US010668071B2

(12) United States Patent
Haßfeld et al.

(10) Patent No.: US 10,668,071 B2
(45) Date of Patent: *Jun. 2, 2020

(54) (AZA)PYRIDOPYRAZOLOPYRIMIDINONES AND INDAZOLOPYRIMIDINONES AND THEIR USE

(71) Applicant: BAYER PHARMA AKTIENGESELLSCHAFT, Berlin (DE)

(72) Inventors: Jorma Haßfeld, Düsseldorf (DE); Tom Kinzel, Düsseldorf (DE); Johannes Köbberling, Neuss (DE); Yolanda Cancho-Grande, Leverkusen (DE); Kristin Beyer, Mainz (DE); Susanne Röhrig, Hilden (DE); Maria Köllnberger, Velbert (DE); Michael Sperzel, Kierspe (DE); Nils Burkhardt, Velbert (DE); Karl-Heinz Schlemmer, Wuppertal (DE); Christian Stegmann, Berlin (DE); Joachim Schuhmacher, Wuppertal (DE); Matthias Werner, Wuppertal (DE); Manuel Ellermann, Wuppertal (DE)

(73) Assignee: BAYER PHARMA AKTIENGESELLSCHAFT, Berlin (DE)

(*) Notice: Subject to any disclaimer, the term of this patent is extended or adjusted under 35 U.S.C. 154(b) by 0 days.

This patent is subject to a terminal disclaimer.

(21) Appl. No.: 16/101,250

(22) Filed: Aug. 10, 2018

(65) Prior Publication Data
US 2018/0344739 A1 Dec. 6, 2018

Related U.S. Application Data

(63) Continuation of application No. 15/416,651, filed on Jan. 26, 2017, now Pat. No. 10,098,883, which is a continuation of application No. 14/533,915, filed on Nov. 5, 2014, now Pat. No. 9,598,417.

(30) Foreign Application Priority Data

Nov. 5, 2013 (EP) ..................................... 13191642

(51) Int. Cl.
A61K 31/519 (2006.01)
A61K 45/06 (2006.01)
C07D 487/04 (2006.01)
C07D 487/12 (2006.01)
C07D 471/14 (2006.01)

(52) U.S. Cl.
CPC ............ A61K 31/519 (2013.01); A61K 45/06 (2013.01); C07D 471/14 (2013.01); C07D 487/04 (2013.01); C07D 487/12 (2013.01)

(58) Field of Classification Search
CPC .... A61K 31/519; A61K 45/06; C07D 471/14; C07D 487/04; C07D 487/12
See application file for complete search history.

(56) References Cited

U.S. PATENT DOCUMENTS 10,098,883 B2 * 10/2018 Ha feld ................ C07D 487/12
2017/0239251 A1 8/2017 Haßfeld et al.

FOREIGN PATENT DOCUMENTS

| WO | WO 2006/023000 | 3/2006 | |
|----|----|----|----|
| WO | WO 2007/088041 | 8/2007 | |
| WO | WO 2010/114780 | 10/2010 | |
| WO | WO 2010/117323 | 10/2010 | |
| WO | WO 2012/047156 | 4/2012 | |
| WO | WO 2012/080237 | 6/2012 | |
| WO | WO 2012/082947 | 6/2012 | |
| WO | WO 2016/173948 | * 11/2016 | ........... C07D 417/04 |

OTHER PUBLICATIONS

"International Preliminary Report on Patentability and Written Opinion", International Application No. PCT/ EP2014/073529, dated May 10, 2016, pp. 1-5.
"International Search Report", International Application No. PCT/ EP2014/073529, dated Dec. 2, 2014, pp. 1-4.
Boström, et al., J Medicinal Chemistry, 56 (8), 2013, pp. 3273-3280.
Cheng, et al., "Discovery of the Fibrinolysis Inhibitor AZD6564, Acting via Interference of a Protein-Protein Interaction", ACS Medicinal Chemistry Letters, 5(5), 2014, pp. 538-543.
Cesarman-Maus et al., "Molecular mechanisms of fibrinolysis," British Journal of Haematology, 2005, 129:307-321.
Day et al., "Direct comparison of binding equilibrium, thermodynamic, and rate constants determined by surface- and solution-based biophysical methods," Protein Science, 2002, 11:1017-1025.
Dunn et al., "Tranexamic Acid A Review of its Use in Surgery and other Indications," Drugs, Jun. 1999, 57 (6):1005-1032.
El-Hemaidi et al., "Menorrhagia and bleeding disorders," Current Opinion in Obstetrics & Gynecology, Dec. 2007, 19(6):513-520.
Flemmig et al., "Serine-proteases as plasminogen activators in terms of fibrinolysis," Journal of Pharmacy and Pharmacology (2012), 64: 1025-1039.

(Continued)

Primary Examiner — Erich A Leeser
(74) Attorney, Agent, or Firm — McBee Moore & Vanik IP, LLC

(57) ABSTRACT

The present application relates to novel substituted (aza) pyridopyrazolopyrimidinones and indazolopyrimidinones, to processes for their preparation, the compounds for use alone or in combinations in a method for the treatment and/or prophylaxis of diseases, in particular for the treatment and/or prophylaxis of acute and recurrent bleeding in patients with or without underlying hereditary or acquired bleeding disorders, wherein the bleeding is associated with a disease or medical intervention selected from the group consisting of menorrhagia, postpartum hemorrhage, hemorrhagic shock, trauma, surgery, transplantation, stroke, liver diseases, hereditary angioedema, nosebleed, and synovitis and cartilage damage following hemarthrosis.

17 Claims, 3 Drawing Sheets

(56) References Cited

OTHER PUBLICATIONS

Fraser et al., "Health-related quality of life and economic burden of abnormal uterine bleeding," Expert Review of Obstetrics and Gynecology, 2009, 4(2):179-189.

Hallberg et al., "Menstrual Blood Loss—A Population Study Variation at different ages and attempts to define normality," Acta Obstetrics and Gynecology Scandinav., 1966, 45{3}:320-351.

Hallberg et al., "Determination of Menstrual Blood Loss," Scandinav. Journal Clin. & Lab. Investigation, 1964, 16:244-248.

Hurskainen et al., "Diagnosis and treatment of menorrhagia," Acta Obstetricia et Gynecologica, 2007, 86:749-757.

Johnsson et al., "Immobilization of Proteins to a Carboxymethyldextran-Modified Gold Surface for Biospecific Interaction Analysis in Surface Plasmon Resonance Sensors," Analytical Biochemistry, 1991, 198:268-277.

Jönsson et al., "Introducing a biosensor based technology for real-time biospecific interaction analysis," Ann Biol. Clin, (Paris) 1993, 51:19-26.

Kadir et al., "Hemostatic disorders in women," Journal of Thrombosis and Haemostasis, 2013, 11 (Suppl. 1):170-179.

Levy, J. H., "Antifibrinolytic therapy: new data and new concepts," The Lancet, Jul. 3, 2010, 376:3-4.

Menhart et al., "Construction, Expression, and Purification of Recombinant Kringle 1 of HumanPlasminogen and Analysis of Its Interaction with w-Amino Acids," Biochemistry, 1991, 30:1948-1957.

Myszka, D. G., "Analysis of small-molecule interactions using Biacore S51 technology," Analytical Biochemistry, 2004, 329:316-323.

NICE (National Institute for Health and Care Excellence), "Heavy menstrual bleeding," NICE Clinical guideline 44, Jan. 2007, pp. 1-34.

Nieuwenhuizen et al., "Antiplasmin, but not amiloride, prevents synovitis and cartilage damage following hemarthrosis in hemophilic mice," Journal of Thrombosis and Haemostasis, 2013, 12:237-245.

O'Flynn et al., "Menorrhagia in general practice—disease or illness," Social Science & Medicine, 2000, 50:651-661.

Shapley et al., "An epidemiological survey of symptoms of menstrual loss in the community," British Journal of General Practice, May 2004, 54:359-363.

Wellington et al., Tranexamic Acid A Review of its Use in the Management of Menorrhagia, Drugs, 2003 63 (13):1417-1433.

West, Anthony R., Solid State Chemistry and its Applications, Wiley, New York, 1988, 358.

Karkouti, et al., "The Risk-Benefit Profile of Aprotinin v. Tranexamic Acid in Cardiac Surgery," Intl. Anesthesia Research Society, (2010), vol. 110, No. 1:21-29.

* cited by examiner

Fig. 1: X-ray diffractogram of the maleate of 10-Chloro-4-(piperidin-4-yl)pyrimido[1,2-b]indazol-2(1H)-one (example 66)
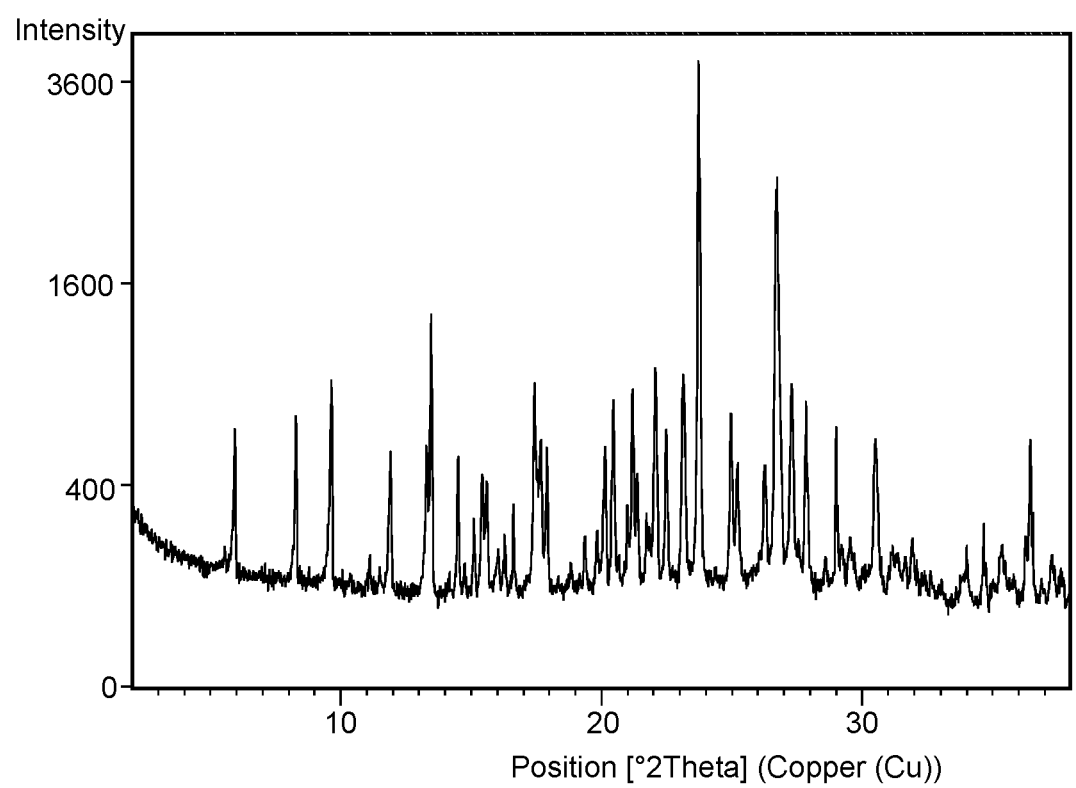

Fig. 2: X-ray diffractogram of the acetate of 10-Chloro-4-(piperidin-4-yl)pyrimido[1,2-b]indazol-2(1H)-one (example 66)
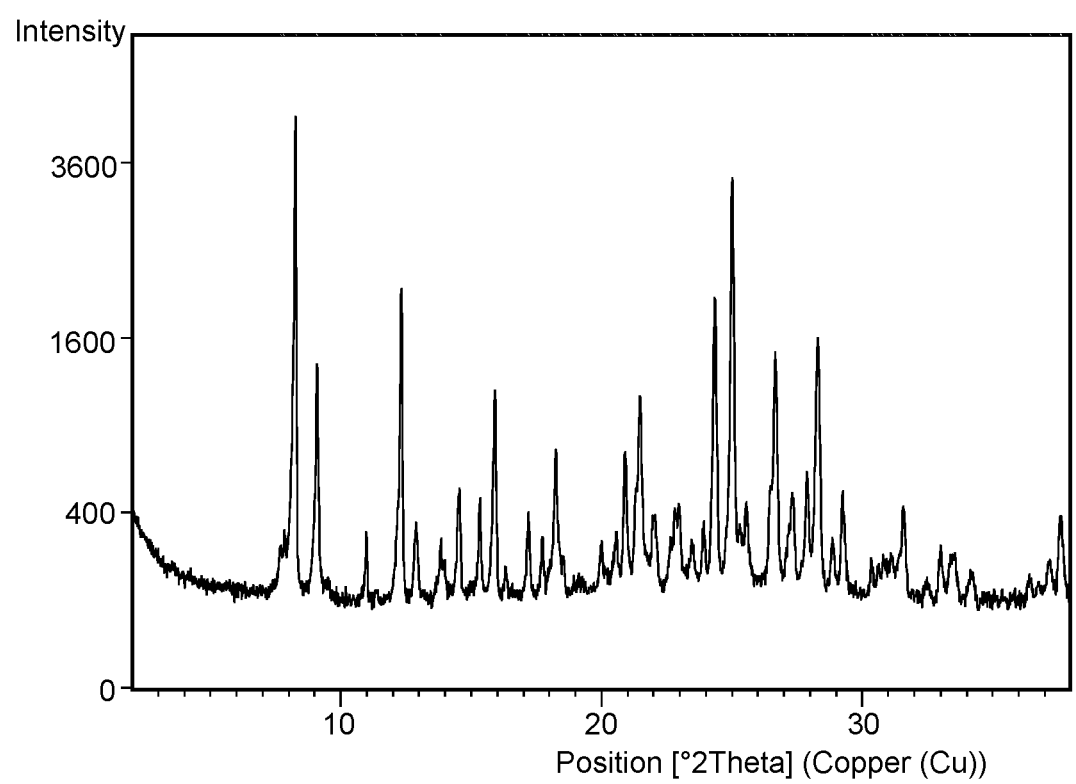

Fig. 3: X-ray diffractogram of the sulfate of 10-Chloro-4-(piperidin-4-yl)pyrimido[1,2-b]indazol-2(1H)-one (example 66)
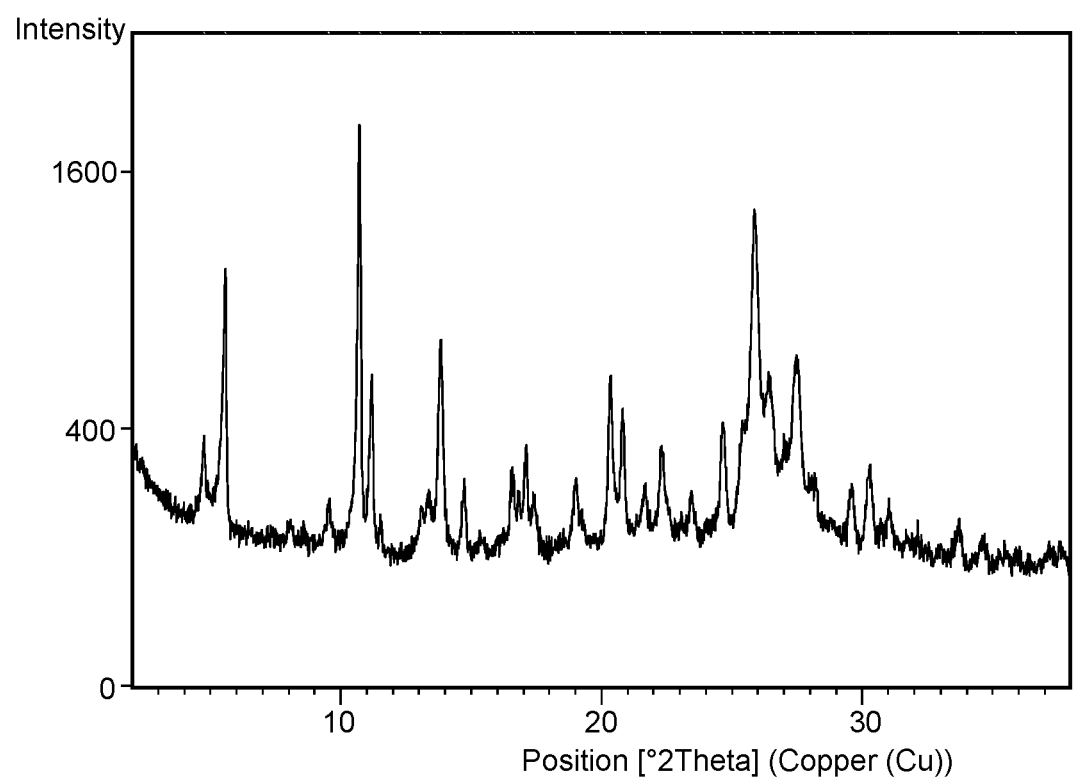

(AZA)PYRIDOPYRAZOLOPYRIMIDINONES AND INDAZOLOPYRIMIDINONES AND THEIR USE

This application is a continuation of U.S. patent application Ser. No. 15/416,651, filed Jan. 26, 2017, now allowed, which was a continuation of U.S. patent application Ser. No. 14/533,915, filed Nov. 5, 2014, now U.S. Pat. No. 9,598, 417, issued Mar. 21, 2017, which claimed priority to European Patent Application No. 13191642.1, filed Nov. 5, 2013, the entire contents of each of which are hereby incorporated by reference.

The present application relates to novel substituted (aza) pyridopyrazolopyrimidinones and indazolopyrimidinones, to processes for their preparation, the compounds for use alone or in combinations in a method for the treatment and/or prophylaxis of diseases, in particular for the treatment and/or prophylaxis of acute and recurrent bleeding in patients with or without underlying hereditary or acquired bleeding disorders. The present invention also relates to medicaments comprising the compounds according to the invention for the treatment and/or prophylaxis of acute and recurrent bleeding in patients with or without underlying hereditary or acquired bleeding disorders, wherein the bleeding is associated with a disease or medical intervention selected from the group consisting of menorrhagia, postpartum hemorrhage, hemorrhagic shock, trauma, surgery, transplantation, stroke, liver diseases, hereditary angioedema, nosebleed, and synovitis and cartilage damage following hemarthrosis.

Bleeding is the common clinical hallmark in hereditary and acquired bleeding disorders, trauma, surgery, stroke, menorrhagia (also termed heavy menstrual bleeding, HMB), postpartum hemorrhage, and liver diseases. When tissue is damaged, vessels can rupture, immediately triggering the hemostatic mechanism, resulting in a stable fibrin network. The fibrinolytic system is activated by the deposition of fibrin and assists in the maintenance of an open lumen in damaged blood vessels. A balance between the formation and lysis of fibrin is required to maintain and remold the hemostatic seal during several days in which the injured vessel wall is repaired.

Fibrinolysis is the physiological mechanism that dissolves clots. The fibrinolytic system comprises plasminogen, the circulating inactive precursor of plasmin, a potent serine protease involved in the dissolution of fibrin blood clots. Tissue-type plasminogen activator (tPA) and urokinase-type plasminogen activator (uPA) are the two major plasminogen activators expressed in many cell types and tissues (Levi J H, Lancet 2010, 376, 9734, 3-4). Plasminogen binds to lysine residues on the surface of fibrin and is converted to plasmin by an activator released from endothelial cells—tPA—that simultaneously binds to fibrin. As part of the hemostatic balance, plasmin generation and activity are also modulated by multiple inhibitors that include plasminogen activator inhibitor (PAI-1), thrombin-activatable fibrinolysis inhibitor (TAFI) and $\alpha_2$-antiplasmin (Cesarman-Maus G, Hajjar K A, Br J Haematol 2005; 129: 307-21).

Activators of fibrinolysis can be therapeutically used to dissolve blood clots in thrombotic conditions like myocardial infarction or ischemic stroke, to avoid degradation of the surrounding tissue (Flemming M, Melzig M F, J Pharm Pharmacol. 2012, 64(8):1025-39). On the other hand inhibition of fibrinolysis can be, and is successfully and safely used in the management of bleeding. After extensive tissue injury that occurs with trauma or surgery, the equilibrium is shifted and fibrinolysis is considered to be an important contributor to bleeding and coagulopathy. In surgical patients, many studies reported the use of antifibrinolytic agents to decrease bleeding and need for allogeneic transfusions. The most commonly used are the lysine analogues, ε-aminocaproic acid and tranexamic acid that interfere with the binding of plasminogen to fibrin, which are necessary for activating plasmin (Levi J H, Lancet 2010, 376, 9734, 3-4).

Antifibrinolytics are a safe and effective proven concept for reducing blood loss and rebleeding, without increased risk for thrombotic events, for example in the management of bleeding disorders like hemophilia and von Willebrand's disease, in menorrhagia (heavy menstrual bleeding, HMB) and in different surgical conditions.

Bleeding due to platelet disorders/dysfunctions like Glantzmann's thrombasthenia and thrombocytopenia as well as anticoagulant-induced bleeding and PAI-1 deficiency might be potential areas of use. Patients with acute promyelocytic leukaemia who frequently develop severe bleeding might also benefit from antifibrinolytics therapy. In addition, it has been suggested that blocking fibrinolysis could potentially be useful to block plasmin-induced proteolysis which may be of biological relevance during athero-thrombosis and inflammatory states, cancer and other diseases.

Further, it has been described that antiplasmin may be used for treating synovitis and cartilage damage following hemarthrosis in patients with underlying bleeding disorders including hemophilia and von Willebrand's disease (L. Nieuwenhuizen L, Roosendaal G, Masterbergen S C, Coeleveld K, Biesma D H, Lafeber F P J G, and Schuthens, R E G, J Thrombosis and Haemostasis 2013, 12: 237-245).

A further potential area of use of antifibrinolytics is the treatment of nosebleed caused by trauma and other causes, also coupled with underlying bleeding disorders including hemophilia and von Willebrand's disease.

Antifibrinolytics have also been successfully applied to the treatment of hereditary angioedema, where a reduction in the number and severity of attacks of edema in patients treated with tranexamic acid could be demonstrated (Dunn C J, Goa K L, Drugs 1999, 57(6): 1005-1032).

Abnormal uterine bleeding (AUB) may be diagnosed when a woman experiences a change in her menstrual blood loss (MBL), or the degree of MBL or vaginal bleeding pattern differs from that experienced by the age-matched general female population (National Collaborating Centre for Women's and Children's Health (NCCWCH): National Institute for Clinical Excellence (NICE) guidelines. CG44 Heavy Menstrual Bleeding: full guideline. 24 Jan. 2007). Normal menstruation occurs at a cycle of 28±7 days, lasting 4±2 days with a mean MBL of 40±20 mL. AUB presents a spectrum of abnormal menstrual bleeding patterns that includes irregular, heavy or prolonged menstrual bleeding or an altered bleeding pattern. AUB may be associated with ovulatory or anovulatory cycles. Terms in use are dysfunctional uterine bleeding (DUB), menorrhagia (abnormally heavy menstrual bleeding at regular intervals which may also be prolonged), metrorrhagia (uterine bleeding at irregular intervals, particularly between the expected menstrual periods), and metromenorrhagia (combination of both).

AUB is one of the most frequent gynecological disorders observed by general practitioners and gynecologists. AUB is an exclusion diagnosis; an organic cause should always be ruled out. Organic causes of AUB include benign uterine neoplasia, especially cervical and endometrial polyps and myoma's, adenomyosis, and malignancies of the cervix and endometrium.

Menorrhagia (heavy menstrual bleeding, HMB) is widely defined in the medical literature as blood loss (MBL) of 80 mL or more per menstrual period (Hallberg L, Nilsson L. Determination of menstrual blood loss. Scandinav J Clin Lab Invest 1964; 16:244-8, Hallberg L, Hogdahl A M, Nilsson L, Rybo G. Menstrual blood loss—a population study. Variation at different ages and attempts to define normality. Acta Obstet Gynecol Scand 1966; 45(3): 320-51, O'Flynn N, Britten N. Menorrhagia in general practice—disease or illness. Soc Sci Med 2000; 50(5): 651-61). Within the meaning of the present invention, menorrhagia is defined as menstrual blood loss of 60 ml or more per cycle, for example 60 to 80 ml per cycle, in particular more than 80 ml per cycle. According to NICE, menorrhagia should be defined for clinical purposes as excessive menstrual blood loss which interferes with the woman's physical, emotional, social and material quality of life, and which can occur alone or in combination with other symptoms. Any interventions should aim to improve quality of life measures. The global prevalence rate of menorrhagia, based on 18 epidemiological studies, ranges from 4% to 52% (Fraser IS, Langham S, Uhl-Hochgraeber K. Health-related quality of life and economic burden of abnormal uterine bleeding. Expert Rev Obstet Gynecol 2009; 4(2): 179-89). The wide variation can be accounted for by different methods of assessment and population samples used by each study. Prevalence rates in studies that use subjective assessments have been found to be consistently higher, compared to 9-11% in studies that directly measured MBL. However an estimated 30% of women suffering from menorrhagia appears to be more representative (Hurskainen R, Grenman S, Komi I, Kujansuu E, Luoto R, Orrainen M, et al. Diagnosis and treatment of menorrhagia. Acta Obstet Gynecol Scand 2007; 86(6): 749-57, El-Hemaidi I, Gharaibeh A, Shehata H. Menorrhagia and bleeding disorders. Curr Opin Obstet Gynecol 2007; 19(6): 513-20). Menorrhagia is more prevalent among women at the extreme ends of the reproductive age spectrum (i.e., adolescent girls and women approaching or going through menopause) (Shapley M, Jordan K, Croft P R. An epidemiological survey of symptoms of menstrual loss in the community. Br J Gen Pract 2004; 54(502): 359-63).

Underlying bleeding disorders, for example hereditary or acquired bleeding disorders, such as hemophilia and von Willebrand's disease, platelet disorders/dysfunctions like Glantzmann's thrombasthenia and thrombocytopenia as well as PAI-1 deficiency, are potential causes of heavy menstrual bleeding. Menstruation and ovulation are unique hemostatic challenges that occur monthly in women of reproductive age. Integral hemostatic systems are required to control excessive bleeding during these events. While men with mild hereditary bleeding disorders are often asymptomatic, women suffer a significant morbidity and impaired quality of life mainly with menstrual-related bleedings. Menorrhagia is often the presenting symptom of an underlying bleeding disorder and can be the only bleeding symptom in women. Menorrhagia was recognized as a valuable predictor for diagnosis of bleeding disorders. A prospective study of 150 women presenting with menorrhagia found the frequency of undiagnosed bleeding disorders of 17% and von Willebrand's disease was the most common with an incidence of 13%. Subsequently, a systematic review of literature confirmed an overall incidence of 13% (95% CI 11%, 15.6%) of von Willebrand's disease among 988 women in 11 studies. Mild platelet function defects are also a frequently found hereditary bleeding disorder in women with menorrhagia. However, disorders of platelet function are more likely to remain undiagnosed due to the complex and specialized testing that requires fresh specimens. There are only a few studies in the literature that assess the incidence of platelet function disorders in women with menorrhagia. These studies reported platelet function defects to be more common than von Willebrand's disease and were found in approximately 50% of women presenting with menorrhagia. Thus, the association of menorrhagia in women and hereditary bleeding disorders is well established (Kadir R A, Davies J. Hemostatic disorders in women. J Thromb Haemost 2013, 11 (Suppl.1): 170-9).

Tranexamic acid is approved for the treatment of menorrhagia and a variety of surgical hemorrhagic conditions. Very high, multiple doses of tranexamic acid are required and the most commonly reported drug-related adverse events after oral administration are gastrointestinal, like nausea, vomiting, diarrhea and dyspepsia (Wellington K, Wagstaff A J, Drugs 2003, 63 (13): 1417-1433), (Dunn C J, Goa K L, Drugs 1999, 57(6): 1005-1032). WO 2006/023000 A1 pertains to modified release oral tranexamic acid formulations and methods of treatment herewith.

WO 2010/117323 A1 and WO 2012/047156 A1 pertain to isoxazol-3(2H)-one analogs as plasminogen inhibitors and their use in the treatment of fibrinolysis related diseases, including hereditary bleeding disorders, stroke, menorrhagia and liver diseases. The compounds described in WO 2010/117323 A1 and WO 2012/047156 A1 are structurally unrelated to the compounds of the present invention.

WO 2012/080237 pertains to substituted pyrimido[1,2-B]indazoles and their use as modulators of the PI3K/AKT pathway for the treatment of cancer. The compounds of formula (I-A) or (I-B) according to the present invention are structurally distinct from the compounds of formula (I) of WO 2012/080237.

It was an object of the present invention to provide novel substances which act as inhibitors of fibrinolysis and, as such, are suitable for the treatment and/or prophylaxis of diseases.

The present invention provides compounds of the general formula (I-A)

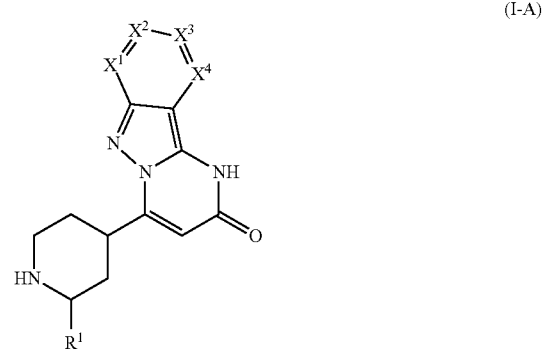

(I-A)

in which
$R^1$ is selected from hydrogen and $C_1$-$C_4$ alkyl;
$X^1$ is selected from nitrogen and C—$R^2$;
$X^2$ is selected from nitrogen and C—$R^3$;
$X^3$ is selected from nitrogen and C—$R^4$;
$X^4$ is selected from nitrogen and C—$R^5$;
with the proviso that 0, 1 or 2 of $X^1$ to $X^4$ are nitrogen; and
$R^2$, $R^3$, $R^4$, and $R^5$ are independently from each other selected from hydrogen, halogen, $C_1$-$C_4$ alkyl, $C_1$-$C_4$ alkenyl, $C_1$-$C_4$ haloalkyl, $C_1$-$C_4$ alkoxy, $C_1$-$C_4$ haloalkoxy, cyano, amino, nitro, mono- or dialkylamino, hydroxy, thiol, carboxyl, $C_3$-$C_7$ cycloalkyl, 5 to 6 membered heteroaryl, the 5 to 6 membered heteroaryl being optionally substituted with one, two, or three substituents selected from $C_1$-$C_4$ alkyl, and phenyl, the phenyl being optionally substituted with one, two, or three substituents selected from halogen, $C_1$-$C_4$ alkyl, $C_1$-$C_4$ haloalkyl, $C_1$-$C_4$ alkoxy, and $C_1$-$C_4$ haloalkoxy, or a group of a formula selected from —CO—$NR^7R^8$, —NH—CO—$R^9$, —CO—O—$R^9$, —CO—$R^9$, —$SO_2R^{10}$, —$SO_2NR^{11}R^{12}$, —$SR^{10}$, $CH_2CN$, —$CH_2NR^{11}R^{12}$, —$CH_2OR^{10}$, wherein $R^7$ and $R^8$ independently from each other represent hydrogen, $C_1$-$C_4$ alkyl, $C_6$ aryl, and 5-6 membered heteroaryl;

$R^9$ represents $C_1$-$C_4$ alkyl, $C_6$ aryl, and 5-6 membered heteroaryl;

$R^{10}$ represents $C_1$-$C_4$ alkyl;

$R^{11}$ and $R^{12}$ independently from each other represent hydrogen, and $C_1$-$C_4$ alkyl;

with the proviso that zero, one, two, or three of $R^2$ to $R^5$ are different from hydrogen, and salts, solvates, and solvates of the salts.

The present invention provides compounds of the general formula (I-B)

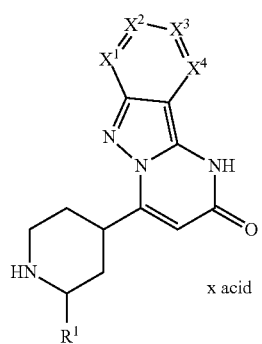

(I-B)

in which $R^1$, $X^1$, $X^2$, $X^3$, and $X^4$ are as defined above, and salts, solvates, and solvates of the salts.

Compounds according to the invention are the compounds of the formulae (I-A) or (I-B) and their salts, solvates and solvates of the salts, the compounds included in the formulae (I-A) or (I-B) of the formulae mentioned in the following and their salts, solvates and solvates of the salts, and the compounds included in the formulae (I-A) or (I-B) and mentioned in the following as embodiment examples and their salts, solvates and solvates of the salts, where the compounds included in the formulae (I-A) or (I-B) and mentioned in the following are not already salts, solvates and solvates of the salts.

Within the meaning of the present invention, the term "x acid" in any of the formulae does not indicate any defined stoichiometric ratio of acid and the respective compound. Thus, depending e.g. on the alkalinity of the respective compound, the term "x acid" denotes different ratios of the compound to the acid, such as 10:1 to 1:10, 8:1 to 1:8, 7:1 to 1:7, 5:1 to 1:5, 4.5:1 to 1:4.5, 4:1 to 1:4, 3.5:1 to 1:3.5, 3:1 to 1:3, 2.5:1 to 1:2.5, 2:1 to 1:2, 1.5:1 to 1:1.5, and 1:1.

Preferred salts in the context of the present invention are physiologically acceptable salts of the compounds of formula (I-A) or (I-B) according to the invention. Salts which are not themselves suitable for pharmaceutical uses but can be used, for example, for isolation or purification of the compounds of formula (I-A) or (I-B) according to the invention are also included.

Physiologically acceptable salts of the compounds of formula (I-A) or (I-B) according to the invention include acid addition salts of mineral acids, carboxylic acids and sulphonic acids, e.g. salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, formic acid, acetic acid, trifluoroacetic acid, propionic acid, lactic acid, tartaric acid, malic acid, citric acid, fumaric acid, maleic acid, benzoic acid, oxalic acid, ascorbic acid, and salicylic acid.

Physiologically acceptable salts of the compounds of formula (I-A) or (I-B) according to the invention also include salts of conventional bases, such as, by way of example and preferably, alkali metal salts (e.g. sodium and potassium salts), alkaline earth metal salts (e.g. calcium and magnesium salts) and ammonium salts derived from ammonia or organic amines having 1 to 16 carbon atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, and N-methylpiperidine.

According to an embodiment of the invention, physiologically acceptable salts of the compounds of formula (I-A) or (I-B) according to the invention include salts of hydrochloric acid, sulphuric acid, maleic acid, acetic acid, trifluoroacetic acid, phosphoric acid, tartaric acid, citric acid, fumaric acid, oxalic acid, ascorbic acid, salicylic acid, and lysine.

According to an embodiment of the invention, physiologically acceptable salts of the compounds of formula (I-A) or (I-B) according to the invention include salts of hydrochloric acid, sulphuric acid, maleic acid, acetic acid, trifluoroacetic acid, tartaric acid, ascorbic acid, and salicylic acid.

According to an embodiment of the invention, physiologically acceptable salts of the compounds of formula (I-A) or (I-B) according to the invention include salts of hydrochloric acid, and trifluoroacetic acid.

According to an embodiment of the invention, the physiologically acceptable salts of the compounds of formula (I-A) or (I-B) according to the invention are the salts of hydrochloric acid.

An embodiment of the invention is also the compound 10-Chloro-4-(piperidin-4-yl)pyrimido[1,2-b]indazol-2(1H)-one (example 66) in form of its physiologically acceptable salts as defined above.

An embodiment of the invention is also the compound 10-Chloro-4-(piperidin-4-yl)pyrimido[1,2-b]indazol-2(1H)-one (example 66) in form of its physiologically acceptable salts selected from the group of salts of hydrochloric acid, sulphuric acid, maleic acid, acetic acid, trifluoroacetic acid, phosphoric acid, tartaric acid, citric acid, fumaric acid, oxalic acid, ascorbic acid, salicylic acid, and lysine.

An embodiment of the invention is also the compound 10-Chloro-4-(piperidin-4-yl)pyrimido[1,2-b]indazol-2(1H)-one (example 66) in form of its physiologically acceptable salts selected from the group of salts of hydrochloric acid, sulphuric acid, maleic acid, acetic acid, trifluoroacetic acid, tartaric acid, ascorbic acid, and salicylic acid.

An embodiment of the invention is also the compound 10-Chloro-4-(piperidin-4-yl)pyrimido[1,2-b]indazol-2(1H)-one (example 66) in form of its physiologically acceptable salts selected from the group of salts of hydrochloric acid, and trifluoroacetic acid.

An embodiment of the invention is also the compound 10-Chloro-4-(piperidin-4-yl)pyrimido[1,2-b]indazol-2(1H)- one (example 66) in form of its maleate that shows the following preferred peak maximum of the °2 Theta: 9.6, 13.5, 17.4, 22.1, 23.1, 23.7, and 26.7.

An embodiment of the invention is also the compound 10-Chloro-4-(piperidin-4-yl)pyrimido[1,2-b]indazol-2(1H)-one (example 66) in form of its acetate that shows the following preferred peak maximum of the °2 Theta: 8.3, 9.1, 12.3, 24.3, 25.0, 26.7, 28.3.

An embodiment of the invention is also the compound 10-Chloro-4-(piperidin-4-yl)pyrimido[1,2-b]indazol-2(1H)-one (example 66) in form of its sulfate that shows the following preferred peak maximum of the °2 Theta: 5.6, 10.7, 13.8, 20.3, 20.8, 25.8, 27.6.

An embodiment of the invention is also the compound 10-Chloro-4-(piperidin-4-yl)pyrimido[1,2-b]indazol-2(1H)-one (example 66) in form of its physiologically acceptable salts as defined above.

An embodiment of the invention is also one or more physiologically acceptable salts as defined above of the compound 10-Chloro-4-(piperidin-4-yl)pyrimido[1,2-b]indazol-2(1H)-one (example 66) for the treatment and/or prophylaxis of diseases.

An embodiment of the invention is also one or more physiologically acceptable salts as defined above of the compound 10-Chloro-4-(piperidin-4-yl)pyrimido[1,2-b]indazol-2(1H)-one (example 66) for use in a method for the treatment and/or prophylaxis of acute and recurrent bleeding in patients with or without underlying hereditary or acquired bleeding disorders.

An embodiment of the invention is also one or more physiologically acceptable salts as defined above of the compound 10-Chloro-4-(piperidin-4-yl)pyrimido[1,2-b]indazol-2(1H)-one (example 66) for use in a method for the treatment and/or prophylaxis of acute and recurrent bleeding in patients with underlying hereditary or acquired bleeding disorders.

An embodiment of the invention is also one or more physiologically acceptable salts as defined above of the compound 10-Chloro-4-(piperidin-4-yl)pyrimido[1,2-b]indazol-2(1H)-one (example 66) for use in a method for the treatment and/or prophylaxis of acute and recurrent bleeding in patients with underlying hereditary or acquired hemostatic disorders.

An embodiment of the invention is also one or more physiologically acceptable salts as defined above of the compound 10-Chloro-4-(piperidin-4-yl)pyrimido[1,2-b]indazol-2(1H)-one (example 66) for use in a method for the treatment and/or prophylaxis of acute and recurrent bleeding in patients with underlying rare bleeding disorders.

An embodiment of the invention is also one or more physiologically acceptable salts as defined above of the compound 10-Chloro-4-(piperidin-4-yl)pyrimido[1,2-b]indazol-2(1H)-one (example 66) for use in a method for the treatment and/or prophylaxis of acute and recurrent bleeding in patients with or without underlying hereditary or acquired bleeding disorders, wherein the bleeding is associated with a disease or medical intervention selected from the group consisting of menorrhagia, postpartum hemorrhage, hemorrhagic shock, trauma, surgery, otolaryngological surgery, dental surgery, urinary surgery, prostatic surgery, gynaecological surgery, cardiovascular surgery, spinal surgery, liver or lung transplantation, stroke, liver diseases, hereditary angioedema, nosebleed, and synovitis and cartilage damage following hemarthrosis.

Within the meaning of this invention, the terms "heavy menstrual bleeding, HMB" and "menorrhagia" are interchangeable.

An embodiment of the invention is also one or more physiologically acceptable salts as defined above of the compound 10-Chloro-4-(piperidin-4-yl)pyrimido[1,2-b]indazol-2(1H)-one (example 66) for use in a method for the treatment and/or prophylaxis of acute and recurrent bleeding in patients with or without underlying hereditary or acquired bleeding disorders, wherein the bleeding is associated with a disease or medical intervention selected from the group consisting of heavy menstrual bleeding (HMB), postpartum hemorrhage, hemorrhagic shock, trauma, surgery, otolaryngological surgery, dental surgery, urinary surgery, prostatic surgery, gynaecological surgery, cardiovascular surgery, spinal surgery, liver or lung transplantation, stroke, liver diseases, hereditary angioedema, nosebleed, and synovitis and cartilage damage following hemarthrosis.

An embodiment of the invention is also one or more physiologically acceptable salts as defined above of the compound 10-Chloro-4-(piperidin-4-yl)pyrimido[1,2-b]indazol-2(1H)-one (example 66) for use in a method for the treatment and/or prophylaxis of acute and recurrent bleeding in patients with underlying hereditary or acquired bleeding disorders, wherein the bleeding is associated with a disease or medical intervention selected from the group consisting of menorrhagia, postpartum hemorrhage, hemorrhagic shock, trauma, surgery, otolaryngological surgery, dental surgery, urinary surgery, prostatic surgery, gynaecological surgery, cardiovascular surgery, spinal surgery, liver or lung transplantation, stroke, liver diseases, hereditary angioedema, nosebleed, and synovitis and cartilage damage following hemarthrosis.

In the context of the present invention, the term "medical intervention" includes medical interventions associated with bleeding, such as surgery and transplantation. The definition of the term "medical intervention" also includes minor medical interventions that may cause bleeding, such as tooth extractions, periodontal (gum) surgery, dental implant placement, biopsies, e.g. dental, prostatic, and urinary biopsies, and the removal of urinary stones.

An embodiment of the invention is also the use of one or more physiologically acceptable salts as defined above of the compound 10-Chloro-4-(piperidin-4-yl)pyrimido[1,2-b]indazol-2(1H)-one (example 66) for producing a medicament for the treatment and/or prophylaxis of acute and recurrent bleeding in patients with or without underlying hereditary or acquired bleeding disorders.

An embodiment of the invention is also the use of one or more physiologically acceptable salts as defined above of the compound 10-Chloro-4-(piperidin-4-yl)pyrimido[1,2-b]indazol-2(1H)-one (example 66) for producing a medicament for the treatment and/or prophylaxis of acute and recurrent bleeding in patients with underlying hereditary or acquired bleeding disorders.

An embodiment of the invention is also the use of one or more physiologically acceptable salts as defined above of the compound 10-Chloro-4-(piperidin-4-yl)pyrimido[1,2-b]indazol-2(1H)-one (example 66) for producing a medicament for the treatment and/or prophylaxis of acute and recurrent bleeding in patients with or without underlying hereditary or acquired bleeding disorders, wherein the bleeding is associated with a disease or medical intervention selected from the group consisting of menorrhagia, postpartum hemorrhage, hemorrhagic shock, trauma, surgery, otolaryngological surgery, dental surgery, urinary surgery, prostatic surgery, gynaecological surgery, cardiovascular surgery, spinal surgery, liver or lung transplantation, stroke, liver diseases, hereditary angioedema, nosebleed, and synovitis and cartilage damage following hemarthrosis.

An embodiment of the invention is also the use of one or more physiologically acceptable salts as defined above of the compound 10-Chloro-4-(piperidin-4-yl)pyrimido[1,2-b]indazol-2(1H)-one (example 66) for producing a medicament for the treatment and/or prophylaxis of acute and recurrent bleeding in patients with underlying hereditary or acquired bleeding disorders, wherein the bleeding is associated with a disease or medical intervention selected from the group consisting of menorrhagia, postpartum hemorrhage, hemorrhagic shock, trauma, surgery, otolaryngological surgery, dental surgery, urinary surgery, prostatic surgery, gynaecological surgery, cardiovascular surgery, spinal surgery, liver or lung transplantation, stroke, liver diseases, hereditary angioedema, nosebleed, and synovitis and cartilage damage following hemarthrosis.

An embodiment of the invention is also a medicament comprising one or more physiologically acceptable salts as defined above of the compound 10-Chloro-4-(piperidin-4-yl)pyrimido[1,2-b]indazol-2(1H)-one (example 66) in combination with an inert, non-toxic, pharmaceutically suitable auxiliary.

An embodiment of the invention is also a medicament comprising one or more physiologically acceptable salts as defined above of the compound 10-Chloro-4-(piperidin-4-yl)pyrimido[1,2-b]indazol-2(1H)-one (example 66) in combination with a further active compound selected from the group consisting of Factor VIII, Factor IX, Factor VIIa, activated prothrombin complex concentrates (aPCC) or prothrombin complex concentrates (PCCs), ε-aminocaproic acid, ethamsylate, paraaminobutyl benzoic acid, tranexamic acid, desmopressin, danazol, combined oral contraceptive pills (COCPs), progestin intrauterine system, glucocorticoid receptor agonists, analgesics, and nonsteroidal anti-inflammatory drugs (NSAIDs).

An embodiment of the invention is also a medicament comprising one or more physiologically acceptable salts as defined above of the compound 10-Chloro-4-(piperidin-4-yl)pyrimido[1,2-b]indazol-2(1H)-one (example 66) for the treatment and/or prophylaxis of acute and recurrent bleeding in patients with or without underlying hereditary or acquired bleeding disorders.

An embodiment of the invention is also a medicament comprising one or more physiologically acceptable salts as defined above of the compound 10-Chloro-4-(piperidin-4-yl)pyrimido[1,2-b]indazol-2(1H)-one (example 66) for the treatment and/or prophylaxis of acute and recurrent bleeding in patients with underlying hereditary or acquired bleeding disorders.

An embodiment of the invention is also a medicament comprising one or more physiologically acceptable salts as defined above of the compound 10-Chloro-4-(piperidin-4-yl)pyrimido[1,2-b]indazol-2(1H)-one (example 66) for the treatment and/or prophylaxis of acute and recurrent bleeding in patients with or without underlying hereditary or acquired bleeding disorders, wherein the bleeding is associated with a disease or medical intervention selected from the group consisting of menorrhagia, postpartum hemorrhage, hemorrhagic shock, trauma, surgery, otolaryngological surgery, dental surgery, urinary surgery, prostatic surgery, gynaecological surgery, cardiovascular surgery, spinal surgery, liver or lung transplantation, stroke, liver diseases, hereditary angioedema, nosebleed, and synovitis and cartilage damage following hemarthrosis.

An embodiment of the invention is also a medicament comprising one or more physiologically acceptable salts as defined above of the compound 10-Chloro-4-(piperidin-4-yl)pyrimido[1,2-b]indazol-2(1H)-one (example 66) for the treatment and/or prophylaxis of acute and recurrent bleeding in patients with underlying hereditary or acquired bleeding disorders, wherein the bleeding is associated with a disease or medical intervention selected from the group consisting of menorrhagia, postpartum hemorrhage, hemorrhagic shock, trauma, surgery, otolaryngological surgery, dental surgery, urinary surgery, prostatic surgery, gynaecological surgery, cardiovascular surgery, spinal surgery, liver or lung transplantation, stroke, liver diseases, hereditary angioedema, nosebleed, and synovitis and cartilage damage following hemarthrosis.

An embodiment of the invention is also a method for the treatment and/or prophylaxis of acute and recurrent bleeding in humans and animals with or without underlying hereditary or acquired bleeding disorders, using an effective amount of one or more physiologically acceptable salts as defined above of the compound 10-Chloro-4-(piperidin-4-yl)pyrimido[1,2-b]indazol-2(1H)-one (example 66).

An embodiment of the invention is also a method for the treatment and/or prophylaxis of acute and recurrent bleeding in humans and animals with underlying hereditary or acquired bleeding disorders, using an effective amount of one or more physiologically acceptable salts as defined above of the compound 10-Chloro-4-(piperidin-4-yl)pyrimido[1,2-b]indazol-2(1H)-one (example 66).

An embodiment of the invention is also a method for the treatment and/or prophylaxis of acute and recurrent bleeding in humans and animals with or without underlying hereditary or acquired bleeding disorders, wherein the bleeding is associated with a disease or medical intervention selected from the group consisting of menorrhagia, postpartum hemorrhage, hemorrhagic shock, trauma, surgery, otolaryngological surgery, dental surgery, urinary surgery, prostatic surgery, gynaecological surgery, cardiovascular surgery, spinal surgery, liver or lung transplantation, stroke, liver diseases, hereditary angioedema, nosebleed, and synovitis and cartilage damage following hemarthrosis, using an effective amount of one or more physiologically acceptable salts as defined above of the compound 10-Chloro-4-(piperidin-4-yl)pyrimido[1,2-b]indazol-2(1H)-one (example 66).

An embodiment of the invention is also a method for the treatment and/or prophylaxis of acute and recurrent bleeding in humans and animals with underlying hereditary or acquired bleeding disorders, wherein the bleeding is associated with a disease or medical intervention selected from the group consisting of menorrhagia, postpartum hemorrhage, hemorrhagic shock, trauma, surgery, otolaryngological surgery, dental surgery, urinary surgery, prostatic surgery, gynaecological surgery, cardiovascular surgery, spinal surgery, liver or lung transplantation, stroke, liver diseases, hereditary angioedema, nosebleed, and synovitis and cartilage damage following hemarthrosis, using an effective amount of one or more physiologically acceptable salts as defined above of the compound 10-Chloro-4-(piperidin-4-yl)pyrimido[1,2-b]indazol-2(1H)-one (example 66).

Solvates in the context of the invention are designated as those forms of the compounds of formula (I-A) or (I-B) according to the invention which form a complex in the solid or liquid state by coordination with solvent molecules. Hydrates are a specific form of solvates, in which the coordination takes place with water. Hydrates are preferred solvates in the context of the present invention.

The compounds of formula (I-A) or (I-B) according to the invention can exist in different stereoisomeric forms depending on their structure, i.e. in the form of configuration isomers or optionally also as conformation isomers (enantiomers and/or diastereomers, including those in the case of atropisomers).

The present invention therefore includes the enantiomers and diastereomers and their particular mixtures. The stereoisomerically uniform constituents can be isolated from such mixtures of enantiomers and/or diastereomers in a known manner; chromatography processes are preferably used for this, in particular HPLC chromatography on an achiral or chiral phase.

Where the compounds of formula (I-A) or (I-B) according to the invention can occur in tautomeric forms, the present invention includes all the tautomeric forms.

Examples of stereoisomeric forms of the compounds of formula (I-A) or (I-B) or (IV) according to the invention are compounds of the formulae (I-A) or (I-B) as defined above, and compounds of the formula (IV) as defined below, wherein the substituent $R^1$ has the meaning of $C_1$-$C_4$ alkyl.

Formula (I-A), wherein the substituent $R^1$ has the meaning of $C_1$-$C_4$ alkyl, comprises the following trans-isomers:

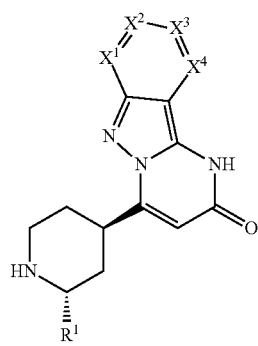
(I-A)

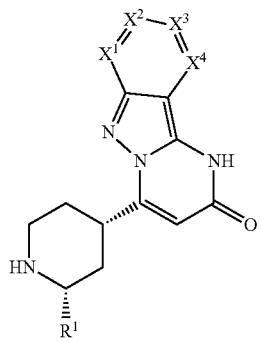
(I-A)

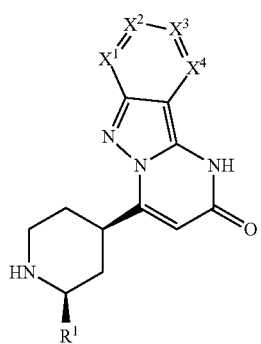
(I-A)

Formula (I-B), wherein the substituent $R^1$ has the meaning of $C_1$-$C_4$ alkyl, comprises the following trans-isomers:

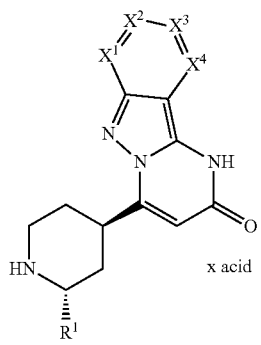
(I-B)

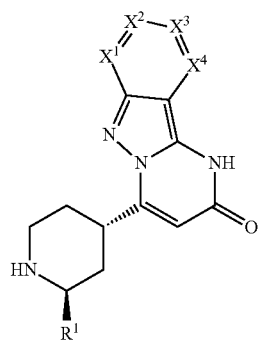
(I-A)

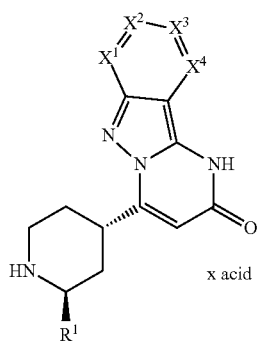
(I-B)

Formula (I-A), wherein the substituent $R^1$ has the meaning of $C_1$-$C_4$ alkyl, further comprises the following cis-isomers:

Formula (I-B), wherein the substituent $R^1$ has the meaning of $C_1$-$C_4$ alkyl, further comprises the following cis-isomers:

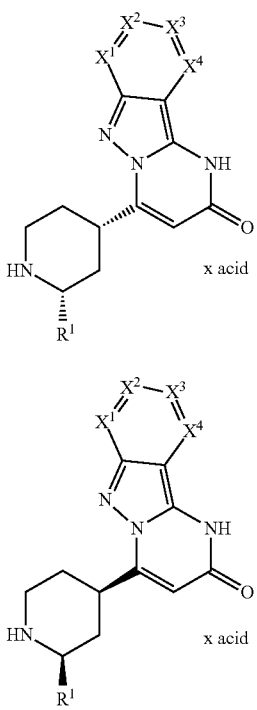
(I-B)

(I-B)

Formula (IV), wherein the substituent R¹ has the meaning of C₁-C₄ alkyl, comprises the following trans-isomers:

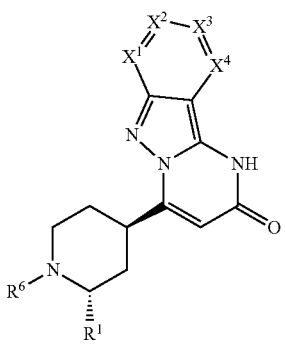
(IV)

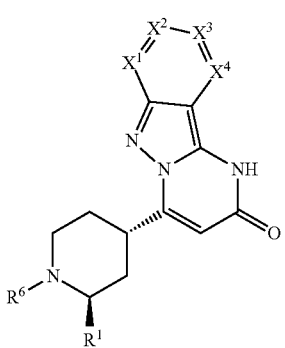
(IV)

Formula (IV), wherein the substituent R¹ has the meaning of C₁-C₄ alkyl, further comprises the following cis-isomers:

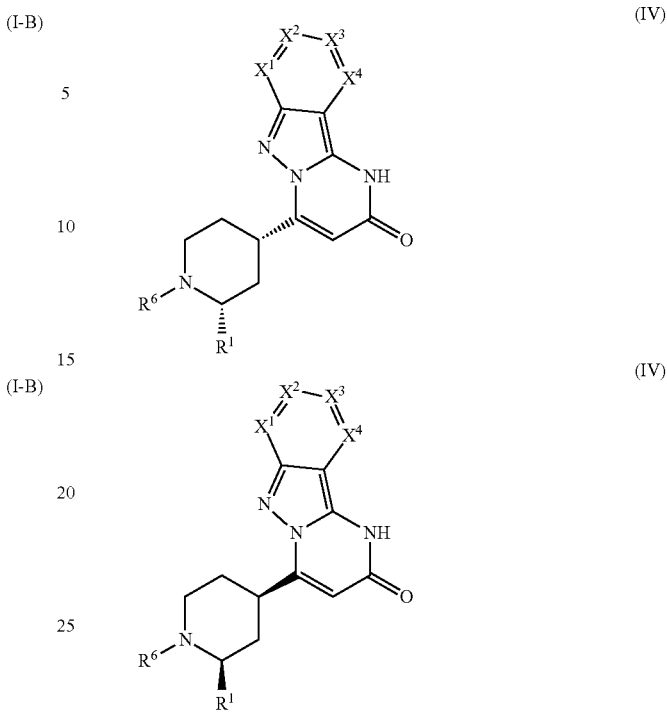
(IV)

(IV)

The present invention comprises all possible stereoisomeric forms, also in cases where no stereoisomerism is indicated.

According to an embodiment of the invention, the compounds of formulae (I-A), (I-B), and (IV), wherein the substituent R¹ has the meaning of C₁-C₄ alkyl, are present as mixtures of cis- and trans-isomers.

According to an embodiment of the invention, the compounds of formulae (I-A), (I-B), and (IV), wherein the substituent R¹ has the meaning of C₁-C₄ alkyl, are present as mixtures of cis- and trans-isomers, wherein more than 50%, more than 55%, more than 60%, more than 65%, more than 70%, more than 75%, more than 80%, more than 85%, more than 90%, more than 95%, more than 97%, more than 98%, or more than 99%, of the compounds of formulae (I-A), (I-B), and (IV) are present as trans-isomer.

According to an embodiment of the invention, the compounds of formulae (I-A), (I-B), and (IV), wherein the substituent R¹ has the meaning of C₁-C₄ alkyl, are present as the enantiomerically pure trans-isomers.

The present invention also encompasses all suitable isotopic variants of the compounds of formula (I-A) or (I-B) according to the invention. An isotopic variant of a compound according to the invention is understood here to mean a compound in which at least one atom within the compound according to the invention has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, phosphorus, sulphur, fluorine, chlorine, bromine and iodine, such as ²H (deuterium), ³H (tritium), ¹³C, ¹⁴C, ¹⁵N, ¹⁷O, ¹⁸O, ³²P, ³³P, ³³S, ³⁴S, ³⁵S, ³⁶S, ¹⁸F, ³⁶Cl, ⁸²Br, ¹²³I, ¹²⁴I, ¹²⁹I and ¹³¹I. Particular isotopic variants of a compound according to the invention, especially those in which one or more radioactive isotopes have been incorporated, may be beneficial, for example, for the examination of the mechanism of action or of the active compound distribution in the body; due to comparatively easy preparability and detectability, especially compounds labelled with $^3H$ or $^{14}C$ isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of the compounds of formula (I-A) or (I-B) according to the invention may therefore in some cases also constitute a preferred embodiment of the present invention. Isotopic variants of the compounds of formula (I-A) or (I-B) according to the invention can be prepared by processes known to those skilled in the art, for example by the methods described below and the methods described in the working examples, by using corresponding isotopic modifications of the particular reagents and/or starting compounds therein.

The present invention moreover also includes prodrugs of the compounds of formula (I-A) or (I-B) according to the invention. The term "prodrugs" here designates compounds which themselves can be biologically active or inactive, but are converted (for example metabolically or hydrolytically) into compounds of formula (I-A) or (I-B) according to the invention during their dwell time in the body.

In the context of the present invention, the substituents have the following meaning, unless specified otherwise:

Alkyl in the context of the invention represents a straight-chain or branched alkyl radical having the number of carbon atoms stated in each case. The following may be mentioned by way of example and by way of preference: methyl, ethyl, n-propyl, isopropyl, n-butyl, isobutyl, 1-methylpropyl, tert-butyl, n-pentyl, isopentyl, 1-ethylpropyl, 1-methylbutyl, 2-methylbutyl, 3-methylbutyl, n-hexyl, 1-methylpentyl, 2-methylpentyl, 3-methylpentyl, 4-methylpentyl, 3,3-dimethylbutyl, 1-ethylbutyl, 2-ethylbutyl.

Haloalkyl in the context of the invention represents an alkyl radical as defined above being mono- or polyhalogenated up to the maximum possible number of substituents. In the case of polyhalogenation, the halogen atoms can be identical or different. Here, halogen represents fluorine, chlorine, bromine or iodine, in particular fluorine, chlorine or bromine.

Cycloalkyl or carbocycle in the context of the invention represents a monocyclic saturated alkyl radical having the number of ring carbon atoms stated in each case. The following may be mentioned by way of example and by way of preference: cyclopropyl, cyclobutyl, cyclopentyl, cyclohexyl and cycloheptyl.

Alkenyl in the context of the invention represents a straight-chain or branched alkenyl radical having 2 to 6 carbon atoms and one or two double bonds. Preference is given to a straight-chain or branched alkenyl radical having 2 to 4 carbon atoms and one double bond. The following may be mentioned by way of example and by way of preference: vinyl, allyl, isopropenyl and n-but-2-en-1-yl.

Alkoxy in the context of the invention represents a straight-chain or branched alkoxy radical having 1 to 4 carbon atoms. The following may be mentioned by way of example and by way of preference: methoxy, ethoxy, n-propoxy, isopropoxy, 1-methylpropoxy, n-butoxy, isobutoxy and tert-butoxy.

Haloalkoxy in the context of the invention represents an alkoxy radical as defined above being mono- or polyhalogenated up to the maximum possible number of substituents. In the case of polyhalogenation, the halogen atoms can be identical or different. Here, halogen represents fluorine, chlorine, bromine or iodine, in particular fluorine, chlorine or bromine.

Alkylamino in the context of the invention includes mono- and dialkylamino and represents an amino group wherein one or two hydrogen atoms are substituted with alkyl radicals.

A 5 to 6-membered Heteroaryl in the context of the invention represents a monocyclic aromatic heterocycle (heteroaromatic) which has a total of 5 or 6 ring atoms, which contains up to three identical or different ring heteroatoms from the group consisting of N, O and S and is attached via a ring carbon atom or, if appropriate, a ring nitrogen atom. The following may be mentioned by way of example and by way of preference: furyl, pyrrolyl, thienyl, pyrazolyl, imidazolyl, thiazolyl, oxazolyl, isoxazolyl, isothiazolyl, triazolyl, oxadiazolyl, thiadiazolyl, pyridyl, pyrimidinyl, pyridazinyl, pyrazinyl and triazinyl.

Halogen in the context of the invention includes fluorine, chlorine, bromine and iodine. Preference is given to chlorine, bromine, or fluorine.

If radicals in the compounds of formula (I-A) or (I-B) according to the invention are substituted, the radicals may, unless specified otherwise, be mono- or polysubstituted. In the context of the present invention, all radicals which occur more than once are defined independently of one another.

Substitution by one, two or three identical or different substituents is preferred.

In the context of the present invention, the term "treatment" or "treat" includes the inhibition, delay, arrest, amelioration, attenuation, limitation, reduction, suppression, reversal or cure of a disease, a condition, a disorder, an injury and a health impairment, of the development, course or the progression of such states and/or the symptoms of such states. Here, the term "therapy" is understood to be synonymous with the term "treatment".

In the context of the present invention, the terms "prevention", "prophylaxis" or "precaution" are used synonymously and refer to the avoidance or reduction of the risk to get, to contract, to suffer from or to have a disease, a condition, a disorder, an injury or a health impairment, a development or a progression of such states and/or the symptoms of such states.

The treatment or the prevention of a disease, a condition, a disorder, an injury or a health impairment may take place partially or completely.

According to an embodiment of the present invention, the compounds of the formulae (I-A) or (I-B) are defined as follows:

$R^1$ is selected from hydrogen and $C_1$-$C_4$ alkyl;
$X^1$ is selected from nitrogen and C—$R^2$;
$X^2$ is selected from nitrogen and C—$R^3$;
$X^3$ is selected from nitrogen and C—$R^4$;
$X^4$ is selected from nitrogen and C—$R^5$;
with the proviso that 0, 1 or 2 of $X^1$ to $X^4$ are nitrogen; and $R^2$, $R^3$, $R^4$, and $R^5$ are independently from each other selected from hydrogen, halogen, $C_1$-$C_4$ alkyl, $C_1$-$C_4$ alkenyl, $C_1$-$C_4$ haloalkyl, $C_1$-$C_4$ alkoxy, $C_1$-$C_4$ haloalkoxy, cyano, amino, nitro, mono- or dialkylamino, $C_3$-$C_7$ cycloalkyl, 5 to 6 membered heteroaryl, the 5 to 6 membered heteroaryl being optionally substituted with one, two, or three substituents selected from $C_1$-$C_4$ alkyl, and phenyl, the phenyl being optionally substituted with one, two, or three substituents selected from halogen, $C_1$-$C_4$ alkyl, $C_1$-$C_4$ haloalkyl, $C_1$-$C_4$ alkoxy, and $C_1$-$C_4$ haloalkoxy;
with the proviso that zero, one, two, or three of $R^2$ to $R^5$ are different from hydrogen, and salts, solvates, and solvates of the salts.

According to an embodiment of the present invention, the compounds of the formulae (I-A) or (I-B) are defined as follows:
$R^1$ is selected from hydrogen and $C_1$-$C_4$ alkyl;
$X^1$ is selected from nitrogen and C—$R^2$;
$X^2$ is selected from nitrogen and C—$R^3$;
$X^3$ is selected from nitrogen and C—$R^4$;
$X^4$ is selected from nitrogen and C—$R^5$;
with the proviso that 0, 1 or 2 of $X^1$ to $X^4$ are nitrogen; and $R^2$, $R^3$, $R^4$, and $R^5$ are independently from each other selected from hydrogen, halogen, $C_1$-$C_4$ alkyl, $C_1$-$C_4$ alkenyl, $C_1$-$C_4$ haloalkyl, $C_1$-$C_4$ alkoxy, $C_1$-$C_4$ haloalkoxy, cyano, amino, nitro, mono- or dialkylamino, hydroxy, carboxyl, $C_3$-$C_7$ cycloalkyl, 5 to 6 membered heteroaryl, the 5 to 6 membered heteroaryl being optionally substituted with one, two, or three substituents selected from $C_1$-$C_4$ alkyl, and phenyl, the phenyl being optionally substituted with one, two, or three subst333ituents selected from halogen, $C_1$-$C_4$ alkyl, $C_1$-$C_4$ haloalkyl, $C_1$-$C_4$ alkoxy, and $C_1$-$C_4$ haloalkoxy;
with the proviso that zero, one, two, or three of $R^2$ to $R^5$ are different from hydrogen,
and salts, solvates, and solvates of the salts.

According to an embodiment of the present invention, the compounds of the formulae (I-A) or (I-B) are defined as follows:
$R^1$ is selected from hydrogen and methyl;
$X^1$ is selected from nitrogen and C—$R^2$
$X^2$ is selected from nitrogen and C—$R^3$
$X^3$ is selected from nitrogen and C—$R^4$
$X^4$ is selected from nitrogen and C—$R^5$
with the proviso that 0, 1 or 2 of $X^1$ to $X^4$ are nitrogen; and $R^2$, $R^3$, $R^4$, and $R^5$ are independently from each other selected from hydrogen, halogen, $C_1$-$C_4$ alkyl, $C_1$-$C_4$ haloalkyl, $C_1$-$C_4$ alkoxy, $C_1$-$C_4$ haloalkoxy, cyano, amino, nitro, dialkylamino, hydroxy, carboxyl, $C_3$-$C_7$ cycloalkyl, triazolyl (bonded via N), thiazolyl, thienyl, pyridyl, pyrazolyl (bonded via N or C), the pyrazolyl being optionally substituted with one or two substituents selected from $C_1$-$C_4$ alkyl, imidazolyl, pyrrolyl, and phenyl, the phenyl being optionally substituted with one or two substituents selected from halogen, $C_1$-$C_4$ alkyl, $C_1$-$C_4$ haloalkyl, $C_1$-$C_4$ alkoxy, and $C_1$-$C_4$ haloalkoxy;
with the proviso that zero, one, or two of $R^2$ to $R^5$ are different from hydrogen,
and its salts, solvates, and solvates of the salts.

According to an embodiment of the present invention, the compounds of the formulae (I-A) or (I-B) are defined as follows:
$R^1$ is selected from hydrogen and methyl;
$X^1$ is selected from nitrogen and C—$R^2$
$X^2$ is selected from nitrogen and C—$R^3$
$X^3$ is selected from nitrogen and C—$R^4$
$X^4$ is selected from nitrogen and C—$R^5$
with the proviso that 0, 1 or 2 of $X^1$ to $X^4$ are nitrogen; and $R^2$, $R^3$, $R^4$, and $R^5$ are independently from each other selected from hydrogen, halogen, methyl, isopropyl, isobutyl, sec-butyl, tert-butyl, trifluoromethyl, methoxy, ethoxy, isopropoxy, trifluoromethoxy, trifluoroethoxy, cyano, amino, nitro, dimethylamino, hydroxy, carboxyl, cyclopropyl, cyclopentyl, triazolyl (bonded via N), thiazolyl, thienyl, pyridyl, pyrazolyl (bonded via N or C), the pyrazolyl being optionally substituted with one or two methyl groups, imidazolyl, pyrrolyl, and phenyl, the phenyl optionally being substituted with one or two substituents selected from methyl, trifluoromethyl, methoxy, ethoxy, isopropoxy, trifluoromethoxy, fluorine and chlorine;
with the proviso that zero, one, or two of $R^2$ to $R^5$ are different from hydrogen,
and its salts, solvates, and solvates of the salts.

According to an embodiment of the present invention, the compounds of the formulae (I-A) or (I-B) are defined as follows:
$R^1$ is selected from hydrogen and methyl;
$X^1$ is selected from nitrogen and C—$R^2$
$X^2$ is selected from nitrogen and C—$R^3$
$X^3$ is selected from nitrogen and C—$R^4$
$X^4$ is selected from nitrogen and C—$R^5$
with the proviso that 0, 1 or 2 of $X^1$ to $X^4$ are nitrogen; and $R^2$, $R^3$, $R^4$, and $R^5$ are independently from each other selected from hydrogen, halogen, and phenyl, the phenyl being optionally substituted with one, two, or three substituents selected from halogen, $C_1$-$C_4$ alkyl, $C_1$-$C_4$ haloalkyl, $C_1$-$C_4$ alkoxy, and $C_1$-$C_4$ haloalkoxy;
with the proviso that zero, one, or two of $R^2$ to $R^5$ are different from hydrogen,
and its salts, solvates, and solvates of the salts.

According to an embodiment of the present invention, the compounds of the formulae (I-A) or (I-B) are defined as follows:
$R^1$ is selected from hydrogen and $C_1$-$C_4$ alkyl;
$X^1$ is selected from nitrogen and C—$R^2$;
$X^2$ is selected from nitrogen and C—$R^3$;
$X^3$ is selected from nitrogen and C—$R^4$;
$X^4$ is selected from nitrogen and C—$R^5$;
with the proviso that 0, 1 or 2 of $X^1$ to $X^4$ are nitrogen; and $R^2$, $R^3$ and $R^4$ are hydrogen, and $R^5$ is selected from hydrogen, halogen, $C_1$-$C_4$ alkyl, $C_1$-$C_4$ alkenyl, $C_1$-$C_4$ haloalkyl, $C_1$-$C_4$ alkoxy, $C_1$-$C_4$ haloalkoxy, cyano, amino, nitro, mono- or dialkylamino, hydroxy, thiol, carboxyl, $C_3$-$C_7$ cycloalkyl, 5 to 6 membered heteroaryl, the 5 to 6 membered heteroaryl being optionally substituted with one, two, or three substituents selected from $C_1$-$C_4$ alkyl, and phenyl, the phenyl being optionally substituted with one, two, or three substituents selected from halogen, $C_1$-$C_4$ alkyl, $C_1$-$C_4$ haloalkyl, $C_1$-$C_4$ alkoxy, and $C_1$-$C_4$ haloalkoxy, or
a group of a formula selected from —CO—NR$^7$R$^8$, —NH—CO—R$^9$, —CO—O—R$^9$, —CO—R$^9$, —SO$_2$R$^1$—SO$_2$NR$^{11}$R$^{12}$, —SR$^{10}$, CH$_2$CN, —CH$_2$NR$^{11}$R$^{12}$, —CH$_2$OR$^{10}$, wherein
$R^7$ and $R^8$ independently from each other represent hydrogen, $C_1$-$C_4$ alkyl, $C_6$ aryl, and 5-6 membered heteroaryl;
$R^9$ represents hydrogen, $C_1$-$C_4$ alkyl, $C_6$ aryl, and 5-6 membered heteroaryl;
$R^{10}$ represents $C_1$-$C_4$ alkyl;
$R^{11}$ and $R^{12}$ independently from each other represent hydrogen, and $C_1$-$C_4$ alkyl;
with the proviso that zero, one, two, or three of $R^2$ to $R^5$ are different from hydrogen, and salts, solvates, and solvates of the salts.

According to an embodiment of the present invention, the compounds of the formulae (I-A) or (I-B) are defined as follows:
$R^1$ is selected from hydrogen and methyl;
$X^1$ is C—$R^2$
$X^2$ is C—$R^3$
$X^3$ is C—$R^4$
$X^4$ is C—$R^5$; and
$R^2$, $R^3$, $R^4$, and $R^5$ are independently from each other selected from hydrogen, halogen, $C_1$-$C_4$ alkyl, $C_1$-$C_4$ alkenyl, $C_1$-$C_4$ haloalkyl, $C_1$-$C_4$ alkoxy, $C_1$-$C_4$ haloalkoxy, cyano, amino, nitro, mono- or dialkylamino, hydroxy, carboxyl, $C_3$-$C_7$ cycloalkyl, 5 to 6 membered heteroaryl, the 5 to 6 membered heteroaryl being optionally substituted with one, two, or three substituents selected from $C_1$-$C_4$ alkyl, and phenyl, the phenyl being optionally substituted with one, two, or three substituents selected from halogen, $C_1$-$C_4$ alkyl, $C_1$-$C_4$ haloalkyl, $C_1$-$C_4$ alkoxy, and $C_1$-$C_4$ haloalkoxy;
with the proviso that zero, one, or two of $R^2$ to $R^5$ are different from hydrogen,
and its salts, solvates, and solvates of the salts.

According to an embodiment of the present invention, the compounds of the formulae (I-A) or (I-B) are defined as follows:
$R^1$ is selected from hydrogen and methyl;
$X^1$ is C—$R^2$
$X^2$ is C—$R^3$
$X^3$ is C—$R^4$
$X^4$ is C—$R^5$; and
$R^2$, $R^3$, $R^4$, and $R^5$ are independently from each other selected from hydrogen, halogen, $C_1$-$C_4$ alkyl, $C_1$-$C_4$ haloalkyl, $C_1$-$C_4$ alkoxy, $C_1$-$C_4$ haloalkoxy, cyano, amino, nitro, dialkylamino, $C_3$-$C_7$ cycloalkyl, triazolyl (bonded via N), thiazolyl, thienyl, pyridyl, pyrazolyl (bonded via N or C), the pyrazolyl being optionally substituted with one or two substituents selected from $C_1$-$C_4$ alkyl, and phenyl, the phenyl being optionally substituted with one or two substituents selected from halogen, $C_1$-$C_4$ alkyl, $C_1$-$C_4$ haloalkyl, $C_1$-$C_4$ alkoxy, and $C_1$-$C_4$ haloalkoxy;
with the proviso that zero, one, or two of $R^2$ to $R^5$ are different from hydrogen,
and its salts, solvates, and solvates of the salts.

According to an embodiment of the present invention, the compounds of the formulae (I-A) or (I-B) are defined as follows:
$R^1$ is selected from hydrogen and methyl;
$X^1$ is C—$R^2$
$X^2$ is C—$R^3$
$X^3$ is C—$R^4$
$X^4$ is C—$R^5$; and
$R^2$, $R^3$, $R^4$, and $R^5$ are independently from each other selected from hydrogen, halogen, $C_1$-$C_4$ alkyl, $C_1$-$C_4$ haloalkyl, $C_1$-$C_4$ alkoxy, $C_1$-$C_4$ haloalkoxy, cyano, amino, nitro, dialkylamino, hydroxy, carboxyl, $C_3$-$C_7$ cycloalkyl, triazolyl (bonded via N), thiazolyl, thienyl, pyridyl, pyrazolyl (bonded via N or C), the pyrazolyl being optionally substituted with one or two substituents selected from $C_1$-$C_4$ alkyl, imidazolyl, pyrrolyl, and phenyl, the phenyl being optionally substituted with one or two substituents selected from halogen, $C_1$-$C_4$ alkyl, $C_1$-$C_4$ haloalkyl, $C_1$-$C_4$ alkoxy, and $C_1$-$C_4$ haloalkoxy;
with the proviso that zero, one, or two of $R^2$ to $R^5$ are different from hydrogen,
and its salts, solvates, and solvates of the salts.

According to an embodiment of the present invention, the compounds of the formulae (I-A) or (I-B) are defined as follows:
$R^1$ is selected from hydrogen and methyl;
$X^1$ is C—$R^2$
$X^2$ is C—$R^3$
$X^3$ is C—$R^4$
$X^4$ is C—$R^5$; and
$R^2$, $R^3$, $R^4$, and $R^5$ are independently from each other selected from hydrogen, halogen, methyl, isopropyl, isobutyl, sec-butyl, tert-butyl, trifluoromethyl, methoxy, ethoxy, isopropoxy, trifluoromethoxy, trifluoroethoxy cyano, amino, nitro, dimethylamino, hydroxy, carboxyl, cyclopropyl, cyclopentyl, triazolyl (bonded via N), thiazolyl, thienyl, pyridyl, pyrazolyl (bonded via N or C), the pyrazolyl being optionally substituted with one or two methyl groups, imidazolyl, pyrrolyl, and phenyl, the phenyl optionally being substituted with one or two substituents selected from methyl, trifluoromethyl, methoxy, ethoxy, isopropoxy, trifluoromethoxy, fluorine and chlorine;
with the proviso that zero, one, or two of $R^2$ to $R^5$ are different from hydrogen,
and its salts, solvates, and solvates of the salts.

According to an embodiment of the present invention, the compounds of the formulae (I-A) or (I-B) are defined as follows:
$R^1$ is selected from hydrogen and methyl;
$X^1$ is C—$R^2$
$X^2$ is C—$R^3$
$X^3$ is C—$R^4$
$X^4$ is C—$R^5$;
$R^2$, $R^3$, and $R^4$, are independently from each other selected from hydrogen, and fluorine; $R^5$ is selected from hydrogen, halogen, $C_1$-$C_4$ alkyl, $C_1$-$C_4$ haloalkyl, $C_1$-$C_4$ alkoxy, $C_1$-$C_4$ haloalkoxy, cyano, amino, nitro, dialkylamino, hydroxy, carboxyl, $C_3$-$C_7$ cycloalkyl, triazolyl (bonded via N), thiazolyl, thienyl, pyridyl, pyrazolyl (bonded via N or C), the pyrazolyl being optionally substituted with one or two substituents selected from $C_1$-$C_4$ alkyl, imidazolyl, pyrrolyl, and phenyl, the phenyl being optionally substituted with one or two substituents selected from halogen, $C_1$-$C_4$ alkyl, $C_1$-$C_4$ haloalkyl, $C_1$-$C_4$ alkoxy, and $C_1$-$C_4$ haloalkoxy;
with the proviso that zero, one, or two of $R^2$ to $R^5$ are different from hydrogen,
and its salts, solvates, and solvates of the salts.

According to an embodiment of the present invention, the compounds of the formulae (I-A) or (I-B) are defined as follows:
$R^1$ is selected from hydrogen and methyl;
$X^1$ is C—$R^2$
$X^2$ is C—$R^3$
$X^3$ is C—$R^4$
$X^4$ is C—$R^5$;
$R^2$ is fluorine; $R^3$, and $R^4$, are hydrogen; $R^5$ is selected from hydrogen, halogen, $C_1$-$C_4$ alkyl, $C_1$-$C_4$ haloalkyl, $C_1$-$C_4$ alkoxy, $C_1$-$C_4$ haloalkoxy, cyano, amino, nitro, dialkylamino, hydroxy, carboxyl, $C_3$-$C_7$ cycloalkyl, triazolyl (bonded via N), thiazolyl, thienyl, pyridyl, pyrazolyl (bonded via N or C), the pyrazolyl being optionally substituted with one or two substituents selected from $C_1$-$C_4$ alkyl, imidazolyl, pyrrolyl, and phenyl, the phenyl being optionally substituted with one or two substituents selected from halogen, $C_1$-$C_4$ alkyl, $C_1$-$C_4$ haloalkyl, $C_1$-$C_4$ alkoxy, and $C_1$-$C_4$ haloalkoxy;
with the proviso that zero, one, or two of $R^2$ to $R^5$ are different from hydrogen,
and its salts, solvates, and solvates of the salts.

According to an embodiment of the present invention, the compounds of the formulae (I-A) or (I-B) are defined as follows:
$R^1$ is selected from hydrogen and methyl;
$X^1$ is C—$R^2$
$X^2$ is C—$R^3$
$X^3$ is C—$R^4$
$X^4$ is C—$R^5$; and
$R^2$, $R^3$, $R^4$, and $R^5$ are independently from each other selected from hydrogen, halogen, and phenyl, the phenyl optionally being substituted with one or two substituents selected from methyl, trifluoromethyl, methoxy, ethoxy, isopropoxy, trifluoromethoxy, fluorine and chlorine;

with the proviso that zero, one, or two of $R^2$ to $R^5$ are different from hydrogen,
and its salts, solvates, and solvates of the salts.

According to an embodiment of the present invention, the compounds of the formulae (I-A) or (I-B) are defined as follows:
$X^1$ is C—$R^2$
$X^2$ is C—$R^3$
$X^3$ is C—$R^4$,
$X^4$ is C—$R^5$, and
$R^1$, $R^2$, $R^3$, $R^4$, and $R^5$ are as defined above.

According to an embodiment of the present invention, the compounds of the formulae (I-A) or (I-B) are defined as follows:
$R^1$ is hydrogen or methyl;
$X^1$ is C—$R^2$
$X^2$ is C—$R^3$
$X^3$ is C—$R^4$
$X^4$ is C—$R^5$
$R^2$ to $R^4$ are selected from hydrogen and fluorine, and
$R^5$ is selected from halogen;
and its salts, solvates, and solvates of the salts.

According to an embodiment of the present invention, the compounds of the formulae (I-A) or (I-B) are defined as follows:
$R^1$ is hydrogen or methyl;
$X^1$ is C—$R^2$
$X^2$ is C—$R^3$
$X^3$ is C—$R^4$
$X^4$ is C—$R^5$
$R^2$ to $R^4$ are selected from hydrogen and fluorine, and
$R^5$ is selected from chlorine and bromine;
and its salts, solvates, and solvates of the salts.

According to an embodiment of the present invention, the compounds of the formulae (I-A) or (I-B) are defined as follows:
$R^1$ is hydrogen;
$X^1$ is C—$R^2$
$X^2$ is C—$R^3$
$X^3$ is C—$R^4$
$X^4$ is C—$R^5$
$R^2$ to $R^4$ are hydrogen, and
$R^5$ is chlorine;
and its salts, solvates, and solvates of the salts.

According to an embodiment of the present invention, the compounds of the formulae (I-A) or (I-B) are defined as follows:
$R^1$ is hydrogen;
$X^1$ is C—$R^2$
$X^2$ is C—$R^3$
$X^3$ is C—$R^4$
$X^4$ is C—$R^5$; and
$R^2$, $R^3$, and $R^4$ are hydrogen, $R^5$ is chlorine, in form of its hydrochloride salt.

According to an embodiment of the present invention, the compounds of the formulae (I-A) or (I-B) are defined as follows:
$R^1$ is selected from hydrogen and methyl;
$X^1$, $X^2$, $X^3$ and $X^4$ are as defined above,
and its salts, solvates, and solvates of the salts.

According to an embodiment of the present invention, the compounds of the formulae (I-A) or (I-B) are defined as follows:
$R^1$ is hydrogen,
$X^1$, $X^2$, $X^3$ and $X^4$ are as defined above,
and its salts, solvates, and solvates of the salts.

According to an embodiment of the present invention, the compounds of the formulae (I-A) or (I-B) are defined as follows:
$X^1$ is N
$X^2$ is C—$R^3$
$X^3$ is C—$R^4$,
$X^4$ is C—$R^5$, and
$R^1$, $R^3$, $R^4$, and $R^5$ are as defined above,
and its salts, solvates, and solvates of the salts.

According to an embodiment of the present invention, the compounds of the formulae (I-A) or (I-B) are defined as follows:
$X^1$ is C—$R^2$
$X^2$ is N,
$X^3$ is C—$R^4$,
$X^4$ is C—$R^5$, and
$R^1$, $R^2$, $R^4$, and $R^5$ are as defined above,
and its salts, solvates, and solvates of the salts.

According to an embodiment of the present invention, the compounds of the formulae (I-A) or (I-B) are defined as follows:
$X^1$ is C—$R^2$
$X^2$ is C—$R^3$,
$X^3$ is N,
$X^4$ is C—$R^5$, and
$R^1$, $R^2$, $R^3$, and $R^5$ are as defined above,
and its salts, solvates, and solvates of the salts.

According to an embodiment of the present invention, the compounds of the formulae (I-A) or (I-B) are defined as follows:
$X^1$ is C—$R^2$
$X^2$ is C—$R^3$,
$X^3$ is C—$R^4$,
$X^4$ is N, and
$R^1$, $R^2$, $R^3$, and $R^4$ are as defined above.
and its salts, solvates, and solvates of the salts.

According to an embodiment of the present invention, the compounds of the formulae (I-A) or (I-B) are defined as follows:
$X^1$ is N,
$X^2$ is C—$R^3$,
$X^3$ is C—$R^4$,
$X^4$ is N, and
$R^1$, $R^3$, and $R^4$ are as defined above,
and its salts, solvates, and solvates of the salts.

According to an embodiment of the present invention, the compounds of the formulae (I-A) or (I-B) are defined as follows:
$X^1$ is N,
$X^2$ is N,
$X^3$ is C—$R^4$,
$X^4$ is C—$R^5$, and
$R^1$, $R^4$ and $R^5$ are as defined above,
and its salts, solvates, and solvates of the salts.

The definitions of radicals indicated specifically in the respective combinations of radicals are replaced as desired irrespective of the particular combinations indicated for the radicals also by definitions of radicals of other combinations.

According to an embodiment of the invention, two or more of the embodiments mentioned above are combined.

The invention furthermore provides a process for preparing the compounds of the formula (IV)

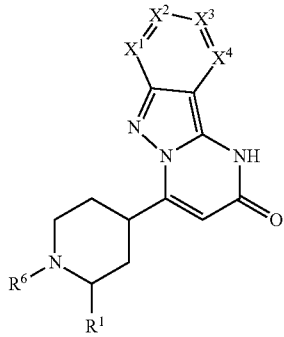

in which $R^1$, $X^1$, $X^2$, $X^3$, and $X^4$ each have the meaning given above and $R^6$ represents an amino protective group, wherein
[A] a compound of the formula (II-A)

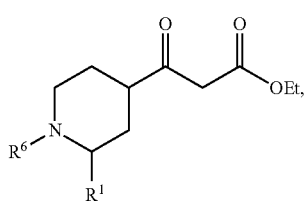

in which $R^1$ and $R^6$ each have the meaning given above, is reacted with a compound of the formula (III)

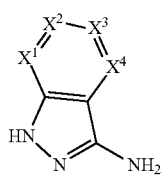

in which $X^1$, $X^2$, $X^3$, and $X^4$ each have the meaning given above in an inert solvent, optionally in the presence of a base, to give a compound of the formula (IV)

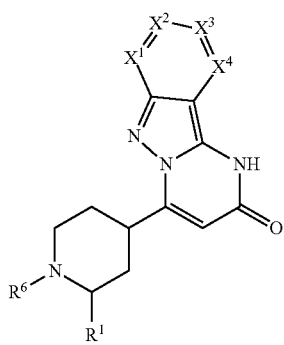

in which $R^1$, $R^6$, $X^1$, $X^2$, $X^3$, and $X^4$ each have the meaning given above,
or
[B] a compound of the formula (II-B)

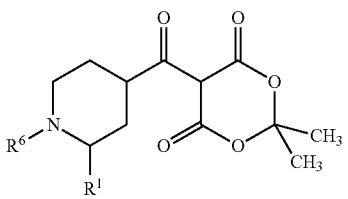

in which $R^1$ has the meaning given above and $R^6$ represents an amino protective group, is reacted with a compound of the formula (III)

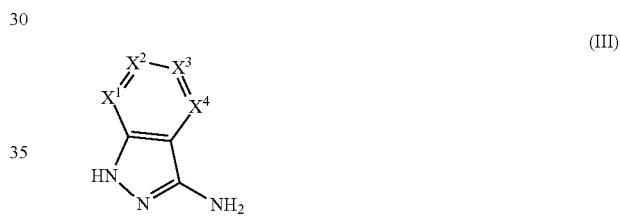

in which $X^1$, $X^2$, $X^3$, and $X^4$ each have the meaning given above in an inert solvent, optionally in the presence of a base, to give a compound of the formula (IV)

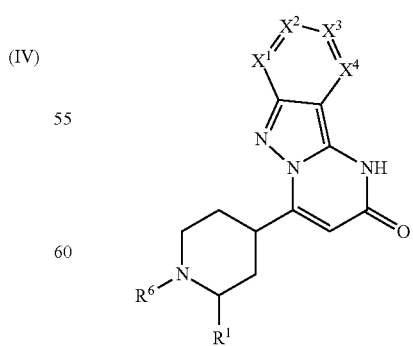

in which $R^1$, $R^6$, $X^1$, $X^2$, $X^3$, and $X^4$ each have the meaning given above.

The invention furthermore provides a process for preparing the compounds of the formula (IV)

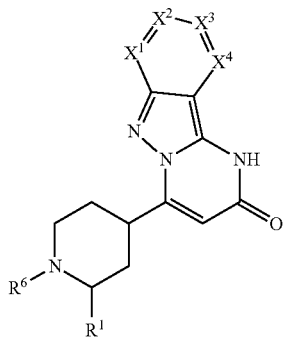
(IV)

in which $R^1$, $X^1$, $X^2$, $X^3$, and $X^4$ each have the meaning given above and $R^6$ represents an amino protective group, wherein
[B] a compound of the formula (II-B)

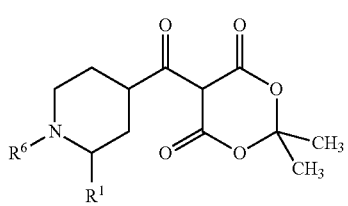
(II-B)

in which $R^1$ and $R^6$ each have the meaning given above, is reacted with a compound of the formula (III)

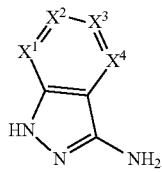
(III)

in which $X^1$, $X^2$, $X^3$, and $X^4$ each have the meaning given above in an inert solvent, optionally in the presence of a base, to give a compound of the formula (IV)

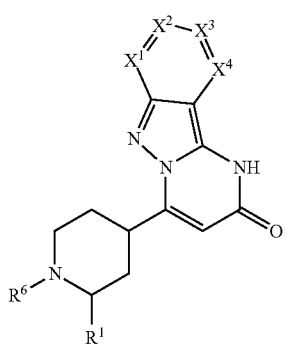
(IV)

in which $R^1$, $R^6$, $X^1$, $X^2$, $X^3$, and $X^4$ each have the meaning given above.

The invention furthermore provides a regioselective process for preparing the compounds of the formula (IV)

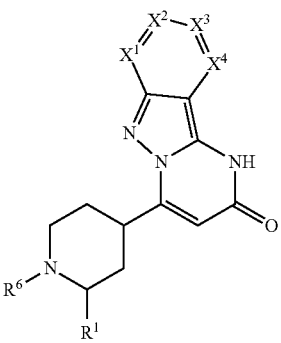
(IV)

in which $R^1$, $X^1$, $X^2$, $X^3$, and $X^4$ each have the meaning given above and $R^6$ represents an amino protective group, wherein
[B] a compound of the formula (II-B)

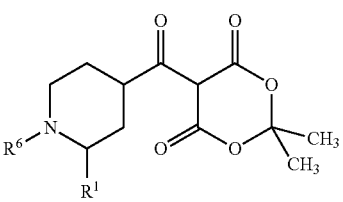
(II-B)

in which $R^1$ has the meaning given above and $R^6$ represents an amino protective group, is reacted with a compound of the formula (III)

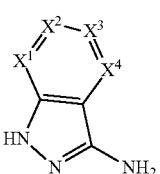
(III)

in which $X^1$, $X^2$, $X^3$, and $X^4$ each have the meaning given above in an inert solvent, optionally in the presence of a base, to give a compound of the formula (IV)

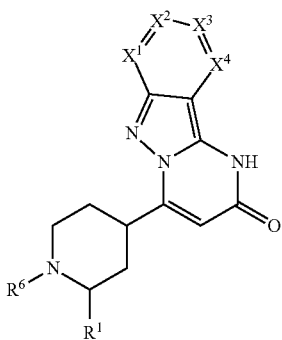

in which $R^1$, $X^1$, $X^2$, $X^3$, and $X^4$ each have the meaning given above, and $R^6$ represents an amino protective group.

The term "regioselective process" within the meaning of the invention is defined as a process that yields a compound of formula (IV) wherein less than 20%, less than 15%, less than 10%, less than 5%, less than 3%, less than 2%, less than 1%, less than 0.5%, less than 0.1% or 0% of the compound of formula (IV) is present as the regioisomer of the compound of formula IV shown below

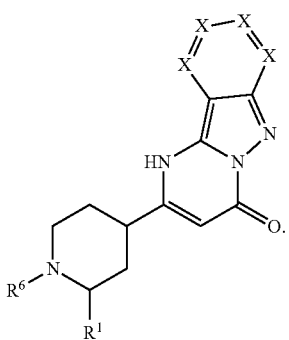

Regioisomer of (IV)

According to an embodiment of the invention, $R^6$ is an acid cleavable amino protective group, such as tert-butoxycarbonyl (Boc), and the compound of the formula (IV) obtained in reaction [A] or [B] is reacted to the compound of the formula (I-B) by addition of an acid.

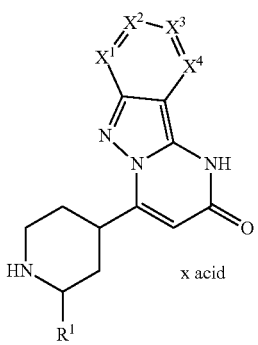

According to an embodiment of the invention, the compound of the formula (I-A) is obtained by treating the compound of the formula (I-B) with a base.

According to an embodiment of the invention, the compound of the formula (I-A) is obtained by treating the compound of formula (I-B) by a suitable chromatographic method by using a basic eluent.

According to an embodiment of the invention, $R^6$ is not cleavable by an acid and the compound of the formula (I-A) is obtained from the compound of formula (IV) by cleaving the amino protective group of the compound of formula (IV) for example by hydrogenation. Examples for this reaction are the cleavage of benzyloxycarbonyl (Cbz), and of optionally substituted benzyl.

According to an embodiment of the invention, the compound of the formula (I-B) is obtained by treating the compound of formula (I-A) with an acid.

The resulting compounds of the formulae (I-A) or (I-B) are optionally converted with the appropriate (i) solvents and/or (ii) acids or bases into their solvates, salts and/or solvates of the salts.

The present invention also provides compounds of the general formula (IV)

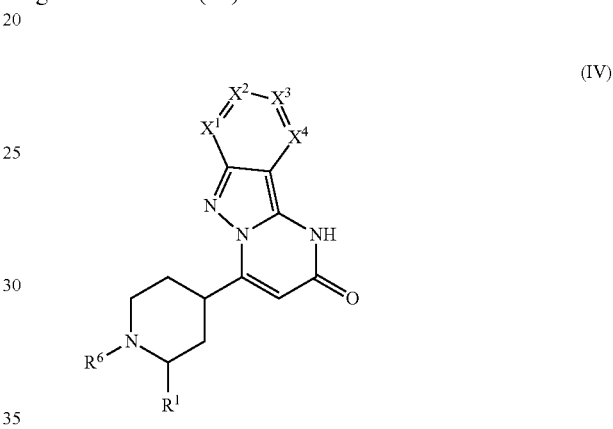

wherein $R^1$, $R^6$, $X^1$, $X^2$, $X^3$, and $X^4$ each have the meaning given above. The present invention also provides a compound of the general formula (II-B)

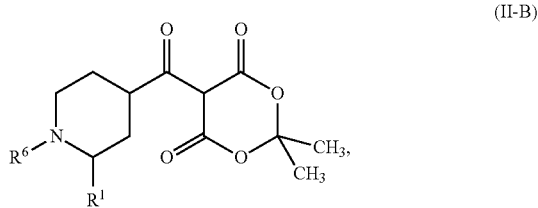

wherein
$R^1$ is selected from hydrogen and $C_1$-$C_4$ alkyl and
$R^6$ is an amino protective group.

The present invention also provides a compound of the general formula (II-B)

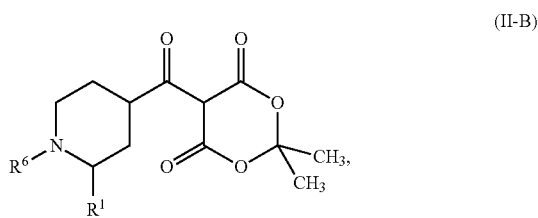

wherein

R[1] is selected from hydrogen and methyl and

R[6] is selected from tert-butoxycarbonyl (Boc), and benzyloxycarbonyl (Cbz).

The present invention also provides a compound of the general formula (II-B)

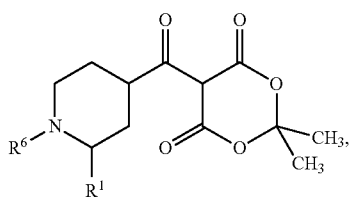

(II-B)

wherein

R[1] is selected from hydrogen and $C_1$-$C_4$ alkyl and

R[6] is tert-butoxycarbonyl (Boc).

Further compounds of formula (I-A) or (I-B) according to the invention can optionally also be prepared by converting functional groups of individual substituents, starting with the compounds of the formula (I-A) and (I-B) obtained by the above processes. These conversions are carried out by customary methods known to the person skilled in the art and include, for example, reactions such as nucleophilic and electrophilic substitutions, oxidations, reductions, hydrogenations, transition metal-catalyzed coupling reactions, eliminations, alkylation, amination, esterification, ester cleavage, etherification, ether cleavage, formation of carboxamides, and also the introduction and removal of temporary protective groups.

The preparation processes described can be illustrated in an exemplary manner by the synthesis schemes below (Schemes 1 and 2).

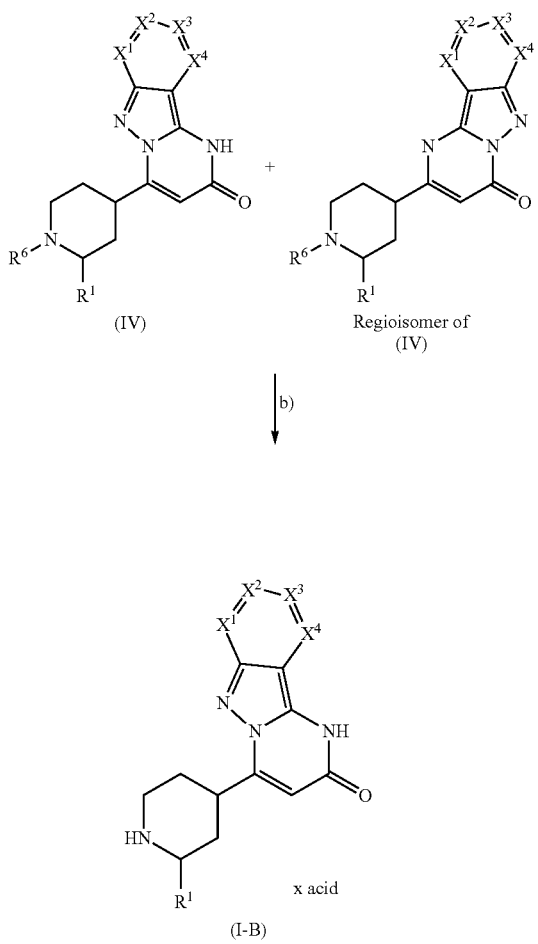

[a] 1-methoxy-2-propanol, potassium phosphate, microwave, 15 minutes, 180° C., b) HCl 4N in dioxane, RT or TFA, dichloromethane, RT]

$X^1 = C—R^2$ or N
$X^2 = C—R^3$ or N
$X^3 = C—R^4$ or N
$X^4 = C—R^5$ or N

Scheme 2 (Reaction [B1]) Synthesis of (aza)pyridopyrazolopyrimidinones or indazolpyrimidinones via the piperidinyl Meldrum's acid derivatives Scheme 1 (Reaction [A1]) Synthesis of (aza)pyridopyrazolopyrimidinones or indazolopyrimidinones via the piperidinyl-beta-ketoester

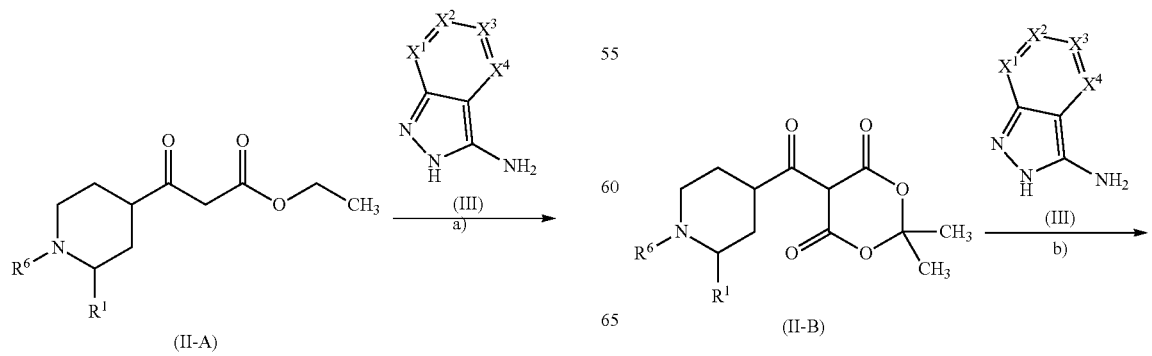

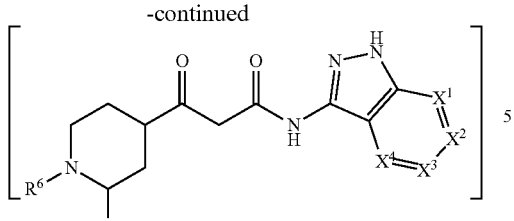

(V)

|  c), d)

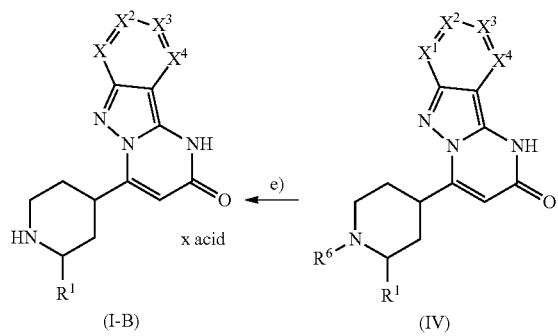

(I-B)    (IV)

[b) acetonitrile, 60° C.; c) evaporation of the solvent d) 1-methoxy-2-propanol, potassium phosphate, 110° C., e) HCl 4N in dioxane, RT or TFA, dichloromethane, RT.]

$X^1 = C—R^2$ or N
$X^2 = C—R^3$ or N
$X^3 = C—R^4$ or N
$X^4 = C—R^5$ or N

Suitable amino protecting groups (substituent $R^6$) in formulae (II-A), (II-B), and (IV) are tert-butoxycarbonyl (Boc), removed by a concentrated strong acid, benzyloxycarbonyl (Cbz), removed by hydrogenolysis, methyl or ethylcarbamate, removed by TMSI in $CHCl_3$ or HBr in AcOH, Trimethylsilylethyl carbamate (Teoc), removed by fluoride, p-Methoxybenzyl carbamate (Moz or MeOZ), removed by hydrogenolysis, 9-Fluorenylmethyl carbamate (F-moc), removed by a base, and optionally substituted benzyl or benzylamine, removed by hydrogenolysis. Preferred for use as amino protective group is tert-butoxycarbonyl (Boc).

According to an embodiment of the invention, the amino protective group $R^6$ is selected from tert-butoxycarbonyl (Boc), and benzyloxycarbonyl (Cbz). Preferred for use as amino protective group is tert-butoxycarbonyl (Boc).

The reaction can also be carried out without protecting the amino group. In this case, $R^6$ is hydrogen.

According to an embodiment of the invention, the reaction is carried out without protecting the amino group. In this embodiment, $R^6$ is hydrogen.

The invention furthermore provides a process for preparing the compounds of the formula (IV)

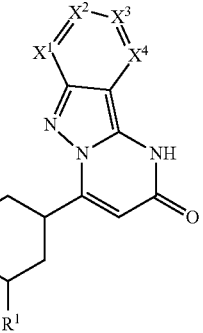

(IV)

in which $R^1$, $X^1$, $X^2$, $X^3$, and $X^4$ each have the meaning given above and $R^6$ is hydrogen, wherein

[A] a compound of the formula (II-A)

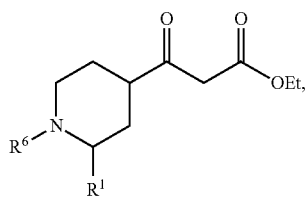

(II-A)

in which $R^1$ has the meaning given above and $R^6$ is hydrogen, is reacted with a compound of the formula (III)

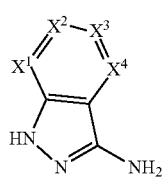

(III)

in which $X^1$, $X^2$, $X^3$, and $X^4$ each have the meaning given above in an inert solvent, optionally in the presence of a base, to give a compound of the formula (IV)

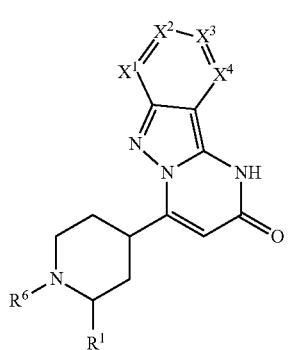

(IV)

in which $R^1$, $X^1$, $X^2$, $X^3$, and $X^4$ each have the meaning given above and $R^6$ is hydrogen, or

[B] a compound of the formula (II-B)

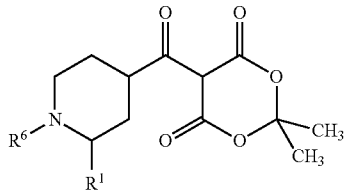
(II-B)

in which $R^1$ has the meaning given above and $R^6$ is hydrogen, is reacted with a compound of the formula (III)

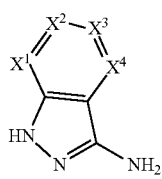
(III)

in which $X^1$, $X^2$, $X^3$, and X each have the meaning given above in an inert solvent, optionally in the presence of a base, to give a compound of the formula (IV)

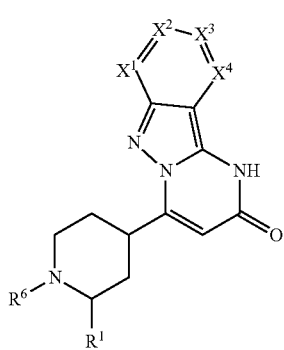
(IV)

in which $R^1$, $X^1$, $X^2$, $X^3$, and $X^4$ each have the meaning given above, and $R^6$ is hydrogen.

Suitable solvents for the process steps (II-A)+(III)→(IV)+ (regioisomer of (IV)) are inert solvents, for example, aliphatic alcohols such as methanol, ethanol, iso-propanol, 1-methoxy-2-propanol or tert-butanol, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halogenated hydrocarbons such as dichloromethane, trichloromethane, carbon tetrachloride, 1,2-dichloroethane, trichloroethylene or chlorobenzene, or other solvents such as acetone, ethyl acetate, acetonitrile, pyridine, dimethyl sulphoxide, N,N-dimethylformamide, N,N-dimethylacetamide, N,N'-dimethylpropyleneurea (DMPU) or N-methylpyrrolidone (NMP). It is also possible to use mixtures of the solvents mentioned. Preference is given to polar solvents with high boiling points, such as toluene, 1-methoxy-2-propanol, and dioxane, or mixtures of these solvents.

The condensation process (II-A)+(III)→(IV)+(regioisomer of IV) may proceed in the absence of a base, in the presence of organic bases such as triethylamine or diisopropylethylamine, or in the presence of inorganic bases. Inorganic bases include alkali metal or alkali earth metal phosphates and carbonates such as potassium phosphate, potassium carbonate, cesium carbonate, sodium phosphate, or calcium carbonate. Preference is given to the presence of potassium phosphate.

According to an embodiment of the invention, the compounds of formulae (II-A) and (III) are reacted in the presence of a base, in particular in the presence of an inorganic base, preferably in the presence of potassium phosphate.

The condensation process (II-A)+(III)→(IV)+(regioisomer of IV) is generally carried out in a temperature range from 50° C. to 250° C., preferably within 100° C. to 200° C. Heating options include conventional heating below the boiling point of the solvent, under reflux, or above the boiling point of the solvent in a closed vial, or in a closed vial with the aid of a microwave reactor. Preference is given to heating the reaction in a microwave vial from 160° C. to 200° C.

According to an embodiment of the invention, the compounds of formulae (II-A) and (III) are reacted at a temperature of 50° C. to 250° C., preferably at a temperature of 100° C. to 200° C.

The condensation process (II-A)+(III)→(IV)+(regioisomer of IV) can be carried out at atmospheric, elevated or reduced pressure (for example from 0.5 to 25 bar). In general, the reactions are in each case carried out at atmospheric pressure to 15 bar.

According to an embodiment of the invention, the compounds of formulae (II-A) and (III) are reacted at a pressure between atmospheric pressure and 15 bar.

Typically, the condensation process (II-A)+(III)→(IV)+ (regioisomer of IV) yields mixtures of regioisomers. The desired regioisomer is isolated by a suitable chromatographic method such as chromatography on silica gel, reverse-phase high-performance liquid chromatography, or preparative thin-layer chromatography. Inert solvents used as liquid phase include ethyl acetate, cyclohexane, dichloromethane, methanol, supercritical carbon dioxide, water, acetonitrile, and mixtures thereof. The desired regioisomer can further be isolated by crystallisation.

According to an embodiment of the invention, the compound of formula (IV) is isolated from the mixture of regioisomers.

The condensation process (II-B)+(III)→[(V)]→(IV) can be carried out in one single step without isolation of the intermediate (V), in two separate steps by changing the reaction conditions for the formation of (V) from (II-B) and (III) and the formation of (IV) from (V) but without purification of the intermediate (V), or in two separate steps involving the purification of intermediate (V). Preference is given to a procedure with two separate steps without purification of the intermediate.

According to an embodiment of the invention, the compounds of formulae (II-B) and (III) are reacted in a first step to a compound of formula (V). The compound of formula (V) is reacted in a second step to the compound of formula (IV) without separation and purification of the intermediate (V). According to a further embodiment of the invention, the solvent is changed between the first and the second step.

Suitable solvents for the process steps (II-B)+(III)→(V) are, for example, aliphatic alcohols such as methanol, ethanol, iso-propanol, 1-methoxy-2-propanol or tert-butanol, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halogenated hydrocarbons such as dichloromethane, trichloromethane, carbon tetrachloride, 1,2-dichloroethane, trichloroethylene or chlorobenzene, or other solvents such as acetone, ethyl acetate, acetonitrile, pyridine, dimethyl sulphoxide, N,N-dimethylformamide, N,N-dimethylacetamide, N,N'-dimethylpropyleneurea (DMPU) or N-methylpyrrolidone (NMP). It is also possible to use mixtures of the solvents mentioned. Preference is given to using acetonitrile or toluene as solvents, or mixtures of these solvents.

Suitable solvents for the process steps (V)→(IV) are, for example, aliphatic alcohols such as methanol, ethanol, isopropanol, 1-methoxy-2-propanol or tert-butanol, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halogenated hydrocarbons such as dichloromethane, trichloromethane, carbon tetrachloride, 1,2-dichloroethane, trichloroethylene or chlorobenzene, or other solvents such as acetone, ethyl acetate, acetonitrile, pyridine, dimethyl sulphoxide, N,N-dimethylformamide, N,N-dimethylacetamide, N,N'-dimethylpropyleneurea (DMPU) or N-methylpyrrolidone (NMP). It is also possible to use mixtures of the solvents mentioned. Preference is given to using 1-methoxy-2-propanol or toluene as solvents, or mixtures of these solvents.

The process (II-B)+(III)→(V) may proceed in the absence of a base, in the presence of organic bases such as triethylamine or diisopropylethylamine, or in the presence of inorganic bases. Inorganic bases include alkali metal or alkali earth metal phosphates and carbonates such as potassium phosphate, potassium carbonate, cesium carbonate, sodium phosphate, or calcium carbonate. Preference is given to reacting the compounds of formulae (II-B) and (III) in the absence of a base.

According to an embodiment of the invention, the compounds of formulae (II-B) and (III) are reacted in the absence of a base.

The condensation process (V)→(IV) may proceed in the absence of a base, in the presence of organic bases such as triethylamine or diisopropylethylamine, or in the presence of inorganic bases. Inorganic bases include alkali metal or alkali earth metal phosphates and carbonates such as potassium phosphate, potassium carbonate, cesium carbonate, sodium phosphate, or calcium carbonate. Preference is given to reacting the compound of formula (V) to the compound of formula (IV) in the presence of potassium phosphate.

According to an embodiment of the invention, the compound of formula (V) is reacted to the compound of formula (IV) in the presence of a base, in particular in the presence of potassium phosphate.

According to an embodiment of the invention, wherein the compounds of formulae (II-B) and (III) are reacted to the compound of formula (V) and the compound of formula (V) is reacted to the compound of formula (IV) in one single step without isolation of the intermediate (V), the reaction is carried out in the presence of a base.

The process (II-B)+(III)→(V) is generally carried out in a temperature range of 0° C. to 100° C., preferably from 40° C. to 80° C.

According to an embodiment of the invention, the compounds of formulae (II-B) and (III) are reacted at a temperature of 0° C. to 100° C., preferably of 40° C. to 80° C.

The process (V)→(IV) is generally carried out in a temperature range of 0° C. to 150° C., preferably from 60° C. to 130° C.

According to an embodiment of the invention, the compound of formula (V) is reacted to a compound of formula (IV) at a temperature of 0° C. to 150° C., preferably of 60° C. to 130° C.

According to an embodiment of the invention, wherein $R^6$ is an acid cleavable amino protective group, such as tert-butoxycarbonyl, the compound of the formula (IV) obtained in reaction [A] or [B] is reacted to the compound of the formula (I-B) by addition of an acid. This reaction is carried out in a suitable solvent, e.g. dioxane.

Generally, the salts of formula (I-B) may be transformed to the respective free bases of formula (I-A) by any way known to the person skilled in art.

The compound of formula (I-B) may be reacted to the compound of formula (I-A) by treating the compound of formula (I-B) with a base. Preferred bases are ammonia, sodium hydroxide, $NaHCO_3$, and $Na_2CO_3$. This may also be achieved by a suitable chromatographic method by using a basic eluent.

According to an embodiment of the invention, the acid used to obtain the compound of the formula (I-B) from the compound of the formula (IV) is selected from hydrochloric acid, trifluoroacetic acid, acetic acid, sulphuric acid, maleic acid, tartaric acid, ascorbic acid, and salicylic acid.

According to an embodiment of the invention, wherein $R^6$ is not cleaved by an acid, the compound of the formula (I-A) is obtained from the compound of formula (IV) by cleaving the amino protection group of the compound of formula (IV) for example by hydrogenation. Examples for this reaction are the cleavage of benzyloxycarbonyl (Cbz), and of optionally substituted benzyl.

The compounds of the formulae (II-A), (III) and (II-B) are commercially available, known from the literature or can be prepared analogously to processes known from the literature or described in schemes 3 to 7 below. Schemes 8 and 9 relate to processes to obtain alkyl or (hetero)aryl compounds from the respective halogenated compounds.

Scheme 3 Synthesis of the methylpiperidinyl Meldrum's acid derivative

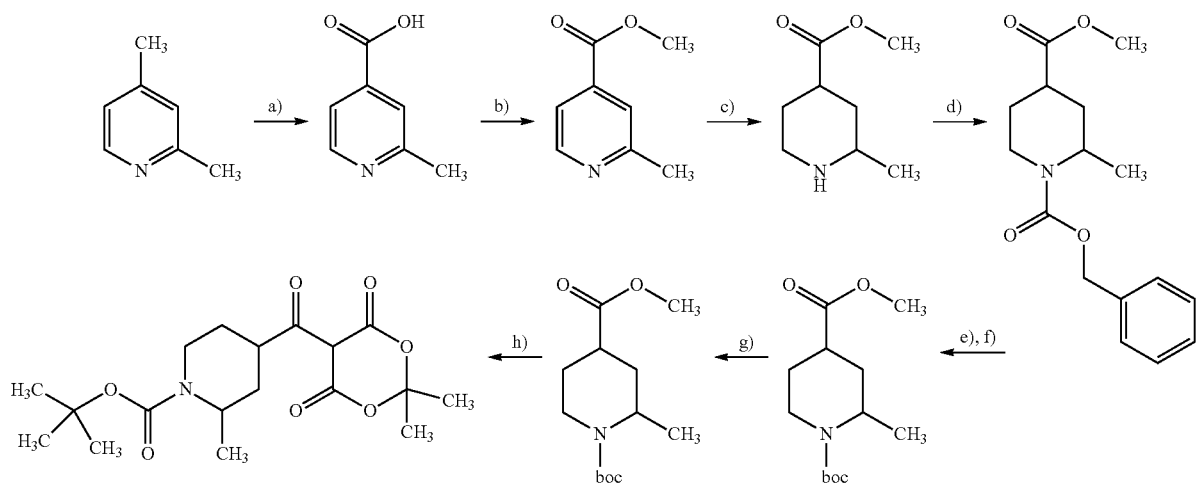

a) 2,4-lutidine, KMnO4, water, 80° C.; b) thionyl chloride, methanol, reflux; c) AcOH, platinum(IV)oxide, 20 bar, RT; d) benzyl chloroformate, diisopropylethylamine, dichloromethane, RT, then separation of the stereoisomers by chromatography on chiral phase; e) Pd/C, H2, ethanol, RT; f) di-tert-butyl dicarbonate, tetrahydrofurane, RT; g) lithium hydroxide, tetrahydrofuran/water, RT; h) 2,2-dimethyl-1,3-dioxane-4,6-dione, DMAP, EDCl, dichloromethane, RT.

Scheme 4 Synthesis of substituted (aza)aminoindazoles via SNAr of Fluoro-Cyano-Arenes with hydrazine

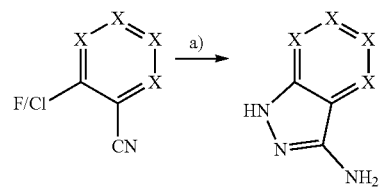

X = C—R or N
a) Hydrazine hydrate, ethanol, 70° C., 8 h.

Scheme 5 Synthesis of 4-(hetero)arylaminoindazoles via Suzuki reactions with 4-chloroaminoindazol

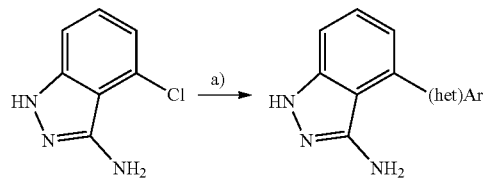

a) (Hetero)aryl boronic aicd or boronic acid ester, (2-dicyclohexylphosphino-2',4',6'-triisopropyl-1,1'-biphenyl)[2-(2'-amino-1,1'-biphenyl)]palladium(II) methanesulfonate (= Xphos precatalyst), ethanol/water/toluene 1:1:1, 1M aqueous K3PO4-solution, 80° C., 4 h.

Scheme 6 Synthesis of 4-di/triazolylamioindazoles

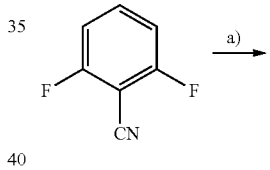

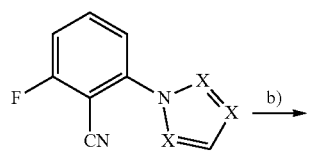

a) Diazole or triazole, dimethylsulfoxide, Cs2CO3, 50° C., 11 h. b) hydrazine hydrate, ethanol, 70° C., 7 h.
X = C—H, N Scheme 7 Synthesis of methyl- and fluoro-analogs of 4-chloro and 4-bromoaminoindazoles

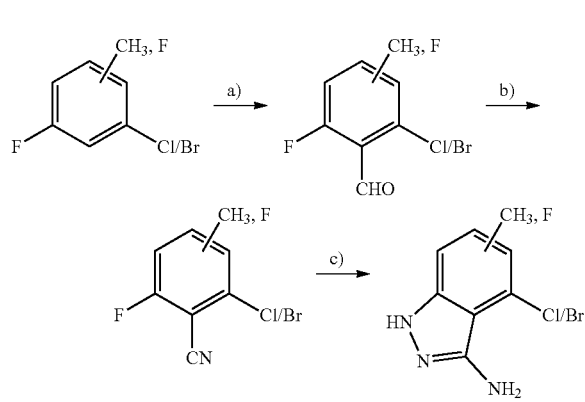

a) lithium diisopropyl amide, tetrahydrofuran, dimethyl formamide, -78° C., then acetic acid, water b) sodium lauryl sulfate, (diacetoxyiodo)benzene, ammonium acetate, water, 70° C., 30 min c) hydrazine hydrate, ethanol, 70° C., 7 h.

Scheme 8 Synthesis of 10-alkylindazolopyrimidinones via Negishi coupling of the chloro intermediate

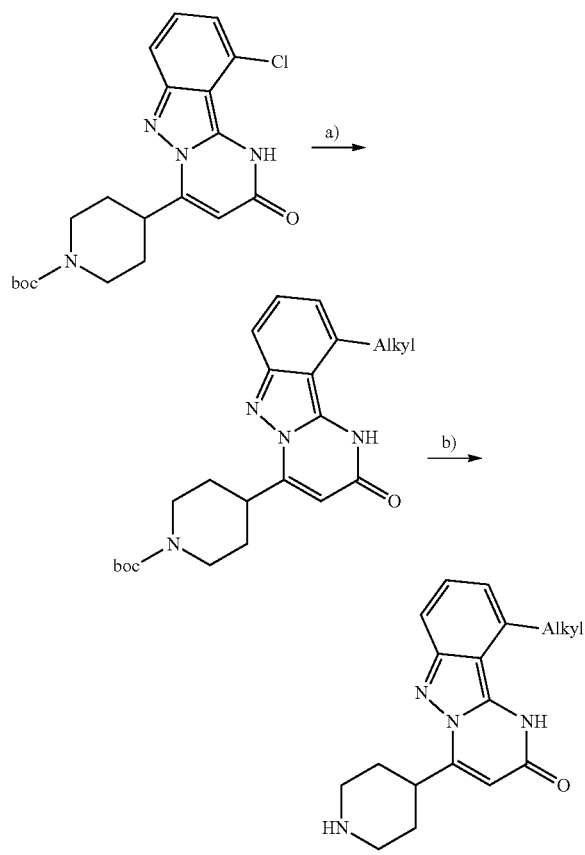

a) Alkylzinc bromide, [(2-dicyclohexylphosphino-2′,6′-bis(N,N-dimethylamino)-1,1′-biphenyl)-2-(2′-amino-1,1′-biphenyl)] palladium (II) methanesulfonate ( = CPhos precatalyst), 2-dicyclohexylphosphino-2′,6′-bis(N,N-dimethylamino)biphenyl (= CPhos), tetrahydrofuran, RT, 16 h. b) 4N HCl in dioxane Scheme 9 Synthesis of 10-(het)arylindazolopyrimidinones via Suzuki coupling of the bromo intermediate

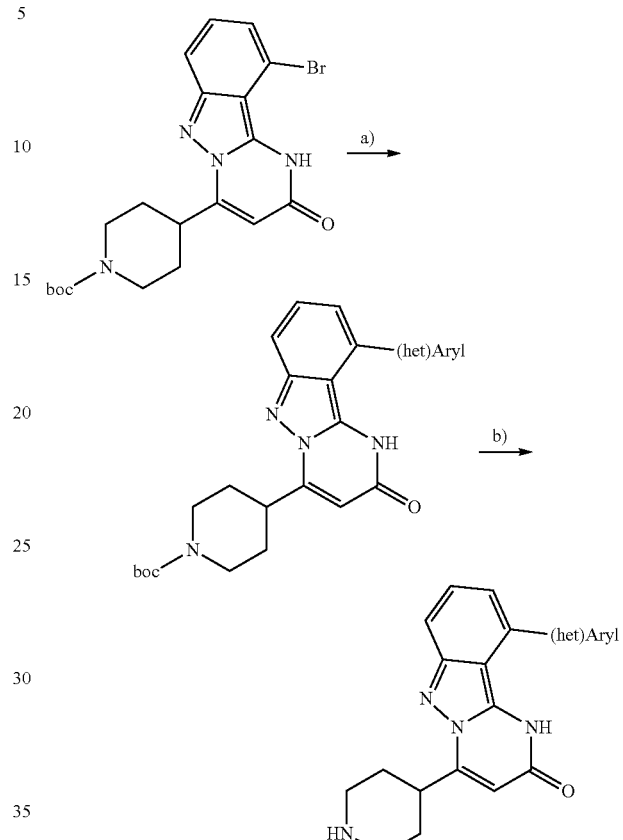

a) (Hetero)aryl boronic acid or boronic acid ester, (2-dicyclohexylphosphino-2′,4′,6′-triisopropyl-1,1′-biphenyl)[2-(2′-amino-1,1′-biphenyl)]palladium (II) methanesulfonate ( = Xphos precatalyst), tetrahydrofuran, 1M aqueous $K_3PO_4$-solution, 40° C., 3 h. b) 4N HCl in dioxane.

EXPLANATION OF THE FIGURES

FIG. 1: X-ray diffractogram of the acetate of 10-Chloro-4-(piperidin-4-yl)pyrimido[1,2-b]indazol-2(1H)-one (example 66).

FIG. 2: X-ray diffractogram of the maleate of 10-Chloro-4-(piperidin-4-yl)pyrimido[1,2-b]indazol-2(1H)-one (example 66).

FIG. 3: X-ray diffractogram of the sulfate of 10-Chloro-4-(piperidin-4-yl)pyrimido[1,2-b]indazol-2(1H)-one (example 66).

The compounds of formula (I-A) or (I-B) according to the invention have useful pharmacological properties and can be employed for the prevention and treatment of disorders in humans and animals.

The compounds of formula (I-A) or (I-B) according to the invention open up a further treatment alternative and are therefore an enrichment of pharmacy.

The compounds of formula (I-A) or (I-B) according to the invention bring about an inhibition of clot lysis (fibrinolysis), lead to an increase in clot stability (clot firmness) and thereby to a reduction of bleeding, re-bleeding and blood loss. These effects are due to direct inhibition of plasminogen, the central precursor of plasmin, a potent serine protease involved in the dissolution of fibrin blood clots.

The compounds of formula (I-A) or (I-B) according to the invention are suitable for the treatment and/or prophylaxis of acute and recurrent bleeding in patients with or without underlying hereditary or acquired bleeding disorders. The compounds of formula (I-A) or (I-B) according to the invention are also suitable for the treatment and/or prophylaxis of acute and recurrent bleeding in patients with or without underlying hereditary or acquired hemostatic disorders. The compounds of formula (I-A) or (I-B) according to the invention are also suitable for the treatment and/or prophylaxis of acute and recurrent bleeding in patients with or without underlying hereditary rare bleeding disorders. The compounds of formula (I-A) or (I-B) according to the invention are also suitable for the treatment and/or prophylaxis of hereditary or acquired bleeding disorders, hereditary or acquired hemostatic disorders, and rare bleeding disorders.

Within the meaning of the present invention, the term underlying hereditary or acquired bleeding disorders comprises von Willebrand's disease, platelet disorders/dysfunctions like Glantzmann's thrombasthenia and thrombocytopenia, and vitamin K deficiency, PAI-1 deficiency, mild and moderate hemophilia, including hemophilia A (factor VIII deficiency), hemophilia B (factor IX deficiency), and hemophilia C (factor XI deficiency), symptomatic carriers of hemophilia and other hereditary bleeding disorders, autoimmune disorders that lead to the formation of antibodies against the coagulation factor, blood cancers, bone marrow diseases, infections, kidney failure, liver disease, medications, medications, including heparin, low molecular weight heparin, and coumarin derivatives, like warfarin, accidental injuries and surgical interventions leading to massive blood loss and resulting in a critical reduction in the level of coagulation factors which can lead to additional non-surgical bleeding complications (e.g. coagulopathic bleeding), acquired von Willebrand syndrome (AVWS), characterized by structural or functional defects of von Willebrand factor (VWF) that are secondary to autoimmune, lymphoproliferative or myeloproliferative, malignant, cardiovascular, or other disorders.

Within the meaning of the present invention, the term mild hemophilia is defined as a level of clotting factor activity of the respective deficient factor of 5% to 50% of the normal level, the term moderate hemophilia is defined as a level of clotting factor activity of the respective deficient factor of 1% to 5% of the normal level.

Within the meaning of the present invention, the term underlying hereditary or acquired hemostatic disorders is defined as pathological processes resulting in abnormal bleeding or clotting.

Within the meaning of the present invention, the term underlying hereditary rare bleeding disorders (RBD) is defined as bleeding disorders caused by hereditary disorders, that are less common than e.g. hemophilia A and B or von Willebrand disease. Rare bleeding disorders include deficiency of fibrinogen, prothrombin, factors V, combined factors V+VIII, factor VII, factor X, factor XI or factor XIII.

The compounds of formula (I-A) or (I-B) according to the invention can be used in a wide range of hemorrhagic conditions like upper gastrointestinal bleeding, hemorrhages caused by antifibrinolytics, and gynecological bleeding indications including menorrhagia (heavy menstrual bleeding, HMB), placental bleeding, postpartum hemorrhage and conisation of the cervix.

Within the meaning of the present invention, menorrhagia (heavy menstrual bleeding, HMB) is defined as menstrual blood loss of 60 ml or more per cycle, for example 60 to 80 ml per cycle, in particular more than 80 ml per cycle. Also within the meaning of the present invention and according to National Institute for Clinical Excellence (NICE) guidelines, menorrhagia is defined for clinical purposes as excessive menstrual blood loss which interferes with the woman's physical, emotional, social and material quality of life, and which can occur alone or in combination with other symptoms.

In particular, the compounds of formula (I-A) or (I-B) according to the invention can be used in menorrhagia (heavy menstrual bleeding, HMB) caused by underlying bleeding disorders, for example hereditary or acquired bleeding disorders, such as von Willebrand's disease, platelet disorders/dysfunctions like Glantzmann's thrombasthenia and thrombocytopenia, and vitamin K deficiency, PAI-1 deficiency, mild and moderate hemophilia, including hemophilia A (factor VIII deficiency), hemophilia B (factor IX deficiency), and hemophilia C (factor XI deficiency), symptomatic carriers of hemophilia and other hereditary bleeding disorders, such as deficiency of fibrinogen, prothrombin, factors V, combined factors V+VIII, factor VII, factor X, factor XI, or factor XIII, autoimmune disorders, blood cancers, bone marrow diseases, infections, kidney failure, liver disease, medications, including heparin, low molecular weight heparin, and coumarin derivatives, like warfarin, accidental injuries and surgical interventions leading to massive blood loss and resulting in a critical reduction in the level of coagulation factors, and acquired von Willebrand syndrome (AVWS).

The compounds of formula (I-A) or (I-B) according to the invention can also be used for reducing peri- and postoperative blood loss and rebleeding during and after different surgical interventions, including cardiovascular surgery, including coronary artery bypass surgery, spinal surgery, trauma surgery, transplantation, including orthotopic liver transplantation, and hysterectomy, as well as transfusion requirements in patients with or without underlying bleeding disorders. Moreover, the compounds of formula (I-A) or (I-B) according to the invention can be used for the prevention of recurrence of bleeding in patients after elective minor surgery like prostatic surgery including prostatectomy and transurethral prostatic surgery, gynaecological surgery, urinary surgery, otolaryngological (ENT) surgery including tonsillectomy, and adenoidectomy, oral surgery, and dental surgery, in patients with or without underlying hereditary or acquired bleeding disorders.

The compounds of formula (I-A) or (I-B) according to the invention can also be used for treatment and/or prophylaxis of acute and recurrent bleeding in patients with liver diseases, including patients with end-stage liver diseases in patients with or without underlying bleeding disorders.

The compounds of formula (I-A) or (I-B) according to the invention can also be used for treatment and/or prophylaxis of acute and recurrent bleeding in patients with trauma and/or traumatic hyphaema, hemorrhagic stroke, acute promyelocytic leukaemia, and to block plasmin-induced proteolysis which may be of biological relevance during atherothrombosis and inflammatory states, cancer and other diseases in patients with or without underlying hereditary or acquired bleeding disorders.

The compounds of formula (I-A) or (I-B) according to the invention can also be used for the treatment and/or prophylaxis of hereditary or acquired bleeding disorders in patients including von Willebrand's disease, platelet disorders/dysfunctions like Glantzmann's thrombasthenia and thrombocytopenia, and vitamin K deficiency, PAI-1 deficiency, mild and moderate hemophilia, including hemophilia A (factor VIII deficiency), hemophilia B (factor IX deficiency), and hemophilia C (factor XI deficiency), symptomatic carriers of hemophilia and other hereditary bleeding disorders, such as deficiency of fibrinogen, prothrombin, factors V, combined factors V+VIII, factor VII, factor X, factor XI or factor XIII, autoimmune disorders, blood cancers, bone marrow diseases, infections, kidney failure, liver disease, medications, medications, including heparin, low molecular weight heparin, and coumarin derivatives, like warfarin, accidental injuries and surgical interventions leading to massive blood loss and resulting in a critical reduction in the level of coagulation factors, and acquired von Willebrand syndrome (AVWS).

The compounds of the present invention can be used either alone as monotherapy or in combination with other therapies to address a bleeding disorder. For instance, co-administration of one or more compounds of the invention with a plasma-derived or recombinant coagulation factor such as factor VIIa, factor VIII, factor IX or desmopressin is believed useful for treating hemophilia.

The compounds of formula (I-A) or (I-B) according to the invention can also be used for treating synovitis, wherein the synovitis may be associated with cartilage damage and is associated with hemarthrosis in patients with or without underlying hereditary or acquired bleeding disorders.

The compounds of formula (I-A) or (I-B) according to the invention can also be used for the treatment of nosebleed (epistaxis) caused by trauma or other causes in patients with or without underlying hereditary or acquired bleeding disorders.

The compounds of formula (I-A) or (I-B) according to the invention can also be used for the treatment and/or prophylaxis of hereditary or acquired bleeding disorders in patients.

The present invention further relates to the use of the compounds of formula (I-A) or (I-B) according to the invention for the treatment and/or prophylaxis of diseases, in particular the aforementioned diseases.

An embodiment of the present invention is also a compound of formula (I-A) or (I-B) according to the invention for use in a method for the treatment and/or prophylaxis of diseases.

An embodiment of the present invention is also a compound of formula (I-A) or (I-B) according to the invention for use in a method for the treatment and/or prophylaxis of acute and recurrent bleeding in patients with or without underlying hereditary or acquired bleeding disorders.

An embodiment of the present invention is also a compound of formula (I-A) or (I-B) according to the invention for use in a method for the treatment and/or prophylaxis of acute and recurrent bleeding in patients with underlying hereditary or acquired bleeding disorders.

An embodiment of the present invention is also a compound of formula (I-A) or (I-B) according to the invention for use in a method for the treatment and/or prophylaxis of acute and recurrent bleeding in patients with or without underlying hereditary or acquired bleeding disorders, wherein the bleeding is associated with a disease or medical intervention selected from the group consisting of menorrhagia, postpartum hemorrhage, hemorrhagic shock, trauma, surgery, including otolaryngological, cardiovascular, and spinal surgery, liver or lung transplantation, stroke, liver diseases, hereditary angioedema, nosebleed, and synovitis.

An embodiment of the present invention is also a compound of formula (I-A) or (I-B) according to the invention for use in a method for the treatment and/or prophylaxis of acute and recurrent bleeding in patients with underlying hereditary or acquired bleeding disorders, wherein the bleeding is associated with a disease or medical intervention selected from the group consisting of menorrhagia, postpartum hemorrhage, hemorrhagic shock, trauma, surgery, including otolaryngological, cardiovascular, and spinal surgery, liver or lung transplantation, stroke, liver diseases, hereditary angioedema, nosebleed, and synovitis.

An embodiment of the present invention is also a medicament comprising a compound of the formula (I-A) or (I-B) according to the invention in combination with an inert, non-toxic, pharmaceutically suitable auxiliary.

An embodiment of the present invention is also a medicament comprising a compound of the formula (I-A) or (I-B) according to the invention in combination with a further active compound selected from the group consisting of Factor VIII, Factor IX, Factor VIIa, activated prothrombin complex concentrates (aPCC) or prothrombin complex concentrates (PCCs), ε-aminocaproic acid, ethamsylate, paraaminobutyl benzoic acid, tranexamic acid, desmopressin, danazol, combined oral contraceptive pills (COCPs), progestin intrauterine system, glucocorticoid receptor agonists, analgesics, and nonsteroidal anti-inflammatory drugs (NSAIDs).

An embodiment of the present invention is also a medicament comprising a compound of the formula (I-A) or (I-B) according to the invention as described above for the treatment and/or prophylaxis of acute and recurrent bleeding in patients with or without underlying hereditary or acquired bleeding disorders.

An embodiment of the present invention is also a medicament comprising a compound of the formula (I-A) or (I-B) according to the invention as described above for the treatment and/or prophylaxis of acute and recurrent bleeding in patients with underlying hereditary or acquired bleeding disorders.

An embodiment of the present invention is also a medicament comprising a compound of the formula (I-A) or (I-B) according to the invention as defined above for the treatment and/or prophylaxis of acute and recurrent bleeding in patients with or without underlying hereditary or acquired bleeding disorders, wherein the bleeding is associated with a disease or medical intervention selected from the group consisting of menorrhagia, postpartum hemorrhage, hemorrhagic shock, trauma, surgery, otolaryngological surgery, dental surgery, urinary surgery, prostatic surgery, gynaecological surgery, cardiovascular surgery, spinal surgery, liver or lung transplantation, stroke, liver diseases, hereditary angioedema, nosebleed, and synovitis and cartilage damage following hemarthrosis.

An embodiment of the present invention is also a medicament comprising a compound of the formula (I-A) or (I-B) according to the invention as defined above for the treatment and/or prophylaxis of acute and recurrent bleeding in patients with underlying hereditary or acquired bleeding disorders, wherein the bleeding is associated with a disease or medical intervention selected from the group consisting of menorrhagia, postpartum hemorrhage, hemorrhagic shock, trauma, surgery, otolaryngological surgery, dental surgery, urinary surgery, prostatic surgery, cardiovascular surgery, spinal surgery, liver or lung transplantation, stroke, liver diseases, hereditary angioedema, nosebleed, and synovitis and cartilage damage following hemarthrosis.

An embodiment of the present invention is also a method for the treatment and/or prophylaxis of acute and recurrent bleeding in patients with or without underlying hereditary or acquired bleeding disorders in humans and animals using an effective amount of at least one compound of the formula (I-A) or (I-B) according to the invention or a medicament comprising a compound of the formula (I-A) or (I-B) according to the invention as defined above.

An embodiment of the present invention is also a method for the treatment and/or prophylaxis of acute and recurrent bleeding in patients with underlying hereditary or acquired bleeding disorders in humans and animals using an effective amount of at least one compound of the formula (I-A) or (I-B) according to the invention or a medicament comprising a compound of the formula (I-A) or (I-B) according to the invention as defined above.

An embodiment of the present invention is also a method for the treatment and/or prophylaxis of acute and recurrent bleeding in patients with or without underlying hereditary or acquired bleeding disorders in humans and animals using an effective amount of at least one compound of the formula (I-A) or (I-B) according to the invention or a medicament comprising a compound of the formula (I-A) or (I-B) according to the invention as defined above, wherein the bleeding is associated with a disease or medical intervention selected from the group consisting of menorrhagia, postpartum hemorrhage, hemorrhagic shock, trauma, surgery, otolaryngological surgery, dental surgery, urinary surgery, prostatic surgery, cardiovascular surgery, spinal surgery, liver or lung transplantation, stroke, liver diseases, hereditary angioedema, nosebleed, and synovitis and cartilage damage following hemarthrosis.

An embodiment of the present invention is also a method for the treatment and/or prophylaxis of acute and recurrent bleeding in patients with underlying hereditary or acquired bleeding disorders in humans and animals using an effective amount of at least one compound of the formula (I-A) or (I-B) according to the invention or a medicament comprising a compound of the formula (I-A) or (I-B) according to the invention as defined above, wherein the bleeding is associated with a disease or medical intervention selected from the group consisting of menorrhagia, postpartum hemorrhage, hemorrhagic shock, trauma, surgery, otolaryngological surgery, dental surgery, urinary surgery, prostatic surgery, cardiovascular surgery, spinal surgery, liver or lung transplantation, stroke, liver diseases, hereditary angioedema, nosebleed, and synovitis and cartilage damage following hemarthrosis.

The efficacy of the compounds of formula (I-A) and (I-B) according to the invention for the treatment and/or prophylaxis of hereditary or acquired bleeding disorders, and of acute and recurrent bleeding in patients with or without underlying hereditary or acquired bleeding disorders, wherein the bleeding is associated with a disease or medical intervention selected from the group consisting of menorrhagia, postpartum hemorrhage, hemorrhagic shock, trauma, surgery, otolaryngological surgery, dental surgery, urinary surgery, prostatic surgery, cardiovascular surgery, spinal surgery, liver or lung transplantation, stroke, liver diseases, hereditary angioedema, nosebleed, and synovitis and cartilage damage following hemarthrosis, can be demonstrated for example by a reduction in blood loss (quantitative and laboratory values), by a shortened duration of bleeding, by an increased clot firmness, by a lower incidence of recurrent bleeding, by an improved quality of life, which may in the case of menorrhagia be determined by the Menorrhagia Impact Questionnaire, the number of medical visits, and/or by improved compliance due to less frequent dosing as compared to e.g. lysine analogs, including tranexamic acid and ε-aminocaproic acid.

The compound of formula (I-A) or (I-B) need not be, but is optionally administered with one or more agents currently used to prevent or treat the disorder in question. The effective amount of such other agents depends on the amount of compound of the invention present, the type of disorder or treatment.

These are generally used in the same dosages and with administration routes as used hereinbefore or about from 1 to 99% of the heretofore employed dosages. The present invention further relates to medicaments containing at least one of the compounds of formula (I-A) or (I-B) according to the invention and one or more further active substances, in particular for the treatment and/or prophylaxis of the aforementioned diseases. As suitable combination active substances, we may mention for example and preferably:

Factor VIII, Factor IX, Factor VIIa, activated prothrombin complex concentrates (aPCC) or prothrombin complex concentrates (PCCs), ε-aminocaproic acid, ethamsylate, paraaminobutyl benzoic acid, tranexamic acid, desmopressin, danazol, combined oral contraceptive pills (COCPs), progestin intrauterine systems, glucocorticoid receptor agonists, analgesics, and nonsteroidal anti-inflammatory drugs (NSAIDs).

In an embodiment of the invention, the compounds of formula (I-A) or (I-B) according to the invention are administered in a combination with the coagulation factor commonly known as Factor VIII, any derivatives, fragments, muteins or conjugates thereof.

In an embodiment of the invention, the compounds of formula (I-A) or (I-B) according to the invention are administered in a combination with the coagulation factor commonly known as Factor IX, any derivatives, fragments, muteins or conjugates thereof.

In an embodiment of the invention, the compounds of formula (I-A) or (I-B) according to the invention are administered in a combination with the coagulation factor commonly known as Factor VIIa, any derivatives, fragments, muteins or conjugates thereof.

In an embodiment of the invention, the compounds of formula (I-A) or (I-B) according to the invention are administered in a combination with activated prothrombin complex concentrates (aPCCs) or prothrombin complex concentrates (PCCs).

In an embodiment of the invention, the compounds of formula (I-A) or (I-B) according to the invention are administered in a combination with antifibrinolytic agents such as, by way of example and preferably, ε-aminocaproic acid, ethamsylate, paraaminobutyl benzoic acid, and tranexamic acid.

In an embodiment of the invention, the compounds of formula (I-A) or (I-B) according to the invention are administered in a combination with desmopressin.

In an embodiment of the invention, the compounds of formula (I-A) or (I-B) according to the invention are administered in a combination with danazol.

In an embodiment of the invention, the compounds of formula (I-A) or (I-B) according to the invention are administered in combination with combined oral contraceptive pills (COCPs) such as, by way of example and preferably, combinations of an estrogen, for example the synthetic estrogen ethinylestradiol or the natural estrogens estradiol and estradiolderivatives, preferably estradiolester, such as estradiolvalerate and estradiolhydrate, and a gestagen for example progesterone, trimegestone, medroxyprogesterone acetate, megestrol acetate, cyproterone acetate, chlormadinone acetate, nestorone, levonorgestrel, norgestimate, desogestrel, ethonogestrel (3-Ketodesogestrel), nomegestrol acetate (NOMAC), norethisterone acetate (NETA), drospirenone, gestodene, dienogest, norethindrone acetate, danazole, norgestrel, and tanaproget.

In an embodiment of the invention, the compounds of formula (I-A) or (I-B) according to the invention are administered in combination with intrauterine devices, including progestine impregnated intrauterine devices, e.g. LNG-IUS levonorgestrel intrauterine system.

In an embodiment of the invention, the compounds of formula (I-A) or (I-B) according to the invention are administered in combination with a glucocorticoid receptor agonist, such as, by way of example and preferably, cortisol, cortisone, hydrocortisone, prednisone, methyl-prednisolone, prednylidene, deflazacort, fluocortolone, triamcinolone, dexamethasone or betamethasone.

In an embodiment of the invention, the compounds of formula (I-A) or (I-B) according to the invention are administered in combination with nonsteroidal anti-inflammatory drugs (NSAIDs), such as by way of example and preferably acetylsalicylic acid, diclofenac, flurbiprofen, ibuprofen, indomethacin, mefenamic acid, meclofenamic acid, and naproxen.

In an embodiment of the invention, the compounds of formula (I-A) or (I-B) according to the invention are administered in combination with analgesics, such as by way of example and preferably, acetaminophen, acetanilide, aminobenzoic acid, antipyrine, calcium or choline salicylate, codeine, phenatecin, phenyltoloxamine citrate, salicylamide, sodium salicylate, and sodium para-aminobenzoate.

An embodiment of the invention is also a medicament, comprising a compound of the formula (I-A) or (I-B) as defined above in combination with a further active compound selected from the group consisting of Factor VIII, Factor IX, Factor VIIa, activated prothrombin complex concentrates (aPCC) or prothrombin complex concentrates (PCCs), ε-aminocaproic acid, ethamsylate, paraaminobutyl benzoic acid, tranexamic acid, desmopressin, danazol, hormonal treatments, including combined oral contraceptive pills (COCPs), progestin intrauterine system, glucocorticoid receptor agonists, analgesics, and nonsteroidal anti-inflammatory drugs (NSAIDs).

An embodiment of the invention is also a medicament as defined above for the treatment and/or prophylaxis of hereditary or acquired bleeding disorders, trauma, surgery, stroke, menorrhagia, including heavy menstrual bleeding in women with underlying bleeding disorders, postpartum hemorrhage, liver diseases, and hereditary angioedema.

An embodiment of the invention is also a method for the treatment and/or prophylaxis of hereditary or acquired bleeding disorders, trauma, surgery, stroke, menorrhagia, including heavy menstrual bleeding in women with underlying bleeding disorders, postpartum hemorrhage, liver diseases, and hereditary angioedema in humans and animals using an effective amount of at least one compound of the formula (I-A) or (I-B) as defined above or a medicament as defined above.

The present invention further relates to medicaments that contain at least one compound of formula (I-A) or (I-B) according to the invention, usually together with one or more inert, non-toxic, pharmaceutically suitable auxiliaries, and use thereof for the aforementioned purposes.

The compounds of formula (I-A) or (I-B) according to the invention may be effective after systemic and/or local administration. For this purpose they can be applied in a suitable way, e.g. by oral, parenteral, pulmonary, nasal, sublingual, lingual, buccal, rectal, dermal, transdermal, conjunctival, or otic administration or as implant or stent.

For these routes of application, the compounds of formula (I-A) or (I-B) according to the invention can be administered in suitable dosage forms.

Dosage forms functioning according to the prior art, for rapid and/or modified release of the compounds according to the invention, which contain the compounds of formula (I-A) or (I-B) according to the invention in crystalline and/or amorphized and/or dissolved form, e.g. tablets (uncoated or coated tablets, for example with enteric coatings or coatings with delayed dissolution or insoluble coatings, which control the release of the compound formula (I-A) or (I-B) according to the invention), tablets or films/wafers that disintegrate rapidly in the oral cavity, films/lyophilizates, capsules (for example hard or soft gelatin capsules), sugar-coated pills, granules, pellets, powders, emulsions, suspensions, aerosols or solutions, are suitable for oral administration.

Parenteral administration can take place avoiding an absorption step (e.g. intravenous, intraarterial, intracardiac, intraspinal or intralumbar) or including absorption (e.g. intramuscular, subcutaneous, intracutaneous, percutaneous or intraperitoneal). Injection and infusion preparations in the form of solutions, suspensions, emulsions, lyophilizates or sterile powders are suitable, among others, as dosage forms for parenteral application. Intravenous administration can take place for example by bolus administration or by continuous infusion.

Inhaled pharmaceutical forms (including powder inhalers, nebulizers), nasal drops, nasal solutions or nasal sprays, tablets, films/wafers or capsules for lingual, sublingual or buccal application, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, dusting powders, implants or stents for example are suitable for other routes of administration.

In one embodiment, the compounds of formula (I-A) or (I-B) according to the invention can be administered in the form of nasal drops, nasal solutions or nasal sprays for the treatment and/or prophylaxis of acute and recurrent nosebleed in patients, in particular in patients with underlying hereditary or acquired bleeding disorders.

In one embodiment, the compounds of formula (I-A) or (I-B) according to the invention can be administered in the form of patches soaked with the compounds of formula (I-A) or (I-B) according to the invention and applied to the wound for the treatment and/or prophylaxis of acute and recurrent bleeding in patients, in particular in patients with underlying hereditary or acquired bleeding disorders.

In one embodiment, the compounds of formula (I-A) or (I-B) according to the invention are administered intramuscular, rectal or transvaginal for the treatment and/or prophylaxis of acute and recurrent bleeding in patients with trauma and other forms of acute bleeding, in particular in patients with underlying hereditary or acquired bleeding disorders.

In one embodiment, the compounds of formula (I-A) or (I-B) according to the invention are administered in form of a swish and swallow or a lozenge for the treatment and/or prophylaxis of acute and recurrent mouth bleeding in patients, in particular in patients with underlying hereditary or acquired bleeding disorders. A swish and swallow route of administration is defined as the administration of a liquid substance to the oral mucosa by swishing the drug inside the mouth for a certain amount of time then allowed to be swallowed. The drug action is both topical and systemic.

The compounds of formula (I-A) or (I-B) according to the invention can also be used in vitro or ex vivo to inhibit fibrinolysis, for example for in vitro/ex vivo assays, to inhibit fibrinolysis in blood and plasma products, to pretreat catheters and other medicinal devices and equipment, for surface coatings or in biological samples.

The compounds of formula (I-A) or (I-B) according to the invention can be transformed to the aforementioned dosage forms. This can take place in a manner known per se by mixing with inert, non-toxic, pharmaceutically suitable auxiliaries. These auxiliaries include inter alia carriers (for example microcrystalline cellulose, lactose, mannitol), solvents (e.g. liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (e.g. antioxidants such as ascorbic acid), colorants (e.g. inorganic pigments, for example iron oxides) and taste and/or odour correctants.

An embodiment of the invention are pharmaceutical compositions comprising at least one compound of formula (I-A) or (I-B) according to the invention, preferably together with at least one inert, non-toxic, pharmaceutically suitable auxiliary, and the use of these pharmaceutical compositions for the above cited purposes.

For the prevention or treatment of disease, the appropriate dosage of a compound of the invention (when used alone or in combination with other agents) will depend on the type of disease to be treated, the type of compound, the severity and course of the disease, whether the compound is administered for preventive or therapeutic purposes, previous therapy, the patient's clinical history and response to the compound, and the discretion of the attending physician. The compound is suitably administered to the patient at one time or over a series of treatments. Depending on the type and severity of disease, about 0.1 µg/kg to 100 mg/kg of the compound is an initial candidate dosage for administration to the patient, whether for example, by one or more separate administrations, or by continuous infusion. A typical daily dosage might range from about 0.1 µg/kg to 100 mg/kg or more, depending on the factors mentioned above. For repeated administrations over several days or longer, depending on the condition, the treatment is sustained until a desired suppression of disease symptoms occurs. An initial higher loading dose, followed by one or more lower doses may be administered. However, other dosing regimen may be useful. The progress of this therapy is easily monitored by conventional techniques and assays.

In general, it has proved advantageous, in the case of parenteral administration, to administer amounts of about 2 to 300 mg/kg body weight every 24 hours to achieve effective results. For oral application, the dosage is about 2 to 600 mg/kg body weight every 24 hours.

According to a further embodiment, it has proved advantageous, in the case of oral or parenteral administration, to administer amounts in a range of from 0.1 to 300 or from 0.5 to 50 or from 1 to 50 or from 2 to 10 mg/kg body weight every 24 hours to achieve effective results.

Nevertheless, it may optionally be necessary to deviate from the stated amounts, namely depending on body weight, route of administration, individual response to the active substance, type of preparation and time point or interval when application takes place. Thus, in some cases it may be sufficient to use less than the aforementioned minimum amount, whereas in other cases the stated upper limit must be exceeded. When applying larger amounts, it may be advisable to distribute these in several individual doses throughout the day.

According to a further embodiment, the compounds of formula (I-A) or (I-B) according to the invention are administered orally once or twice or three times a day. According to a further embodiment, the compounds of formula (I-A) or (I-B) according to the invention are administered orally once or twice a day. According to a further embodiment, the compounds of formula (I-A) or (I-B) according to the invention are administered orally once a day. For the oral administration, a rapid release or a modified release dosage form may be used.

According to a further embodiment, the compounds of formula (I-A) or (I-B) according to the invention are administered orally once or twice or three times a day on 1 or 2 or 3 or 4 or 5 or 6 or 7 or 8 or 9 or 10 days per month. According to a further embodiment, the compounds of formula (I-A) or (I-B) according to the invention are administered orally once or twice or three times a day on 2 or 3 or 4 or 5 or 6 or 7 or 8 or 9 or 10 consecutive days per month. According to a further embodiment, the compounds of formula (I-A) or (I-B) according to the invention are administered orally once or twice or three times a day on 3 or 4 or 5 or 6 or 7 days per month. According to a further embodiment, the compounds of formula (I-A) or (I-B) according to the invention are administered orally once or twice or three times a day on 3 or 4 or 5 or 6 or 7 consecutive days per month.

The following practical examples explain the invention. The invention is not limited to the examples.

The percentages in the following tests and examples are percentages by weight, unless stated otherwise; parts are parts by weight. Proportions of solvents, dilution ratios and concentrations for liquid/liquid solutions refer in each case to the volume.

A. EXAMPLES

Abbreviations and Acronyms

[α] specific rotation value
AcOH acetic acid
Boc tert-butoxycarbonyl
br. broad signal (NMR coupling pattern)
CDI N,N'-carbonyldiimidazole
Conc. concentrated
CPhos 2-dicyclohexylphosphino-2',6'-bis(N,N-dimethylamino)-1,1'-biphenyl
δ NMR shift in ppm
d doublet (NMR coupling pattern)
DCM dichloromethane
DIPEA diisopropyl ethyl amine
DMAP 4-N,N-dimethylaminopyridine
DMF N,N-dimethylformamide
DMSO dimethylsulfoxide
EDCI N-ethyl-N'-(3-dimethylaminopropyl)carbodiimide hydrochloride
ESI electrospray ionisation (MS)
GC-MS gas chromatography coupled to mass spectrometry
HATU 1-[Bis(dimethylamino)methylene]-1H-1,2,3-triazolo[4,5-b]pyridinium 3-oxid hexafluorophosphate
HOBt 1-hydroxybenzotriazole hydrate
HPLC high performance liquid chromatography
LC-MS liquid chromatography coupled to mass spectrometry
m multiplet (NMR coupling pattern)
MS mass spectrometry
MTBE tert-butyl methyl ether
NMR nuclear magnetic resonance
q quartet (NMR coupling pattern)
$R_t$ retention time
RT room temperature
s singlet (NMR coupling pattern)

t triplet (NMR coupling pattern)
TFA trifluoroacetic acid
UV ultraviolet
WL wavelength
XPhos 2-dicyclohexylphosphino-2',4',6'-triisopropylbiphenyl
Preparative HPLC
Method 1A
  Column: Chromatorex C18 48 μm 100×30 5 μm, Flow: 50 mL/min, Eluent: A: acetonitrile B: water/0.1% formic acid, Gradient 20% A→90% A
Method 2A
  Column: Xbridge 100×30 5 μm, Flow: 50 mL/min, Eluent: A: acetonitrile B: water/0.2% ammonia, Gradient 10% A→95% A
LC-MS-Methods:
Method 1B
  Instrument: Waters ACQUITY SQD UPLC system; column: Waters Acquity UPLC HSS T3 1.8μ 50×1 mm; eluent A: 1 l water+0.25 ml 99% HCOOH, eluent B: 1 l acetonitrile+0.25 ml 99% HCOOH; gradient: 0.0 min 90% A→1.2 min 5% A→2.0 min 5% A; oven: 50° C.; flow: 0.40 ml/min; UV-detection: 208-400 nm.
Method 2B
  Instrument MS: Waters (Micromass) QM; Instrument HPLC: Agilent 1100 series; column: Agilent ZORBAX Extend-C18 3.0×50 mm 3.5 μm; Eluent A: 1 l water+0.01 mol ammonium carbonate, eluent B: 1 l acetonitrile; gradient: 0.0 min 98% A→0.2 min 98% A→3.0 min 5% A→4.5 min 5% A; Oven: 40° C.; Flow: 1.75 ml/min; UV-detection: 210 nm
Method 3B
  Instrument: Micromass Quattro Premier with Waters UPLC Acquity; Column: Thermo Hypersil GOLD 1.9μ 50×1 mm; Eluent A: 1 l Wasser+0.5 ml 50% formic acid, Eluent B: 1 l Acetonitril+0.5 ml 50% formix acid; Gradient: 0.0 min 97% A→0.5 min 97% A→3.2 min 5% A→4.0 min 5% A Oven: 50° C.; Flow: 0.3 ml/min; UV-detection: 210 nm.
Method 4B
  Instrument MS: Waters (Micromass) ZQ; Instrument HPLC: Agilent 1100 Series; Column: Agilent ZORBAX Extend-C18 3.0×50 mm 3.5-Micron; Eluent A: 1 L water+0.01 mol ammonium carbonate, Eluent B: 1 L acetonitrile; Gradient: 0.0 min 98% A→0.2 min 98% A→3.0 min 5% A→4.5 min 5% A; Oven: 40° C.; Flow: 1.75 ml/min; UV-detection: 210 nm
Method 5B
  Instrument: Waters ACQUITY SQD UPLC system; column: Waters Acquity UPLC HSS T3 1.8μ 30×2 mm; eluent A: 1 l water+0.25 ml 99% formic acid, eluent B: 1 l acetonitrile+0.25 ml 99% formic acid; gradient: 0.0 min 90% A→1.2 min 5% A→2.0 min 5% A oven: 50° C.; flow: 0.60 ml/min; UV-detection: 208-400 nm.
Method 6B
  Instrument: Waters ACQUITY SQD UPLC system; column: Waters Acquity UPLC HSS T3 1.8μ 50×1 mm; eluent A: 1 l water+0.25 ml 99% formic acid, eluent B: 1 l acetonitrile+0.25 ml 99% formic acid; gradient: 0.0 min 95% A→6.0 min 5% A→7.5 min 5% A oven: 50° C.; flow: 0.35 ml/min; UV-detection: 210-400 nm.
Method 7B
  Instrument MS: Waters (Micromass) QM; Instrument HPLC: Agilent 1100 Series; Column: Agilent ZORBAX Extend-C18 3.0×50 mm 3.5-Micron; Eluent A: 1 L water+0.01 mol ammonium carbonate, Eluent B: 1 L acetonitrile; Gradient: 0.0 min 98% A→0.2 min 98% A→3.0 min 5% A→4.5 min 5% A; Oven: 40° C.; Flow: 1.75 ml/min; UV-detection: 210 nm.
Method 8B
  Instrument: Agilent MS Quad 6150; HPLC: Agilent 1290; Column: Waters Acquity UPLC HSS T3 1.8 50×2.1 mm; Eluent A: 1 l water+0.25 ml 99% formic acid, Eluent B: 1 l acetonitrile+0.25 ml 99% formic acid; Gradient: 0.0 min 90% A→0.3 min 90% A→1.7 min 5% A→3.0 min 5% A Oven: 50° C.; Flow: 1.20 ml/min; UV-Detection: 205-305 nm.
Preparative Separation of Diastereomers:
Method 1C
  Phase: Chiracel OD-H, 5 μm 25 mm×50 mm, eluent: $CO_2$/methanol 81:19; pressure: 135 bar, temperature eluent: 38° C.; temperature zyklon: 40° C., pressure zyklon: 24 bar, flow: 200 g/min; UV-Detection: 210 nm.
Method 2C
  Phase: Daicel AD-H, 5 μm 250 mm×20 mm, eluent: iso-hexane/ethanol 7/3; temperature: 25° C.; flow: 20 ml/min; UV-Detection: 230 nm.
Method 3C
  Phase: Daicel Chiralpak AZ-H, 5 μm 250 mm×20 mm, eluent: iso-hexane/ethanol 6:4; temperature: 25° C.; flow: 15 ml/min; UV-Detection: 220 nm.
Method 4C
  Phase: Daicel Chiralpak AZ-H, 5 μm 250 mm×30 mm, eluent: iso-hexane/isopropanol 1/1; temperature: 25° C.; flow: 35 ml/min; UV-Detection: 230 nm.
Method 5C
  Phase: Daicel Chiralpak AS-H 5 μm 25 mm×20 mm; eluent: iso-hexane/ethanol 70:30; temperature: 25° C.; flow: 20 ml/min; UV-Detection: 220 nm.
Preparative Separation of Enantiomers:
Method 1D
  Phase: Daicel Chiralpak IC, 5 μm 250 mm×20 mm, eluent: iso-hexan/isopropanol 70:30; temperature: 30° C.; flow: 20 ml/min; UV-Detection: 230 nm.
Analytical Separation of Diastereomers:
Method 1E
  Phase: 250 mm×4.6 mm Chiracel OD-H 5 μm, eluent: methanol, temperature: 35° C., flow: 4 ml/min, UV-Detection: 210 nm
Method 2E
  Phase: 250 mm×4.6 mm Daicel Chiralpak AD-H 5 μm, eluent: iso-hexane/ethanol 1/1, temperature: 30° C., flow: 1.0 ml/min; UV-Detection: 220 nm
Method 3E
  Phase: 250 mm×4.6 mm Daicel Chiralpak AZ-H 5 μm, eluent: iso-hexane/ethanol/TFA/$H_2O$ 60%/40%/0.2%/1%, temperature: 40° C., flow: 1.0 ml/min; UV-Detection: 220 nm
Method 4E
  Phase: 250 mm×4.6 mm Daicel Chiralpak AZ-H 5 μm, eluent: iso-hexane/2-propanol 1/1, temperature: 30° C., flow: 1.0 ml/min; UV-Detection: 220 nm
Method 5E
  Phase: Daicel Chiralpak AS-H 5 μm 25 mm×4.6 mm; eluent: iso-hexane/ethanol 70:30; temperature: 30° C., flow: 1 ml/min, UV-Detection: 220 nm
Analytical Separation of Enantiomers:
Method 1F
  Phase: 250 mm×4.6 mm Daicel Chiralpak AY-H 5 μm, eluent: iso-hexan/ethanol 9/1, temperature: 45° C., flow: 1.0 ml/min; UV-Detection: 220 nm GC-MS-Methods:
Method 1G Instrument: Thermo Scientific DSQII, Thermo Scientific Trace GC Ultra; Column: Restek RTX-35MS, 15 m×200 μm×0.33 μm; constant Helium flow: 1.20 ml/min; Oven: 60° C.; Inlet: 220° C.; Gradient: 60° C., 30° C./min→300° C. (hold for 3.33 min).

Method 2G

Instrument: Thermo DFS, Trace GC Ultra; Column: Restek RTX-35, 15 m×200 μm×0.33 μm; constant Helium flow: 1.20 ml/min; Oven: 60° C.; Inlet: 220° C.; Gradient: 60° C., 30° C./min→300° C. (hold for 3.33 min).

Other Remarks

Microwave Instrument: Biotage Initiator

Starting Materials and Intermediates

General Procedures

General Procedure 1A: Condensation of (Aza)Aminoindazoles Under Standard Conditions A mixture of tert-butyl 4-[(2,2-dimethyl-4,6-dioxo-1,3-dioxan-5-yl)carbonyl]piperidine-1-carboxylate (1 eq) and the corresponding (aza)aminoindazol (1 eq.) in acetonitrile was stirred at 60° C. until HPLC and/or LC-MS indicated complete consumption of the starting material. After evaporating the solvent under vacuo the crude product was dissolved in 1-methoxy-2-propanol and then potassium phosphate (2 eq) was added in to the mixture. The reaction mixture was stirred at 110° C. until complete consumption of the intermediate. The work-up is described individually for each example.

Example 1A

Tert-butyl 4-(3-ethoxy-3-oxopropanoyl)piperidine-1-carboxylate

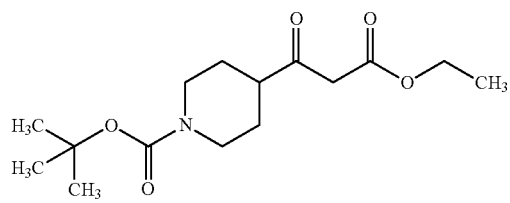 [SMILES: CCOC(=O)CC(=O)C1CCN(C(=O)OC(C)(C)C)CC1]

To a solution of boc-isonipecotic acid (150 g, 654 mmol) in tetrahydrofuran (2100 mL) was added di-1H-imidazol-1-ylmethanone (159 g, 981 mmol) and N,N-dimethylpyridin-4-amine (40.0 g, 327 mmol) at RT. The mixture was stirred at RT for 15 h (CAUTION: moderate gas evolution). In a second flask, a suspension of potassium 3-ethoxy-3-oxopropanoate (200 g, 1.18 mol) and magnesium dichloride (112 g, 1.18 mol) in tetrahydrofuran (2100 mL) was heated to 50° C. for 15 h. The resulting warm suspension was slowly added to the first flask under extensive stirring. The resulting mixture was stirred at RT for 20 h. Tetrahydrofuran was evaporated in vacuo, water (1500 mL) and ethyl acetate (1500 mL) were added. The mixture was cooled to 10° C. and 3N aqueous HCl was added until pH 1 was achieved. The organic phase was separated, the aqueous phase was extracted with ethyl acetate (1500 mL) and the combined organic phases were washed with 10% aq. NaHCO$_3$ (750 mL) and 10% aq. NaCl (750 mL), dried over magnesium sulfate, filtered and evaporated in vacuo to yield the title compound (182 g, 505 mmol) in a purity of 83%.

LC-MS (Method 1B): R$_t$=1.00 min, MS (ESIPos): m/z=300 [M+H]$^+$

Example 2A

Tert-butyl 4-[(2,2-dimethyl-4,6-dioxo-1,3-dioxan-5-yl)carbonyl]piperidine-1-carboxylate

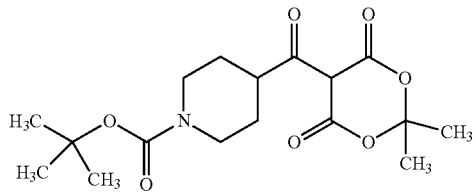 [SMILES: CC(C)(C)OC(=O)N1CCC(C(=O)C2C(=O)OC(C)(C)OC2=O)CC1]

To a solution of 1-(tert-butoxycarbonyl)piperidine-4-carboxylic acid (10 g, 43.6 mmol) and 2,2-dimethyl-1,3-dioxane-4,6-dione (6.9 g, 47.98 mmol) in 100 ml dichloromethane was added 4-dimethylaminopyridin (8.0 g, 65.42 mmol). After cooling the mixture to 0° C. 1-(3-dimethylaminopropyl)-3-ethylcarbodiimide hydrochloride (11.7 g, 61.1 mmol) was added in portions and then the reaction mixture was stirred at RT for 16 h. The mixture was treated with 50 ml of water and then the layers were separated. The organic layer was extracted with HCl 1M, dried over magnesium sulfate, filtered and evaporated under vacuo to yield the title compound (14 g, 86% of theory).

LC-MS (Method 1B): R$_t$=1.10 min, MS (ESIPos): m/z=354 [M−H]$^-$

Example 3A

2-Methylisonicotinic Acid

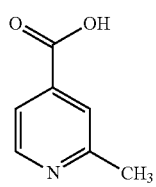

To a solution of 2,4-lutidine (280 g, 2.61 mol) in water (3.0 l) at 80° C. was added potassium permanganate (826 g, 5.23 mol) in small portions over 3 h. The reaction mixture was stirred at 80° C. overnight. The mixture was filtered through silica gel and then the filtrate was evaporated under vacuo until a volume of approximately of 20 ml was achieved. Then the solution was treated with HCl 37% (450 ml) until pH 3-4 was achieved. The solution was kept 1 h at 0° C. and then the resulting solid was filtered, washed with water at 0° C. and finally dried under vacuo overnight over phosphorus pentoxide to yield the title product (130 g, 36% of theory).

LC-MS (Method 3B): R$_t$=0.20 min, MS (ESIPos): m/z=138 [M+H]$^+$

Example 4A

Methyl 2-methylisonicotinate

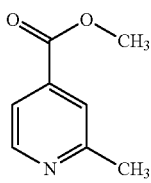

To methanol (1.54 l) at −10° C. was added slowly thionyl chloride (401 g, 3.37 mol) and the solution was stirred 10 minutes at 0° C. Then was added 2-methylisonicotinic acid (154 g, 1.20 mol) and the reaction mixture was stirred at reflux temperature overnight. The mixture was evaporated under vacuo, then diluted in ethyl acetated and finally treated with a 10% sodium hydrogen carbonate aqueous solution until pH 7 was achieved. After separation of the layers the aqueous phase was extracted with ethyl acetate. All collected organic phases were dried over magnesium sulfate, evaporated under dried under vacuo. The crude product was used in the next step without further purification (113.0 g, 48% of theory), 72% purity).

LC-MS (Method 1B): $R_t$=0.43 min, MS (ESIPos): m/z=152 [M+H]$^+$

Example 5A

Methyl 2-methylpiperidine-4-carboxylate

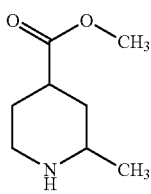

To acetic acid (700 ml) were added methyl 2-methylisonicotinate (79 g, 523 mmol) and platinum (IV) oxide (7.83 g, 34.5 mmol). The mixture was hydrogenated in the autoclave at RT and 20 bar during two days. After this time platinum (IV) oxide (5.00 g, 22.2 mmol) was added again and the mixture was hydrogenated during two days more at RT and 20 bar. After filtration of the catalyst the filtrate was evaporated under vacuo to obtain the title compound in quantitative yield.

LC-MS (Method 2B): $R_t$=1.15 min, MS (ESIPos): m/z=158 [M+H]$^+$

Example 6A

(−)-Cis-1-benzyl 4-methyl 2-methylpiperidine-1,4-dicarboxylate and (+)-Cis-1-benzyl 4-methyl 2-methylpiperidine-1,4-dicarboxylate

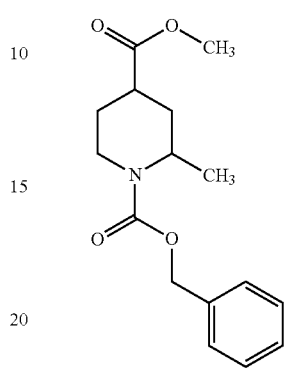

To a solution of methyl 2-methylpiperidine-4-carboxylate (138 g, 394 mmol) in dichloromethane (620 ml) was added N,N-diisopropylethylamine (331 g, 2.56 mol). The mixture was cooled to 0° C. and then benzyl chloroformate (80.6 g, 473 mmol) was added slowly. The reaction mixture was stirred 30 min at RT and then water was added in to the mixture. After separation of the layers the aqueous phase was extracted with dichloromethane and the collected organic layers were washed with water, dried over magnesium sulfate and evaporated. The crude product was purified by silica gel chromatography with petrolether/ethyl acetate 8/2 and finally the stereoisomers were separated by chromatography on chiral phase (Method 1D) to yield the title compounds in enantiomerically pure form. (−)-Cis-1-benzyl 4-methyl 2-methylpiperidine-1,4-dicarboxylate:
Yield: (26.7 g, 23% of theory)
HPLC (Method 1F): $R_t$=14.48 min
$[\alpha]^{23}_D$=−54.2 (c 0.9, acetonitrile)

(+)-Cis-1-benzyl 4-methyl 2-methylpiperidine-1,4-dicarboxylate

Yield: (23.3 g, 20% of theory)
HPLC (Method 1F): $R_t$=11.21 min
$[\alpha]^{23}_D$=+60.0 (c 0.365, acetonitrile) Example 7A Cis-methyl 2-methylpiperidine-4-carboxylate

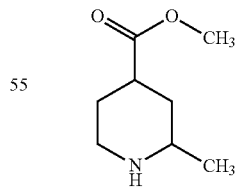

A solution of (−)-cis-1-benzyl 4-methyl 2-methylpiperidine-1,4-dicarboxylate (25.00 g, 85.8 mmol) in ethanol (250 ml) was treated with palladium on charcoal 10% (1.83 g, 1.72 mmol) under hydrogen atmosphere at normal pressure and RT for 16 h. The mixture was filtered through celite and the filtrate was evaporated and dried under vacuo to yield the title compound (13.95 g, 96% of theory).

LC-MS (Method 2B): $R_t$=1.15 min, MS (ESIPos): m/z=158 [M+H]$^+$

Example 8A

Cis-1-tert-butyl 4-methyl 2-methylpiperidine-1,4-dicarboxylate

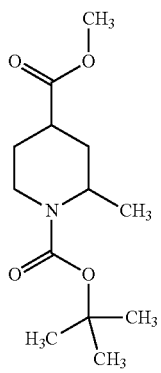

To a solution of cis-methyl 2-methylpiperidine-4-carboxylate obtained in example 7A (12.95 g, 82.34 mmol) in tetrahydrofuran (250 ml) under argon atmosphere was added di-tert-butyl dicarbonate (21.58 g, 98.88 mmol) and the reaction mixture was stirred at RT overnight. The mixture was evaporated under vacuo and the crude product was dissolved in ethyl acetate and treated with a 10% citric acid aqueous solution. After separation of the layers the organic layer was washed with 10% citric acid aqueous solution, with a saturated aqueous solution of sodium hydrogen carbonate and finally with brine. The organic phase was dried over magnesium sulfate, filtered and evaporated to yield the title compound (27.16 g, 96% of theory), 75% pure according NMR). The crude product was used in the next step without further purification.

MS (ESIPos): m/z=258 [M+H]$^+$

Example 9A

Cis-1-(tert-butoxycarbonyl)-2-methylpiperidine-4-carboxylic Acid

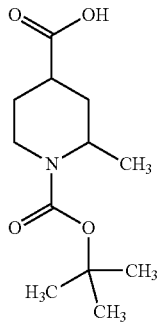

To a solution of cis-1-tert-butyl 4-methyl 2-methylpiperidine-1,4-dicarboxylate obtained in example 8A) (27.16 g, 79.16 mmol, 75% purity) in a mixture of tetrahydrofuran (250 ml) and water (125 ml) was added lithium hydroxide (10.1 g, 422 mmol) and the mixture was stirred overnight at RT. The mixture was evaporated under vacuo and was diluted in water and ethyl acetate. After separation of the layers the aqueous phase was treated with HCl 37% until pH 4 was achieved and then was extracted with ethyl acetate, dried over magnesium sulfate, filtered and evaporated under vacuo to yield the title compound (18.4 g, 95% of theory).

$^1$H-NMR (400 MHz, DMSO-d$_6$): δ=12.27 (bs, 1H), 4.07-3.99 (m, 1H), 3.67-3-61 (m, 1H), 3.06-2.98 (m, 1H), 1.89-1.76 (m, 4H), 1.62-1.53 (m, 1H), 1.39 (s, 9H), 1.04 (d, 3H).

Example 10A (−)-Cis-tert-butyl 4-[(2,2-dimethyl-4,6-dioxo-1,3-dioxan-5-yl)carbonyl]-2-methylpiperidine-1-carboxylate

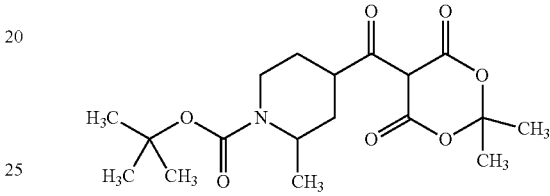

To a solution of cis-1-(tert-butoxycarbonyl)-2-methylpiperidine-4-carboxylic acid obtained in example 9A (17.3 g, 71.0 mmol) and 2,2-dimethyl-1,3-dioxane-4,6-dione (11.3 g, 78.0 mmol) in dichloromethane (190 ml) was added 4-dimethylaminopyridin (13.1 g, 107 mmol). After cooling the mixture to 0° C., 1-(3-dimethylaminopropyl)-3-ethylcarbodiimide hydrochloride (19.13 g, 100.0 mmol) was added in portions and then the reaction mixture was stirred at RT for 16 h. The mixture was treated with water and then the layers were separated. The organic layer was washed with HCl 1M, dried over magnesium sulfate, filtered and evaporated under vacuo to yield the title compound (20.8 g, 79% of theory).

LC-MS (Method 1B): $R_t$=1.16 min, MS (ESIPos): m/z=370 [M+H]$^+$

[α]$^{20}$=−71.36 (c. 0.625, methanol) WL=589 nm

Example 11A

6-Fluoro-1H-pyrazolo[4,3-b]pyridin-3-amine

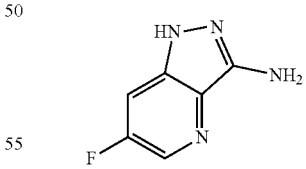

To a solution of 3,5-difluoro-2-pyridincarbonitrile (2.00 g 14.3 mmol, 1 eq) in ethanol (36 mL) was 5 added hydrazine hydrate (1.04 mL, 21.4 mmol, 1.5 eq) at RT. The mixture was heated to 70° C. for 15 h. After cooling to RT, the resulting suspension was evaporated. The residue was triturated with ethyl acetate (20 mL), filtered, the residue was washed with ethyl acetate (5 mL) and dried for 16 h at 50° C. in vacuo to yield the title compound 6-fluoro-1H-pyrazolo[4,3-b]pyridin-3-amine (0.56 g, 80% purity, 80% of theory).

LC-MS (Method 2B): $R_t$=1.10 min, MS (ESIPos): m/z=153 [M+H]$^+$ $^1$H-NMR (400 MHz, DMSO-d$_6$): δ=11.75 (br. s, 1H), 8.26 (dt, 1H), 7.58 (dd, 1H), 5.47 (br. s, 2H).

Example 12A

4-Ethoxy-1H-indazol-3-amine

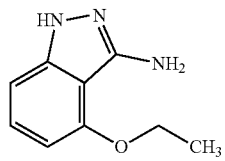

To a solution of 2-ethoxy-6-fluorobenzonitrile (2.00 g, 12.1 mmol, 1 eq) in ethanol (30 mL) was added hydrazine hydrate (0.884 mL, 18.1 mmol, 1.5 eq) at RT. The mixture was heated to 70° C. for 30 h. After cooling to RT, water (20 mL) was added, the mixture was extracted with ethyl acetate (2×50 mL), the combined organic phases were washed with brine (50 mL), dried over MgSO4, filtered and evaporated in vacuo. The residue was triturated with MTBE (10 mL), filtered and the residue was dried for 16 h at 50° C. in vacuo to yield the title compound 4-ethoxy-1H-indazol-3-amine (1.01 g, 47% of theory).

LC-MS (Method 2B): $R_t$=1.76 min, MS (ESIPos): m/z=178 [M+H]$^+$ $^1$H-NMR (400 MHz, DMSO-d$_6$): δ=11.36 (s, 1H), 7.08 (dd, 1H), 6.74 (d, 1H), 6.28 (d, 1H), 4.94 (s, 2H), 4.11 (q, 2H), 1.41 (t, 3H).

Example 13A

7-Bromo-1H-pyrazolo[4,3-c]pyridin-3-amine

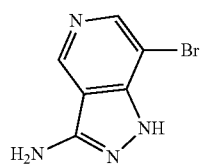

A solution of 3,5-dibromopyridine-4-carbonitrile (2.10 g, 8.02 mmol) and hydrazine hydrate (0.90 g, 17.6 mmol) in ethanol (18 mL) was heated in a microwave at 125° C. for 1 h. The precipitate was collected and washed with a mixture of petrol ether and ethanol to obtain the title compound (1.27 g, 72% of theory).

LC-MS (Method 1B): $R_t$=0.37 min, MS (ESIPos): m/z=213 [M+H]$^+$

Example 14A

7-Fluoro-1H-indazol-3-amine

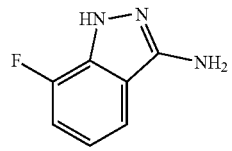 [SMILES: Nc1n[nH]c2c(F)cccc12]

2,3-Difluorobenzonitril (1.00 g, 7.19 mmol) was dissolved in ethanol (10 mL) and treated with hydrazine hydrate (0.54 g, 10.7 mmol). After stirring at 70° C. for 16 h, the mixture was cooled to RT and concentrated in vacuo. The residue was dissolved in a mixture of water and ethyl acetate. The aqueous layer was extracted once more with ethyl acetate. The combined organic layers were washed with water and with brine, dried over magnesium sulfate, concentrated in vacuo and dried to yield the title compound (0.98 g, 91% of theory)

LC-MS (Method 2B): $R_t$=1.45 min, MS (ESIPos): m/z=152 [M+H]$^+$

Example 15A

1H-Pyrazolo[3,4-c]pyridin-3-amine

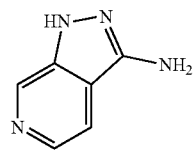

3-Fluoro-isonicotinonitrile (0.50 g, 4.10 mmol) was dissolved in ethanol (8 mL) and treated with hydrazine hydrate (0.31 g, 6.1 mmol). After stirring at 70° C. for 16 h, the mixture was cooled to RT and concentrated in vacuo and dried to yield the title compound (0.66 g, 100% of theory).

LC-MS (Method 2B): $R_t$=0.51 min, MS (ESIPos): m/z=135 [M+H]$^+$

Example 16A 7-(Trifluoromethyl)-1H-indazol-3-amine

2-Fluoro-3-(trifluoromethyl)-benzonitrile (1.00 g, 5.29 mmol) was dissolved in ethanol (11 mL) and treated with hydrazine hydrate (0.40 g, 7.9 mmol). After stirring at reflux for 16 h, the mixture was cooled to RT, concentrated in vacuo and dried to yield the title compound (1.07 g, 100% of theory).

LC-MS (Method 1B): $R_t$=0.74 min, MS (ESIPos): m/z=202 [M+H]$^+$

Example 17A

Tert-butyl 4-(4-oxo-1,4-dihydropyrimido[1,2-b]indazol-2-yl)piperidine-1-carboxylate

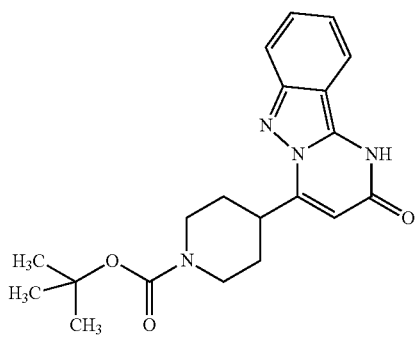 [SMILES: CC(C)(C)OC(=O)N1CCC(c2cc(=O)[nH]c3c4ccccc4nn23)CC1]

Tert-butyl 4-(3-ethoxy-3-oxopropanoyl)piperidine-1-carboxylate (1.50 g, 5.01 mmol, 1 eq), 1H-indazol-3-amine (1.00 g, 7.52 mmol, 1.5 eq) and potassium phosphate (2.13 g, 10.0 mmol, 2 eq) were suspended in 1-methoxy-2-propanol (15 mL) in a 20 mL microwave vial. The vial was capped and the mixture was heated in a microwave to 180° C. for 15 min. After cooling to RT, the suspension was neutralized (pH 6-7) by the addition of 1N HCl, diluted with water (60 mL), and extracted with ethyl acetate (2×, 100 mL and 50 mL). The combined organic phases were washed with brine (25 mL), dried over sodium sulfate, filtered and evaporated in vacuo. The residue was triturated with acetonitrile (5 mL). The precipitate was filtered, washed with acetonitrile (8 mL) and dried for 2 h at 50° C. in vacuo to give the title compound (239 mg, 13% of theory).

LC-MS (Method 1B): $R_t$=0.98 min, MS (ESIPos): m/z=369 [M+H]$^+$

Example 18A

Tert-butyl 4-[2-oxo-9-(trifluoromethyl)-1,2-dihydropyrimido[1,2-b]indazol-4-yl]piperidine-1-carboxylate

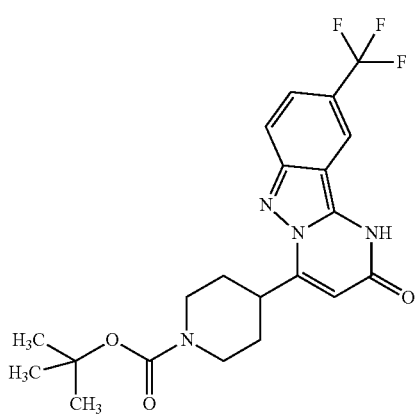 [SMILES: CC(C)(C)OC(=O)N1CCC(c2cc(=O)[nH]c3c4cc(C(F)(F)F)ccc4nn23)CC1]

Tert-butyl 4-(3-ethoxy-3-oxopropanoyl)piperidine-1-carboxylate (450 mg, 81% purity, 1.22 mmol, 1 eq), 5-(trifluoromethyl)-1H-indazol-3-amine (245 mg, 1.22 mmol, 1.0 eq) and potassium phosphate (517 mg, 2.43 mmol, 2 eq) were suspended in dioxane (4.3 mL) in a 20 mL microwave vial. The vial was capped and the mixture was heated in a microwave to 150° C. for 1 h. Another 1 eq of tert-butyl 4-(3-ethoxy-3-oxopropanoyl)piperidine-1-carboxylate was added and the mixture was heated in a microwave to 150° C. for 1 h. Again, 1 eq of tert-butyl 4-(3-ethoxy-3-oxopropanoyl)piperidine-1-carboxylate was added and the mixture was heated in a microwave to 150° C. for 1 h. The solvent was evaporated in vacuo and the residue was diluted with water (20 mL), and extracted with ethyl acetate (2×, 50 mL and 25 mL). The combined organic phases were dried over sodium sulfate, filtered and evaporated in vacuo. The residue was purified by preparative HPLC (Method 1A). The combined product fractions were neutralized with aqueous ammonium hydroxide and acetonitrile was evaporated in vacuo. The aqueous phase was extracted with ethyl acetate (30 mL), dried over sodium sulfate, filtered and evaporated in vacuo to yield the title compound (47 mg, 9% of theory) as solid.

LC-MS (Method 1B): $R_t$=1.17 min, MS (ESIPos): m/z=437 [M+H]$^+$

Example 19A

Tert-butyl 4-(10-chloro-4-oxo-1,4-dihydropyrimido[1,2-b]indazol-2-yl)piperidine-1-carboxylate

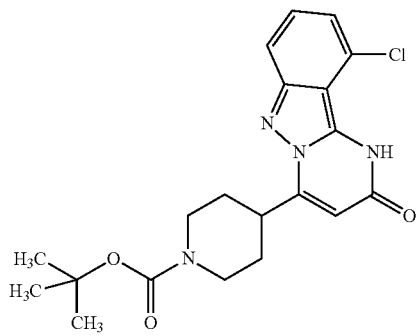

Tert-butyl 4-(3-ethoxy-3-oxopropanoyl)piperidine-1-carboxylate (9.11 g, 30.4 mmol, 1.5 eq), 4-chloro-1H-indazol-3-amine (3.4 g, 20.3 mmol, 1 eq) and potassium phosphate (8.61 g, 40.6 mmol, 2 eq) were suspended in 1-methoxy-2-propanol (70 mL) and split to seven 20 mL microwave vials. The vials were capped and the mixture was heated in a microwave to 180° C. for 15 min. Another 1.5 eq of tert-butyl 4-(3-ethoxy-3-oxopropanoyl)piperidine-1-carboxylate was added in 1-methoxy-2-propanol (2 mL for each vial), and the mixture was heated in a microwave to 180° C. for 15 min again. After cooling to RT, the combined suspensions were evaporated in vacuo, diluted with water (150 mL), neutralized (pH 6) by the addition of 1N HCl, and extracted with ethyl acetate (2×, 200 mL). The combined organic phases were washed with water (2×100 mL) and brine (50 mL) and evaporated in vacuo. The partially crystalline residue was triturated with ethyl acetate (50 mL). The precipitate was filtered, washed with ethyl acetate (20 mL) and acetonitrile (10 mL) and dried for 16 h at 50° C. in vacuo to yield the title compound (2.63 g, 96% purity, 31% of theory).

LC-MS (Method 1B): $R_t$=1.12 min, MS (ESIPos): m/z=403 [M+H]$^+$

Example 20A

Tert-butyl 4-(10-fluoro-4-oxo-1,4-dihydropyrimido[1,2-b]indazol-2-yl)piperidine-1-carboxylate

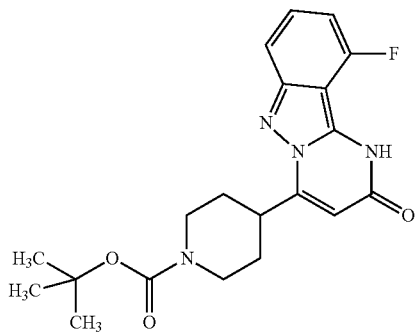 [SMILES: CC(C)(C)OC(=O)N1CCC(c2cc(=O)[nH]c3c4c(Cl)cccc4nn23)CC1]

Tert-butyl 4-(3-ethoxy-3-oxopropanoyl)piperidine-1-carboxylate (0.66 g, 2.2 mmol, 1 eq), 4-fluoro-1H-indazol-3-amine (0.50 g, 3.31 mmol, 1.5 eq) and potassium phosphate (0.936 g, 4.41 mmol, 2 eq) were suspended in 1-methoxy-2-propanol (9 mL) in a 20 mL microwave vial. The vial was capped and the mixture was heated in a microwave to 180° C. for 15 min. After cooling to RT, the suspension was diluted with water (15 mL), neutralized (pH 5-6) by the addition of 1N HCl, and extracted with ethyl acetate (2×, 15 mL). The combined organic phases were evaporated in vacuo. The residue was triturated with water (30 mL), filtered, and the residue was resuspended in acetonitrile (30 mL). The precipitate was filtered, washed with acetonitrile (2 mL) and dried for 16 h at 50° C. in vacuo to yield the title compound (62 mg, 7% of theory).

LC-MS (Method 1B): $R_t$=1.02 min, MS (ESIPos): m/z=387 [M+H]$^+$

Example 21A

Tert-butyl 4-(9-chloro-4-oxo-1,4-dihydropyrimido[1,2-b]indazol-2-yl)piperidine-1-carboxylate

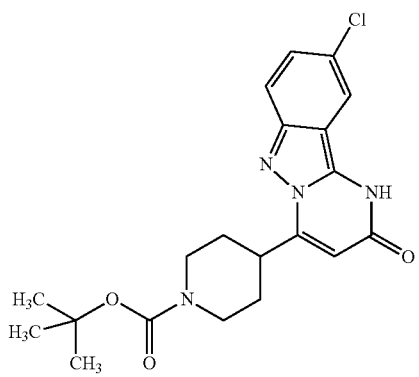 [SMILES: CC(C)(C)OC(=O)N1CCC(c2cc(=O)[nH]c3c4cc(Cl)ccc4nn23)CC1]

Tert-butyl 4-(3-ethoxy-3-oxopropanoyl)piperidine-1-carboxylate (450 mg, 81% purity, 1.22 mmol, 1 eq), 5-chloro-1H-indazol-3-amine (204 mg, 1.22 mmol, 1.0 eq) and potassium phosphate (517 mg, 2.43 mmol, 2 eq) were suspended in dioxane (4.3 mL) in a 20 mL microwave vial. The vial was capped and the mixture was heated in a microwave to 150° C. for 1 h. Another 1 eq of tert-butyl 4-(3-ethoxy-3-oxopropanoyl)piperidine-1-carboxylate was added and the mixture was heated in a microwave to 150° C. for 1 h. The solvent was evaporated in vacuo, the residue was diluted with water (20 mL) and extracted with ethyl acetate (2×, 50 mL and 25 mL). The combined organic phases were dried over sodium sulfate, filtered and evaporated in vacuo. The residue was purified by preparative HPLC (Method 1A). The combined product fractions were neutralized with aqueous ammonium hydroxide and acetonitrile was evaporated in vacuo. The aqueous phase was extracted with ethyl acetate (30 mL), dried over sodium sulfate, filtered and evaporated in vacuo to yield the title compound (30 mg, 6% of theory) as solid.

LC-MS (Method 2B): $R_t$=1.97 min, MS (ESIPos): m/z=403 [M+H]$^+$

Example 22A

Tert-butyl 4-(8,10-dichloro-4-oxo-1,4-dihydropyrimido[1,2-b]indazol-2-yl)piperidine-1-carboxylate

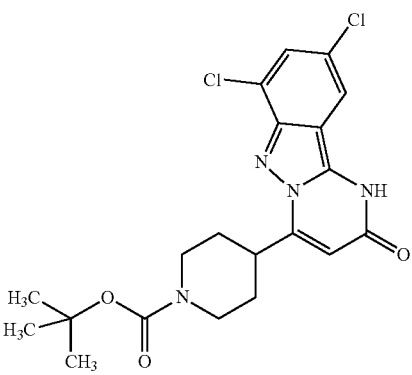 [SMILES: CC(C)(C)OC(=O)N1CCC(c2cc(=O)[nH]c3c4cc(Cl)cc(Cl)c4nn23)CC1]

Tert-butyl 4-(4-oxo-1,4-dihydropyrimido[1,2-b]indazol-2-yl)piperidine-1-carboxylate (50 mg, 0.136 mmol) and N-chlorosuccinimid (27 mg, 0.204 mmol) were dissolved in DMF (1.5 mL) in a 5 mL microwave vial. The vial was capped and the mixture was heated in a microwave to 50° C. for 30 min. The reaction mixture was purified by preparative HPLC (Method 1A). The combined product fractions were neutralized with aqueous ammonium hydroxide and acetonitrile was evaporated in vacuo. The resulting suspension was filtered, the residue was washed with water (10 ml) and dried for 16 h at 50° C. in vacuo to give the title compound (17.3 mg, 29% of theory).

LC-MS (Method 1B): $R_t$=1.22 min, MS (ESIPos): m/z=437 [M+H]$^+$

Example 23A

Tert-butyl 4-(9-fluoro-4-oxo-1,4-dihydropyrimido[1,2-b]indazol-2-yl)piperidine-1-carboxylate

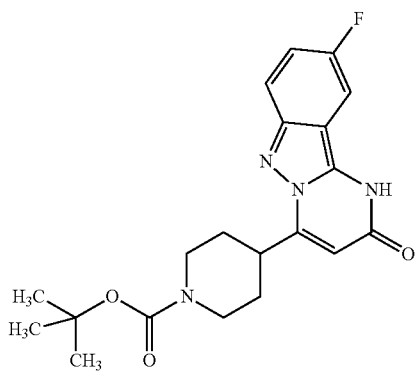

Tert-butyl 4-(3-ethoxy-3-oxopropanoyl)piperidine-1-carboxylate (264 mg, 0.882 mmol, 1 eq), 5-fluoro-1H-indazol-3-amine (200 mg, 1.32 mmol, 1.5 eq) and potassium phosphate (374 mg, 1.76 mmol, 2 eq) were suspended in 1-methoxy-2-propanol (2.6 mL) in a microwave vial. The vial was capped and the mixture was heated in a microwave to 180° C. for 15 min. After cooling to RT, the suspension was diluted with water (20 mL), neutralized (pH 5-6) by the addition of 1N HCl, and extracted with ethyl acetate (2×15 mL). The combined organic phases were evaporated in vacuo. The residue was triturated with acetonitrile (10 mL). The precipitate was filtered, washed with acetonitrile (2 mL) and dried for 2 h at 50° C. in vacuo to yield the title compound (61.3 mg, 18% of theory).

LC-MS (Method 1B): $R_t$=1.02 min, MS (ESIPos): m/z=387 [M+H]$^+$

Example 24A

Tert-butyl 4-(10-methoxy-4-oxo-1,4-dihydropyrimido[1,2-b]indazol-2-yl)piperidine-1-carboxylate

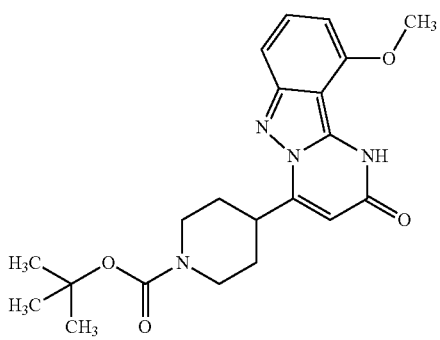 [SMILES: COc1cccc2nn3c(C4CCN(C(=O)OC(C)(C)C)CC4)cc(=O)[nH]c3c12]

Tert-butyl 4-(3-ethoxy-3-oxopropanoyl)piperidine-1-carboxylate (1.00 g, 3.34 mmol, 1.5 eq), 4-methoxy-1H-indazol-3-amine (363 mg, 2.23 mmol, 1.5 eq) and potassium phosphate (945 mg, 10.2 mmol, 2 eq) were suspended in 1-methoxy-2-propanol (10 mL) in a 20 mL microwave vial. The vial was capped and the mixture was heated in a microwave to 180° C. for 15 min. After cooling to RT, the suspension was diluted with water (20 mL), neutralized (pH 5-6) by the addition of 1N HCl, and extracted with ethyl acetate (2×50 mL). The combined organic phases were washed with brine (20 mL), dried over magnesium sulfate, filtered and evaporated in vacuo. The residue was purified by preparative HPLC (Method 1A). The combined product fractions were neutralized with aqueous ammonium hydroxide and acetonitrile was evaporated in vacuo. The resulting suspension was filtered, the residue was washed with water (10 ml) and dried for 16 h at 50° C. in vacuo to give the title compound (128 mg, 14% of theory) as light yellow solid.

LC-MS (Method 1B): $R_t$=1.04 min, MS (ESIPos): m/z=399 [M+H]$^+$

Example 25A

Tert-butyl 4-(9-oxo-9,10-dihydropyrido[3',2':3,4]pyrazolo[1,5-a]pyrimidin-7-yl)piperidine-1-carboxylate

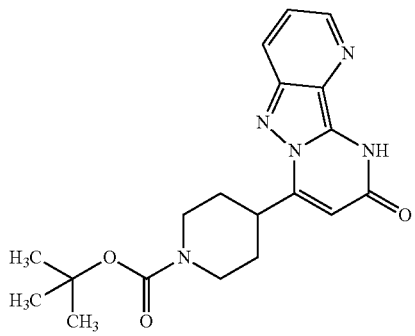 [SMILES: CC(C)(C)OC(=O)N1CCC(c2cc(=O)[nH]c3c4ncccc4nn23)CC1]

Tert-butyl 4-(3-ethoxy-3-oxopropanoyl)piperidine-1-carboxylate (49 mg, 0.497 mmol, 1 eq), 1H-pyrazolo[4,3-b]pyridin-3-amine (100 mg, 0.745 mmol, 1.5 eq) and potassium phosphate (210 mg, 0.993 mmol, 2 eq) were suspended in 1-methoxy-2-propanol (1.5 mL) in a microwave vial. The vial was capped and the mixture was heated in a microwave to 180° C. for 15 min. After cooling to RT, the suspension was diluted with water (20 mL), neutralized (pH 5-6) by the addition of 1N HCl, and extracted with ethyl acetate (2×15 mL). The combined organic phases were evaporated in vacuo. The residue was triturated with water (40 mL). The precipitate was filtered, triturated with acetonitrile (6 mL), filtered, washed with acetonitrile (2 mL) and dried for 16 h at 50° C. The crude product was purified by preparative HPLC (Method 1A). The combined product fractions were neutralized with aqueous ammonium hydroxide and acetonitrile was evaporated in vacuo. The aqueous phase was extracted with ethyl acetate (2×15 mL), dried over magnesium sulfate, filtered and evaporated in vacuo to yield the title compound (15 mg, 8% of theory).

LC-MS (Method 1B): $R_t$=0.91 min, MS (ESIPos): m/z=370 [M+H]$^+$

Example 26A

Tert-butyl 4-(10-bromo-4-oxo-1,4-dihydropyrimido[1,2-b]indazol-2-yl)piperidine-1-carboxylate

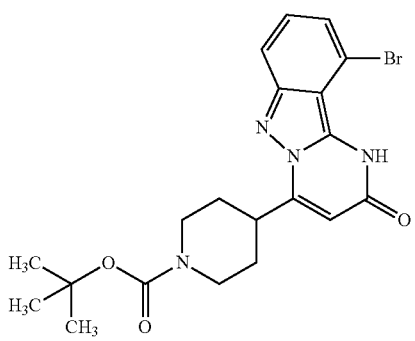

Tert-butyl 4-(3-ethoxy-3-oxopropanoyl)piperidine-1-carboxylate (1.00 g, 3.34 mmol, 1.5 eq), 4-bromo-1H-indazol-3-amine (472 mg, 2.27 mmol, 1 eq) and potassium phosphate (945 mg, 4.45 mmol, 2 eq) were suspended in 1-methoxy-2-propanol (11.8 mL) in a 20 mL microwave vial. The vial was capped and the mixture was heated in a microwave to 180° C. for 15 min. After cooling to RT, the suspension was diluted with water (20 mL) and neutralized (pH 6) by the addition of 1N HCl. The precipitate was filtered, washed with water (10 mL), MTBE (4 mL) and dried for 16 h at 50° C. in vacuo to yield the title compound (222 mg, 22% of theory).

LC-MS (Method 1B): $R_t$=1.13 min, MS (ESIPos): m/z=447 [M+H]$^+$

Example 27A

Tert-butyl 4-[2-oxo-8-(trifluoromethyl)-1,2-dihydropyrimido[1,2-b]indazol-4-yl]piperidine-1-carboxylate

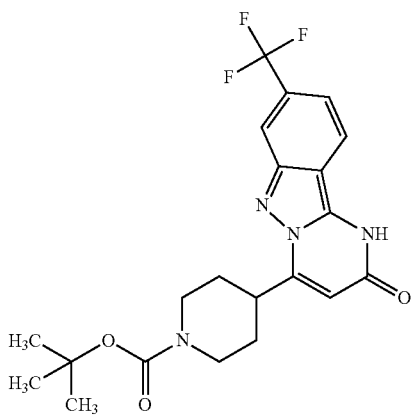 [SMILES: CC(C)(C)OC(=O)N1CCC(c2cc(=O)[nH]c3c4ccc(C(F)(F)F)cc4nn23)CC1]

Tert-butyl 4-(3-ethoxy-3-oxopropanoyl)piperidine-1-carboxylate (1.00 g, 3.34 mmol, 1.5 eq), 6-(trifluoromethyl)-1H-indazol-3-amine (448 mg, 2.27 mmol, 1 eq) and potassium phosphate (945 mg, 4.45 mmol, 2 eq) were suspended in 1-methoxy-2-propanol (11.8 mL) in a 20 mL microwave vial. The vial was capped and the mixture was heated in a microwave to 180° C. for 15 min. After cooling to RT, the suspension was diluted with water (50 mL) and neutralized (pH 5-6) by the addition of 1N HCl and extracted with ethyl acetate (2×100 mL). The combined organic phases were washed with brine (25 mL), dried over sodium sulfate, filtered and evaporated in vacuo. The brown residue was triturated with MTBE (4 mL) under ultrasound irradiation. The precipitate was filtered, washed with water (20 mL) and dried for 16 h at 50° C. in vacuo to yield the title compound (381 mg, 95% purity, 37% of theory) as off-white solid.

LC-MS (Method 1B): $R_t$=1.15 min, MS (ESIPos): m/z=437 [M+H]$^+$

Example 28A

Tert-butyl 4-(10-(trifluoromethyl)-4-oxo-1,4-dihydropyrimido[1,2-b]indazol-2-yl)piperidine-1-carboxylate

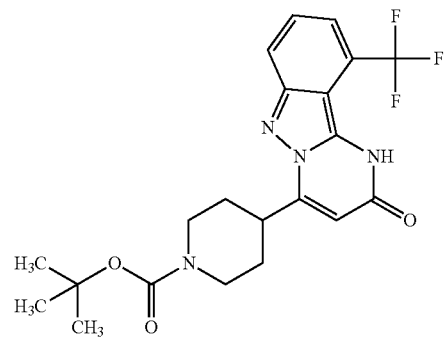 [SMILES: CC(C)(C)OC(=O)N1CCC(c2cc(=O)[nH]c3c4c(C(F)(F)F)cccc4nn23)CC1]

Tert-butyl 4-(3-ethoxy-3-oxopropanoyl)piperidine-1-carboxylate (1.00 g, 3.34 mmol, 1.5 eq), 4-(trifluoromethyl)-1H-indazol-3-amine (448 mg, 2.27 mmol, 1 eq) and potassium phosphate (945 mg, 4.45 mmol, 2 eq) were suspended in 1-methoxy-2-propanol (11.8 mL) in a 20 mL microwave vial. The vial was capped and the mixture was heated in a microwave to 180° C. for 15 min. After cooling to RT, the suspension was diluted with water (20 mL) and neutralized (pH 5) by the addition of 1N HCl and extracted with ethyl acetate (2×30 mL). The combined organic phases were washed with brine (10 mL), dried over sodium sulfate, filtered and evaporated in vacuo. The brown residue was purified by preparative HPLC (Method 1A). The combined product fractions were evaporated in vacuo to remove acetonitrile. The resulting suspension was filtered, the residue was washed with water (2 ml) and dried for 16 h at 50° C. in vacuo to yield the title compound (116 mg, 12% of theory) as colorless solid.

LC-MS (Method 1B): $R_t$=1.19 min, MS (ESIPos): m/z=437 [M+H]$^+$

Example 29A

Tert-butyl 4-(8-tert-butyl-4-oxo-1,4-dihydropyrido[2',3':3,4]pyrazolo[1,5-a]pyrimidin-2-yl)piperidine-1-carboxylate

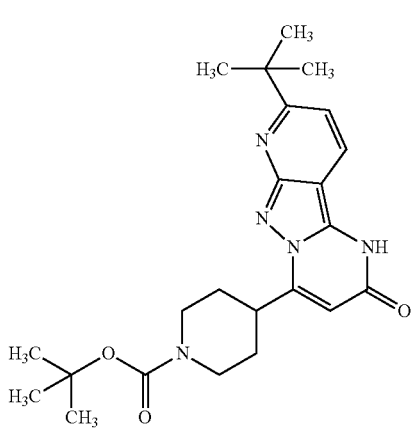 [SMILES: CC(C)(C)OC(=O)N1CCC(c2cc(=O)[nH]c3c4ccc(C(C)(C)C)nc4nn23)CC1]

Tert-butyl 4-(3-ethoxy-3-oxopropanoyl)piperidine-1-carboxylate (1.00 g, 3.34 mmol, 1.5 eq), 6-tert-butyl-1H-pyrazolo[3,4-b]pyridin-3-amine (448 mg, 2.27 mmol, 1 eq) and potassium phosphate (945 mg, 4.45 mmol, 2 eq) were suspended in 1-methoxy-2-propanol (11.8 mL) in a 20 mL microwave vial. The vial was capped and the mixture was heated in a microwave to 180° C. for 15 min. After cooling to RT, the suspension was diluted with water (20 mL) and neutralized (pH 6) by the addition of 1N HCl and extracted with ethyl acetate (2×50 mL). The combined organic phases were washed with water (2×20 mL), brine (20 mL), dried over sodium sulfate, filtered and evaporated in vacuo. The brown residue was purified by preparative HPLC (Method 1A). The combined product fractions were evaporated in vacuo to remove acetonitrile. The resulting suspension was filtered, the residue was washed with water (2 ml) and dried for 16 h at 50° C. in vacuo to yield the title compound (56.6 mg, 90% purity, 5% of theory).

LC-MS (Method 2B): $R_t$=2.07 min, MS (ESIPos): m/z=426 [M+H]$^+$

Example 30A

Tert-butyl 4-(8-(trifluoromethyl)-4-oxo-1,4-dihydropyrido[2',3':3,4]pyrazolo[1,5-a]pyrimidin-2-yl)piperidine-1-carboxylate

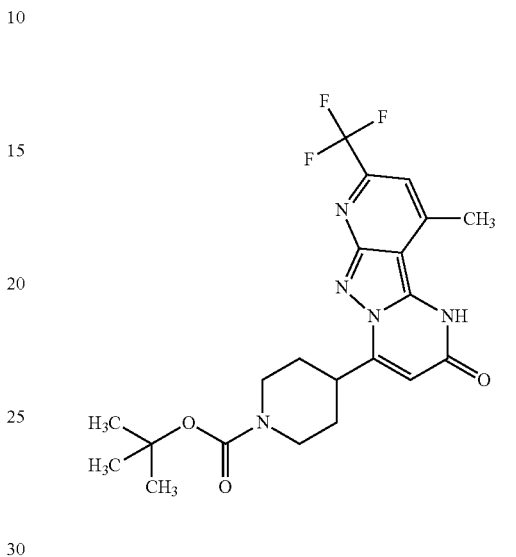

Tert-butyl 4-(3-ethoxy-3-oxopropanoyl)piperidine-1-carboxylate (1.00 g, 3.34 mmol, 1.5 eq), 4-methyl-6-(trifluoromethyl)-1H-pyrazolo[3,4-b]pyridin-3-amine (448 mg, 2.27 mmol, 1 eq) and potassium phosphate (945 mg, 4.45 mmol, 2 eq) were suspended in 1-methoxy-2-propanol (11.8 mL) in a 20 mL microwave vial. The vial was capped and the mixture was heated in a microwave to 180° C. for 15 min.

After cooling to RT, the suspension was diluted with water (20 mL) and neutralized (pH 5-6) by the addition of 1N HCl. The precipitate was filtered and washed with water (10 mL). The combined filtrates were extracted with ethyl acetate (2×30 mL), adjusted to pH 8-9 by the addition of 1N NaOH, and extracted with ethyl acetate (20 mL). The combined organic phases were washed with water (2×10 mL), brine (10 mL), dried over sodium sulfate, filtered and evaporated in vacuo. The yellow residue was triturated with MTBE (5 mL) under ultrasound irradiation, filtered and washed with MTBE (4 mL) and ethyl acetate (1 mL). The filtrate was evaporated in vacuo and purified by preparative HPLC (Method 1A). The combined product fractions were evaporated in vacuo to remove acetonitrile. The resulting suspension was filtered, the residue was washed with water (2 ml) and dried for 16 h at 50° C. in vacuo to yield the title compound (123 mg, 12% of theory) as off-white solid.

LC-MS (Method 1B): $R_t$=1.08 min, MS (ESIPos): m/z=452 [M+H]$^+$

Example 31A

Tert-butyl 4-(9-methyl-4-oxo-1,4-dihydropyrimido[1,2-b]indazol-2-yl)piperidine-1-carboxylate

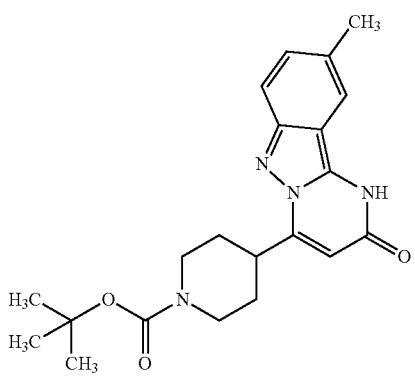 [SMILES: Cc1ccc2nn3c(C4CCN(C(=O)OC(C)(C)C)CC4)cc(=O)[nH]c3c2c1]

Tert-butyl 4-(3-ethoxy-3-oxopropanoyl)piperidine-1-carboxylate (1.00 g, 3.34 mmol, 1.5 eq), 5-methyl-1H-indazol-3-ylamine (328 mg, 2.27 mmol, 1 eq) and potassium phosphate (945 mg, 4.45 mmol, 2 eq) were suspended in 1-methoxy-2-propanol (11 mL) in a 20 mL microwave vial. The vial was capped and the mixture was heated in a microwave to 180° C. for 15 min. After cooling to RT, the suspension was diluted with 20 mL dichloromethane/methanol (4:1), filtered through a short pad of silica gel with 100 mL dichloromethane/methanol (4:1) and evaporated in vacuo. The yellow residue was triturated with MTBE (5 mL), filtered, washed with ethyl acetate (1 mL) and dried for 16 h at 50° C. in vacuo to yield the title compound (148 mg, 95% purity, 17% of theory) as yellow solid.

LC-MS (Method 1B): $R_t$=1.04 min, MS (ESIPos): m/z=383 [M+H]$^+$

Example 32A

Tert-butyl 4-(8-amino-4-oxo-1,4-dihydropyrimido[1,2-b]indazol-2-yl)piperidine-1-carboxylate

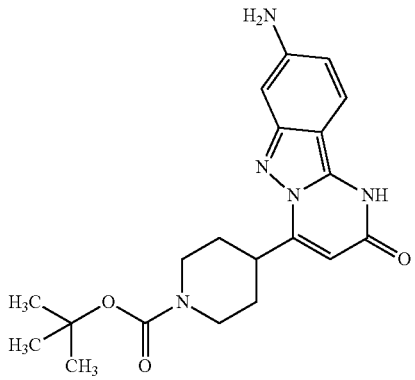 [SMILES: CC(C)(C)OC(=O)N1CCC(c2cc(=O)[nH]c3c4ccc(N)cc4nn23)CC1]

Tert-butyl 4-(3-ethoxy-3-oxopropanoyl)piperidine-1-carboxylate (1.00 g, 3.34 mmol, 1.5 eq), 6-amino-1H-indazol-3-ylamine (330 mg, 2.27 mmol, 1 eq) and potassium phosphate (945 mg, 4.45 mmol, 2 eq) were suspended in 1-methoxy-2-propanol (11 mL) in a 20 mL microwave vial. The vial was capped and the mixture was heated in a microwave to 180° C. for 15 min. After cooling to RT, the suspension was diluted with 20 mL dichloromethane/methanol (4:1), filtered through a short pad of silica gel with 100 mL dichloromethane/methanol (4:1) and evaporated in vacuo. The yellow residue was triturated with acetonitrile (4 mL), filtered, washed with acetonitrile (2 mL) and dried for 16 h at 50° C. in vacuo to yield the title compound (31 mg, 4% of theory) as yellow solid.

LC-MS (Method 1B): $R_t$=0.81 min, MS (ESIPos): m/z=384 [M+H]$^+$

Example 33A

Tert-butyl 4-(3,4-dimethyl-8-oxo-5,8-dihydropyrimido[1',2':1,5]pyrazolo[3,4-c]pyridazin-6-yl)piperidine-1-carboxylate

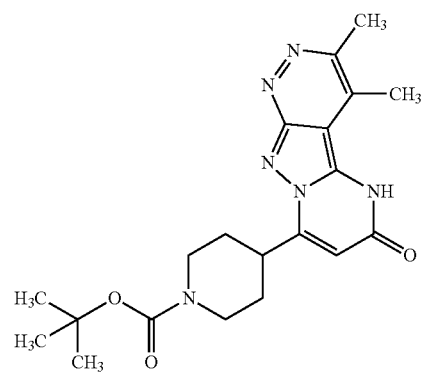 [SMILES: Cc1nnc2nn3c(C4CCN(C(=O)OC(C)(C)C)CC4)cc(=O)[nH]c3c2c1C]

Tert-butyl 4-(3-ethoxy-3-oxopropanoyl)piperidine-1-carboxylate (1.00 g, 0.334 mmol, 1.5 eq), 4,5-dimethyl-1H-pyrazolo[3,4-C]pyridazin-3-amine (363 mg, 2.27 mmol, 1 eq) and potassium phosphate (945 mg, 4.45 mmol, 2 eq) were suspended in 1-methoxy-2-propanol (11 mL) in a 20 mL microwave vial. The vial was capped and the mixture was heated in a microwave to 180° C. for 15 min. After cooling to RT, the suspension was diluted with 20 mL dichloromethane/methanol (4:1), filtered through a short pad of silica gel with 100 mL dichloromethane/methanol (4:1) and evaporated in vacuo. The residue was triturated with MTBE (4 mL), filtered, washed with ethyl acetate (1 mL). The filtrate was evaporated in vacuo and purified by preparative HPLC (Method 1A). The combined product fractions were evaporated in vacuo to remove acetonitrile and lyophilized to give the title compound (62.3 mg, 7% of theory).

LC-MS (Method 1B): $R_t$=0.75 min, MS (ESIPos): m/z=399 [M+H]$^+$

Example 34A

Tert-butyl 4-(8-fluoro-4-oxo-1,4-dihydropyrimido[1,2-b]indazol-2-yl)piperidine-1-carboxylate

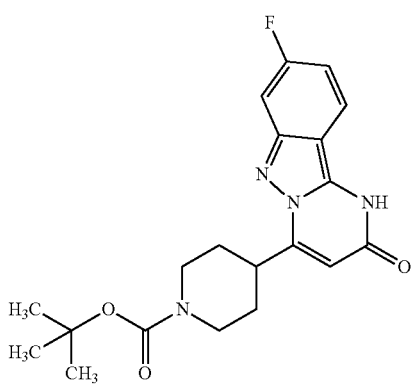 [SMILES: CC(C)(C)OC(=O)N1CCC(c2cc(=O)[nH]c3c4ccc(F)cc4nn23)CC1]

Tert-butyl 4-(3-ethoxy-3-oxopropanoyl)piperidine-1-carboxylate (1.00 g, 3.34 mmol, 1.5 eq), 6-fluoro-1H-indazol-3-ylamine (337 mg, 2.27 mmol, 1 eq) and potassium phosphate (945 mg, 4.45 mmol, 2 eq) were suspended in 1-methoxy-2-propanol (11 mL) in a 20 mL microwave vial. The vial was capped and the mixture was heated in a microwave to 180° C. for 15 min. After cooling to RT, the suspension was diluted with 20 mL dichloromethane/methanol (4:1), filtered through a short pad of silica gel with 100 mL dichloromethane/methanol (4:1) and evaporated in vacuo. The residue was triturated with 4 mL MTBE/ethyl acetate (1:1), filtered, washed with ethyl acetate (2 mL) and dried for 16 h at 50° C. in vacuo to yield the title compound (66 mg, 7% of theory) as colorless solid.

LC-MS (Method 1B): $R_t$=1.01 min, MS (ESIPos): m/z=387 [M+H]$^+$

Example 35A

Tert-butyl 4-(9-bromo-4-oxo-1,4-dihydropyrimido[1,2-b]indazol-2-yl)piperidine-1-carboxylate

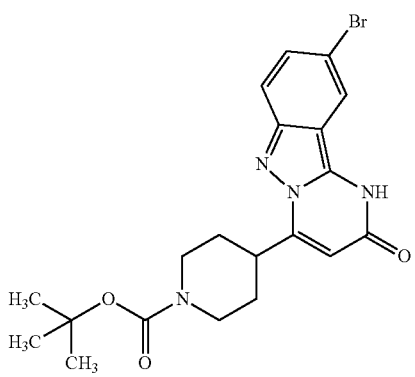 [SMILES: CC(C)(C)OC(=O)N1CCC(c2cc(=O)[nH]c3c4cc(Br)ccc4nn23)CC1]

Tert-butyl 4-(3-ethoxy-3-oxopropanoyl)piperidine-1-carboxylate (1.00 g, 3.34 mmol, 1.5 eq), 5-bromo-1H-indazol-3-ylamine (472 mg, 2.27 mmol, 1 eq) and potassium phosphate (945 mg, 4.45 mmol, 2 eq) were suspended in 1-methoxy-2-propanol (11 mL) in a 20 mL microwave vial. The vial was capped and the mixture was heated in a microwave to 180° C. for 15 min. After cooling to RT, the suspension was diluted with 20 mL dichloromethane/methanol (4:1), filtered through a short pad of silica gel with 100 mL dichloromethane/methanol (4:1) and evaporated in vacuo. The residue was triturated with 4 mL MTBE/ethyl acetate (1:1), filtered, washed with ethyl acetate (2 mL) and dried for 16 h at 50° C. in vacuo to yield the title compound (37 mg, 3% of theory).

LC-MS (Method 1B): $R_t$=1.11 min, MS (ESIPos): m/z=447 [M+H]$^+$

Example 36A

Tert-butyl 4-(10-iodo-4-oxo-1,4-dihydropyrimido[1,2-b]indazol-2-yl)piperidine-1-carboxylate

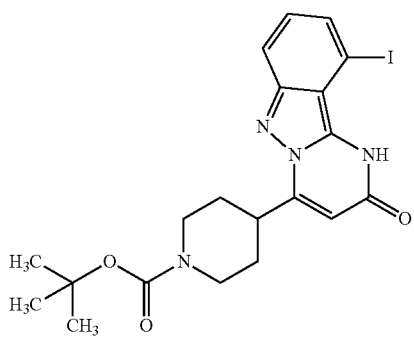 [SMILES: CC(C)(C)OC(=O)N1CCC(c2cc(=O)[nH]c3c4c(I)cccc4nn23)CC1]

Tert-butyl 4-(3-ethoxy-3-oxopropanoyl)piperidine-1-carboxylate (0.750 g, 2.50 mmol, 1.5 eq), 4-iodo-1H-indazol-3-ylamine (472 mg, 1.67 mmol, 1 eq) and potassium phosphate (709 mg, 3.34 mmol, 2 eq) were suspended in 1-methoxy-2-propanol (11 mL) in a 20 mL microwave vial. The vial was capped and the mixture was heated in a microwave to 180° C. for 15 min. After cooling to RT, the suspension was diluted with 20 mL dichloromethane/methanol (4:1), filtered through a short pad of silica gel with 100 mL dichloromethane/methanol (4:1) and evaporated in vacuo. The residue was purified by preparative HPLC (Method 1A). The combined product fractions were evaporated in vacuo to remove acetonitrile. The resulting suspension was filtered, the residue was washed with water (2 ml) and dried for 16 h at 50° C. in vacuo to yield the title compound (56 mg, 7% of theory).

LC-MS (Method 1B): $R_t$=1.19 min, MS (ESIPos): m/z=495 [M+H]$^+$

Example 37A

Tert-butyl 4-(8-bromo-4-oxo-1,4-dihydropyrimido[1,2-b]indazol-2-yl)piperidine-1-carboxylate

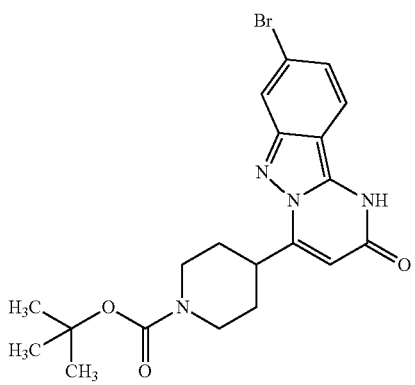 [SMILES: CC(C)(C)OC(=O)N1CCC(c2cc(=O)[nH]c3c4ccc(Br)cc4nn23)CC1]

Tert-butyl 4-(3-ethoxy-3-oxopropanoyl)piperidine-1-carboxylate (1.00 g, 3.34 mmol, 1.5 eq), 6-bromo-1H-indazol-3-ylamine (472 mg, 2.27 mmol, 1 eq) and potassium phosphate (945 mg, 4.45 mmol, 2 eq) were suspended in 1-methoxy-2-propanol (11 mL) in a 20 mL microwave vial. The vial was capped and the mixture was heated in a microwave to 180° C. for 15 min. After cooling to RT, the suspension was diluted with 20 mL dichloromethane/methanol (4:1), filtered through a short pad of silica gel with 100 mL dichloromethane/methanol (4:1) and evaporated in vacuo. The residue was purified by preparative HPLC (Method 1A). The combined product fractions were evaporated in vacuo to remove acetonitrile. The resulting suspension was filtered, the residue was washed with water (2 ml) and dried for 16 h at 50° C. in vacuo to yield the title compound (94 mg, 9% of theory) as yellowish solid.

LC-MS (Method 1B): $R_t$=1.12 min, MS (ESIPos): m/z=447 [M+H]$^+$

Example 38A

Tert-butyl 4-(7-chloro-4-oxo-1,4-dihydropyrimido[1,2-b]indazol-2-yl)piperidine-1-carboxylate

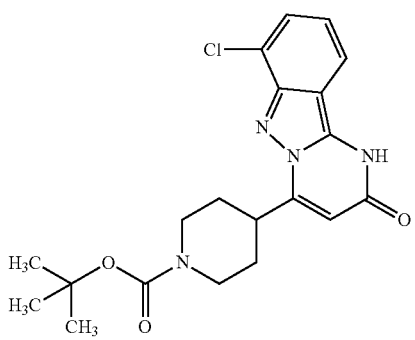

Tert-butyl 4-(3-ethoxy-3-oxopropanoyl)piperidine-1-carboxylate (1.00 g, 3.34 mmol, 1.5 eq), 7-chloro-1H-indazol-3-ylamine (373 mg, 2.27 mmol, 1 eq) and potassium phosphate (945 mg, 4.45 mmol, 2 eq) were suspended in 1-methoxy-2-propanol (10 mL) in a 20 mL microwave vial. The vial was capped and the mixture was heated in a microwave to 180° C. for 15 min. After cooling to RT, the suspension was diluted with 20 mL dichloromethane/methanol (4:1), filtered through a short pad of silica gel with 100 mL dichloromethane/methanol (4:1) and concentrated in vacuo to 5 mL. The resulting suspension was filtered, washed with ethyl acetate (5 mL) and dried for 16 h at 50° C. in vacuo to yield the title compound (83 mg, 9% of theory).

LC-MS (Method 1B): $R_t$=1.09 min, MS (ESIPos): m/z=403 [M+H]$^+$

Example 39A

Tert-butyl 4-(8,10-difluoro-4-oxo-1,4-dihydropyrimido[1,2-b]indazol-2-yl)piperidine-1-carboxylate

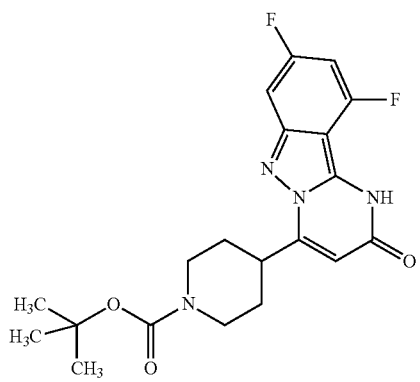 [SMILES: CC(C)(C)OC(=O)N1CCC(c2cc(=O)[nH]c3c4c(F)cc(F)cc4nn23)CC1]

Tert-butyl 4-(3-ethoxy-3-oxopropanoyl)piperidine-1-carboxylate (1.00 g, 3.34 mmol, 1.5 eq), 4,6-difluoro-1H-indazol-3-ylamine (377 mg, 2.27 mmol, 1 eq) and potassium phosphate (945 mg, 4.45 mmol, 2 eq) were suspended in 1-methoxy-2-propanol (10 mL) in a 20 mL microwave vial. The vial was capped and the mixture was heated in a microwave to 180° C. for 15 min. After cooling to RT, the suspension was diluted with 20 mL dichloromethane/methanol (4:1), filtered through a short pad of silica gel with 100 mL dichloromethane/methanol (4:1) and evaporated in vacuo. The residue was purified by preparative HPLC (Method 1A). The combined product fractions were evaporated in vacuo to remove acetonitrile. The resulting suspension was filtered, the residue was washed with water (2 ml) and dried for 16 h at 50° C. in vacuo to yield the title compound (27 mg, 90% purity, 3% of theory).

LC-MS (Method 2B): $R_t$=1.92 min, MS (ESIPos): m/z=405 [M+H]$^+$

Example 40A

Tert-butyl 4-(8-methyl-4-oxo-1,4-dihydropyrido[2',3':3,4]pyrazolo[1,5-a]pyrimidin-2-yl)piperidine-1-carboxylate

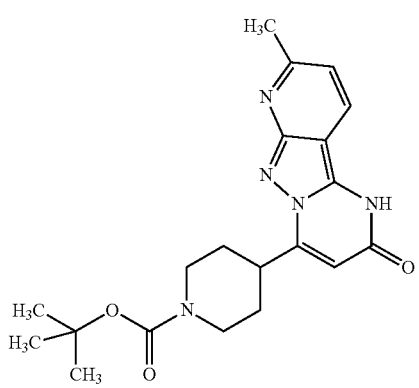 [SMILES: Cc1ccc2c(n1)nn1c(C3CCN(C(=O)OC(C)(C)C)CC3)cc(=O)[nH]c21]

Tert-butyl 4-(3-ethoxy-3-oxopropanoyl)piperidine-1-carboxylate (1.00 g, 3.34 mmol, 1.5 eq), 6-methyl-1H-pyrazolo[3,4-b]pyridin-3-amine (330 mg, 2.27 mmol, 1 eq) and potassium phosphate (945 mg, 4.45 mmol, 2 eq) were suspended in 1-methoxy-2-propanol (10 mL) in a 20 mL microwave vial. The vial was capped and the mixture was heated in a microwave to 180° C. for 15 min. After cooling to RT, the suspension was diluted with 20 mL dichloromethane/methanol (4:1), filtered through a short pad of silica gel with 100 mL dichloromethane/methanol (4:1) and evaporated in vacuo. The residue was purified by preparative HPLC (Method 2A). The combined product fractions were lyophilized to give the title compound (64 mg, 7% of theory).

LC-MS (Method 2B): $R_t$=1.64 min, MS (ESIPos): m/z=384 [M+H]$^+$

Example 41A

Tert-butyl 4-(3-fluoro-9-oxo-9,10-dihydropyrido[3',2':3,4]pyrazolo[1,5-a]pyrimidin-7-yl)piperidine-1-carboxylate

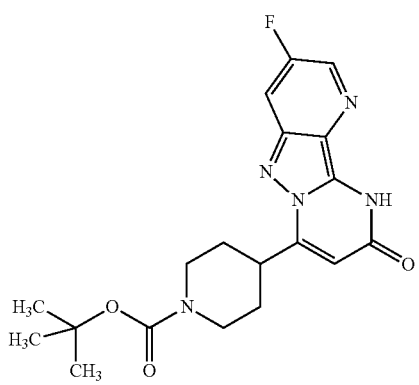 [SMILES: CC(C)(C)OC(=O)N1CCC(c2cc(=O)[nH]c3c4ncc(F)cc4nn23)CC1]

Tert-butyl 4-(3-ethoxy-3-oxopropanoyl)piperidine-1-carboxylate (932 mg, 3.11 mmol, 1.5 eq), 6-fluoro-1H-pyrazolo[4,3-b]pyridin-3-amine (395 mg, 80% purity, 2.07 mmol, 1 eq) and potassium phosphate (881 mg, 4.15 mmol, 2 eq) were suspended in 1-methoxy-2-propanol (10 mL) in a 20 mL microwave vial. The vial was capped and the mixture was heated in a microwave to 180° C. for 15 min. After cooling to RT, the suspension was diluted with 20 mL dichloromethane/methanol (4:1), filtered through a short pad of silica gel with 100 mL dichloromethane/methanol (4:1) and evaporated in vacuo. The residue was purified by preparative HPLC (Method 1A). The combined product fractions were concentrated in vacuo to remove acetonitrile. The resulting suspension was filtered, the residue was washed with water (2 ml) and dried for 16 h at 50° C. in vacuo to give the title compound (59.2 mg, 95% purity, 7% of theory) as yellowish solid.

LC-MS (Method 1B): $R_t$=0.96 min, MS (ESIPos): m/z=388 [M+H]$^+$

Example 42A

Tert-butyl 4-(10-ethoxy-2-oxo-1,2-dihydropyrimido[1,2-b]indazol-4-yl)piperidine-1-carboxylate

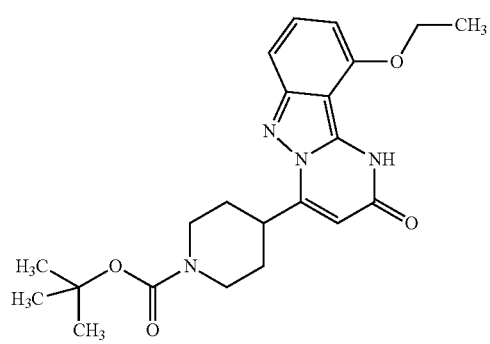 [SMILES: CCOc1cccc2nn3c(C4CCN(C(=O)OC(C)(C)C)CC4)cc(=O)[nH]c3c12]

Tert-butyl 4-(3-ethoxy-3-oxopropanoyl)piperidine-1-carboxylate (1.07 g, 3.58 mmol, 1.5 eq), 4-ethoxy-1H-indazol-3-amine (423 mg, 2.39 mmol, 1 eq) and potassium phosphate (1.01 g, 4.78 mmol, 2 eq) were suspended in 1-methoxy-2-propanol (10 mL) in a 20 mL microwave vial. The vial was capped and the mixture was heated in a microwave to 180° C. for 15 min. After cooling to RT, the suspension was diluted with 20 mL dichloromethane/methanol (4:1), filtered through a short pad of silica gel with 100 mL dichloromethane/methanol (4:1) and evaporated in vacuo. The residue was triturated with MTBE (15 mL), filtered, washed with MTBE (2 mL) and dried for 16 h at 50° C. in vacuo to yield the title compound (161 mg, 15% of theory).

LC-MS (Method 1B): $R_t$=1.11 min, MS (ESIPos): m/z=413 [M+H]$^+$

Example 43A

Tert-butyl 4-(7-bromo-2-oxo-1,2-dihydropyrido[4',3':3,4]pyrazolo[1,5-a]pyrimidin-4-yl)piperidine-1-carboxylate

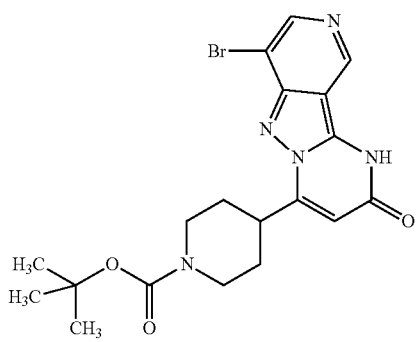 [SMILES: CC(C)(C)OC(=O)N1CCC(c2cc(=O)[nH]c3c4cncc(Br)c4nn23)CC1]

Tert-butyl 4-(3-ethoxy-3-oxopropanoyl)piperidine-1-carboxylate (1.00 g, 3.34 mmol, 1.5 eq), 7-bromo-1H-pyrazolo[4,3-c]pyridin-3-amine (474 mg, 2.27 mmol, 1 eq) and potassium phosphate (945 mg, 4.45 mmol, 2 eq) were suspended in 1-methoxy-2-propanol (10 mL) in a 20 mL microwave vial. The vial was capped and the mixture was heated in a microwave to 180° C. for 15 min. After cooling to RT, the suspension was diluted with 20 mL dichloromethane/methanol (4:1), filtered through a short pad of silica gel with 100 mL dichloromethane/methanol (4:1) and evaporated in vacuo. The residue was triturated with acetonitrile (10 mL) and filtered. The residue was triturated with DMSO (6 mL), washed with acetonitrile (8 mL) and dried for 16 h at 50° C. in vacuo to yield the title compound (116 mg, 12% of theory).

LC-MS (Method 1B): $R_t$=0.98 min, MS (ESIPos): m/z=448 [M+H]$^+$

Example 44A

Tert-butyl 4-(7-fluoro-2-oxo-1,2-dihydropyrimido[1,2-b]indazol-4-yl)piperidine-1-carboxylate

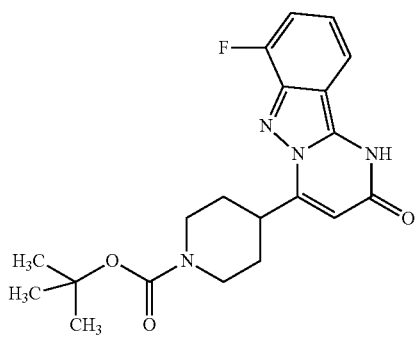 [SMILES: CC(C)(C)OC(=O)N1CCC(c2cc(=O)[nH]c3c4cccc(F)c4nn23)CC1]

Tert-butyl 4-(3-ethoxy-3-oxopropanoyl)piperidine-1-carboxylate (1.00 g, 3.34 mmol, 1.5 eq), 7-fluoro-1H-indazol-3-amine (336 mg, 2.27 mmol, 1 eq) and potassium phosphate (945 mg, 4.45 mmol, 2 eq) were suspended in 1-methoxy-2-propanol (10 mL) in a 20 mL microwave vial. The vial was capped and the mixture was heated in a microwave to 180° C. for 15 min. After cooling to RT, the suspension was diluted with water (20 mL) and neutralized (pH 6) by the addition of 1N HCl. The mixture was extracted with ethyl acetate (2×30 mL). The combined organic phases were washed with brine (10 mL), dried over sodium sulfate, filtered and evaporated in vacuo. The residue was triturated with MTBE (5 mL), filtered and washed with MTBE (2 mL). The residue was purified by preparative HPLC (Method 1A). The combined product fractions were evaporated in vacuo to remove acetonitrile. The resulting suspension was filtered, the residue was washed with water (2 ml) and dried for 2 h at 50° C. in vacuo to the title compound (92 mg, 11% of theory) as off-white solid.

LC-MS (Method 1B): $R_t$=1.03 min, MS (ESIPos): m/z=387 [M+H]$^+$

Example 45A

Tert-butyl 4-(2-oxo-1,2-dihydropyrido[3',4':3,4]pyrazolo[1,5-a]pyrimidin-4-yl)piperidine-1-carboxylate

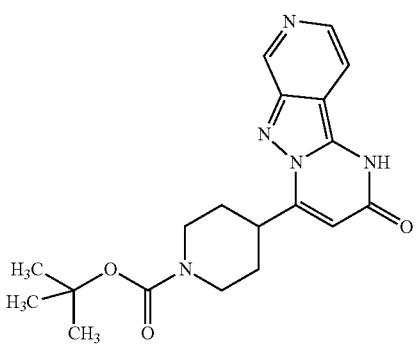 [SMILES: CC(C)(C)OC(=O)N1CCC(c2cc(=O)[nH]c3c4ccncc4nn23)CC1]

Tert-butyl 4-(3-ethoxy-3-oxopropanoyl)piperidine-1-carboxylate (1.00 g, 3.34 mmol, 1.5 eq), 1H-pyrazolo[3,4-c]pyridin-3-amine (299 mg, 2.27 mmol, 1 eq) and potassium phosphate (945 mg, 4.45 mmol, 2 eq) were suspended in 1-methoxy-2-propanol (10 mL) in a 20 mL microwave vial. The vial was capped and the mixture was heated in a microwave to 180° C. for 15 min. After cooling to RT, the suspension was diluted with water (20 mL) and neutralized (pH 7) by the addition of 1N HCl. The precipitate was filtered, washed with water (10 mL) and dried for 16 h at 50° C. in vacuo to yield the title compound (169 mg, 75% purity, 16% of theory).

LC-MS (Method 1B): $R_t$=0.73 min, MS (ESIPos): m/z=370 [M+H]$^+$

Example 46A

Tert-butyl 4-[2-oxo-7-(trifluoromethyl)-1,2-dihydropyrimido[1,2-b]indazol-4-yl]piperidine-1-carboxylate

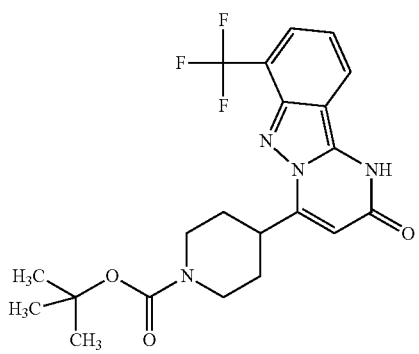 [SMILES: CC(C)(C)OC(=O)N1CCC(c2cc(=O)[nH]c3c4cccc(C(F)(F)F)c4nn23)CC1]

Tert-butyl 4-(3-ethoxy-3-oxopropanoyl)piperidine-1-carboxylate (1.00 g, 3.34 mmol, 1.5 eq), 7-(trifluoromethyl)-1H-indazol-3-amine (299 mg, 2.27 mmol, 1 eq) and potassium phosphate (945 mg, 4.45 mmol, 2 eq) were suspended in 1-methoxy-2-propanol (10 mL) in a 20 mL microwave vial. The vial was capped and the mixture was heated in a microwave to 180° C. for 15 min. After cooling to RT, the suspension was diluted with water (20 mL), neutralized (pH 6) by the addition of 1N HCl and extracted with ethyl acetate (2×50 mL). The combined organic phases were washed with water (30 mL), brine (30 mL), dried over magnesium sulfate, filtered and evaporated in vacuo. The residue was triturated with MTBE (5 mL), filtered, washed with MTBE (2 mL)) and dried for 16 h at 50° C. in vacuo to yield the title compound (122 mg, 12% of theory).

LC-MS (Method 1B): $R_t$=1.16 min, MS (ESIPos): m/z=437 [M+H]$^+$

Example 47A

Tert-butyl 4-[10-nitro-2-oxo-8-(trifluoromethyl)-1,2-dihydropyrimido[1,2-b]indazol-4-yl]piperidine-1-carboxylate

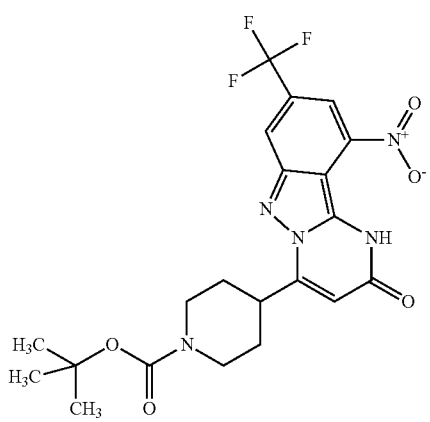 [SMILES: CC(C)(C)OC(=O)N1CCC(c2cc(=O)[nH]c3c4c([N+](=O)[O-])cc(C(F)(F)F)cc4nn23)CC1]

Tert-butyl 4-(3-ethoxy-3-oxopropanoyl)piperidine-1-carboxylate (1.00 g, 3.34 mmol, 1.5 eq), 4-nitro-6-(trifluoromethyl)-1H-indazol-3-amine (548 mg, 2.23 mmol, 1 eq) and potassium phosphate (945 mg, 4.45 mmol, 2 eq) were suspended in 1-methoxy-2-propanol (10 mL) in a 20 mL microwave vial. The vial was capped and the mixture was heated in a microwave to 180° C. for 15 min. After cooling to RT, the suspension was diluted with 20 mL dichloromethane/methanol (4:1), filtered through a short pad of silica gel with 100 mL dichloromethane/methanol (4:1) and evaporated in vacuo. The residue was purified by preparative HPLC (Method 1A). The combined product fractions were concentrated in vacuo to remove acetonitrile. The resulting suspension was filtered, the residue was washed with water (2 ml) and dried for 16 h at 50° C. in vacuo to give the title compound (90.8 mg, 8% of theory).

LC-MS (Method 1B): $R_t$=1.16 min, MS (ESIPos): m/z=482 [M+H]$^+$

Example 48A

Tert-butyl 4-(8,10-dimethyl-4-oxo-1,4-dihydropyrido[2',3':3,4]pyrazolo[1,5-a]pyrimidin-2-yl)piperidine-1-carboxylate

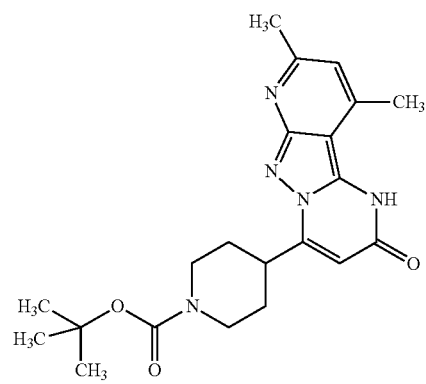 [SMILES: Cc1cc(C)c2c(n1)nn1c(C3CCN(C(=O)OC(C)(C)C)CC3)cc(=O)[nH]c21]

Tert-butyl 4-(3-ethoxy-3-oxopropanoyl)piperidine-1-carboxylate (1.00 g, 3.34 mmol, 1.5 eq), 4,6-Dimethyl-1H-pyrazolo[3,4-b]pyridin-3-amine (361 mg, 2.27 mmol, 1 eq) and potassium phosphate (945 mg, 4.45 mmol, 2 eq) were suspended in 1-methoxy-2-propanol (9 mL) in a 20 mL microwave vial. The vial was capped and the mixture was heated in a microwave to 180° C. for 15 min. After cooling to RT, the suspension was diluted with water (50 mL), neutralized (pH 5-6) by the addition of 1N HCl and extracted with ethyl acetate (2×100 mL). The combined organic phases were washed with water, (2×25 mL), brine (25 mL), dried over sodium sulfate, filtered and evaporated in vacuo. The residue was triturated with acetonitrile (4 mL) and DMSO (4 mL). The precipitate was filtered, washed with acetonitrile (2×2 mL) and dried for 2 h at 50° C. in vacuo to yield the title compound (50 mg, 5% of theory) as yellow solid.

LC-MS (Method 1B): $R_t$=0.92 min, MS (ESIPos): m/z=398 [M+H]$^+$

Example 49A

Tert-butyl 4-(10-chloro-2-oxo-1,2-dihydropyrimido[1,2-b]indazol-4-yl)-2-methylpiperidine-1-carboxylate [Enantiomerically Pure Trans-Isomer]

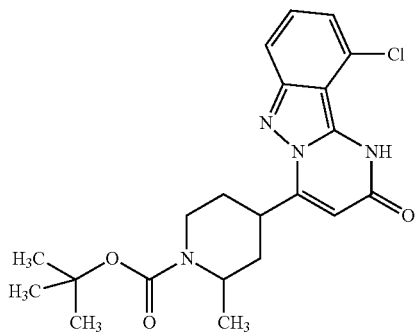 [SMILES: CC1CC(c2cc(=O)[nH]c3c4c(Cl)cccc4nn23)CCN1C(=O)OC(C)(C)C]

The title compound was prepared according to General Procedure A starting from 0.92 g (5.13 mmol) 4-chloro-1H-indazol-3-amine and 2.02 g (5.13 mmol) (−)-cis-tert-butyl 4-[(2,2-dimethyl-4,6-dioxo-1,3-dioxan-5-yl)carbonyl]-2-methylpiperidine-1-carboxylate. Then the mixture was evaporated and the crude product was treated HCl 1N and extracted with ethyl acetates several times. The organic layer was washed with water and dried over sodium sulfate, filtered, evaporated and dried under vacuo. The crude product was stirred in acetonitrile and then was filtered and dried under vacuo to yield the title compound as a mixture of two diastereoisomers (950 mg, 100% of theory). The mixture was dissolved in methanol (6.6 ml) and then was treated with HCl 4N in dioxane (6.6 ml). The reaction mixture was sonicated at RT for 15 minutes. The solvent was evaporated under vacuo and the crude product was stirred in methanol. The resulting solid was filtered, washed with dioxane and dried under vacuo to yield a crude product with the two deprotected diastereomers (677 mg) which could not be separated from each other through chromatography. For this reason the crude product was dissolved again in dichloromethane (15 ml) and was treated with di-tert-butyl dicarbonate (0.38 g, 1.78 mmol) and triethylamine (0.18 g, 1.77 mol). The reaction mixture was stirred 15 minutes at RT and was left without stirring at RT for 39 h. Then the solvent was evaporated under vacuo and the crude product was treated with water and extracted several times with ethyl acetate. The collected organic phases were washed with an 10% aq. solution of citric acid, with water and brine. After that the organic layer was dried over sodium sulfate, filtered, evaporated and dried under vacuo. At that point the mixture could be separated by Method 4C to yield the title compound (273 mg, 37% of theory).

LC-MS (Method 1B): RT=1.18 min, MS (ESIPos): m/z=417 (M+H)$^+$

HPLC (Method 4E): R$_t$=8.77 min

Example 50A

Tert-butyl 4-(7-bromo-2-oxo-1,2-dihydropyrimido[1,2-b]indazol-4-yl)piperidine-1-carboxylate

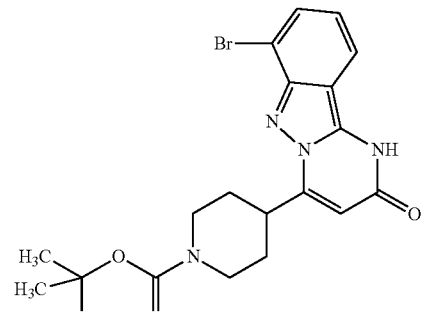

Tert-butyl 4-(3-ethoxy-3-oxopropanoyl)-2-methylpiperidine-1-carboxylate (750 mg, 2.50 mmol, 1.5 eq), 7-bromo-1H-indazol-3-amine (354 mg, 1.67 mmol, 1 eq) and potassium phosphate (709 mg, 3.34 mmol, 2 eq) were suspended in 1-methoxy-2-propanol (10 mL) in a 20 mL microwave vial. The vial was capped and the mixture was heated in a microwave to 180° C. for 15 min. After cooling to RT, the suspension was diluted with water (20 mL) and neutralized (pH 6-7) by the addition of 1N HCl. The resulting aqueous suspension filtered, the residue was washed with ethyl acetate (10 mL) and acetonitrile (5 mL) and dried for 16 h at 50° C. in vacuo to give the title compound (42.3 mg, 7% of theory).

LC-MS (Method 1B): R$_t$=1.12 min, MS (ESIPos): m/z=447 [M+H]$^+$

Example 51A

Tert-butyl 4-(2-oxo-1,2-dihydropyrido[2',3':3,4]pyrazolo[1,5-a]pyrimidin-4-yl)piperidine-1-carboxylate

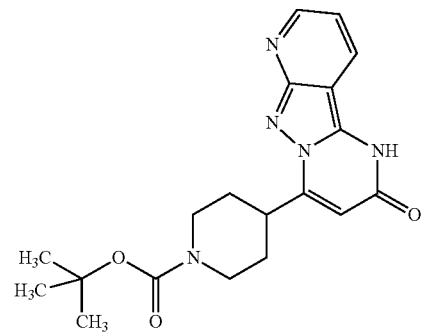 [SMILES: CC(C)(C)OC(=O)N1CCC(c2cc(=O)[nH]c3c4cccnc4nn23)CC1]

Tert-butyl 4-(3-ethoxy-3-oxopropanoyl)piperidine-1-carboxylate (1.00 g, 3.34 mmol, 1.5 eq), 1H-Pyrazolo[3,4-b]pyridin-3-amine (299 mg, 2.27 mmol, 1 eq) and potassium phosphate (945 mg, 4.45 mmol, 2 eq) were suspended in 1-methoxy-2-propanol (10 mL) in a 20 mL microwave vial. The vial was capped and the mixture was heated in a microwave to 180° C. for 15 min. After cooling to RT, the mixture was diluted with water (20 mL) and acidified (pH 5)

by the addition of 1N HCl. The resulting suspension was filtered, washed with water (20 mL) and the residue was purified by preparative HPLC (Method 2A). The combined product fractions were lyophilized to give the title compound (36.3 mg, 4% of theory).

LC-MS (Method 1B): $R_t$=0.78 min, MS (ESIPos): m/z=370 [M+H]$^+$

Example 52A

Tert-butyl 4-(10-methyl-2-oxo-1,2-dihydropyrimido[1,2-b]indazol-4-yl)piperidine-1-carboxylate

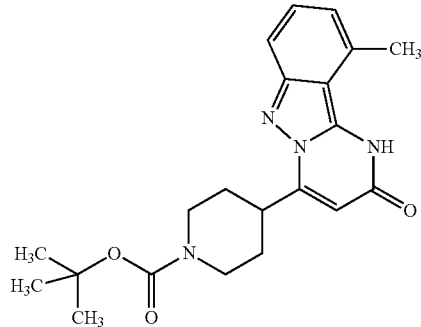 [SMILES: Cc1cccc2nn3c(C4CCN(C(=O)OC(C)(C)C)CC4)cc(=O)[nH]c3c12]

Tert-butyl 4-(3-ethoxy-3-oxopropanoyl)piperidine-1-carboxylate (750 mg, 2.50 mmol, 1.5 eq), 4-methyl-1H-indazol-3-amine (246 mg, 1.67 mmol, 1 eq) and potassium phosphate (709 mg, 3.34 mmol, 2 eq) were suspended in 1-methoxy-2-propanol (10 mL) in a 20 mL microwave vial. The vial was capped and the mixture was heated in a microwave to 180° C. for 15 min. After cooling to RT, the suspension was diluted with water (20 mL), neutralized (pH 6) by the addition of 1N HCl and extracted with ethyl acetate (2×30 mL). The combined organic phases were washed with water, (50 mL), brine (25 mL), dried over magnesium sulfate, filtered and evaporated in vacuo. The residue was purified by preparative HPLC (Method 1A). The combined product fractions were concentrated in vacuo to remove acetonitrile. The resulting suspension was filtered, the residue was washed with water (2 ml) and dried for 16 h at 50° C. in vacuo to give the title compound (63.8 mg, 10% of theory).

LC-MS (Method 1B): $R_t$=1.07 min, MS (ESIPos): m/z=383 [M+H]$^+$

Example 53A

Tert-butyl 4-[2-oxo-10-(trifluoromethoxy)-1,2-dihydropyrimido[1,2-b]indazol-4-yl]piperidine-1-carboxylate

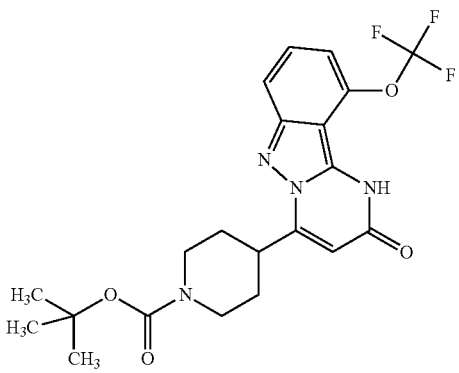 [SMILES: CC(C)(C)OC(=O)N1CCC(c2cc(=O)[nH]c3c4c(OC(F)(F)F)cccc4nn23)CC1]

Tert-butyl 4-(3-ethoxy-3-oxopropanoyl)piperidine-1-carboxylate (750 mg, 2.50 mmol, 1.5 eq), 4-(trifluoromethoxy)-1H-indazol-3-amine (363 mg, 1.67 mmol, 1 eq) and potassium phosphate (709 mg, 3.34 mmol, 2 eq) were suspended in 1-methoxy-2-propanol (10 mL) in a 20 mL microwave vial. The vial was capped and the mixture was heated in a microwave to 180° C. for 15 min. After cooling to RT, the suspension was diluted with water (20 mL), neutralized (pH 6) by the addition of 1N HCl and extracted with ethyl acetate (2×30 mL). The combined organic phases were washed with water, (50 mL), brine (25 mL), dried over magnesium sulfate, filtered and evaporated in vacuo. The residue was purified by preparative HPLC (Method 1A). The combined product fractions were concentrated in vacuo to remove acetonitrile. The resulting suspension was filtered, the residue was washed with water (2 ml) and dried for 16 h at 50° C. in vacuo to give the title compound (64 mg, 8% of theory) as off-white solid.

LC-MS (Method 2B): $R_t$=2.51 min, MS (ESIPos): m/z=453 [M+H]$^+$

Example 54A

Tert-butyl 4-(9-oxo-9,10-dihydropyrazino[2',3':3,4]pyrazolo[1,5-a]pyrimidin-7-yl)piperidine-1-carboxylate

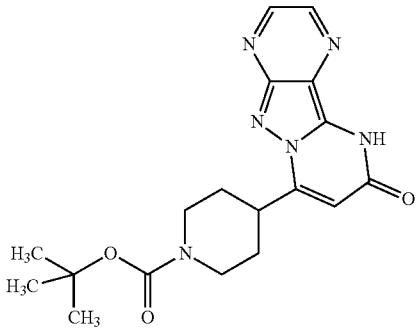 [SMILES: CC(C)(C)OC(=O)N1CCC(c2cc(=O)[nH]c3c4nccnc4nn23)CC1]

Tert-butyl 4-(3-ethoxy-3-oxopropanoyl)piperidine-1-carboxylate (750 mg, 2.50 mmol, 1.5 eq), 1H-pyrazolo[3,4-b]pyrazin-3-amine (226 mg, 1.67 mmol, 1 eq) and potassium phosphate (709 g, 3.34 mmol, 2 eq) were suspended in 1-methoxy-2-propanol (10 mL) in a 20 mL microwave vial. The vial was capped and the mixture was heated in a microwave to 180° C. for 15 min. After cooling to RT, the suspension was diluted with 20 mL dichloromethane/methanol (3:1), filtered through a short pad of silica gel with 150 mL dichloromethane/methanol (3:1) and evaporated in vacuo. The residue was purified by preparative HPLC (Method 1A). The combined product fractions were lyophilized to give the title compound (31.1 mg, 5% of theory) as yellow solid.

LC-MS (Method 1B): $R_t$=0.85 min, MS (ESIPos): m/z=371 [M+H]$^+$

Example 55A

Tert-butyl 4-(8-chloro-4-oxo-1,4-dihydropyrimido[1,2-b]indazol-2-yl)piperidine-1-carboxylate

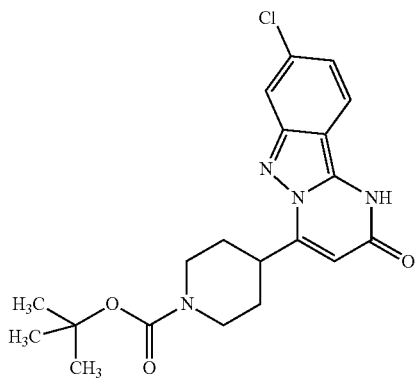 [SMILES: CC(C)(C)OC(=O)N1CCC(c2cc(=O)[nH]c3c4ccc(Cl)cc4nn23)CC1]

Tert-butyl 4-(3-ethoxy-3-oxopropanoyl)piperidine-1-carboxylate (450 mg, 81% purity, 1.22 mmol, 1 eq), 6-chloro-1H-indazol-3-amine (204 mg, 1.22 mmol, 1.0 eq) and potassium phosphate (517 mg, 2.43 mmol, 2 eq) were suspended in dioxane (4.3 mL) in a 20 mL microwave vial. The vial was capped and the mixture was heated in a microwave to 150° C. for 1 h. The solvent was evaporated in vacuo, the residue was diluted with water (20 mL) and extracted with ethyl acetate (2×, 50 mL and 25 mL). The combined organic phases were dried over sodium sulfate, filtered and evaporated in vacuo. The residue was purified by preparative HPLC (Method 2A). The combined product fractions were evaporated in vacuo. The residue was purified again by preparative HPLC (Method 1A). The combined product fractions were neutralized with aqueous ammonium hydroxide and acetonitrile was evaporated in vacuo. The aqueous phase was extracted with ethyl acetate (30 mL), dried over sodium sulfate, filtered and evaporated in vacuo to yield the title compound (5.2 mg, 1% of theory).

LC-MS (Method 1B): $R_t$=1.13 min, MS (ESIPos): m/z=403 [M+H]$^+$

Example 56A $N^4,N^4$-Dimethyl-1H-pyrazolo[3,4-b]pyridine-3,4-diamine

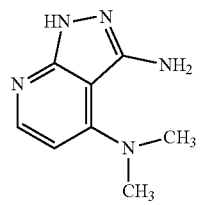

2-Chloro-4-(dimethylamino)nicotinonitrile (500 mg, 2.75 mmol) and sodium acetate (270 mg, 3.30 mmol) were suspended in pyridine (4 ml) under argon atmosphere. The resulting suspension was heated at 100° C. Hydrazine hydrate (1.38 g, 27.53 mmol) was added slowly over a period of 10 minutes and then the reaction mixture was heated at 115° C. for 2h. After cooling to RT the mixture was diluted in water and was extracted with dichlormethane. The collected organic phases were washed with brine, dried over magnesium sulfate, filtered and evaporated. The residue was dried under vacuo to yield the title compound (303 mg, 57% of theory).

LC-MS (Method 2B): $R_t$=1.37 min, MS (ESIPos): m/z=177 [M+H]$^+$

Example 57A

4-Chloro-6-(trifluoromethyl)-1H-indazol-3-amine

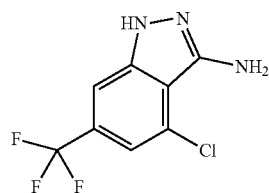 [SMILES: Nc1n[nH]c2cc(C(F)(F)F)cc(Cl)c12]

2,6-Dichloro-4-(trifluoromethyl)benzonitrile (500 mg, 2.08 mmol) and sodium acetate (205 mg, 2.50 mmol) were suspended in pyridine (5 ml) under argon atmosphere. The resulting suspension was heated at 95° C. Hydrazine hydrate (1.04 g, 20.83 mmol) was added slowly over a period of 10 minutes and then the reaction mixture was heated at 115° C. for 2h. After cooling to RT, the mixture was diluted in water and it was acidified by addition of HCl 4N until pH 6 was achieved. The mixture was extracted with ethyl acetate and the collected organic phases were washed water and brine, dried over magnesium sulfate, filtered and evaporated. The residue was dried under vacuo to yield the title compound (0.54 g, 99% of theory).

LC-MS (Method 1B): $R_t$=0.90 min, MS (ESIPos): m/z=236 [M+H]$^+$

Example 58A 6-(4-Fluorophenyl)-4-(trifluoromethyl)-1H-pyrazolo[3,4-b]pyridin-3-amine

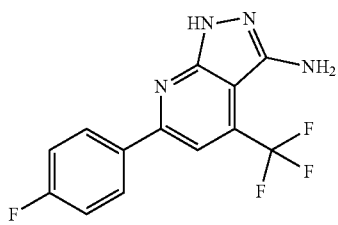 [SMILES: Nc1n[nH]c2nc(-c3ccc(F)cc3)cc(C(F)(F)F)c12]

To a solution of 2-chloro-6-(4-fluorophenyl)-4-(trifluoromethyl)nicotinonitrile (0.40 g, 1.33 mmol) in ethanol (4 ml) under argon atmosphere was added hydrazine hydrate (0.13 g, 2.66 mmol) at RT. The mixture was heated at 70° C. for 15 h. After cooling to RT, water was added and the resulting precipitate was filtered, washed again with water and dried under vacuo 2h at 50° C. to yield the title compound (0.36 g, 89% of theory).

LC-MS (Method 1B): $R_t$=0.99 min, MS (ESIPos): m/z=297 [M+H]$^+$

Example 59A

4-Methyl-1H-pyrazolo[3,4-b]pyridin-3-amine

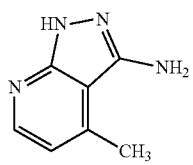

2-Chloro-4-methylnicotinonitrile (500 mg, 3.18 mmol) and sodium acetate (312 mg, 3.81 mmol) were suspended in pyridine (7.5 ml) under argon atmosphere. The resulting suspension was heated at 100° C. Hydrazine hydrate (1.62 g, 31.79 mmol) was added slowly over a period of 10 minutes and then the resulting mixture was heated at 105° C. for 5h. After cooling to RT the mixture was diluted in water and acidified by addition of HCl 1N until pH 6 was achieved. The mixture was extracted with dichloromethane and the collected organic phases were washed with water and brine, dried over sodium sulfate, filtered and evaporated. The residue was dried under vacuo to yield the title compound (0.27 g, 59% of theory).

LC-MS (Method 2B): $R_t$=1.21 min, MS (ESIPos): m/z=149 [M+H]$^+$

Example 60A

1H-Pyrazolo[4,3-c]pyridin-3-amine

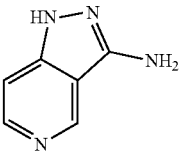

To a solution of 4-chloronicotinonitrile (1.00 g, 7.00 mmol) in ethanol (10 ml) under argon atmosphere was added hydrazine hydrate (0.71 g, 14.00 mmol) at RT. The mixture was heated to 70° C. for 5 h. After cooling to RT the mixture was diluted with water and extracted with ethyl acetate. In the aqueous phase a pale-yellow solid precipitated which was collected by filtration and dried under vacuo to yield the title compound (0.43 g, 46% of theory).

LC-MS (Method 2B): $R_t$=0.49 min, MS (ESIPos): m/z=135 [M+H]$^+$

Example 61A

6-Phenyl-1H-pyrazolo[3,4-b]pyridin-3-amine

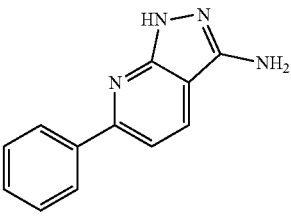 [SMILES: Nc1n[nH]c2nc(-c3ccccc3)ccc12]

To a solution of 2-chloro-6-phenylnicotinonitrile (1.00 g, 4.66 mmol) in ethanol (10 ml) under argon atmosphere was added hydrazine hydrate (0.48 g, 9.32 mmol) at RT. The mixture was heated at 70° C. for 15 h. After that time (0.23 g, 4.65 mmol) hydrazine hydrate were added into the mixture and it was still stirred 2h at 70° C. After cooling to RT the mixture was diluted with water and the resulting precipitate was filtered, washed with water and dried under vacuo to yield the title compound (0.83 g, 84% of theory).

LC-MS (Method 1B): $R_t$=0.69 min, MS (ESIPos): m/z=210 [M+H]$^+$

Example 62A

4-Phenyl-1H-pyrazolo[3,4-b]pyridin-3-amine

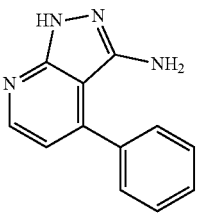 [SMILES: Nc1n[nH]c2nccc(-c3ccccc3)c12]

To a solution of 2-chloro-4-phenylnicotinonitrile (1.00 g, 4.43 mmol) in ethanol (9.5 ml) under argon atmosphere was added hydrazine hydrate (0.45 g, 8.85 mmol) at RT. The mixture was heated at 70° C. for 15 h. After that time (0.11 g, 2.21 mmol) hydrazine hydrate were added into the mixture and it was still stirred at 70° C. for 2h. After cooling to RT the mixture was diluted with water and the resulting precipitate was filtered, washed with water and dried under vacuo to yield the title compound (0.83 g, 89% of theory).

LC-MS (Method 1B): $R_t$=0.67 min, MS (ESIPos): m/z=210 [M+H]$^+$

Example 63A

5-Phenyl-1H-pyrazolo[3,4-b]pyridin-3-amine

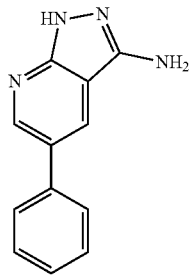

To a solution of 2-chloro-5-phenylnicotinonitrile (1.00 g, 4.66 mmol) in ethanol (10 ml) under argon atmosphere was added hydrazine hydrate (0.48 g, 9.32 mmol) at RT. The mixture was heated at 70° C. for 15 h. After cooling to RT the mixture was diluted with water and the resulting precipitate was filtered, washed with water and dried under vacuo to yield the title compound (0.88 g, 89% of theory).

LC-MS (Method 1B): $R_t$=0.68 min; MS (ESIPos): m/z=210 [M+H]$^+$

Example 64A

Tert-butyl 4-[10-(dimethylamino)-2-oxo-1,2-dihydropyrido[2',3':3,4]pyrazolo[1,5-a]pyrimidin-4-yl]piperidine-1-carboxylate

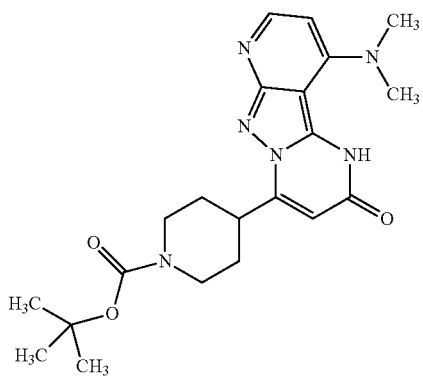 [SMILES: CN(C)c1ccnc2nn3c(C4CCN(C(=O)OC(C)(C)C)CC4)cc(=O)[nH]c3c12]

Tert-butyl 4-(3-ethoxy-3-oxopropanoyl)piperidine-1-carboxylate (842 mg, 2.33 mmol), N$^4$,N$^4$-dimethyl-1H-pyrazolo[3,4-b]pyridine-3,4-diamine (303 mg, 1.56 mmol) and potassium phosphate (661 mg, 3.11 mmol) were suspended in 1-methoxy-2-propanol (7 ml) in a 20 ml microwave vial. The vial was capped and the mixture was heated in a microwave to 180° C. for 15 min. After cooling to RT, the solvent was evaporated and the residue was diluted in water and extracted with ethyl acetate. After separation of the two layers, the aqueous layer was extracted with ethyl acetate. The aqueous layer was acidified with HCl 1N until pH 7 was achieved and then evaporated under vacuo. The crude product was purified by preparative HPLC (Method 1A). The combined product fractions were neutralized with a 33% ammonia solution and then acetonitrile was evaporated. The resulting aqueous phase was extracted with ethyl acetate and the collected organic phases were dried over sodium sulfate, filtrated and evaporated. The resulting solid was dried under vacuo to yield the title compound (11 mg, 2% of theory).

LC-MS (Method 1B): $R_t$=0.77 min, MS (ESIPos): m/z=413 [M+H]$^+$

Example 65A

Tert-butyl 4-[10-chloro-2-oxo-8-(trifluoromethyl)-1,2-dihydropyrimido[1,2-b]indazol-4-yl]piperidine-1-carboxylate

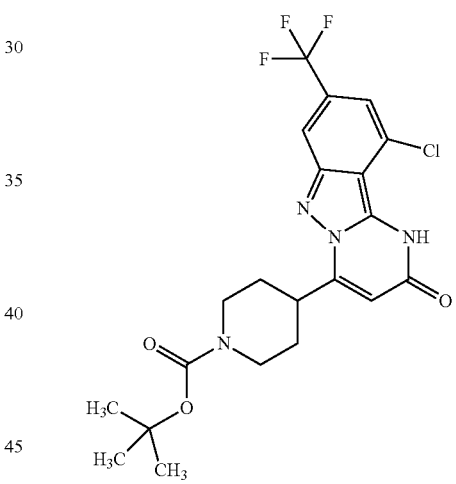

Tert-butyl 4-(3-ethoxy-3-oxopropanoyl)piperidine-1-carboxylate (1.03 g, 2.87 mmol), 4-chloro-6-(trifluoromethyl)-1H-indazol-3-amine (500 mg, 1.91 mmol) and potassium phosphate (811 mg, 3.82 mmol) were suspended in 1-methoxy-2-propanol (9 ml) in a 20 ml microwave vial. The vial was capped and the mixture was heated in a microwave to 180° C. for 15 min. After cooling to RT, the solvent was evaporated and the residue was diluted with water and extracted with ethyl acetate. After separation of the layers the aqueous layer was extracted with ethyl acetate. The collected organic layers were dried over magnesium sulfate, filtrated and evaporated. The crude product was purified by preparative (Method 1A). The combined product fractions were neutralized with a 33% ammonia solution and then acetonitrile was evaporated. The resulting solid in the aqueous phase was filtered and dried under vacuo to yield the title compound (287 mg, 32% of theory).

LC-MS (Method 1B): $R_t$=1.27 min, MS (ESIPos): m/z=471 [M+H]$^+$

Example 66A

Tert-butyl 4-[8-(4-fluorophenyl)-2-oxo-10-(trifluoromethyl)-1,2-dihydropyrido[2'3':3,4]pyrazolo[1,5-a]pyrimidin-4-yl]piperidine-1-carboxylate

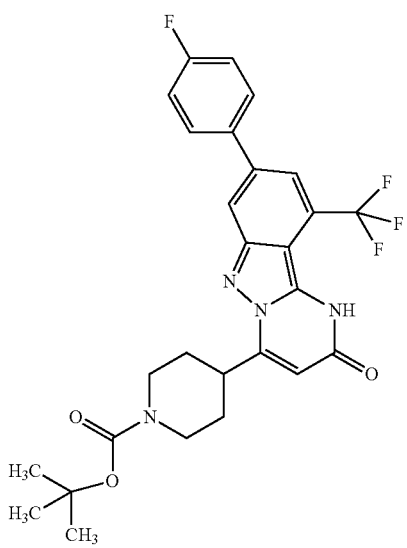 [SMILES: CC(C)(C)OC(=O)N1CCC(c2cc(=O)[nH]c3c4c(C(F)(F)F)cc(-c5ccc(F)cc5)cc4nn23)CC1]

Tert-butyl 4-(3-ethoxy-3-oxopropanoyl)piperidine-1-carboxylate (630 mg, 1.75 mmol), 6-(4-fluorophenyl)-4-(trifluoromethyl)-1H-pyrazolo[3,4-b]pyridin-3-amine (352 mg, 1.17 mmol) and potassium phosphate (494 mg, 2.33 mmol) were suspended in 1-methoxy-2-propanol (10 ml) in a 20 ml microwave vial. The vial was capped and the mixture was heated in a microwave to 180° C. for 15 min. After this period the mixture was additionally heated in the MW at 180° C. for 30 min. After cooling to RT, the solvent was evaporated and the residue was diluted in water and extracted with ethyl acetate. After separation of the layers the aqueous layer was extracted with ethyl acetate. The collected organic layers were dried over sodium sulfate, filtered and evaporated. The crude product was purified by preparative HPLC (Method 1A). The combined product fractions were neutralized with a 33% ammonia solution and then acetonitrile was evaporated. The resulting solid in the aqueous phase was filtered and dried under vacuo to yield the title compound (62 mg, 10% of theory).

LC-MS (Method 1B): R$_t$=1.29 min, MS (ESIPos): m/z=532 [M+H]$^+$

Example 67A

Tert-butyl 4-(10-bromo-2-oxo-1,2-dihydropyrido[3',4':3,4]pyrazolo[1,5-a]pyrimidin-4-yl)piperidine-1-carboxylate

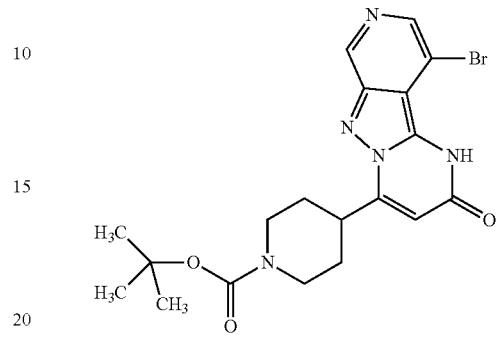

Tert-butyl 4-(3-ethoxy-3-oxopropanoyl)piperidine-1-carboxylate (1.00 g, 3.34 mmol), 4-bromo-1H-pyrazolo[3,4-c]pyridin-3-amine (474 mg, 2.23 mmol) and potassium phosphate (945 mg, 4.45 mmol) were suspended in 1-methoxy-2-propanol (10 ml) in a 20 ml microwave vial. The vial was capped and the mixture was heated in a microwave to 180° C. for 15 min. After cooling to RT, the mixture was diluted with water and neutralized until pH 6 was achieved by the addition of 1N HCl. The resulting solid was filtrated, washed with ethyl acetate and dried under vacuo at 60° C. overnight to yield the first fraction of title compound. After separation of filtrate layers the aqueous layer was extracted with ethyl acetate. The collected organic layers were washed with water und brine solution. The resulting precipitate formed in the organic phase was filtered and dried under vacuo at 60° C. for 2 h to give a second fraction of the title compound. Overall yield (176 mg, 18% of theory).

LC-MS (Method 1B): R$_t$=0.98 min, MS (ESIPos): m/z=450 [M+H]$^+$

Example 68A

Tert-butyl 4-(2-oxo-8-phenyl-1,2-dihydropyrido[2',3':3,4]pyrazolo[1,5-a]pyrimidin-4-yl)piperidine-1-carboxylate

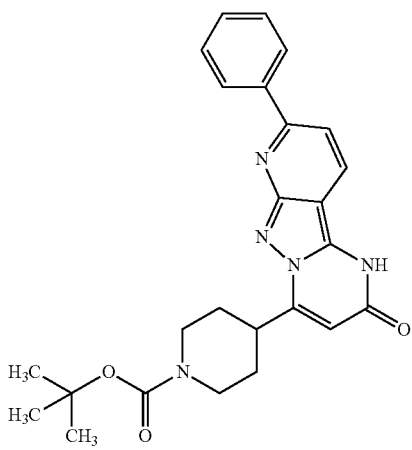 [SMILES: CC(C)(C)OC(=O)N1CCC(c2cc(=O)[nH]c3c4ccc(-c5ccccc5)nc4nn23)CC1]

Tert-butyl 4-(3-ethoxy-3-oxopropanoyl)piperidine-1-carboxylate (1.00 g, 2.77 mmol), 6-phenyl-1H-pyrazolo[3,4-b]pyridin-3-amine (393 mg, 1.85 mmol) and potassium phosphate (785 mg, 3.70 mmol) were suspended in 1-methoxy-2-propanol (10 ml) in a 20 ml microwave vial. The vial was capped and the mixture was heated in a microwave to 180° C. for 15 min. After cooling to RT, the reaction mixture was diluted with water and neutralized (pH 6) by the addition of 1N HCl. The resulting solid was filtrated, washed with ethyl acetate and dried under vacuo. The solid was stirred in a mixture of DMSO/water, filtered and dried under vacuo to yield a first fraction of title compound. The filtrate was purified by preparative HPLC (Method 2A) to yield a second fraction of the title compound. Overall yield: 112 mg, 14%.

LC-MS (Method 1B): $R_t$=1.07 min, MS (ESIPos): m/z=446 [M+H]$^+$

Example 69A

Tert-butyl 4-(2-oxo-9-phenyl-1,2-dihydropyrido[2',3':3,4]pyrazolo[1,5-a]pyrimidin-4-yl)piperidine-1-carboxylate

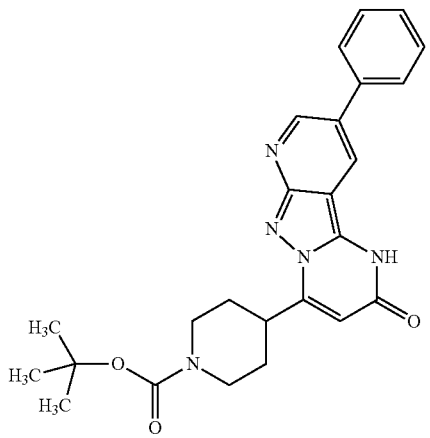 [SMILES: CC(C)(C)OC(=O)N1CCC(c2cc(=O)[nH]c3c4cc(-c5ccccc5)cnc4nn23)CC1]

Tert-butyl 4-(3-ethoxy-3-oxopropanoyl)piperidine-1-carboxylate (1 g, 2.77 mmol), 5-phenyl-1H-pyrazolo[3,4-b]pyridin-3-amine (389 mg, 1.85 mmol) and potassium phosphate (785 mg, 3.70 mmol) were suspended in 1-methoxy-2-propanol (10 ml) in a 20 ml microwave vial. The vial was capped and the mixture was heated in a microwave to 180° C. for 15 min. After cooling to RT, the reaction mixture was diluted with water and neutralized (pH 6) by the addition of 1N HCl. The resulting solid was filtrated, washed with ethyl acetate and water and dried under vacuo. The solid was stirred in a mixture of water and DMSO, filtered und dried under vacuo. The solid was stirred again in a mixture of water, ammonia and acetonitrile. The resulting solid was filtered and the filtrate was purified by preparative HPLC Method 2A) to yield the title compound (70 mg, 8% of theory).

LC-MS (Method 1B): $R_t$=1.02 min, MS (ESIPos): m/z=446 [M+H]$^+$

Example 70A

Tert-butyl 4-(2-oxo-10-phenyl-1,2-dihydropyrido[2',3':3,4]pyrazolo[1,5-a]pyrimidin-4-yl)piperidine-1-carboxylate

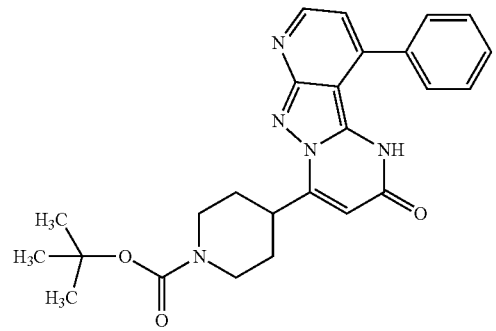 [SMILES: CC(C)(C)OC(=O)N1CCC(c2cc(=O)[nH]c3c4c(-c5ccccc5)ccnc4nn23)CC1]

Tert-butyl 4-(3-ethoxy-3-oxopropanoyl)piperidine-1-carboxylate (1 g, 2.77 mmol), 4-phenyl-1H-pyrazolo[3,4-b]pyridin-3-amine (389 mg, 1.85 mmol) and potassium phosphate (785 mg, 3.70 mmol) were suspended in 1-methoxy-2-propanol (10 ml) in a 20 ml microwave vial. The vial was capped and the mixture was heated in a microwave to 180° C. for 15 min. After cooling to RT, the reaction mixture was diluted with water and neutralized (pH 6) by the addition of 1N HCl. The resulting solid was filtrated, washed with ethyl acetate and water and dried under vacuo. The solid was stirred in a mixture of water, ammonia and acetonitrile. The solid was filtered off and the filtrate was purified by preparative HPLC (Method 2A) to yield the title compound (49 mg, 6% of theory).

LC-MS (Method 1B): $R_t$=0.98 min, MS (ESIPos): m/z=446 [M+H]$^+$

Example 71A

Tert-butyl 4-(2-oxo-1,2-dihydropyrido[4',3':3,4]pyrazolo[1,5-a]pyrimidin-4-yl)piperidine-1-carboxylate

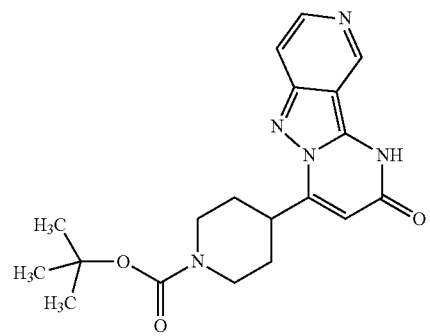 [SMILES: CC(C)(C)OC(=O)N1CCC(c2cc(=O)[nH]c3c4cnccc4nn23)CC1]

The title compound was prepared according to General Procedure 1A starting from 37 mg (0.28 mmol) 1H-pyrazolo[4,3-c]pyridin-3-amine and 100 mg (0.28 mmol) tert-butyl 4-[(2,2-dimethyl-4,6-dioxo-1,3-dioxan-5-yl)carbonyl]piperidine-1-carboxylate.

Work-up: the mixture was diluted with ethyl acetate and treated with HCl 1H. The layers were separated and the aqueous layer was treated with NaOH 1N until pH 10 was achieved. The resulting precipitate was filtered and dried under vacuo to yield the title compound (13 mg, 12% of theory).

LC-MS (Method 1B): $R_t$=0.68 min, MS (ESIPos): m/z=370 [M+H]$^+$

Example 72A

Tert-butyl 4-(10-methyl-2-oxo-1,2-dihydropyrido[2', 3':3,4]pyrazolo[1,5-a]pyrimidin-4-yl)piperidine-1-carboxylate

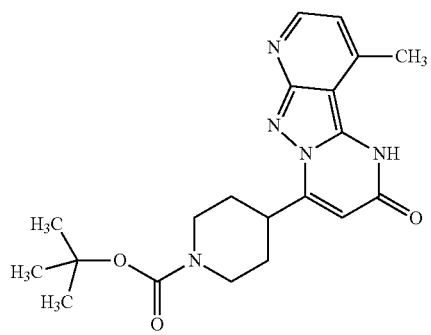 [SMILES: Cc1ccnc2nn3c(C4CCN(C(=O)OC(C)(C)C)CC4)cc(=O)[nH]c3c12]

Tert-butyl 4-(3-ethoxy-3-oxopropanoyl)piperidine-1-carboxylate (818 mg, 2.27 mmol), 4-methyl-1H-pyrazolo[3,4-b]pyridin-3-amine (224 mg, 1.51 mmol) and potassium phosphate (642 mg, 3.02 mmol) were suspended in 1-methoxy-2-propanol (8 ml) in a 20 ml microwave vial. The vial was capped and the mixture was heated in a microwave to 180° C. for 15 min. The reaction mixture was diluted with water and neutralized (pH 6) by the addition of 1N HCl. The resulting solid was filtrated, washed with ethyl acetate and water and dried under vacuo. The solid was stirred in a mixture of water, ammonia and acetonitrile. The solid was filtered off and the filtrate was purified by preparative HPLC (Method 2A) to yield the title compound (40 mg, 7% of theory).

LC-MS (Method 3B): $R_t$=1.75 min, MS (ESIPos): m/z=384 [M+H]$^+$

Example 73A

Tert-butyl 4-(9-iodo-2-oxo-1,2-dihydropyrimido[1,2-b]indazol-4-yl)piperidine-1-carboxylate

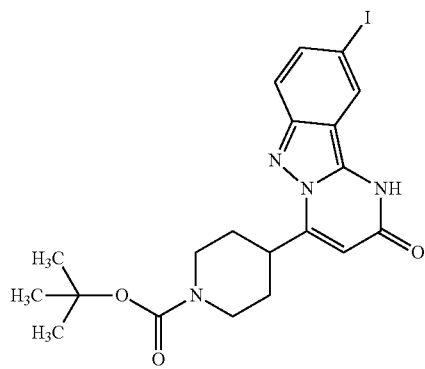 [SMILES: CC(C)(C)OC(=O)N1CCC(c2cc(=O)[nH]c3c4cc(I)ccc4nn23)CC1]

Tert-butyl 4-(3-ethoxy-3-oxopropanoyl)piperidine-1-carboxylate (1 g, 2.27 mmol), 5-iodo-1H-indazol-3-amine (504 mg, 1.85 mmol) and potassium phosphate (785 mg, 3.70 mmol) were suspended in 1-methoxy-2-propanol (10 ml) in a 20 ml microwave vial. The vial was capped and the mixture was heated in a microwave to 180° C. for 15 min. After cooling to RT the residue was diluted with water and extracted with ethyl. The layers were separated and the aqueous layer was extracted with ethyl acetate.

The collected organic phases were dried over magnesium sulfate, filtered and evaporated. The crude product was purified by preparative HPLC (Method 1A). The combined product fractions were neutralized with aqueous ammonium hydroxide. After the evaporation of acetonitrile a white solid was formed in the aqueous phase, which was filtered and dried under vacuo to yield the title compound (108 mg, 12% of theory).

LC-MS (Method 3B): $R_t$=2.46 min, MS (ESIPos): m/z=495 [M+H]$^+$

Example 74A

Tert-butyl-4-(10-bromo-2-oxo-1,2-dihydropyrimido[1,2-b]indazol-4-yl)-2-methylpiperidine-1-carboxylate [Enantiomerically Pure Trans-Isomer]

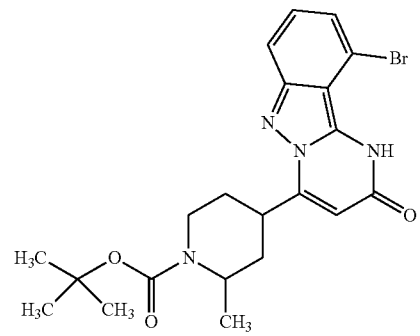 [SMILES: CC1CC(c2cc(=O)[nH]c3c4c(Br)cccc4nn23)CCN1C(=O)OC(C)(C)C]

The title compound was prepared according to General Procedure 1A starting from 1.00 g (4.48 mmol) 4-bromo-1H-indazol-3-amine and 1.77 mg (4.48 mmol) (−)-cis-tert-butyl 4-[(2,2-dimethyl-4,6-dioxo-1,3-dioxan-5-yl)carbonyl]-2-methylpiperidine-1-carboxylate.

Work-up: the mixture was evaporated and the crude product was treated with water and ethyl acetate.

After separation of the layers the organic layer was washed with water, dried over sodium sulfate and evaporated under vacuo. The crude product was purified by preparative HPLC (Method 1A). The combined product fractions were neutralized with a 33% ammonia solution and then acetonitrile was evaporated. In the aqueous phase precipitated a solid which was filtered and dried under vacuo. After reaction epimerization was observed obtaining a mixture of diastereomers which were separated by Method 1C to yield the title compound (1.00 g, 49% of theory).

LC-MS (Method 1B): $R_t$=1.17 min, MS (ESIPos): m/z=463 [M+H]$^+$

HPLC (Method 1E): $R_t$=7.04 min

Example 75A

Tert-butyl 4-(10-ethoxy-2-oxo-1,2-dihydropyrimido[1,2-b]indazol-4-yl)-2-methylpiperidine-1-carboxylate [Enantiomerically Pure Trans-Isomer]

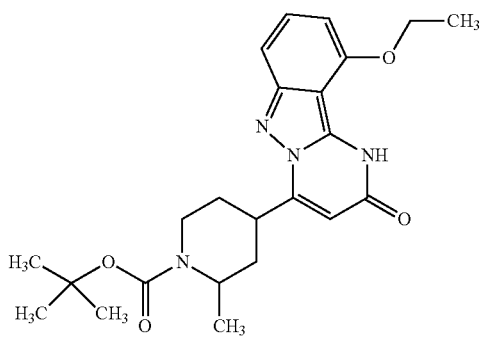 [SMILES: CCOc1cccc2nn3c(C4CCN(C(=O)OC(C)(C)C)C(C)C4)cc(=O)[nH]c3c12]

The title compound was prepared according to General Procedure 1A starting from 0.26 g (1.28 mmol) 4-Ethoxy-1H-pyrazolo[3,4-b]pyridin-3-amine and 0.50 g (1.28 mmol) (−)-cis-tert-butyl 4-[(2,2-dimethyl-4,6-dioxo-1,3-dioxan-5-yl)carbonyl]-2-methylpiperidine-1-carboxylate.

Work-up: the mixture was evaporated and the crude product was treated with water and ethyl acetate. After separation of the layers the aqueous layer was extracted with ethyl acetate and then the collected organic phases were washed with water, dried over sodium sulfate and evaporated under vacuo. The crude product was sonicated 15 minutes at RT in tert-butylmethylether, filtered off and the filtrate was evaporated and then purified by preparative HPLC (Method 1A). The combined product fractions were neutralized with a 33% ammonia solution and then acetonitrile was evaporated. In the aqueous phase precipitated a solid which was filtered and dried under vacuo. After reaction epimerization was observed obtaining a mixture of diastereomers which were separated by Method 2C to yield the title compound (99 mg, 18% of theory).

LC-MS (Method 2B): $R_t$=2.45 min, MS (ESIPos): m/z=427 [M+H]$^+$

HPLC (Method 2E): $R_t$=5.75 min

Example 76A

Tert-butyl 2-methyl-4-(2-oxo-10-phenyl-1,2-dihydropyrido[2',3':3,4]pyrazolo[1,5-a]pyrimidin-4-yl)piperidine-1-carboxylate [Enantiomerically Pure Trans-Isomer]

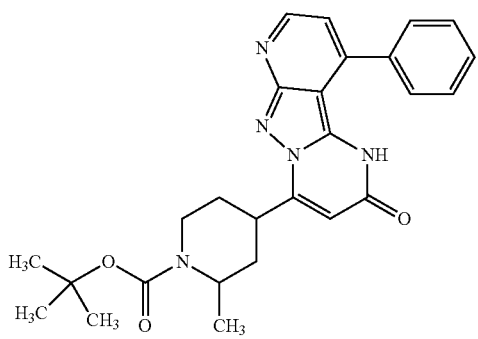 [SMILES: CC1CC(c2cc(=O)[nH]c3c4c(-c5ccccc5)ccnc4nn23)CCN1C(=O)OC(C)(C)C]

The title compound was prepared according to General Procedure 1A starting from 200 mg (0.92 mmol) 4-phenyl-1H-pyrazolo[3,4-b]pyridin-3-amine and 363 mg (0.92 mmol) (−)-cis-tert-butyl 4-[(2,2-dimethyl-4,6-dioxo-1,3-dioxan-5-yl)carbonyl]-2-methylpiperidine-1-carboxylate.

Work-up: the mixture was evaporated and the crude product was treated with water and extracted with ethyl acetate. After separation of the phases a yellow solid precipitated in the aqueous phase. The solid was filtered and dried under vacuo. After reaction epimerization was observed obtaining a mixture of diastereomers which were separated by Method 3C. The fraction containing the title compound was purified again by preparative HPLC (Method 1A). The combined product fractions were neutralized with a 33% ammonia solution and then acetonitrile was evaporated. In the aqueous phase precipitated a solid which was filtered and dried under vacuo to yield the title compound (81 mg, 20% of theory).

LC-MS (Method 1B): $R_t$=1.04 min, MS (ESIPos): m/z=460 [M+H]$^+$

HPLC (Method 3E): $R_t$=8.18 min

Example 77A

3-Amino-1H-indazole-4-carbonitrile

3-Fluorophthalonitrile (1.00 g, 6.84 mmol) was dissolved in ethanol (10 mL) and treated with hydrazine hydrate (1.37 g, 27.4 mmol). After stirring at 70° C. for 8 h, the mixture was cooled to RT and concentrated in vacuo. The residue was dissolved in a mixture of water and ethyl acetate. The aqueous layer was extracted once more with ethyl acetate. The combined organic layers were washed with water and with brine, dried over magnesium sulfate, concentrated in vacuo and dried to yield the title compound (0.51 g, 47% of theory)

LC-MS (Method 2B): $R_t$=1.47 min, MS (ESIPos): m/z=159 [M+H]$^+$

Example 78A

Tert-butyl 4-(10-cyano-2-oxo-1,2-dihydropyrimido[1,2-b]indazol-4-yl)piperidine-1-carboxylate

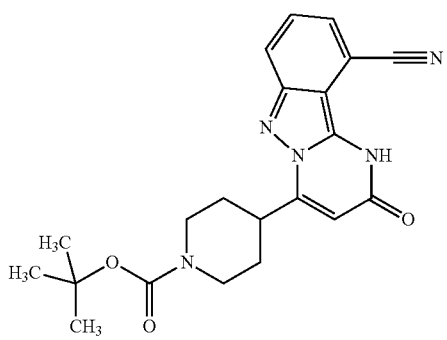 [SMILES: CC(C)(C)OC(=O)N1CCC(c2cc(=O)[nH]c3c4c(C#N)cccc4nn23)CC1]

3-Amino-1H-indazole-4-carbonitrile (0.51 g, 3.20 mmol) and tert-butyl 4-[(2,2-dimethyl-4,6-dioxo-1,3-dioxan-5-yl)carbonyl]piperidine-1-carboxylate (1.27 g, 3.55 mmol) were dissolved in acetonitrile (20 mL) and refluxed for 6 h. After cooling to RT, the solvent was removed in vacuo and the residue was dissolved in 1-methoxy-2-propanol (20 mL). Potassium phosphate (1.37 g, 6.45 mmol) was added and the mixture was stirred at 80° C. for 6 h. Concentration in vacuo and purification by preparative HPLC (Method 1A) afforded the title compound (0.32 g, 25% of theory).

LC-MS (Method 1B): $R_t$=1.07 min, MS (ESIPos): m/z=394 [M+H]$^+$

Example 79A 4-(4-Methoxyphenyl)-1H-indazol-3-amine

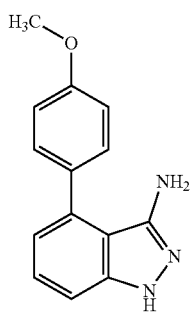

Under argon, 4-chloro-1H-indazol-3-amine (0.50 g, 2.98 mmol), 4-methoxyphenylboronic acid (0.68 g, 4.48 mmol) and (2-dicyclohexylphosphino-2',4',6'-triisopropyl-1,1'-biphenyl) [2-(2'-amino-1,1'-biphenyl)]palladium(II) methanesulfonate (0.07 g, 0.09 mmol) were dissolved in a degassed mixture of ethanol, water, and toluene (1:1:1, 20 mL total volume). Potassium phosphate solution (1 M in water, degassed) (6.00 mL, 6.00 mmol) was added and the mixture was stirred at 80° C. for 4 h. The mixture was concentrated in vacuo and purified by preparative HPLC (Method 1A) to yield the title compound (0.28 g, 40% of theory).

LC-MS (Method 1B): $R_t$=0.84 min, MS (ESIPos): m/z=240 [M+H]$^+$

Example 80A

Tert-butyl-4-[10-(4-methoxyphenyl)-2-oxo-1,2-dihydropyrimido[1,2-b]indazol-4-yl]piperidin-1-carboxylate

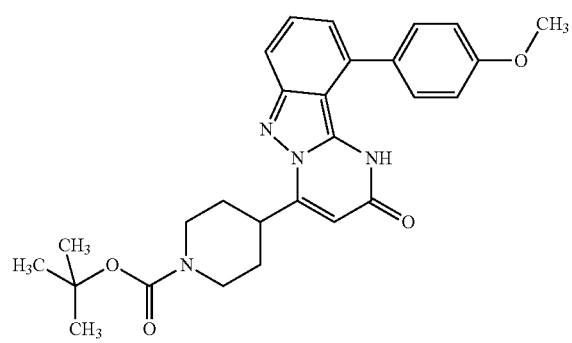 [SMILES: COc1ccc(-c2cccc3nn4c(C5CCN(C(=O)OC(C)(C)C)CC5)cc(=O)[nH]c4c23)cc1]

4-(4-Methoxyphenyl)-1H-indazol-3-amine (0.28 g, 1.18 mmol) and tert-butyl 4-[(2,2-dimethyl-4,6-dioxo-1,3-dioxan-5-yl)carbonyl]piperidine-1-carboxylate (0.46 g, 1.30 mmol) were dissolved in acetonitrile (10 mL) and refluxed for 6 h. After cooling to RT, the solvent was removed in vacuo and the residue was dissolved in 1-methoxy-2-propanol (10 mL). Potassium phosphate (0.52 g, 2.44 mmol) was added and the mixture was stirred at 120° C. for 6 h. Concentration in vacuo and purification by preparative HPLC (Method 1A) afforded the title compound (0.31 g, 54% of theory).

LC-MS (Method 1B): $R_t$=1.27 min, MS (ESIPos): m/z=475 [M+H]$^+$

Example 81A

4-[4-(Trifluoromethyl)phenyl]-1H-indazol-3-amine

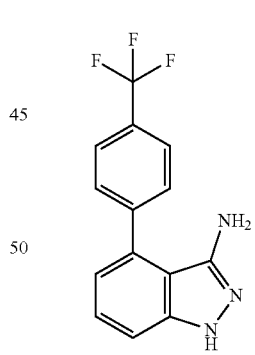

Under argon, 4-chloro-1H-indazol-3-amine (0.50 g, 2.98 mmol), 4-trifluoromethylphenylboronic acid (0.85 g, 4.48 mmol) and (2-dicyclohexylphosphino-2',4',6'-triisopropyl-1,1'-biphenyl)[2-(2'-amino-1,1'-biphenyl)]palladium(II) methanesulfonate (0.07 g, 0.09 mmol) were dissolved in a degassed mixture of ethanol, water, and toluene (1:1:1, 20 mL total volume). Potassium phosphate solution (1 M in water, degassed) (6.00 mL, 6.00 mmol) was added and the mixture was stirred at 80° C. for 4 h. The mixture was concentrated in vacuo and purified by preparative HPLC (Method 1A) to yield the title compound (0.18 g, 22% of theory).

LC-MS (Method 1B): $R_t$=0.99 min, MS (ESIPos): m/z=278 [M+H]$^+$

Example 82A

Tert-butyl 4-{2-oxo-10-[4-(trifluoromethyl)phenyl]-1,2-dihydropyrimido[1,2-b]indazol-4-yl}piperidine-1-carboxylate

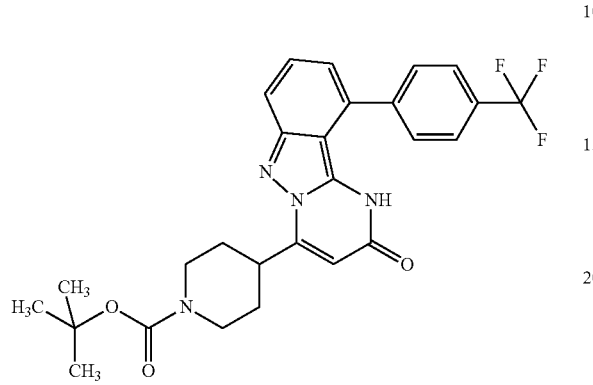

4-[4-(Trifluoromethyl)phenyl]-1H-indazol-3-amine (0.18 g, 0.65 mmol) and tert-butyl 4-[(2,2-dimethyl-4,6-dioxo-1,3-dioxan-5-yl)carbonyl]piperidine-1-carboxylate (0.25 g, 0.71 mmol) were dissolved in acetonitrile (5 mL) and refluxed for 6 h. After cooling to RT, the solvent was removed in vacuo and the residue was dissolved in 1-methoxy-2-propanol (10 mL). Potassium phosphate (0.29 g, 1.36 mmol) was added and the mixture was stirred at 120° C. for 6 h. Concentration in vacuo and purification by preparative HPLC (Method 1A) afforded the title compound (0.18 g, 53% of theory).

LC-MS (Method 1B): $R_t$=1.38 min, MS (ESIPos): m/z=513 [M+H]$^+$

Example 83A

4-Phenyl-1H-indazol-3-amine

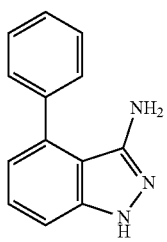 [SMILES: Nc1n[nH]c2cccc(-c3ccccc3)c12]

Under argon, 4-chloro-1H-indazol-3-amine (0.50 g, 2.98 mmol), phenylboronic acid (0.55 g, 4.48 mmol) and (2-dicyclohexylphosphino-2',4',6'-triisopropyl-1,1'-biphenyl) [2-(2'-amino-1,1'-biphenyl)]palladium(II) methanesulfonate (0.07 g, 0.09 mmol) were dissolved in a degassed mixture of ethanol, water, and toluene (1:1:1, 20 mL total volume). Potassium phosphate solution (1 M in water, degassed) (6.00 mL, 6.00 mmol) was added and the mixture was stirred at 80° C. for 4 h. The mixture was concentrated in vacuo and purified by preparative HPLC (Method 1A) to yield the title compound (0.35 g, 57% of theory).

LC-MS (Method 1B): $R_t$=0.83 min, MS (ESIPos): m/z=210 [M+H]$^+$

Example 84A

Tert-butyl 4-(2-oxo-10-phenyl-1,2-dihydropyrimido[1,2-b]indazol-4-yl)piperidine-1-carboxylate

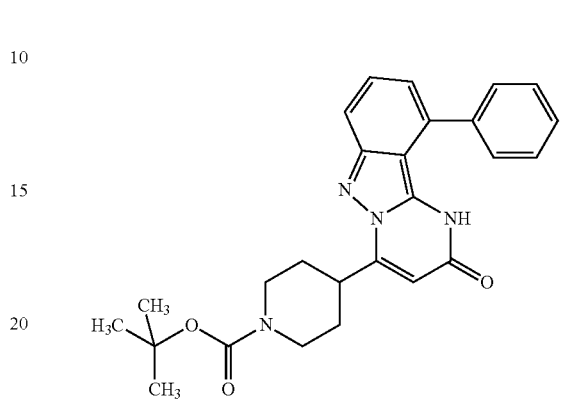

4-Phenyl-1H-indazol-3-amine (0.35 g, 1.69 mmol) and tert-butyl 4-[(2,2-dimethyl-4,6-dioxo-1,3-dioxan-5-yl)carbonyl]piperidine-1-carboxylate (0.66 g, 1.86 mmol) were dissolved in acetonitrile (10 mL) and refluxed for 6 h. After cooling to RT, the solvent was removed in vacuo and the residue was dissolved in 1-methoxy-2-propanol (10 mL). Potassium phosphate (0.75 g, 3.55 mmol) was added and the mixture was stirred at 120° C. for 6 h. Concentration in vacuo and purification by preparative HPLC (Method 1A) afforded the title compound (0.47 g, 60% of theory).

LC-MS (Method 1B): $R_t$=1.23 min, MS (ESIPos): m/z=445 [M+H]$^+$

Example 85A 4-(2-Fluorophenyl)-1H-indazol-3-amine

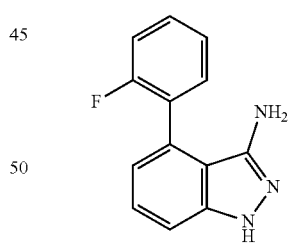

Under argon, 4-chloro-1H-indazol-3-amine (0.50 g, 2.98 mmol), 2-fluorophenylboronic acid (0.63 g, 4.48 mmol) and (2-dicyclohexylphosphino-2',4',6'-triisopropyl-1,1'-biphenyl) [2-(2'-amino-1,1'-biphenyl)]palladium(II) methanesulfonate (0.07 g, 0.09 mmol) were dissolved in a degassed mixture of ethanol, water, and toluene (1:1:1, 20 mL total volume). Potassium phosphate solution (1 M in water, degassed) (6.00 mL, 6.00 mmol) was added and the mixture was stirred at 80° C. for 4 h. The mixture was concentrated in vacuo and purified by preparative HPLC (Method 1A) to yield the title compound (0.45 g, 66% of theory).

LC-MS (Method 2B): $R_t$=2.07 min, MS (ESIPos): m/z=228 [M+H]+

Example 86A

Tert-butyl 4-[10-(2-fluorophenyl)-2-oxo-1,2-dihydropyrimido[1,2-b]indazol-4-yl]piperidine-1-carboxylate

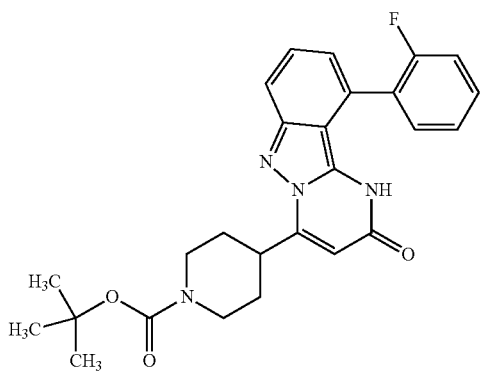 [SMILES: CC(C)(C)OC(=O)N1CCC(c2cc(=O)[nH]c3c4c(-c5ccccc5F)cccc4nn23)CC1]

4-(2-Fluorophenyl)-1H-indazol-3-amine (0.45 g, 1.97 mmol) and tert-butyl 4-[(2,2-dimethyl-4,6-dioxo-1,3-dioxan-5-yl)carbonyl]piperidine-1-carboxylate (0.77 g, 2.17 mmol) were dissolved in acetonitrile (10 mL) and refluxed for 6 h. After cooling to RT, the solvent was removed in vacuo and the residue was dissolved in 1-methoxy-2-propanol (10 mL). Potassium phosphate (0.98 g, 4.60 mmol) was added and the mixture was stirred at 120° C. for 6 h. Concentration in vacuo and purification by preparative HPLC (Method 1A) afforded the title compound (0.59 g, 55% of theory).

LC-MS (Method 3B): $R_t$=2.62 min, MS (ESIPos): m/z=463[M+H]$^+$

Example 87A 4-(Pyridin-3-yl)-1H-indazol-3-amine

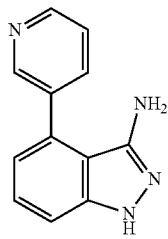

Under argon, 4-chloro-1H-indazol-3-amine (0.50 g, 2.98 mmol), 3-pyridylboronic acid (0.55 g, 4.48 mmol) and (2-dicyclohexylphosphino-2',4',6'-triisopropyl-1,1'-biphenyl) [2-(2'-amino-1,1'-biphenyl)]palladium(II) methanesulfonate (0.07 g, 0.09 mmol) were dissolved in a degassed mixture of ethanol, water, and toluene (1:1:1, 20 mL total volume). Potassium phosphate solution (1 M in water, degassed) (6.00 mL, 6.00 mmol) was added and the mixture was stirred at 80° C. for 4 h. The mixture was concentrated in vacuo and purified by preparative HPLC (Method 1A) to yield the title compound (0.48 g, 77% of theory).

LC-MS (Method 2B): $R_t$=1.63 min, MS (ESIPos): m/z=211 [M+H]$^+$

Example 88A

Tert-butyl 4-[2-oxo-10-(pyridin-3-yl)-1,2-dihydropyrimido[1,2-b]indazol-4-yl]piperidine-1-carboxylate

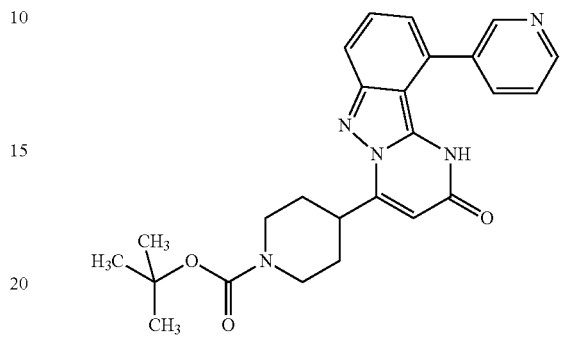

4-(Pyridin-3-yl)-1H-indazol-3-amine (0.48 g, 2.28 mmol) and tert-butyl 4-[(2,2-dimethyl-4,6-dioxo-1,3-dioxan-5-yl)carbonyl]piperidine-1-carboxylate (0.89 g, 2.51 mmol) were dissolved in acetonitrile (20 mL) and refluxed for 6 h. After cooling to RT, the solvent was removed in vacuo and the residue was dissolved in 1-methoxy-2-propanol (30 mL). Potassium phosphate (0.97 g, 4.56 mmol) was added and the mixture was stirred under reflux for 6 h. Concentration in vacuo and purification by preparative HPLC (Method 1A) afforded the title compound (0.48 g, 47% of theory).

Example 89A 4-(Pyridin-4-yl)-1H-indazol-3-amine

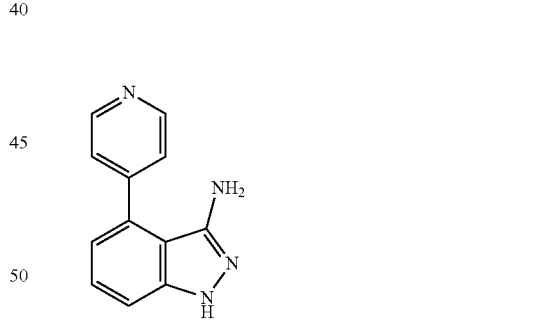

Under argon, 4-chloro-1H-indazol-3-amine (0.50 g, 2.98 mmol), 4-pyridylboronic acid (0.55 g, 4.48 mmol) and (2-dicyclohexylphosphino-2',4',6'-triisopropyl-1,1'-biphenyl) [2-(2'-amino-1,1'-biphenyl)]palladium(II) methanesulfonate (0.07 g, 0.09 mmol) were dissolved in a degassed mixture of ethanol, water, and toluene (1:1:1, 20 mL total volume). Potassium phosphate solution (1 M in water, degassed) (6.00 mL, 6.00 mmol) was added and the mixture was stirred at 80° C. for 4 h. The mixture was concentrated in vacuo and purified by preparative HPLC (Method 1A) to yield the title compound (0.33 g, 53% of theory).

LC-MS (Method 2B): $R_t$=1.62 min, MS (ESIPos): m/z=211 [M+H]$^+$

Example 90A

Tert-butyl 4-(3-oxo-3-{[4-(pyridin-4-yl)-1H-indazol-3-yl]amino}propanoyl)piperidine-1-carboxylate

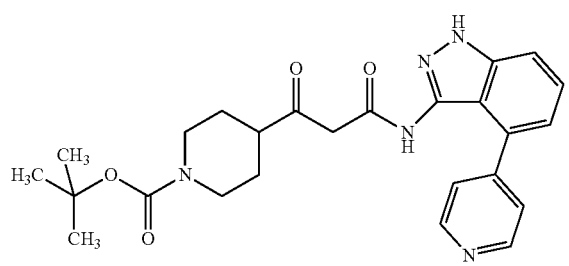 [SMILES: CC(C)(C)OC(=O)N1CCC(C(=O)CC(=O)Nc2n[nH]c3cccc(-c4ccncc4)c23)CC1]

4-(Pyridin-4-yl)-1H-indazol-3-amine (0.33 g, 1.58 mmol) and tert-butyl 4-[(2,2-dimethyl-4,6-dioxo-1,3-dioxan-5-yl)carbonyl]piperidine-1-carboxylate (0.62 g, 1.74 mmol) were dissolved in acetonitrile (15 mL) and refluxed for 6 h. Concentration in vacuo and purification by preparative HPLC (Method 1A) afforded the title compound (0.07 g, 10% of theory).

LC-MS (Method 1B): $R_t$=0.73 min, MS (ESIPos): m/z=464 [M+H]$^+$

Example 91A

Tert-butyl 4-[2-oxo-10-(pyridin-4-yl)-1,2-dihydropyrimido[1,2-b]indazol-4-yl]piperidine-1-carboxylate

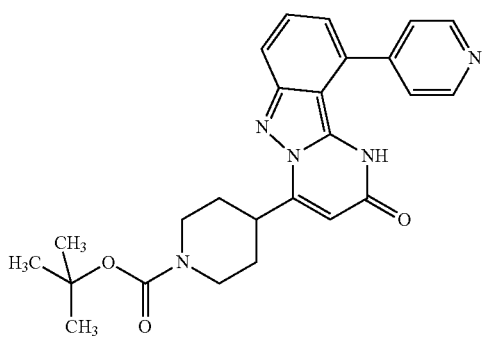 [SMILES: CC(C)(C)OC(=O)N1CCC(c2cc(=O)[nH]c3c4c(-c5ccncc5)cccc4nn23)CC1]

Tert-butyl 4-(3-oxo-3-{[4-(pyridin-4-yl)-1H-indazol-3-yl]amino}propanoyl)piperidine-1-carboxylate (0.07 g, 0.15 mmol) was dissolved in 1-methoxy-2-propanol (2 mL). Potassium phosphate (0.06 g, 0.30 mmol) was added and the mixture was stirred at 100° C. for 4 h. Concentration in vacuo and purification by preparative HPLC (Method 1A) afforded the title compound (0.03 g, 67% of theory).

LC-MS (Method 1B): $R_t$=0.86 min, MS (ESIPos): m/z=446 [M+H]$^+$

Example 92A

Tert-butyl 4-(10-bromo-2-oxo-1,2-dihydropyrimido[1,2-b]indazol-4-yl)piperidine-1-carboxylate

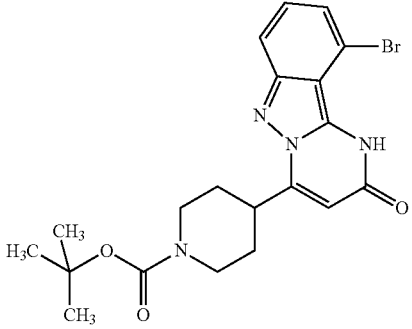 [SMILES: CC(C)(C)OC(=O)N1CCC(c2cc(=O)[nH]c3c4c(Br)cccc4nn23)CC1]

4-Bromo-1H-indazol-3-amine (2.00 g, 9.43 mmol) and tert-butyl 4-[(2,2-dimethyl-4,6-dioxo-1,3-dioxan-5-yl)carbonyl]piperidine-1-carboxylate (3.69 g, 10.38 mmol) were dissolved in acetonitrile (90 mL) and refluxed for 4 h. After cooling to RT, the solvent was removed in vacuo and the residue was dissolved in 1-methoxy-2-propanol (25 mL). Potassium phosphate (4.00 g, 18.9 mmol) was added and the mixture was stirred at reflux for 4 h. After concentration in vacuo, the residue was dissolved in water and extracted with ethyl acetate. The organic phase was washed with brine and dried over magnesium sulfate. Concentration in vacuo and purification by preparative HPLC (Method 1A) afforded the title compound in 93% purity. The solid was suspended in methanol, filtered, and dried to afford the title compound (0.86 g, 20% of theory).

LC-MS (Method 3B): $R_t$=2.37 min, MS (ESIPos): m/z=447 [M+H]$^+$, 449 [M+H]$^+$

Example 93A

Tert-butyl 4-(10-cyclopropyl-2-oxo-1,2-dihydropyrimido[1,2-b]indazol-4-yl)piperidine-1-carboxylate

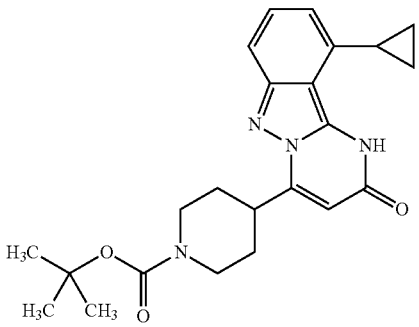 [SMILES: CC(C)(C)OC(=O)N1CCC(c2cc(=O)[nH]c3c4c(C5CC5)cccc4nn23)CC1]

Under argon, a mixture of tert-butyl 4-(10-chloro-2-oxo-1,2-dihydropyrimido[1,2-b]indazol-4-yl)piperidine-1-carboxylate (0.10 g, 0.25 mmol), palladium(II)acetate (1.7 mg, 7 µmol), and 2-dicyclohexylphosphino-2',6'-bis(N,N-dimethylamino)biphenyl (6.5 mg, 15 µmol) in tetrahydrofuran (5 mL) was cooled to 0° C. Cyclopropylzinc bromide (0.5 M in tetrahydrofuran, 1.24 mL, 0.62 mmol) was added dropwise. After stirring for 4 h at RT, additional cyclopropylzinc bromide (0.5 M in tetrahydrofuran, 1.24 mL, 0.62 mmol) was added and the mixture was stirred at RT for 16 h. The mixture was quenched with water, extracted with ethyl acetate and dried over magnesium sulfate. Concentration in vacuo and purification by preparative HPLC (Method 1A) afforded the title compound (20 mg, 20% of theory).

LC-MS (Method 1B): $R_t$=1.16 min, MS (ESIPos): m/z=409 [M+H]$^+$

Example 94A

Tert-butyl 4-(10-isopropyl-2-oxo-1,2-dihydropyrimido[1,2-b]indazol-4-yl)piperidine-1-carboxylate

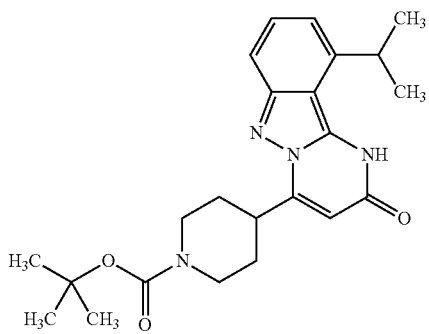 [SMILES: CC(C)c1cccc2nn3c(C4CCN(C(=O)OC(C)(C)C)CC4)cc(=O)[nH]c3c12]

Under argon, a mixture of tert-butyl 4-(10-chloro-2-oxo-1,2-dihydropyrimido[1,2-b]indazol-4-yl)piperidine-1-carboxylate (0.10 g, 0.25 mmol), [(2-dicyclohexylphosphino-2',6'-bis(N,N-dimethylamino)-1,1'-biphenyl)-2-(2'-amino-1,1'-biphenyl)]palladium(II) methanesulfonate (0.04 g, 0.05 mmol), and 2-dicyclohexylphosphino-2',6'-bis(N,N-dimethylamino)biphenyl (0.02 g, 0.05 mmol) was suspended in tetrahydrofuran (5 mL). Lithium chloride (0.5 M in tetrahydrofuran, 5.00 mL, 2.48 mmol) was added and the mixture was cooled to 0° C. Isopropylzinc bromide (0.5 M in tetrahydrofuran, 5.00 mL, 2.48 mmol) was added dropwise. After stirring at RT for 16 h, the mixture was quenched with water, extracted with ethyl acetate and dried over magnesium sulfate. Concentration in vacuo and purification by preparative HPLC (Method 1A) afforded the title compound (0.03 g, 33% of theory).

LC-MS (Method 1B): $R_t$=1.21 min, MS (ESIPos): m/z=411 [M+H]$^+$

Example 95A

Tert-butyl 4-(10-cyclopentyl-2-oxo-1,2-dihydropyrimido[1,2-b]indazol-4-yl)piperidine-1-carboxylate

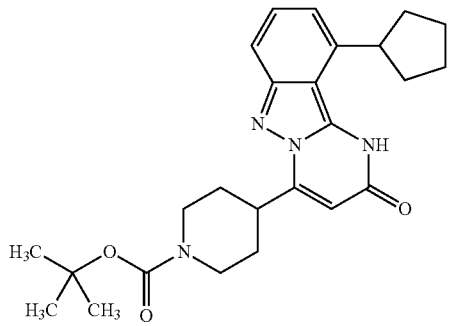 [SMILES: CC(C)(C)OC(=O)N1CCC(c2cc(=O)[nH]c3c4c(C5CCCC5)cccc4nn23)CC1]

Under argon, a mixture of tert-butyl 4-(10-chloro-2-oxo-1,2-dihydropyrimido[1,2-b]indazol-4-yl)piperidine-1-carboxylate (0.10 g, 0.25 mmol), [(2-dicyclohexylphosphino-2',6'-bis(N,N-dimethylamino)-1,1'-biphenyl)-2-(2'-amino-1,1'-biphenyl)]palladium(II) methanesulfonate (0.04 g, 0.05 mmol), and 2-dicyclohexylphosphino-2',6'-bis(N,N-dimethylamino)biphenyl (0.02 g, 0.05 mmol) was suspended in tetrahydrofuran (5 mL). Lithium chloride (0.5 M in tetrahydrofuran, 5.00 mL, 2.48 mmol) was added and the mixture was cooled to 0° C. Cyclopentylzinc bromide (0.5 M in tetrahydrofuran, 5.00 mL, 2.48 mmol) was added dropwise. After stirring at RT for 16 h, the mixture was quenched with water, extracted with ethyl acetate and dried over magnesium sulfate. Concentration in vacuo and purification by preparative HPLC (Method 1A) afforded the title compound (0.02 g, 20% of theory).

LC-MS (Method 1B): $R_t$=1.32 min, MS (ESIPos): m/z=437 [M+H]$^+$

Example 96A 4-(2-Chlorophenyl)-1H-indazol-3-amine

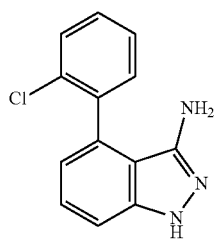 [SMILES: Nc1n[nH]c2cccc(-c3ccccc3Cl)c12]

Under argon, 4-chloro-1H-indazol-3-amine (0.50 g, 2.98 mmol), 2-chlorophenylboronic acid (0.70 g, 4.48 mmol) and (2-dicyclohexylphosphino-2',4',6'-triisopropyl-1,1'-biphenyl)[2-(2'-amino-1,1'-biphenyl)]palladium(II) methanesulfonate (0.07 g, 0.09 mmol) were dissolved in a degassed mixture of ethanol, water, and toluene (1:1:1, 20 mL total volume). Potassium phosphate solution (1 M in water, degassed) (6.00 mL, 6.00 mmol) was added and the mixture was stirred at 80° C. for 4 h. The mixture was concentrated in vacuo and purified by preparative HPLC (Method 1A) to yield the title compound (0.31 g, 42% of theory).

LC-MS (Method 1B): $R_t$=0.86 min, MS (ESIPos): m/z=244 [M+H]$^+$

Example 97A

Tert-butyl 4-[10-(2-chlorophenyl)-2-oxo-1,2-dihydropyrimido[1,2-b]indazol-4-yl]piperidine-1-carboxylate

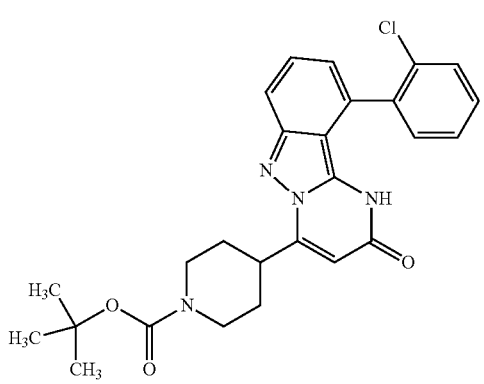

4-(2-Chlorophenyl)-1H-indazol-3-amine (0.30 g, 1.23 mmol) and tert-butyl 4-[(2,2-dimethyl-4,6-dioxo-1,3-dioxan-5-yl)carbonyl]piperidine-1-carboxylate (0.48 g, 1.35 mmol) were dissolved in acetonitrile (6 mL) and refluxed for 6 h. After cooling to RT, the solvent was removed in vacuo and the residue was dissolved in 1-methoxy-2-propanol (5 mL). Potassium phosphate (0.52 g, 2.46 mmol) was added and the mixture was stirred at 120° C. for 6 h. Concentration in vacuo and purification by preparative HPLC (Method 1A) afforded the title compound (0.30 g, 51% of theory).

LC-MS (Method 1B): $R_t$=1.28 min, MS (ESIPos): m/z=479 [M+H]$^+$

Example 98A 4-(2-Methoxyphenyl)-1H-indazol-3-amine

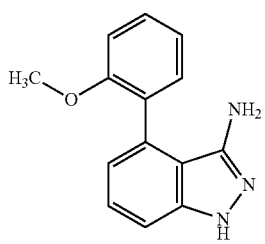 [SMILES: COc1ccccc1-c1cccc2[nH]nc(N)c12]

Under argon, 4-chloro-1H-indazol-3-amine (0.50 g, 2.98 mmol), 2-methoxyphenylboronic acid (0.68 g, 4.48 mmol) and (2-dicyclohexylphosphino-2',4',6'-triisopropyl-1,1'-biphenyl) [2-(2'-amino-1,1'-biphenyl)]palladium(II) methanesulfonate (0.07 g, 0.09 mmol) were dissolved in a degassed mixture of ethanol, water, and toluene (1:1:1, 20 mL total volume). Potassium phosphate solution (1 M in water, degassed) (6.00 mL, 6.00 mmol) was added and the mixture was stirred at 80° C. for 4 h. The mixture was concentrated in vacuo and purified by preparative HPLC (Method 1A) to yield the title compound (0.52 g, 72% of theory).

LC-MS (Method 1B): $R_t$=0.77 min, MS (ESIPos): m/z=240 [M+H]$^+$

Example 99A

Tert-butyl 4-[10-(2-methoxyphenyl)-2-oxo-1,2-dihydropyrimido[1,2-b]indazol-4-yl]piperidine-1-carboxylate

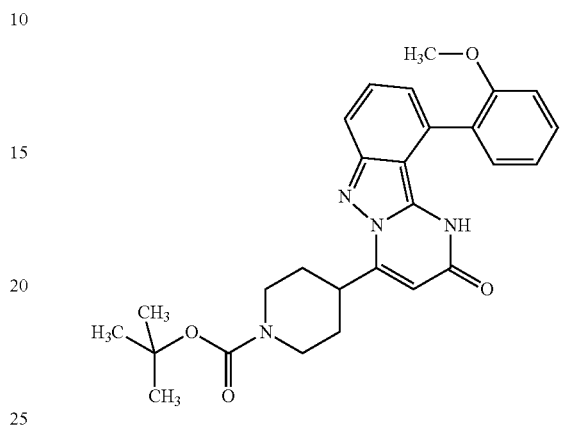

4-(2-Methoxyphenyl)-1H-indazol-3-amine (0.51 g, 2.13 mmol) and tert-butyl 4-[(2,2-dimethyl-4,6-dioxo-1,3-dioxan-5-yl)carbonyl]piperidine-1-carboxylate (0.83 g, 2.35 mmol) were dissolved in acetonitrile (11 mL) and refluxed for 6 h. After cooling to RT, the solvent was removed in vacuo and the residue was dissolved in 1-methoxy-2-propanol (9 mL). Potassium phosphate (0.90 g, 4.26 mmol) was added and the mixture was stirred at 120° C. for 6 h. Concentration in vacuo and purification by preparative HPLC (Method 1A) afforded the title compound (0.20 g, 20% of theory).

LC-MS (Method 1B): $R_t$=1.22 min, MS (ESIPos): m/z=475 [M+H]$^+$

Example 100A

4-[2-(Trifluoromethyl)phenyl]-1H-indazol-3-amine

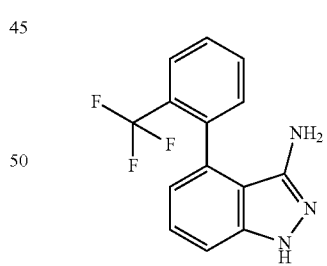

Under argon, 4-chloro-1H-indazol-3-amine (0.50 g, 2.98 mmol), 2-trifluoromethylphenylboronic acid (0.85 g, 4.48 mmol) and (2-dicyclohexylphosphino-2',4',6'-triisopropyl-1,1'-biphenyl)[2-(2'-amino-1,1'-biphenyl)]palladium(II) methanesulfonate (0.07 g, 0.09 mmol) were dissolved in a degassed mixture of ethanol, water, and toluene (1:1:1, 20 mL total volume). Potassium phosphate solution (1 M in water, degassed) (6.00 mL, 6.00 mmol) was added and the mixture was stirred at 80° C. for 4 h. The mixture was concentrated in vacuo and purified by preparative HPLC (Method 1A) to yield the title compound (0.31 g, 37% of theory).

LC-MS (Method 1B): $R_t$=0.89 min, MS (ESIPos): m/z=278 [M+H]$^+$

Example 101A

Tert-butyl 4-{2-oxo-10-[2-(trifluoromethyl)phenyl]-1,2-dihydropyrimido[1,2-b]indazol-4-yl}piperidine-1-carboxylate

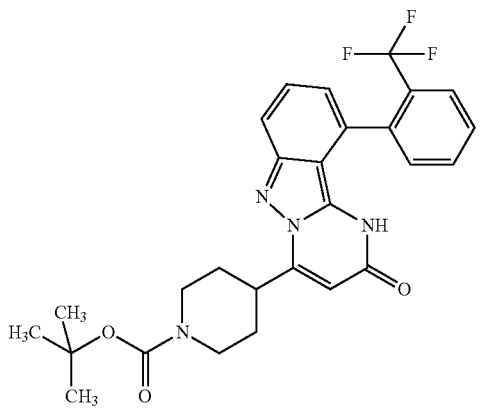 [SMILES: CC(C)(C)OC(=O)N1CCC(c2cc(=O)[nH]c3c4c(-c5ccccc5C(F)(F)F)cccc4nn23)CC1]

4-[2-(Trifluoromethyl)phenyl]-1H-indazol-3-amine (0.31 g, 1.10 mmol) and tert-butyl 4-[(2,2-dimethyl-4,6-dioxo-1,3-dioxan-5-yl)carbonyl]piperidine-1-carboxylate (0.43 g, 1.21 mmol) were dissolved in acetonitrile (6 mL) and refluxed for 6 h. After cooling to RT, the solvent was removed in vacuo and the residue was dissolved in 1-methoxy-2-propanol (5 mL). Potassium phosphate (0.47 g, 2.20 mmol) was added and the mixture was stirred at 120° C. for 6 h. Concentration in vacuo and purification by preparative HPLC (Method 1A) afforded the title compound (0.10 g, 18% of theory).

LC-MS (Method 1B): $R_t$=1.26 min, MS (ESIPos): m/z=513 [M+H]$^+$

Example 102A

2-Chloro-6-fluoro-3-methylbenzaldehyde

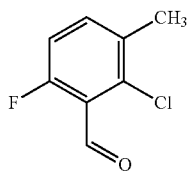

2-Chloro-4-fluoro-1-methylbenzene (5.00 g, 34.6 mmol) was dissolved in tetrahydrofuran (100 mL) and cooled to −78° C. Lithium diisopropyl amide (1.8 M in tetrahydrofuran, 21.1 mL, 38.0 mmol) was added. After stirring at −78° C. for 30 min, N,N-dimethylformamide (3.03 g, 41.5 mmol) was added. After stirring at −78° C. for an additional 15 min, acetic acid (8 mL) and water (100 mL) was added and the mixture was warmed to RT. After extraction with ethyl acetate, the organic phase was washed with 1 M hydrochloride acid solution and brine, and dried over magnesium sulfate. Concentration in vacuo afforded the title compound (3.25 g, 49% of theory) in a purity of 90%.

GC-MS (Method 1G): $R_t$=3.90 min, MS (ESINeg): m/z=171 [M−H]$^−$

Example 103A

2-Chloro-6-fluoro-3-methylbenzonitrile

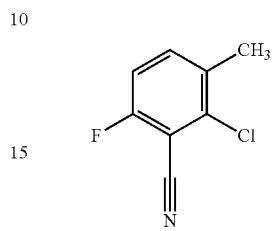

A mixture of 2-chloro-6-fluoro-3-methylbenzaldehyde (90% purity, 3.25 g, 18.8 mmol), sodium lauryl sulfate (1.09 g, 3.77 mmol), (Diacetoxyiodo)benzene (9.10 g, 28.2 mmol) and ammonium acetate (7.26 g, 94.2 mmol) in water (20 mL) was stirred at 70° C. for 30 min. After cooling to RT, a solution of sodium thiosulfate (3.33 g, 21.1 mmol) in water (3.5 mL) was added and the mixture was stirred at RT for 15 min. After extraction with dichloromethane, the organic phase was dried over magnesium sulfate. Concentration in vacuo and purification by preparative HPLC (Method 1A) afforded the title compound (1.26 g, 39% of theory).

GC-MS (Method 1G): $R_t$=3.94 min, MS (ESIPos): m/z=169 [M+H]$^+$

Example 104A

4-Chloro-5-methyl-1H-indazol-3-amine

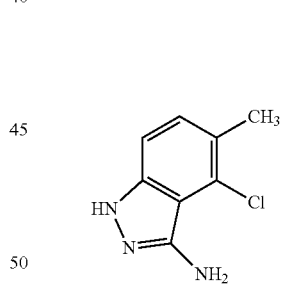

2-chloro-6-fluoro-3-methylbenzonitrile (1.26 g, 7.43 mmol) was dissolved in ethanol (10 mL) and treated with hydrazine hydrate (1.49 g, 29.7 mmol). After stirring at reflux for 4 h, the mixture was cooled to RT and concentrated in vacuo. The residue was dissolved in a mixture of water and ethyl acetate. The aqueous layer was extracted once more with ethyl acetate. The combined organic layers were washed with water and with brine, dried over magnesium sulfate, concentrated in vacuo and dried to yield the title compound (1.06 g, 79% of theory) in a purity of 75%.

LC-MS (Method 2B): $R_t$=1.85 min, MS (ESIPos): m/z=182 [M+H]$^+$

Example 105A

Tert-butyl 4-(10-chloro-9-methyl-2-oxo-1,2-dihydropyrimido[1,2-b]indazol-4-yl)piperidine-1-carboxylate

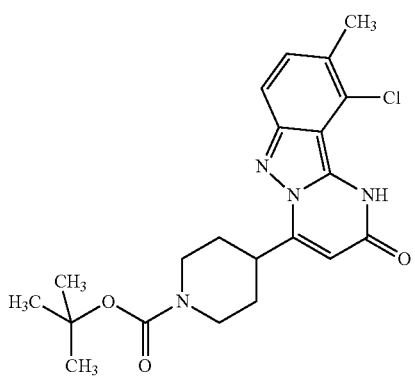 [SMILES: Cc1ccc2nn3c(C4CCN(C(=O)OC(C)(C)C)CC4)cc(=O)[nH]c3c2c1Cl]

4-Chloro-5-methyl-1H-indazol-3-amine (75% purity, 1.06 g, 4.38 mmol) and tert-butyl 4-[(2,2-dimethyl-4,6-dioxo-1,3-dioxan-5-yl)carbonyl]piperidine-1-carboxylate (2.29 g, 6.42 mmol) were dissolved in acetonitrile (50 mL) and refluxed for 4 h. After cooling to RT, the solvent was removed in vacuo and the residue was dissolved in 1-methoxy-2-propanol (20 mL). Potassium phosphate (2.36 g, 11.1 mmol) was added and the mixture was stirred at reflux for 4 h. After concentration in vacuo, the residue was dissolved in water and extracted with ethyl acetate. The organic phase was washed with brine and dried over magnesium sulfate. Concentration in vacuo and recrystallization from acetonitrile/methanol afforded the title compound (0.76 g, 33% of theory).

LC-MS (Method 1B): $R_t$=1.16 min, MS (ESIPos): m/z=417 [M+H]$^+$

Example 106A

2-Bromo-3,6-difluorobenzaldehyde

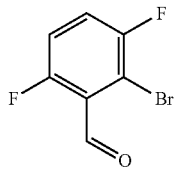 [SMILES: O=Cc1c(F)ccc(F)c1Br]

2-Bromo-1,4-difluorobenzene (5.00 g, 25.9 mmol) was dissolved in tetrahydrofuran (100 mL) and cooled to −78° C. Lithium diisopropyl amide (1.8 M in tetrahydrofuran, 15.8 mL, 28.5 mmol) was added. After stirring at −78° C. for 30 min, N,N-dimethylformamide (2.28 g, 31.1 mmol) was added. After stirring at −78° C. for an additional 15 min, acetic acid (6 mL) and water (100 mL) was added and the mixture was warmed to RT. After extraction with ethyl acetate, the organic phase was washed with 1 M hydrochloride acid solution and brine, and dried over magnesium sulfate. Concentration in vacuo afforded the title compound (2.72 g, 42% of theory) in a purity of 90%.

GC-MS (Method 2G): $R_t$=3.40 min, MS (ESIPos): m/z=221 [M+H]$^+$

Example 107A

2-Bromo-3,6-difluorobenzonitrile

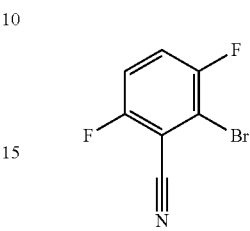

A mixture of 2-bromo-3,6-difluorobenzaldehyde (90% purity, 2.72 g, 11.1 mmol), sodium lauryl sulfate (0.71 g, 2.46 mmol), (Diacetoxyiodo)benzene (5.95 g, 18.5 mmol) and ammonium acetate (4.74 g, 61.5 mmol) in water (13 mL) was stirred at 70° C. for 30 min. After cooling to RT, a solution of sodium thiosulfate (2.18 g, 13.8 mmol) in water (2.3 mL) was added and the mixture was stirred at RT for 15 min. After extraction with dichloromethane, the organic phase was dried over magnesium sulfate. Concentration in vacuo and purification by preparative HPLC (Method 1A) afforded the title compound (1.32 g, 44% of theory).

GC-MS (Method 1G): $R_t$=3.73 min, MS (ESIPos): m/z=217 [M+H]$^+$

Example 108A

4-Bromo-5-fluoro-1H-indazol-3-amine

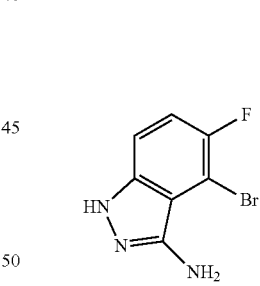

2-Bromo-3,6-difluorobenzonitrile (1.32 g, 6.06 mmol) was dissolved in ethanol (10 mL) and treated with hydrazine hydrate (1.21 g, 24.2 mmol). After stirring at reflux for 4 h, the mixture was cooled to RT and concentrated in vacuo. The residue was dissolved in a mixture of water and ethyl acetate. The aqueous layer was extracted once more with ethyl acetate. The combined organic layers were washed with water and with brine, dried over magnesium sulfate, concentrated in vacuo and dried to yield the title compound (1.25 g, 83% of theory) in a purity of 92%.

LC-MS (Method 2B): $R_t$=1.78 min, MS (ESIPos): m/z=230 [M+H]+

Example 109A

Tert-butyl 4-(10-bromo-9-fluoro-2-oxo-1,2-dihydropyrimido[1,2-b]indazol-4-yl)piperidine-1-carboxylate

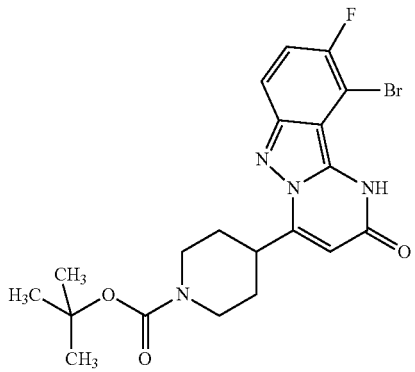 [SMILES: CC(C)(C)OC(=O)N1CCC(c2cc(=O)[nH]c3c4c(Br)c(F)ccc4nn23)CC1]

4-Bromo-5-fluoro-1H-indazol-3-amine (92% purity, 1.25 g, 5.01 mmol) and tert-butyl 4-[(2,2-dimethyl-4,6-dioxo-1,3-dioxan-5-yl)carbonyl]piperidine-1-carboxylate (2.13 g, 6.00 mmol) were dissolved in acetonitrile (50 mL) and refluxed for 4 h. After cooling to RT, the solvent was removed in vacuo and the residue was dissolved in 1-methoxy-2-propanol (20 mL). Potassium phosphate (2.42 g, 11.4 mmol) was added and the mixture was stirred at reflux for 4 h. After concentration in vacuo, the residue was dissolved in water and extracted with ethyl acetate. The organic phase was washed with brine and dried over magnesium sulfate. Concentration in vacuo and recrystallization from acetonitrile/methanol afforded the title compound (0.70 g, 29% of theory).

LC-MS (Method 1B): $R_t$=1.16 min, MS (ESIPos): m/z=466 [M+H]$^+$

Example 110A

6-Bromo-2,3-difluorobenzaldehyde

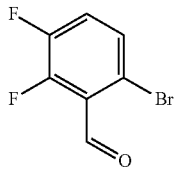 [SMILES: O=Cc1c(Br)ccc(F)c1F]

4-Bromo-1,2-difluorobenzene (5.00 g, 25.9 mmol) was dissolved in tetrahydrofuran (100 mL) and cooled to −78° C. Lithium diisopropyl amide (1.8 M in tetrahydrofuran, 15.8 mL, 28.5 mmol) was added. After stirring at −78° C. for 30 min, N,N-dimethylformamide (2.28 g, 31.1 mmol) was added. After stirring at −78° C. for an additional 15 min, acetic acid (6 mL) and water (100 mL) was added and the mixture was warmed to RT. After extraction with ethyl acetate, the organic phase was washed with 1 M hydrochloride acid solution and brine, and dried over magnesium sulfate. Concentration in vacuo afforded the title compound (2.59 g, 52% of theory).

GC-MS (Method 2G): $R_t$=3.28 min, MS (ESIPos): m/z=221 [M+H]$^+$

Example 111A

6-Bromo-2,3-difluorobenzonitrile

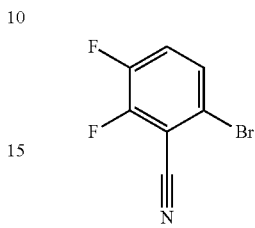

A mixture of 6-bromo-2,3-difluorobenzaldehyde (2.59 g, 11.7 mmol), sodium lauryl sulfate (0.68 g, 2.34 mmol), (Diacetoxyiodo)benzene (5.66 g, 17.6 mmol) and ammonium acetate (4.52 g, 58.6 mmol) in water (12 mL) was stirred at 70° C. for 30 min. After cooling to RT, a solution of sodium thiosulfate (2.08 g, 13.1 mmol) in water (2.2 mL) was added and the mixture was stirred at RT for 15 min. After extraction with dichloromethane, the organic phase was dried over magnesium sulfate. Concentration in vacuo and purification by preparative HPLC (Method 1A) afforded the title compound (0.78 g, 31% of theory).

GC-MS (Method 1G): $R_t$=3.59 min, MS (ESIPos): m/z=217 [M+H]$^+$

Example 112A

4-Bromo-7-fluoro-1H-indazol-3-amine

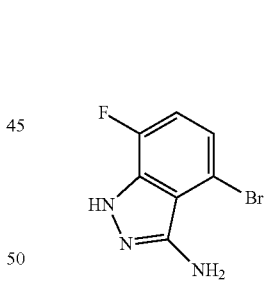

6-Bromo-2,3-difluorobenzonitrile (0.78 g, 3.58 mmol) was dissolved in ethanol (10 mL) and treated with hydrazine hydrate (0.72 g, 14.3 mmol). After stirring at reflux for 4 h, the mixture was cooled to RT and concentrated in vacuo. The residue was dissolved in a mixture of water and ethyl acetate. The aqueous layer was extracted once more with ethyl acetate. The combined organic layers were washed with water and with brine, dried over magnesium sulfate, concentrated in vacuo and dried to yield the title compound (0.77 g, 94% of theory).

LC-MS (Method 2B): $R_t$=1.83 min, MS (ESIPos): m/z=230 [M+H]$^+$

Example 113A

Tert-butyl 4-(10-bromo-7-fluoro-2-oxo-1,2-dihydropyrimido[1,2-b]indazol-4-yl)piperidine-1-carboxylate

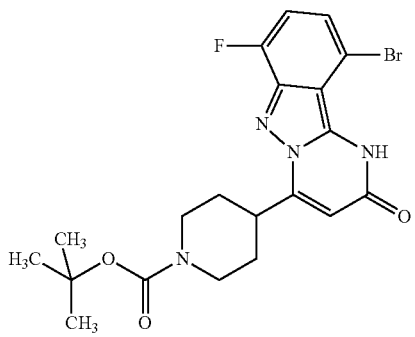 [SMILES: CC(C)(C)OC(=O)N1CCC(c2cc(=O)[nH]c3c4c(Br)ccc(F)c4nn23)CC1]

4-Bromo-7-fluoro-1H-indazol-3-amine (0.77 g, 3.36 mmol) and tert-butyl 4-[(2,2-dimethyl-4,6-dioxo-1,3-dioxan-5-yl)carbonyl]piperidine-1-carboxylate (1.31 g, 3.70 mmol) were dissolved in acetonitrile (30 mL) and refluxed for 4 h. After cooling to RT, the solvent was removed in vacuo and the residue was dissolved in 1-methoxy-2-propanol (10 mL). Potassium phosphate (1.37 g, 6.46 mmol) was added and the mixture was stirred at reflux for 4 h. After concentration in vacuo, the residue was dissolved in water and extracted with ethyl acetate. The organic phase was washed with brine and dried over magnesium sulfate. Concentration in vacuo and recrystallization from acetonitrile/methanol afforded the title compound (0.48 g, 32% of theory).

LC-MS (Method 1B): $R_t$=1.16 min, MS (ESIPos): m/z=465 [M+H]$^+$

Example 114A

Tert-butyl 4-(10-sec-butyl-2-oxo-1,2-dihydropyrimido[1,2-b]indazol-4-yl)piperidine-1-carboxylate

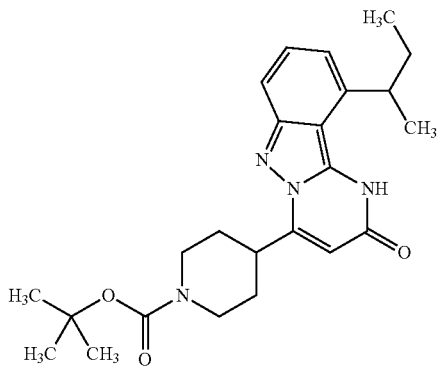 [SMILES: CCC(C)c1cccc2nn3c(C4CCN(C(=O)OC(C)(C)C)CC4)cc(=O)[nH]c3c12]

Under argon, a mixture of tert-butyl 4-(10-chloro-2-oxo-1,2-dihydropyrimido[1,2-b]indazol-4-yl)piperidine-1-carboxylate (0.11 g, 0.27 mmol), [(2-dicyclohexylphosphino-2',6'-bis(N,N-dimethylamino)-1,1'-biphenyl)-2-(2'-amino-1,1'-biphenyl)]palladium(II) methanesulfonate (0.04 g, 0.055 mmol), and 2-dicyclohexylphosphino-2',6'-bis(N,N-dimethylamino)biphenyl (0.02 g, 0.055 mmol) was suspended in tetrahydrofuran (5 mL). Lithium chloride (0.5 M in tetrahydrofuran, 5.50 mL, 2.73 mmol) was added and the mixture was cooled to 0° C. Isopropylzinc bromide (0.5 M in tetrahydrofuran, 5.50 mL, 2.73 mmol) was added dropwise. After stirring at RT for 16 h, the mixture was quenched with water, extracted with ethyl acetate and dried over magnesium sulfate. Concentration in vacuo and purification by preparative HPLC (Method 1A) afforded the title compound (28 mg, 24% of theory).

LC-MS (Method 1B): $R_t$=1.26 min, MS (ESIPos): m/z=425 [M+H]$^+$

Example 115A

Tert-butyl 4-(10-isobutyl-2-oxo-1,2-dihydropyrimido[1,2-b]indazol-4-yl)piperidine-1-carboxylate

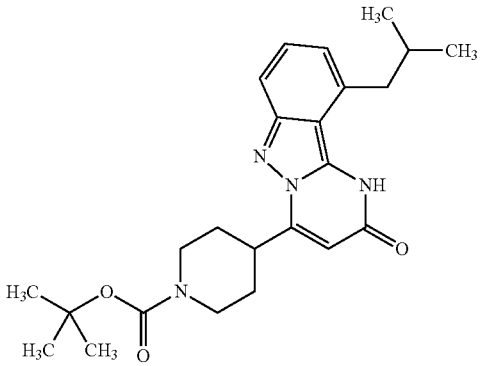 [SMILES: CC(C)Cc1cccc2nn3c(C4CCN(C(=O)OC(C)(C)C)CC4)cc(=O)[nH]c3c12]

Under argon, a mixture of tert-butyl 4-(10-chloro-2-oxo-1,2-dihydropyrimido[1,2-b]indazol-4-yl)piperidine-1-carboxylate (0.20 g, 0.50 mmol), [(2-dicyclohexylphosphino-2',6'-bis(N,N-dimethylamino)-1,1'-biphenyl)-2-(2'-amino-1,1'-biphenyl)]palladium(II) methanesulfonate (0.08 g, 0.10 mmol), and 2-dicyclohexylphosphino-2',6'-bis(N,N-dimethylamino)biphenyl (0.04 g, 0.10 mmol) was suspended in tetrahydrofuran (10 mL). Lithium chloride (0.5 M in tetrahydrofuran, 9.90 mL, 4.96 mmol) was added and the mixture was cooled to 0° C. Isopropylzinc bromide (0.5 M in tetrahydrofuran, 9.90 mL, 4.96 mmol) was added dropwise. After stirring at RT for 16 h, the mixture was quenched with water, extracted with ethyl acetate and dried over magnesium sulfate. Concentration in vacuo and purification by preparative HPLC (Method 1A) afforded the title compound (98 mg, 47% of theory).

LC-MS (Method 1B): $R_t$=1.30 min, MS (ESIPos): m/z=425 [M+H]$^+$

Example 116A

2-Bromo-6-fluoro-3-methylbenzaldehyde

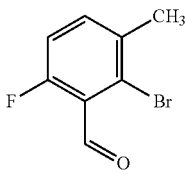

2-Bromo-4-fluoro-1-methylbenzene (5.00 g, 25.9 mmol) was dissolved in tetrahydrofuran (100 mL) and cooled to −78° C. Lithium diisopropyl amide (1.8 M in tetrahydrofuran, 16.2 mL, 29.1 mmol) was added. After stirring at −78° C. for 30 min, N,N-dimethylformamide (2.32 g, 31.7 mmol) was added. After stirring at −78° C. for an additional 15 min, acetic acid (6 mL) and water (100 mL) was added and the mixture was warmed to RT. After extraction with ethyl acetate, the organic phase was washed with 1 M hydrochloride acid solution and brine, and dried over magnesium sulfate. Concentration in vacuo afforded the title compound (6.05 g, 84% of theory) in a purity of 80%.

GC-MS (Method 1G): $R_t$=4.38 min, MS (ESIPos): m/z=217 [M+H]$^+$

Example 117A

2-Bromo-6-fluoro-3-methylbenzonitrile

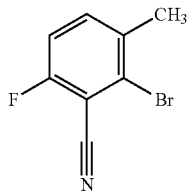

A mixture of 2-bromo-3,6-difluorobenzaldehyde (80% purity, 6.05 g, 22.2 mmol), sodium lauryl sulfate (1.61 g, 5.57 mmol), (Diacetoxyiodo)benzene (13.5 g, 41.8 mmol) and ammonium acetate (10.7 g, 139.4 mmol) in water (30 mL) was stirred at 70° C. for 30 min. After cooling to RT, a solution of sodium thiosulfate (4.94 g, 31.2 mmol) in water (5 mL) was added and the mixture was stirred at RT for 15 min. After extraction with dichloromethane, the organic phase was dried over magnesium sulfate and concentrated in vacuo. A portion of the residue was purified by preparative HPLC (Method 1A) to afford the title compound (1.03 g).

GC-MS (Method 1G): $R_t$=4.46 min, MS (ESIPos): m/z=213 [M+H]$^+$

Example 118A

4-Bromo-5-methyl-1H-indazol-3-amine

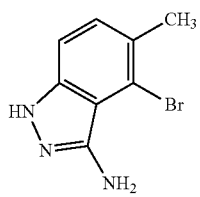

2-Bromo-6-fluoro-3-methylbenzonitrile (0.30 g, 1.40 mmol) was dissolved in ethanol (2 mL) and treated with hydrazine hydrate (0.28 g, 5.6 mmol). After stirring at reflux for 4 h, the mixture was cooled to RT and concentrated in vacuo. The residue was dissolved in a mixture of water and ethyl acetate. The aqueous layer was extracted once more with ethyl acetate. The combined organic layers were washed with water and with brine, dried over magnesium sulfate, concentrated in vacuo and dried to yield the title compound (0.28 g, 62% of theory) in a purity of 70%.

LC-MS (Method 2B): $R_t$=1.90 min, MS (ESIPos): m/z=226 [M+H]$^+$

Example 119A

Tert-butyl 4-(10-bromo-9-methyl-2-oxo-1,2-dihydropyrimido[1,2-b]indazol-4-yl)piperidine-1-carboxylate

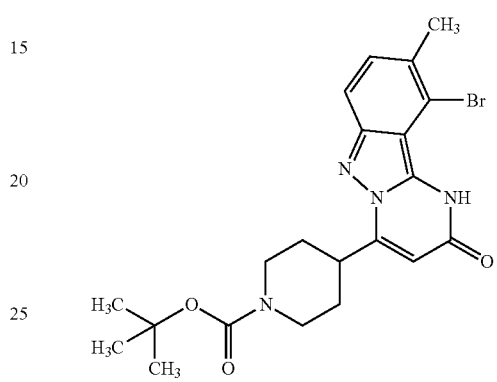

4-Bromo-5-methyl-1H-indazol-3-amine (70% purity, 0.28 g, 0.86 mmol) and tert-butyl 4-[(2,2-dimethyl-4,6-dioxo-1,3-dioxan-5-yl)carbonyl]piperidine-1-carboxylate (0.48 g, 1.36 mmol) were dissolved in acetonitrile (12 mL) and refluxed for 4 h. After cooling to RT, the solvent was removed in vacuo and the residue was dissolved in 1-methoxy-2-propanol (5 mL). Potassium phosphate (0.53 g, 2.47 mmol) was added and the mixture was stirred at 70° C. for 6 h. Concentration in vacuo and purification via preparative HPLC (Method 1A) afforded the title compound (0.22 g, 56% of theory).

LC-MS (Method 1B): $R_t$=1.21 min, MS (ESIPos): m/z=461 [M+H]$^+$

Example 120A

6-Bromo-2-fluoro-3-methylbenzaldehyde

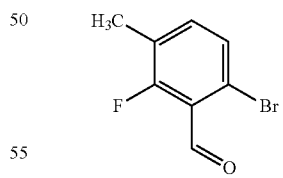

4-Bromo-2-fluoro-1-methylbenzene (5.00 g, 26.5 mmol) was dissolved in tetrahydrofuran (100 mL) and cooled to −78° C. Lithium diisopropyl amide (1.8 M in tetrahydrofuran, 16.2 mL, 29.1 mmol) was added. After stirring at −78° C. for 30 min, N,N-dimethylformamide (2.32 g, 31.7 mmol) was added. After stirring at −78° C. for an additional 15 min, acetic acid (6 mL) and water (100 mL) was added and the mixture was warmed to RT. After extraction with ethyl acetate, the organic phase was washed with 1 M hydrochloride acid solution and brine, and dried over magnesium sulfate. Concentration in vacuo afforded the title compound (5.63 g, 83% of theory) in a purity of 85%.

GC-MS (Method 1G): $R_t$=4.35 min, MS (ESIPos): m/z=217 [M+H]$^+$

Example 121A

6-Bromo-2-fluoro-3-methylbenzonitrile

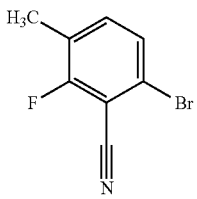

A mixture of 6-bromo-2-fluoro-3-methylbenzaldehyde (85% purity, 5.63 g, 22.1 mmol), sodium lauryl sulfate (1.50 g, 5.19 mmol), (Diacetoxyiodo)benzene (12.5 g, 38.9 mmol) and ammonium acetate (10.0 g, 129.7 mmol) in water (30 mL) was stirred at 70° C. for 30 min. After cooling to RT, a solution of sodium thiosulfate (4.60 g, 29.1 mmol) in water (5 mL) was added and the mixture was stirred at RT for 15 min. After extraction with dichloromethane, the organic phase was dried over magnesium sulfate and concentrated in vacuo. A portion of the residue was purified by preparative HPLC (Method 1A) to afford the title compound (0.45 g).

Example 122A

Tert-butyl 4-(10-bromo-7-methyl-2-oxo-1,2-dihydropyrimido[1,2-b]indazol-4-yl)piperidine-1-carboxylate

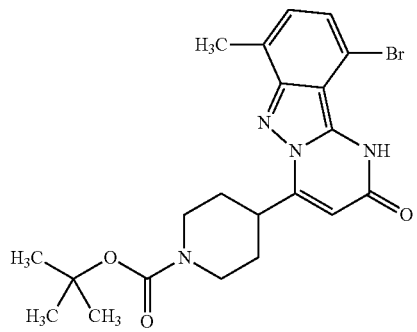 [SMILES: Cc1ccc(Br)c2c1nn1c(C3CCN(C(=O)OC(C)(C)C)CC3)cc(=O)[nH]c21]

6-Bromo-2-fluoro-3-methylbenzonitrile (0.45 g, 2.09 mmol) was dissolved in ethanol (3 mL) and treated with hydrazine hydrate (0.42 g, 8.37 mmol). After stirring at reflux for 4 h, the mixture was cooled to RT and concentrated in vacuo. The residue was dissolved in a mixture of water and ethyl acetate. The aqueous layer was extracted once more with ethyl acetate. The combined organic layers were washed with water and with brine, dried over magnesium sulfate, and concentrated in vacuo.

The residue and tert-butyl 4-[(2,2-dimethyl-4,6-dioxo-1,3-dioxan-5-yl)carbonyl]piperidine-1-carboxylate (0.82 g, 2.30 mmol) were dissolved in acetonitrile (20 mL) and refluxed for 4 h. After cooling to RT, the solvent was removed in vacuo and the residue was dissolved in 1-methoxy-2-propanol (9 mL). Potassium phosphate (0.89 g, 4.17 mmol) was added and the mixture was stirred at 70° C. for 6 h. Concentration in vacuo and purification via preparative HPLC (Method 1A) afforded the title compound (0.47 g, 49% of theory).

LC-MS (Method 1B): $R_t$=1.25 min, MS (ESIPos): m/z=461 [M+H]$^+$

Example 123A

4-Isopropoxy-1H-indazol-3-amine

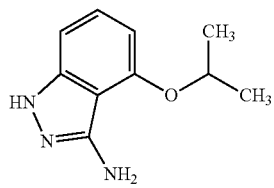

2-Fluoro-6-isopropoxybenzonitrile (0.50 g, 2.79 mmol) was dissolved in ethanol (10 mL) and treated with hydrazine hydrate (0.56 g, 11.2 mmol). After stirring at reflux for 8 h, the mixture was cooled to RT and concentrated in vacuo. The residue was dissolved in a mixture of water and ethyl acetate. The aqueous layer was extracted once more with ethyl acetate. The combined organic layers were washed with water and with brine, dried over magnesium sulfate, concentrated in vacuo and dried to yield the title compound (0.53 g, 90% of theory) in a purity of 90%.

LC-MS (Method 2B): $R_t$=1.90 min, MS (ESIPos): m/z=192 [M+H]$^+$

Example 124A

Tert-butyl 4-(10-isopropoxy-2-oxo-1,2-dihydropyrimido[1,2-b]indazol-4-yl)piperidine-1-carboxylate

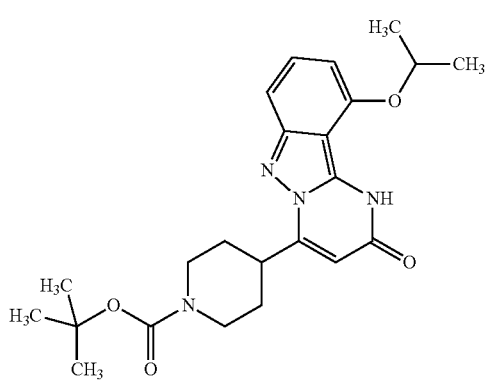 [SMILES: CC(C)Oc1cccc2nn3c(C4CCN(C(=O)OC(C)(C)C)CC4)cc(=O)[nH]c3c12]

4-Isopropoxy-1H-indazol-3-amine (90% purity, 0.52 g, 2.45 mmol) and tert-butyl 4-[(2,2-dimethyl-4,6-dioxo-1,3-dioxan-5-yl)carbonyl]piperidine-1-carboxylate (1.06 g, 2.99 mmol) were dissolved in acetonitrile (25 mL) and refluxed for 4 h. After cooling to RT, the solvent was removed in vacuo and the residue was dissolved in 1-methoxy-2-propanol (20 mL). Potassium phosphate (0.82 g, 3.88 mmol) was added and the mixture was stirred at 70° C. for 6 h. Concentration in vacuo and purification via preparative HPLC (Method 1A) afforded the title compound (0.14 g, 18% of theory).

LC-MS (Method 1B): $R_t$=1.16 min, MS (ESIPos): m/z=427 [M+H]$^+$

Example 125A

Tert-butyl 4-(9-fluoro-2-oxo-10-phenyl-1,2-dihydropyrimido[1,2-b]indazol-4-yl)piperidine-1-carboxylate

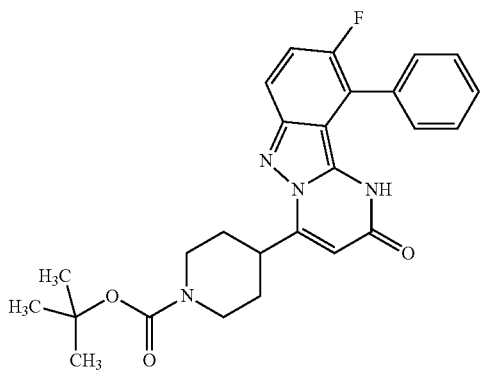 [SMILES: CC(C)(C)OC(=O)N1CCC(c2cc(=O)[nH]c3c4c(-c5ccccc5)c(F)ccc4nn23)CC1]

Under argon, tert-butyl 4-(10-bromo-9-fluoro-2-oxo-1,2-dihydropyrimido[1,2-b]indazol-4-yl)piperidine-1-carboxylate (0.15 g, 0.32 mmol), phenylboronic acid (0.043 g, 0.36 mmol) and (2-dicyclohexylphosphino-2',4',6'-triisopropyl-1,1'-biphenyl) [2-(2'-amino-1,1'-biphenyl)]palladium(II) methanesulfonate (8 mg, 10 μmol) were dissolved in degassed tetrahydrofuran (3 mL). Potassium phosphate solution (1 M in water, degassed) (1.90 mL, 1.90 mmol) was added and the mixture was stirred at 40° C. for 10 min. The mixture was diluted with water, and extracted with dichloromethane. The organic phase was dried over magnesium sulfate and concentrated in vacuo. Purification by preparative HPLC (Method 1A) afforded the title compound (69 mg, 46% of theory).

LC-MS (Method 1B): $R_t$=1.21 min, MS (ESIPos): m/z=463 [M+H]$^+$

Example 126A

2',3,6'-Trifluorobiphenyl-2-carbonitrile

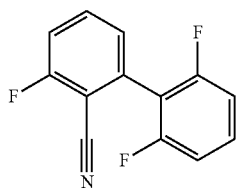

Under argon, 2-bromo-6-fluorobenzonitrile (0.50 g, 2.50 mmol), 2,6-difluorophenylboronic acid (0.443 g, 2.75 mmol) and (2-dicyclohexylphosphino-2',4',6'-triisopropyl-1,1'-biphenyl)[2-(2'-amino-1,1'-biphenyl)]palladium(II) methanesulfonate (63 mg, 0.08 mmol) were dissolved in degassed tetrahydrofuran (30 mL). Potassium phosphate solution (1 M in water, degassed) (14.8 mL, 14.8 mmol) was added and the mixture was stirred at RT for 16 h. The mixture was concentrated in vacuo. Purification by preparative HPLC (Method 1A) afforded the title compound (0.19 g, 32% of theory).

GC-MS (Method 1G): $R_t$=5.34 min, MS (ESIPos): m/z=233 [M]

Example 127A

Tert-butyl 4-[10-(2,6-difluorophenyl)-2-oxo-1,2-dihydropyrimido[1,2-b]indazol-4-yl]piperidine-1-carboxylate

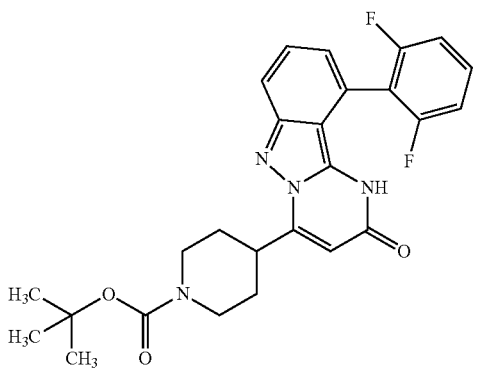 [SMILES: CC(C)(C)OC(=O)N1CCC(c2cc(=O)[nH]c3c4c(-c5c(F)cccc5F)cccc4nn23)CC1]

2',3,6'-Trifluorobiphenyl-2-carbonitrile (0.19 g, 0.79 mmol) was dissolved in ethanol (1 mL) and treated with hydrazine hydrate (0.16 g, 3.17 mmol). After stirring at reflux for 4 h, an additional portion of hydrazine hydrate (0.16 g, 3.17 mmol) was added at RT and stirring was resumed at reflux for 4 h. The mixture was cooled to RT and concentrated in vacuo. The residue was dissolved in a mixture of water and ethyl acetate. The aqueous layer was extracted once more with ethyl acetate. The combined organic layers were washed with water and with brine, dried over magnesium sulfate, and concentrated in vacuo. The residue and tert-butyl 4-[(2,2-dimethyl-4,6-dioxo-1,3-dioxan-5-yl)carbonyl]piperidine-1-carboxylate (0.31 g, 0.87 mmol) were dissolved in acetonitrile (8 mL) and refluxed for 4 h. After cooling to RT, the solvent was removed in vacuo and the residue was dissolved in 1-methoxy-2-propanol (5 mL). Potassium phosphate (0.33 g, 1.58 mmol) was added and the mixture was stirred at 70° C. for 6 h. Concentration in vacuo and purification via preparative HPLC (Method 1A) afforded the title compound (0.11 g, 28% of theory).

LC-MS (Method 1B): $R_t$=1.23 min, MS (ESIPos): m/z=481 [M+H]$^+$

Example 128A

2-Chloro-6-fluoro-4-methylbenzaldehyde

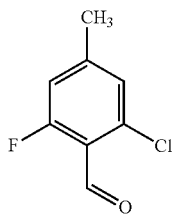

1-Chloro-3-fluoro-5-methylbenzene (5.00 g, 34.6 mmol) was dissolved in tetrahydrofuran (100 mL) and cooled to −78° C. Lithium diisopropyl amide (1.8 M in tetrahydrofuran, 21.1 mL, 38.0 mmol) was added. After stirring at −78° C. for 30 min, N,N-dimethylformamide (3.03 g, 41.5 mmol) was added. After stirring at −78° C. for an additional 15 min, acetic acid (8 mL) and water (100 mL) was added and the mixture was warmed to RT. After extraction with ethyl acetate, the organic phase was washed with 1 M hydrochloride acid solution and brine, and dried over magnesium sulfate. Concentration in vacuo afforded the title compound (2.83 g, 43% of theory) in a purity of 90%.

GC-MS (Method 1G): $R_t$=3.91 min, MS (ESIPos): m/z=171 [M+H]$^+$

Example 129A

2-Chloro-6-fluoro-4-methylbenzonitrile

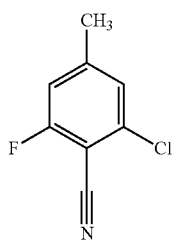

A mixture of 2-chloro-6-fluoro-4-methylbenzaldehyde (90% purity, 2.80 g, 14.6 mmol), sodium lauryl sulfate (0.94 g, 3.25 mmol), (Diacetoxyiodo)benzene (7.4 g, 24.3 mmol) and ammonium acetate (6.25 g, 81.1 mmol) in water (20 mL) was stirred at 70° C. for 30 min. After extraction with dichloromethane, the organic phase was dried over magnesium sulfate and concentrated in vacuo. Purification by preparative HPLC (Method 1A) afforded the title compound (1.34 g).

GC-MS (Method 1G): $R_t$=3.92 min, MS (ESIPos): m/z=169 [M+H]$^+$

Example 130A

4-Chloro-6-methyl-1H-indazol-3-amine

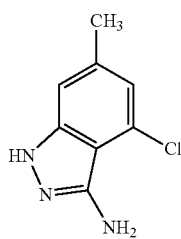

2-Chloro-6-fluoro-4-methylbenzonitrile (1.33 g, 7.84 mmol) was dissolved in ethanol (40 mL) and treated with hydrazine hydrate (1.57 g, 31.3 mmol). After stirring at reflux for 4 h, the mixture was cooled to RT and concentrated in vacuo. The residue was dissolved in a mixture of water and ethyl acetate. The aqueous layer was extracted once more with ethyl acetate. The combined organic layers were washed with water and with brine, dried over magnesium sulfate, concentrated in vacuo and dried to yield the title compound (1.20 g, 85% of theory).

LC-MS (Method 2B): $R_t$=1.88 min, MS (ESIPos): m/z=182 [M+H]$^+$

Example 131A

Tert-butyl 4-(10-chloro-8-methyl-2-oxo-1,2-dihydropyrimido[1,2-b]indazol-4-yl)piperidine-1-carboxylate

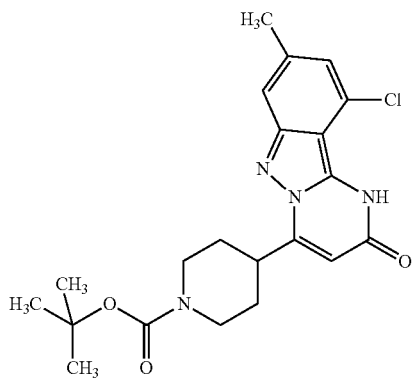 [SMILES: Cc1cc(Cl)c2c(c1)nn1c(C3CCN(C(=O)OC(C)(C)C)CC3)cc(=O)[nH]c21]

4-Chloro-6-methyl-1H-indazol-3-amine (0.40 g, 2.20 mmol) and tert-butyl 4-[(2,2-dimethyl-4,6-dioxo-1,3-dioxan-5-yl)carbonyl]piperidine-1-carboxylate (0.86 g, 2.42 mmol) were dissolved in acetonitrile (18 mL) and refluxed for 2 h. After cooling to RT, the solvent was removed in vacuo and the residue was dissolved in 1-methoxy-2-propanol (18 mL). Potassium phosphate (0.74 g, 3.47 mmol) was added and the mixture was stirred at 70° C. for 6 h. After concentration in vacuo, the residue was taken up in water and extracted with dichloromethane. The organic phase was dried over magnesium sulfate and concentrated in vacuo. Purification via preparative HPLC (Method 1A) afforded the title compound (0.32 g, 45% of theory).

LC-MS (Method 1B): $R_t$=1.15 min, MS (ESIPos): m/z=417 [M+H]$^+$

Example 132A

Tert-butyl 4-{2-oxo-10-[2-(trifluoromethoxy)phenyl]-1,2-dihydropyrimido[1,2-b]indazol-4-yl}piperidine-1-carboxylate

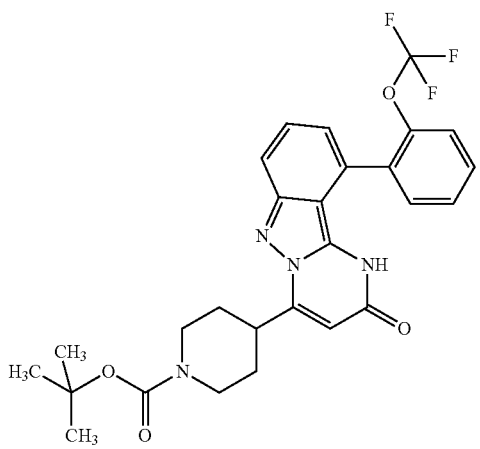 [SMILES: CC(C)(C)OC(=O)N1CCC(c2cc(=O)[nH]c3c4c(-c5ccccc5OC(F)(F)F)cccc4nn23)CC1]

Under argon, tert-butyl 4-(10-bromo-2-oxo-1,2-dihydropyrimido[1,2-b]indazol-4-yl)piperidine-1-carboxylate (0.20 g, 0.48 mmol), 2-trifluoromethoxyphenylboronic acid (0.10 g, 0.49 mmol) and (2-dicyclohexylphosphino-2',4',6'-triisopropyl-1,1'-biphenyl) [2-(2'-amino-1,1'-biphenyl)]palladium(II) methanesulfonate (11 mg, 13 μmol) were dissolved in degassed tetrahydrofuran (4 mL). Potassium phosphate solution (1 M in water, degassed) (2.55 mL, 2.55 mmol) was added and the mixture was stirred at 40° C. for 2.5 h. The mixture was diluted with water, and extracted with ethyl acetate. The organic phase was dried over magnesium sulfate and concentrated in vacuo. Purification by preparative HPLC (Method 1A) afforded the title compound (107 mg, 45% of theory).

LC-MS (Method 1B): $R_t$=1.27 min, MS (ESIPos): m/z=529 [M+H]$^+$

Example 133A

2-Bromo-4,6-difluorobenzaldehyde

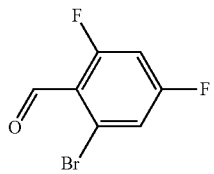 [SMILES: O=Cc1c(F)cc(F)cc1Br]

1-Bromo-3,5-difluoro-2-iodobenzene (5.00 g, 15.7 mmol) was dissolved in 2-methyltetrahydrofuran (30 mL) and cooled to 0° C. Isopropylmagnesium chloride lithium chloride complex (1.3 M in tetrahydrofuran, 12.7 mL, 16.5 mmol) was added dropwise. After stirring at 0° C. for 30 min, 4-formylmorpholine (1.99 g, 17.2 mmol) was added. The mixture was warmed to RT and stirred at RT for 4 h. The mixture was quenched with hydrochloric acid (1M in water), diluted with water, and extracted with ethyl acetate. The organic phase was washed with hydrochloric acid (1M in water), water, and brine, and dried over magnesium sulfate. Concentration in vacuo afforded the title compound (2.70 g, 70% of theory) in a purity of 92%.

GC-MS (Method 1G): $R_t$=3.37 min, MS (ESIPos): m/z=219 [M+H]$^+$

Example 134A

2-Bromo-4,6-difluorobenzonitrile

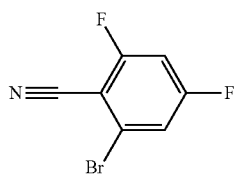 [SMILES: N#Cc1c(F)cc(F)cc1Br]

A mixture of 2-bromo-4,6-difluorobenzaldehyde (92% purity, 2.68 g, 11.1 mmol), sodium lauryl sulfate (0.70 g, 2.43 mmol), (Diacetoxyiodo)benzene (5.86 g, 18.2 mmol) and ammonium acetate (4.67 g, 60.6 mmol) in water (20 mL) was stirred at 70° C. for 30 min. After extraction with dichloromethane, the organic phase was dried over magnesium sulfate and concentrated in vacuo to afford the title compound (0.50 g, 16% of theory) in a purity of 90%.

GC-MS (Method 1G): $R_t$=3.36 min, MS (ESIPos): m/z=217 [M+H]$^+$

Example 135A

4-Bromo-6-fluoro-1H-indazol-3-amine

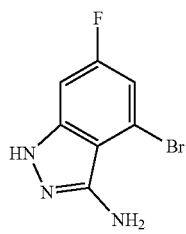

2-Bromo-4,6-difluorobenzonitrile (90% purity, 0.45 g, 1.85 mmol) was dissolved in ethanol (10 mL) and treated with hydrazine hydrate (0.41 g, 8.3 mmol). After stirring at reflux for 4 h, the mixture was cooled to RT and concentrated in vacuo. The residue was dissolved in a mixture of water and ethyl acetate. The aqueous layer was extracted once more with ethyl acetate. The combined organic layers were washed with water and with brine, dried over magnesium sulfate, concentrated in vacuo and dried to yield a mixture containing the title compound (0.38 g, 20% of theory) in a purity of 25% which was taken to the next step without further purification.

LC-MS (Method 2B): $R_t$=1.86 min, MS (ESIPos): m/z=230 [M+H]$^+$

Example 136A

Tert-butyl 4-(10-bromo-8-fluoro-2-oxo-1,2-dihydro-pyrimido[1,2-b]indazol-4-yl)piperidine-1-carboxylate

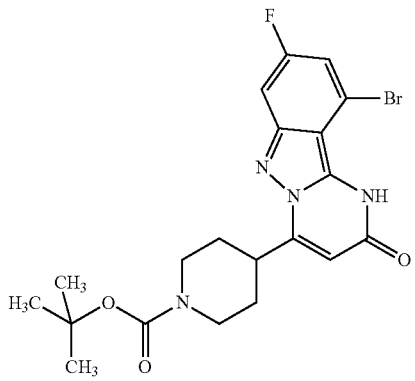

4-Bromo-6-fluoro-1H-indazol-3-amine (25% purity, 0.38 g, 0.41 mmol) and tert-butyl 4-[(2,2-dimethyl-4,6-dioxo-1,3-dioxan-5-yl)carbonyl]piperidine-1-carboxylate (0.65 g, 1.82 mmol) were dissolved in acetonitrile (10 mL) and refluxed for 2 h. After cooling to RT, the solvent was removed in vacuo and the residue was dissolved in 1-methoxy-2-propanol (10 mL). Potassium phosphate (0.49 g, 2.32 mmol) was added and the mixture was stirred at 100° C. for 2 h. After concentration in vacuo, the residue was taken up in water and extracted with ethyl acetate. The organic phase was washed with water and brine, dried over magnesium sulfate, and concentrated in vacuo. Purification via preparative HPLC (Method 1A) afforded the title compound (23 mg, 17% of theory).

LC-MS (Method 1B): $R_t$=1.19 min, MS (ESIPos): m/z=465 [M+H]$^+$

Example 137A

2-Fluoro-6-(pyridin-2-yl)benzonitrile

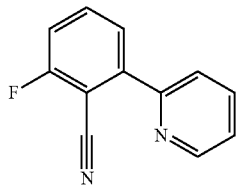 [SMILES: N#Cc1c(F)cccc1-c1ccccn1]

Under argon, 2-pyridylzinc bromide (0.5 M in tetrahydrofuran, 13 mL, 6.5 mmol) was diluted with tetrahydrofuran (10 mL), and 2-bromo-6-fluorobenzonitrile (1.00 g, 5.00 mmol), (2-dicyclohexylphosphino-2',4',6'-triisopropyl-1,1'-biphenyl)[2-(2'-amino-1,1'-biphenyl)]palladium(II) methanesulfonate (127 mg, 150 μmol), 2-dicyclohexylphosphino-2',4',6'-triisopropyl-1,1'-biphenyl (72 mg, 150 μmol) were added. After stirring at RT for 16 h, the mixture was diluted with ethyl acetate. The organic phase was washed with water and brine, dried over magnesium sulfate, and concentrated in vacuo. Purification via preparative HPLC (Method 1A) afforded the title compound (263 mg, 27% of theory).

LC-MS (Method 3B): $R_t$=1.81 min, MS (ESIPos): m/z=199 [M+H]$^+$

Example 138A 4-(Pyridin-2-yl)-1H-indazol-3-amine

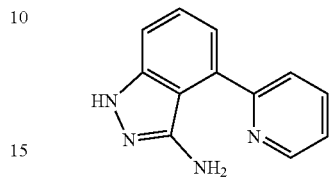

2-Fluoro-6-(pyridin-2-yl)benzonitrile (0.26 g, 1.31 mmol) was dissolved in ethanol (5 mL) and treated with hydrazine hydrate (0.26 g, 5.25 mmol). After stirring at reflux for 2 h, the mixture was cooled to RT and concentrated in vacuo. The residue was dissolved in a mixture of water and ethyl acetate. The aqueous layer was extracted once more with ethyl acetate. The combined organic layers were washed with water and with brine, dried over magnesium sulfate, concentrated in vacuo and dried to afford the title compound (0.31 g, 83% of theory) in a purity of 75%.

LC-MS (Method 1B): $R_t$=0.53 min, MS (ESIPos): m/z=211 [M+H]$^+$

Example 139A

Tert-butyl 4-[2-oxo-10-(pyridin-2-yl)-1,2-dihydro-pyrimido[1,2-b]indazol-4-yl]piperidine-1-carboxylate

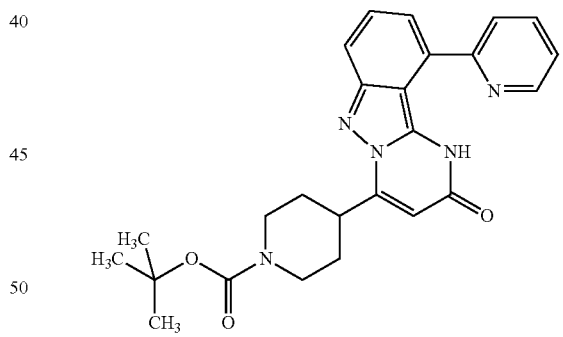

4-(Pyridin-2-yl)-1H-indazol-3-amine (75% purity, 0.31 g, 1.09 mmol) and tert-butyl 4-[(2,2-dimethyl-4,6-dioxo-1,3-dioxan-5-yl)carbonyl]piperidine-1-carboxylate (0.57 g, 1.60 mmol) were dissolved in acetonitrile (10 mL) and refluxed for 2 h. After cooling to RT, the solvent was removed in vacuo and the residue was dissolved in 1-methoxy-2-propanol (15 mL). Potassium phosphate (0.80 g, 3.75 mmol) was added and the mixture was stirred at 100° C. for 2 h. After concentration in vacuo, the residue was taken up in water and extracted with ethyl acetate. The organic phase was washed with water and brine, dried over magnesium sulfate, and concentrated in vacuo. Purification via preparative HPLC (Method 1A) afforded the title compound (0.34 g, 54% of theory).

LC-MS (Method 1B): $R_t$=1.14 min, MS (ESIPos): m/z=446 [M+H]$^+$

Example 140A

2-Fluoro-6-(1,3-thiazol-2-yl)benzonitrile

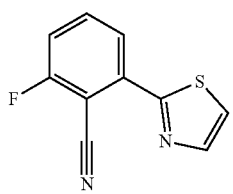 [SMILES: N#Cc1c(F)cccc1-c1nccs1]

Under argon, 2-thiazolozinc bromide (0.5 M in tetrahydrofuran, 13 mL, 6.5 mmol) was diluted with tetrahydrofuran (10 mL), and 2-bromo-6-fluorobenzonitrile (1.00 g, 5.00 mmol), (2-dicyclohexylphosphino-2',4',6'-triisopropyl-1,1'-biphenyl)[2-(2'-amino-1,1'-biphenyl)]palladium(II) methanesulfonate (127 mg, 150 µmol), 2-dicyclohexylphosphino-2',4',6'-triisopropyl-1,1'-biphenyl (72 mg, 150 µmol) were added. After stirring at RT for 16 h, the mixture was diluted with ethyl acetate. The organic phase was washed with water and brine, dried over magnesium sulfate, and concentrated in vacuo. Purification via preparative HPLC (Method 1A) afforded the title compound (248 mg, 24% of theory).

LC-MS (Method 1B): $R_t$=0.87 min, MS (ESIPos): m/z=205 [M+H]$^+$

Example 141A 4-(1,3-Thiazol-2-yl)-1H-indazol-3-amine

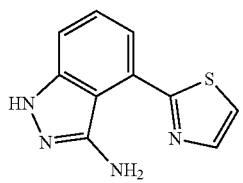

2-Fluoro-6-(1,3-thiazol-2-yl)benzonitrile (0.25 g, 1.21 mmol) was dissolved in ethanol (5 mL) and treated with hydrazine hydrate (0.24 g, 4.86 mmol). After stirring at reflux for 2 h, the mixture was cooled to RT and concentrated in vacuo. The residue was dissolved in a mixture of water and ethyl acetate. The aqueous layer was extracted once more with ethyl acetate. The combined organic layers were washed with water and with brine, dried over magnesium sulfate, concentrated in vacuo and dried to afford the title compound (0.29 g, 76% of theory) in a purity of 70%.

LC-MS (Method 1B): $R_t$=0.66 min, MS (ESIPos): m/z=217 [M+H]$^+$

Example 142A

Tert-butyl 4-[2-oxo-10-(1,3-thiazol-2-yl)-1,2-dihydropyrimido[1,2-b]indazol-4-yl]piperidine-1-carboxylate

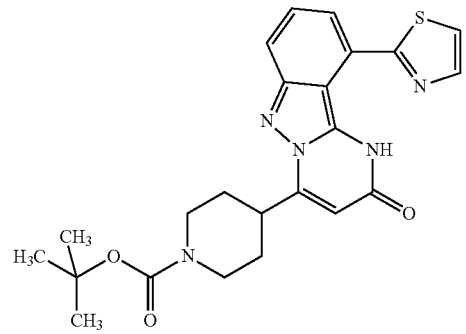 [SMILES: CC(C)(C)OC(=O)N1CCC(c2cc(=O)[nH]c3c4c(-c5nccs5)cccc4nn23)CC1]

4-(1,3-Thiazol-2-yl)-1H-indazol-3-amine (70% purity, 0.29 g, 0.98 mmol) and tert-butyl 4-[(2,2-dimethyl-4,6-dioxo-1,3-dioxan-5-yl)carbonyl]piperidine-1-carboxylate (0.55 g, 1.55 mmol) were dissolved in acetonitrile (10 mL) and refluxed for 2 h. After cooling to RT, the solvent was removed in vacuo and the residue was dissolved in 1-methoxy-2-propanol (15 mL). Potassium phosphate (0.74 g, 3.49 mmol) was added and the mixture was stirred at 100° C. for 2 h. After concentration in vacuo, the residue was taken up in water and extracted with ethyl acetate. The organic phase was washed with water and brine, dried over magnesium sulfate, and concentrated in vacuo. Purification via preparative HPLC (Method 1A) afforded the title compound (0.28 g, 50% of theory).

LC-MS (Method 1B): $R_t$=1.21 min, MS (ESIPos): m/z=452 [M+H]$^+$

Example 143A

Tert-butyl 4-[2-oxo-10-(3-thienyl)-1,2-dihydropyrimido[1,2-b]indazol-4-yl]piperidine-1-carboxylate

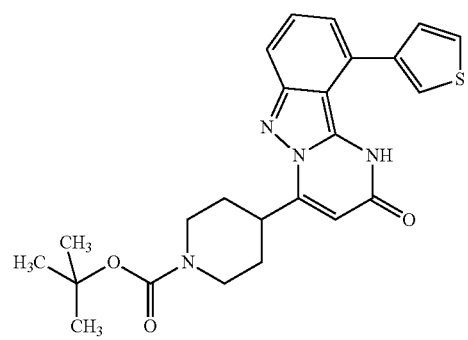 [SMILES: CC(C)(C)OC(=O)N1CCC(c2cc(=O)[nH]c3c4c(-c5ccsc5)cccc4nn23)CC1]

Under argon, tert-butyl 4-(10-bromo-2-oxo-1,2-dihydropyrimido[1,2-b]indazol-4-yl)piperidine-1-carboxylate (0.20 g, 0.48 mmol), 3-thienylboronic acid (63 mg, 0.49 mmol) and (2-dicyclohexylphosphino-2',4',6'-triisopropyl-1,1'-biphenyl) [2-(2'-amino-1,1'-biphenyl)]palladium(II) methanesulfonate (11 mg, 13 µmol) were dissolved in degassed tetrahydrofuran (4 mL). Potassium phosphate solution (1 M

Example 144A

Tert-butyl 4-[10-(2-methylphenyl)-2-oxo-1,2-dihydropyrimido[1,2-b]indazol-4-yl]piperidine-1-carboxylate

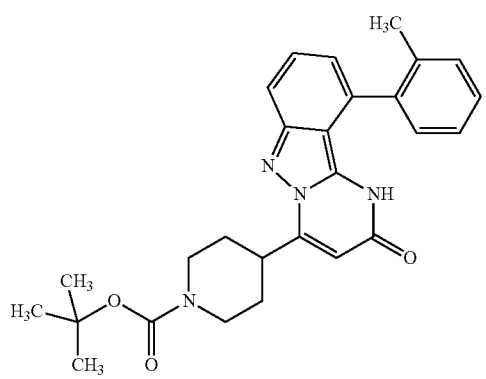 [SMILES: Cc1ccccc1-c1cccc2nn3c(C4CCN(C(=O)OC(C)(C)C)CC4)cc(=O)[nH]c3c12]

Under argon, tert-butyl 4-(10-bromo-2-oxo-1,2-dihydropyrimido[1,2-b]indazol-4-yl)piperidine-1-carboxylate (0.20 g, 0.48 mmol), 2-methylphenylboronic acid (67 mg, 0.49 mmol) and (2-dicyclohexylphosphino-2',4',6'-triisopropyl-1,1'-biphenyl) [2-(2'-amino-1,1'-biphenyl)]palladium(II) methanesulfonate (11 mg, 13 µmol) were dissolved in degassed tetrahydrofuran (4 mL). Potassium phosphate solution (1 M in water, degassed) (2.55 mL, 2.55 mmol) was added and the mixture was stirred at 40° C. for 16 h. The mixture was diluted with water, and extracted with dichloromethane. The organic phase was dried over magnesium sulfate and concentrated in vacuo. Purification by preparative HPLC (Method 1A) afforded the title compound (150 mg, 73% of theory).

LC-MS (Method 1B): $R_t$=1.26 min, MS (ESIPos): m/z=459 [M+H]$^+$

Example 145A

Tert-butyl 4-[10-(1-methyl-1H-pyrazol-5-yl)-2-oxo-1,2-dihydropyrimido[1,2-b]indazol-4-yl]piperidine-1-carboxylate

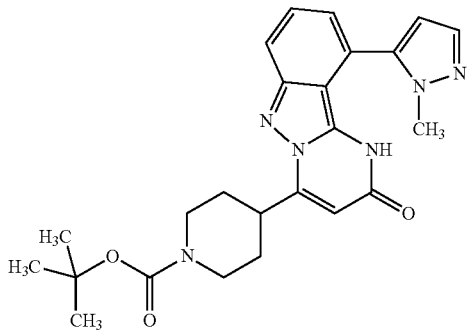 [SMILES: Cn1nccc1-c1cccc2nn3c(C4CCN(C(=O)OC(C)(C)C)CC4)cc(=O)[nH]c3c12]

Under argon, tert-butyl 4-(10-bromo-2-oxo-1,2-dihydropyrimido[1,2-b]indazol-4-yl)piperidine-1-carboxylate (0.20 g, 0.48 mmol), 1-methyl-5-(4,4,5,5-tetramethyl-1,3,2-dioxaborolan-2-yl)-1H-pyrazole (102 mg, 0.49 mmol) and (2-dicyclohexylphosphino-2',4',6'-triisopropyl-1,1'-biphenyl)[2-(2'-amino-1,1'-biphenyl)]palladium(II) methanesulfonate (11 mg, 13 mol) were dissolved in degassed tetrahydrofuran (4 mL). Potassium phosphate solution (1 M in water, degassed) (2.55 mL, 2.55 mmol) was added and the mixture was stirred at 40° C. for 48 h. Additional (2-dicyclohexylphosphino-2',4',6'-triisopropyl-1,1'-biphenyl)[2-(2'-amino-1,1'-biphenyl)]palladium(II) methanesulfonate (11 mg, 13 µmol) was added and the mixture was stirred at reflux for 16 h. The phases were separated and the organic phase was subjected to preparative HPLC (Method 1A) to afford the title compound (140 mg, 70% of theory).

LC-MS (Method 1B): $R_t$=1.05 min, MS (ESIPos): m/z=449 [M+H]$^+$

Example 146A

Tert-butyl 4-[10-(1-methyl-1H-pyrazol-4-yl)-2-oxo-1,2-dihydropyrimido[1,2-b]indazol-4-yl]piperidine-1-carboxylate

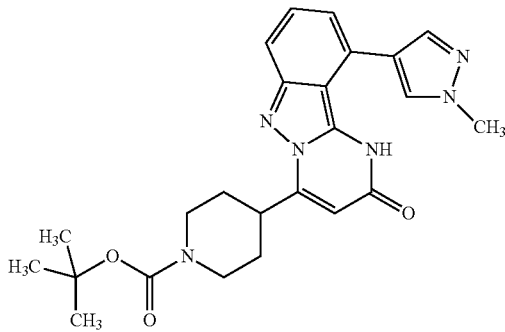 [SMILES: Cn1cc(-c2cccc3nn4c(C5CCN(C(=O)OC(C)(C)C)CC5)cc(=O)[nH]c4c23)cn1]

Under argon, tert-butyl 4-(10-bromo-2-oxo-1,2-dihydropyrimido[1,2-b]indazol-4-yl)piperidine-1-carboxylate (0.20 g, 0.48 mmol), (1-methyl-1H-pyrazol-4-yl)boronic acid (62 mg, 0.49 mmol) and (2-dicyclohexylphosphino-2',4',6'-tri-

--- in water, degassed) (2.55 mL, 2.55 mmol) was added and the mixture was stirred at 40° C. for 16 h. The mixture was diluted with water, and extracted with dichloromethane. The organic phase was dried over magnesium sulfate and concentrated in vacuo. Purification by preparative HPLC (Method 1A) afforded the title compound (98 mg, 49% of theory).

LC-MS (Method 1B): $R_t$=1.18 min, MS (ESIPos): m/z=451 [M+H]$^+$ isopropyl-1,1'-biphenyl) [2-(2'-amino-1,1'-biphenyl)]palladium(II) methanesulfonate (11 mg, 13 µmol) were dissolved in degassed tetrahydrofuran (4 mL). Potassium phosphate solution (1 M in water, degassed) (2.55 mL, 2.55 mmol) was added and the mixture was stirred at 40° C. for 48 h. Additional (2-dicyclohexylphosphino-2',4',6'-triisopropyl-1,1'-biphenyl)[2-(2'-amino-1,1'-biphenyl)]palladium(II) methanesulfonate (11 mg, 13 µmol) was added and the mixture was stirred at reflux for 16 h. The phases were separated and the organic phase was subjected to preparative HPLC (Method 1A) to afford the title compound (121 mg, 60% of theory).

LC-MS (Method 1B): $R_t$=1.03 min, MS (ESIPos): m/z=449 [M+H]$^+$

Example 147A

Tert-butyl 4-[2-oxo-10-(2-thienyl)-1,2-dihydropyrimido[1,2-b]indazol-4-yl]piperidine-1-carboxylate

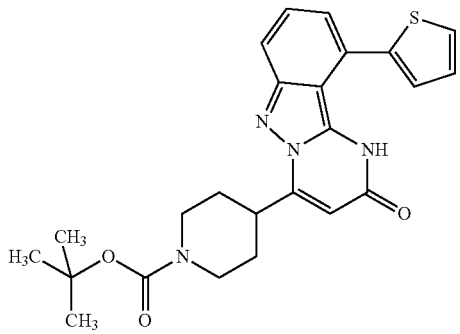 [SMILES: CC(C)(C)OC(=O)N1CCC(c2cc(=O)[nH]c3c4c(-c5cccs5)cccc4nn23)CC1]

Under argon, tert-butyl 4-(10-bromo-2-oxo-1,2-dihydropyrimido[1,2-b]indazol-4-yl)piperidine-1-carboxylate (0.20 g, 0.48 mmol), 2-thienylboronic acid (63 mg, 0.49 mmol) and (2-dicyclohexylphosphino-2',4',6'-triisopropyl-1,1'-biphenyl) [2-(2'-amino-1,1'-biphenyl)]palladium(II) methanesulfonate (11 mg, 13 µmol) were dissolved in degassed tetrahydrofuran (4 mL). Potassium phosphate solution (1 M in water, degassed) (2.55 mL, 2.55 mmol) was added and the mixture was stirred at 40° C. for 48 h. Additional (2-dicyclohexylphosphino-2',4',6'-triisopropyl-1,1'-biphenyl)[2-(2'-amino-1,1'-biphenyl)]palladium(II) methanesulfonate (11 mg, 13 µmol) was added and the mixture was stirred at reflux for 16 h. The phases were separated and the organic phase was subjected to preparative HPLC (Method 1A) to afford the title compound (121 mg, 60% of theory).

LC-MS (Method 1B): $R_t$=1.21 min, MS (ESIPos): m/z=451 [M+H]$^+$

Example 148A

2-Bromo-6-fluoro-4-methylbenzaldehyde

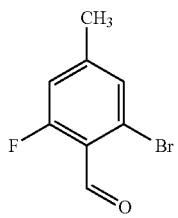

1-Bromo-3-fluoro-5-methylbenzene (5.00 g, 26.5 mmol) was dissolved in tetrahydrofuran (100 mL) and cooled to −78° C. Lithium diisopropyl amide (1.8 M in tetrahydrofuran, 16.2 mL, 29.1 mmol) was added. After stirring at −78° C. for 30 min, N,N-dimethylformamide (2.32 g, 31.7 mmol) was added.

After stirring at −78° C. for an additional 15 min, acetic acid (6 mL) and water (100 mL) was added and the mixture was warmed to RT. After extraction with ethyl acetate, the organic phase was washed with 1 M hydrochloride acid solution and brine, and dried over magnesium sulfate. Concentration in vacuo afforded the title compound (5.45 g, 95% of theory).

GC-MS (Method 1G): $R_t$=4.39 min, MS (ESIPos): m/z=217 [M+H]$^+$

Example 149A

2-Bromo-6-fluoro-4-methylbenzonitrile

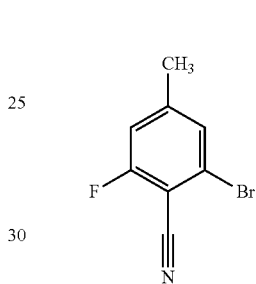

A mixture of 2-bromo-6-fluoro-4-methylbenzaldehyde (5.45 g, 25.1 mmol), sodium lauryl sulfate (1.45 g, 5.03 mmol), (Diacetoxyiodo)benzene (12.1 g, 37.7 mmol) and ammonium acetate (9.68 g, 125.6 mmol) in water (25 mL) was stirred at 70° C. for 30 min. After extraction with dichloromethane, the organic phase was dried over magnesium sulfate and concentrated in vacuo. Purification via preparative HPLC (Method 1A) afforded the title compound (4.26 g, 79% of theory).

GC-MS (Method 1G): $R_t$=4.43 min, MS (ESIPos): m/z=215 [M+H]$^+$

Example 150A

4-Bromo-6-methyl-1H-indazol-3-amine

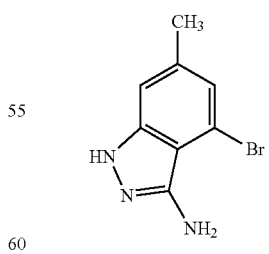

2-Bromo-6-fluoro-4-methylbenzonitrile (4.26 g, 19.9 mmol) was dissolved in ethanol (100 mL) and treated with hydrazine hydrate (3.99 g, 79.6 mmol). After stirring at reflux for 4 h, the mixture was cooled to RT and concentrated in vacuo. The residue was dissolved in a mixture of water and ethyl acetate. The aqueous layer was extracted once more with ethyl acetate. The combined organic layers were washed with water and with brine, dried over magnesium sulfate, concentrated in vacuo and dried to yield the title compound (4.40 g, 41% of theory) in a purity of 42%.

LC-MS (Method 1B): $R_t$=0.72 min, MS (ESIPos): m/z=226 [M+H]$^+$

Example 151A

Tert-butyl 4-(10-bromo-8-methyl-2-oxo-1,2-dihydropyrimido[1,2-b]indazol-4-yl)piperidine-1-carboxylate

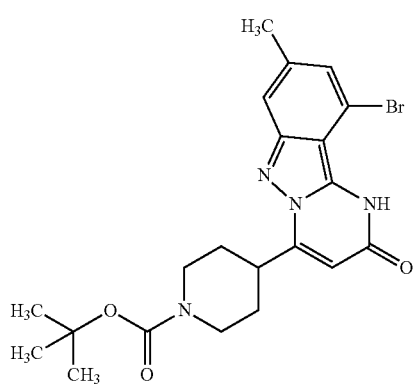 [SMILES: Cc1cc(Br)c2c(c1)nn1c(C3CCN(C(=O)OC(C)(C)C)CC3)cc(=O)[nH]c21]

4-Bromo-6-methyl-1H-indazol-3-amine (42% purity, 300 mg, 0.42 mmol) and tert-butyl 4-[(2,2-dimethyl-4,6-dioxo-1,3-dioxan-5-yl)carbonyl]piperidine-1-carboxylate (0.52 g, 1.46 mmol) were dissolved in acetonitrile (13 mL) and refluxed for 4 h. After cooling to RT, the solvent was removed in vacuo and the residue was dissolved in 1-methoxy-2-propanol (15 mL). Potassium phosphate (0.56 g, 2.65 mmol) was added and the mixture was stirred at 70° C. for 6 h. After concentration in vacuo, the residue was taken up in water and extracted with ethyl acetate. The organic phase was washed with water and brine, dried over magnesium sulfate, and concentrated in vacuo. Purification via preparative HPLC (Method 1A) afforded the title compound (0.40 g, 89% of theory).

LC-MS (Method 1B): $R_t$=1.19 min, MS (ESIPos): m/z=461 [M+H]$^+$

Example 152A

2-Chloro-3,6-difluorobenzaldehyde

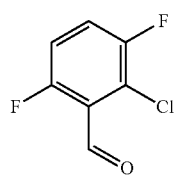

2-Chloro-1,4-difluorobenzene (1.78 g, 12.0 mmol) was dissolved in tetrahydrofuran (50 mL) and cooled to −78° C. Lithium diisopropyl amide (1.8 M in tetrahydrofuran, 7.3 mL, 13.2 mmol) was added. After stirring at −78° C. for 30 min, N,N-dimethylformamide (1.05 g, 14.4 mmol) was added. After stirring at −78° C. for an additional 15 min, acetic acid (3 mL) and water (100 mL) was added and the mixture was warmed to RT. After extraction with ethyl acetate, the organic phase was washed with 1 M hydrochloride acid solution and brine, and dried over magnesium sulfate. Concentration in vacuo afforded the title compound (1.51 g, 71% of theory).

GC-MS (Method 1G): $R_t$=3.25 min, MS (ESIPos): m/z=177 [M+H]$^+$

Example 153A

2-Chloro-3,6-difluorobenzonitrile

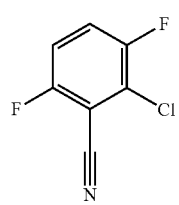

A mixture of 2-chloro-3,6-difluorobenzaldehyde (1.51 g, 8.5 mmol), sodium lauryl sulfate (0.49 g, 1.71 mmol), (Diacetoxyiodo)benzene (4.12 g, 12.8 mmol) and ammonium acetate (3.29 g, 42.7 mmol) in water (9 mL) was stirred at 70° C. for 30 min. After extraction with dichloromethane, the organic phase was dried over magnesium sulfate and concentrated in vacuo. Purification via preparative HPLC (Method 1A) afforded the title compound (0.42 g, 28% of theory) in a purity of 60%.

GC-MS (Method 1G): $R_t$=2.80 min, MS (ESIPos): m/z=175 [M+H]$^+$

Example 154A

4-Chloro-5-fluoro-1H-indazol-3-amine

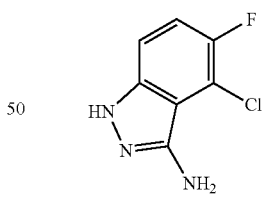

2-chloro-3,6-difluorobenzonitrile (purity 60%, 0.42 g, 1.45 mmol) was dissolved in ethanol (12 mL) and treated with hydrazine hydrate (0.49 g, 9.68 mmol). After stirring at reflux for 4 h, the mixture was cooled to RT and concentrated in vacuo. The residue was dissolved in a mixture of water and ethyl acetate. The aqueous layer was extracted once more with ethyl acetate. The combined organic layers were washed with water and with brine, dried over magnesium sulfate, concentrated in vacuo and dried to yield the title compound (0.32 g, 99% of theory) in a purity of 85%.

LC-MS (Method 1B): $R_t$=0.63 min, MS (ESIPos): m/z=186 [M+H]$^+$

Example 155A

Tert-butyl 4-(10-chloro-9-fluoro-2-oxo-1,2-dihydropyrimido[1,2-b]indazol-4-yl)piperidine-1-carboxylate

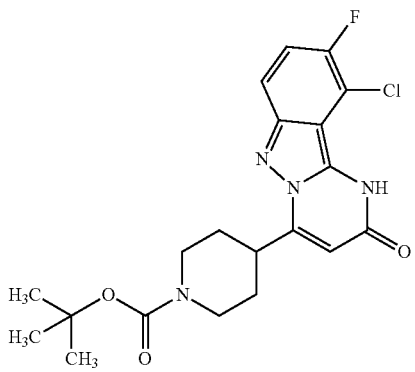 [SMILES: CC(C)(C)OC(=O)N1CCC(c2cc(=O)[nH]c3c4c(Cl)c(F)ccc4nn23)CC1]

4-Chloro-5-fluoro-1H-indazol-3-amine (85% purity, 319 mg, 1.46 mmol) and tert-butyl 4-[(2,2-dimethyl-4,6-dioxo-1,3-dioxan-5-yl)carbonyl]piperidine-1-carboxylate (0.67 g, 1.89 mmol) were dissolved in acetonitrile (16 mL) and refluxed for 4 h. After cooling to RT, the solvent was removed in vacuo and the residue was dissolved in 1-methoxy-2-propanol (15 mL). Potassium phosphate (0.73 g, 3.43 mmol) was added and the mixture was stirred at 70° C. for 6 h. After concentration in vacuo, the residue was taken up in water and extracted with ethyl acetate. The organic phase was washed with water and brine, dried over magnesium sulfate, and concentrated in vacuo. Purification via preparative HPLC (Method 1A) afforded the title compound (0.43 g, 70% of theory).

LC-MS (Method 1B): $R_t$=1.12 min, MS (ESIPos): m/z=421 [M+H]$^+$

Example 156A

2-Fluoro-6-(1H-1,2,4-triazol-1-yl)benzonitrile

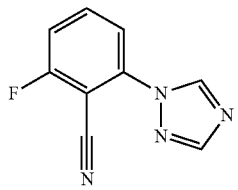 [SMILES: N#Cc1c(F)cccc1-n1cncn1]

Under argon, 2,6-difluorobenzonitrile (1.00 g, 7.19 mmol) was dissolved in dimethylsulfoxide (4 mL), and 1,2,4-triazole (0.52 g, 7.48 mmol) and cesium carbonate (2.44 g, 7.48 mmol) were added. The mixture was stirred at 50° C. for 5 h. After cooling to RT, water (20 mL) was added and stirring was continued for 15 min. The precipitate was filtered and washed with water (10 mL). The solid was taken up in dichloromethane/water and extracted with dichloromethane. The combined organic phases were washed with brine, and concentrated in vacuo. Purification via column chromatography (silica gel, cyclohexane/ethyl acetate, Gradient) afforded the title compound (0.25 g, 18% of theory).

LC-MS (Method 1B): $R_t$=0.62 min, MS (ESIPos): m/z=189 [M+H]+

Example 157A 4-(1H-1,2,4-Triazol-1-yl)-1H-indazol-3-amine

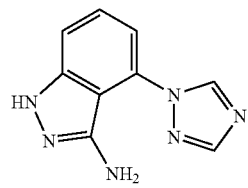

2-Fluoro-6-(1H-1,2,4-triazol-1-yl)benzonitrile (0.25 g, 1.3 mmol) was dissolved in ethanol (2.5 mL) and treated with hydrazine hydrate (0.27 g, 5.3 mmol). After stirring at 70° C. for 9 h, the mixture was cooled to RT and concentrated in vacuo. The residue was dissolved in a mixture of water and ethyl acetate. The aqueous layer was extracted once more with ethyl acetate. The combined organic layers were washed with water and with brine, dried over sodium sulfate, concentrated in vacuo and dried to yield the title compound (0.18 g, 66% of theory).

GC-MS (Method 1G): $R_t$=8.04 min, MS (ESIPos): m/z=200 [M+H]$^+$

Example 158A

Tert-butyl 4-[2-oxo-10-(1H-1,2,4-triazol-1-yl)-1,2-dihydropyrimido[1,2-b]indazol-4-yl]piperidine-1-carboxylate

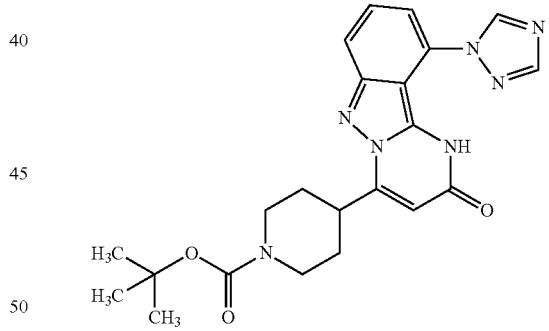

4-(1H-1,2,4-Triazol-1-yl)-1H-indazol-3-amine (180 mg, 0.88 mmol) and tert-butyl 4-[(2,2-dimethyl-4,6-dioxo-1,3-dioxan-5-yl)carbonyl]piperidine-1-carboxylate (0.34 g, 0.97 mmol) were dissolved in acetonitrile (8.5 mL) and refluxed for 5 h. After cooling to RT, the solvent was removed in vacuo and the residue was dissolved in 1-methoxy-2-propanol (5 mL). Potassium phosphate (0.39 g, 1.85 mmol) was added and the mixture was stirred at 110° C. for 4 h. After cooling to RT, water (24 mL) was added, and the mixture was neutralized with aqueous hydrogen chloride solution (1 M). The precipitate was collected via filtration, washed with water and acetonitrile, and dried to afford the title compound (96 mg, 23% of theory).

LC-MS (Method 1B): $R_t$=0.95 min, MS (ESIPos): m/z=436 [M+H]$^+$

Example 159A

Tert-butyl 4-[9-fluoro-10-(2-fluorophenyl)-2-oxo-1,2-dihydropyrimido[1,2-b]indazol-4-yl]piperidine-1-carboxylate

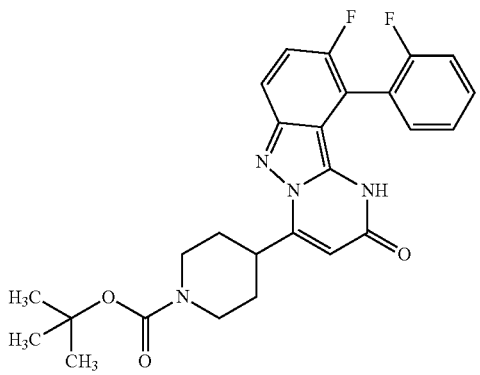 [SMILES: CC(C)(C)OC(=O)N1CCC(c2cc(=O)[nH]c3c4c(-c5ccccc5F)c(F)ccc4nn23)CC1]

Under argon, tert-butyl 4-(10-bromo-9-fluoro-2-oxo-1,2-dihydropyrimido[1,2-b]indazol-4-yl)piperidine-1-carboxylate (purity 70%, 0.10 g, 0.16 mmol), 2-fluorophenylboronic acid (24 mg, 0.17 mmol) and (2-dicyclohexylphosphino-2',4',6'-triisopropyl-1,1'-biphenyl) [2-(2'-amino-1,1'-biphenyl)]palladium(II) methanesulfonate (4 mg, 5 µmol) were dissolved in degassed tetrahydrofuran (2 mL). Potassium phosphate solution (1 M in water, degassed) (0.90 mL, 0.90 mmol) was added and the mixture was stirred at RT for 15 min. The mixture was diluted with ethyl acetate. The organic phase was washed with water and brine, dried over magnesium sulfate, and concentrated in vacuo. Purification by preparative HPLC (Method 1A) afforded the title compound (43 mg, 57% of theory).

LC-MS (Method 1B): $R_t$=1.21 min, MS (ESIPos): m/z=481 [M+H]$^+$

Example 160A

Tert-butyl 4-[10-(2-ethoxyphenyl)-2-oxo-1,2-dihydropyrimido[1,2-b]indazol-4-yl]piperidine-1-carboxylate

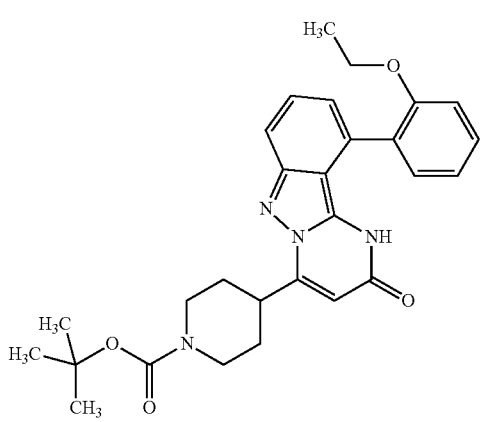 [SMILES: CCOc1ccccc1-c1cccc2nn3c(C4CCN(C(=O)OC(C)(C)C)CC4)cc(=O)[nH]c3c12]

Under argon, tert-butyl 4-(10-bromo-2-oxo-1,2-dihydropyrimido[1,2-b]indazol-4-yl)piperidine-1-carboxylate (0.20 g, 0.48 mmol), 2-ethoxyphenylboronic acid (82 mg, 0.49 mmol) and (2-dicyclohexylphosphino-2',4',6'-triisopropyl-1,1'-biphenyl)[2-(2'-amino-1,1'-biphenyl)]palladium(II) methanesulfonate (11 mg, 13 µmol) were dissolved in degassed tetrahydrofuran (4 mL). Potassium phosphate solution (1 M in water, degassed) (2.65 mL, 2.65 mmol) was added and the mixture was stirred at 40° C. for 16 h. The phases were separated and the organic phase was subjected to preparative HPLC (Method 1A) to afford the title compound (151 mg, 69% of theory).

LC-MS (Method 1B): $R_t$=1.23 min, MS (ESIPos): m/z=489 [M+H]$^+$

Example 161A

Tert-butyl 4-[10-(2-isopropoxyphenyl)-2-oxo-1,2-dihydropyrimido[1,2-b]indazol-4-yl]piperidine-1-carboxylate

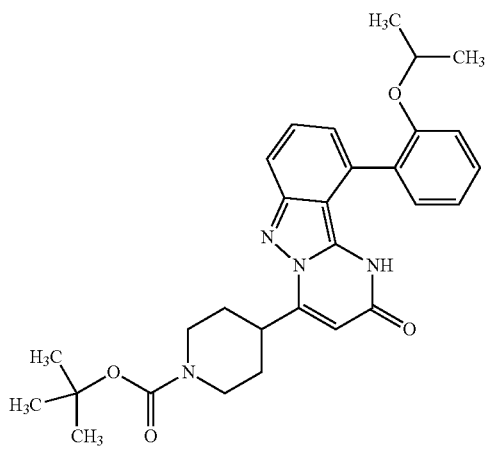 [SMILES: CC(C)Oc1ccccc1-c1cccc2nn3c(C4CCN(C(=O)OC(C)(C)C)CC4)cc(=O)[nH]c3c12]

Under argon, tert-butyl 4-(10-bromo-2-oxo-1,2-dihydropyrimido[1,2-b]indazol-4-yl)piperidine-1-carboxylate (0.20 g, 0.48 mmol), 2-isopropoxyphenylboronic acid (89 mg, 0.49 mmol) and (2-dicyclohexylphosphino-2',4',6'-triisopropyl-1,1'-biphenyl)[2-(2'-amino-1,1'-biphenyl)]palladium(II) methanesulfonate (11 mg, 13 µmol) were dissolved in degassed tetrahydrofuran (4 mL). Potassium phosphate solution (1 M in water, degassed) (2.65 mL, 2.65 mmol) was added and the mixture was stirred at 40° C. for 16 h. The phases were separated and the organic phase was subjected to preparative HPLC (Method 1A) to afford the title compound (134 mg, 59% of theory).

LC-MS (Method 1B): $R_t$=1.33 min, MS (ESIPos): m/z=503 [M+H]$^+$

Example 162A

2-Fluoro-6-(1H-pyrazol-1-yl)benzonitrile

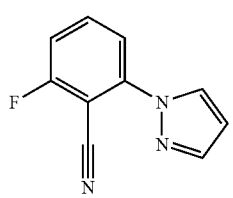 [SMILES: N#Cc1c(F)cccc1-n1cccn1]

Under argon, 2,6-difluorobenzonitrile (4.00 g, 28.8 mmol) was dissolved in dimethylsulfoxide (16 mL), and pyrazole (2.04 g, 29.9 mmol) and cesium carbonate (9.74 g, 29.9 mmol) were added. After stirring the mixture at 50° C. for 11 h, additional pyrazole (1.18 g, 17.3 mmol) was added and stirring was resumed at 50° C. for 6 h. After cooling to RT, water (80 mL) was added and stirring was continued for 15 min. The mixture was extracted with ethyl acetate. The combined organic phases were washed with brine, dried over sodium sulfate, and concentrated in vacuo. Purification via column chromatography (silica gel, cyclohexane/ethyl acetate, Gradient) afforded the title compound (4.16 g, 70% of theory) in a purity of 90%.

GC-MS (Method 1G): $R_t$=5.28 min, MS (ESIPos): m/z=187 [M+H]$^+$

Example 163A 4-(1H-Pyrazol-1-yl)-1H-indazol-3-amine

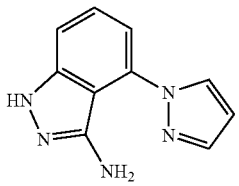 [SMILES: Nc1n[nH]c2cccc(-n3cccn3)c12]

2-Fluoro-6-(1H-pyrazol-1-yl)benzonitrile (purity 90%, 4.16 g, 20.2 mmol) was dissolved in ethanol (45 mL) and treated with hydrazine hydrate (4.05 g, 80.9 mmol). After stirring at 70° C. for 7 h, the mixture was cooled to RT and concentrated in vacuo. The residue was dissolved in a mixture of water and ethyl acetate. The aqueous layer was extracted once more with ethyl acetate. The combined organic layers were washed with water and with brine, dried over sodium sulfate, concentrated in vacuo and dried. Purification via column chromatography (silica gel, cyclohexane/ethyl acetate, Gradient) afforded the title compound (2.65 g, 66% of theory).

LC-MS (Method 1B): $R_t$=0.59 min, MS (ESIPos): m/z=200 [M+H]$^+$

Example 164A

Tert-butyl 4-[2-oxo-10-(1H-pyrazol-1-yl)-1,2-dihydropyrimido[1,2-b]indazol-4-yl]piperidine-1-carboxylate

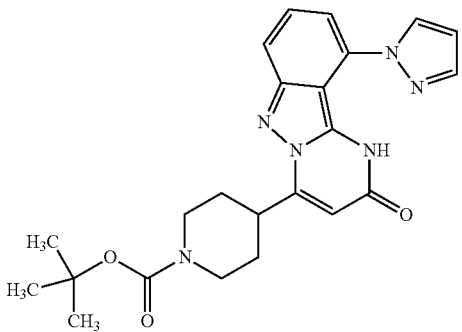 [SMILES: CC(C)(C)OC(=O)N1CCC(c2cc(=O)[nH]c3c4c(-n5cccn5)cccc4nn23)CC1]

4-(1H-Pyrazol-1-yl)-1H-indazol-3-amine (500 mg, 2.51 mmol) and tert-butyl 4-[(2,2-dimethyl-4,6-dioxo-1,3-dioxan-5-yl)carbonyl]piperidine-1-carboxylate (0.98 g, 2.76 mmol) were dissolved in acetonitrile (8.5 mL) and refluxed for 5 h. After cooling to RT, the solvent was removed in vacuo and the residue was dissolved in 1-methoxy-2-propanol (5 mL). Potassium phosphate (0.39 g, 1.85 mmol) was added and the mixture was stirred at 110° C. for 4 h. After cooling to RT, water (24 mL) was added, and the mixture was neutralized with aqueous hydrogen chloride solution (1 M). The precipitate was collected via filtration, washed with water and acetonitrile, and dried to afford the title compound (96 mg, 23% of theory).

LC-MS (Method 1B): $R_t$=0.95 min, MS (ESIPos): m/z=436 [M+H]$^+$

Example 165A

Tert-butyl 4-[10-(2-fluoro-6-methoxyphenyl)-2-oxo-1,2-dihydropyrimido[1,2-b]indazol-4-yl]piperidine-1-carboxylate

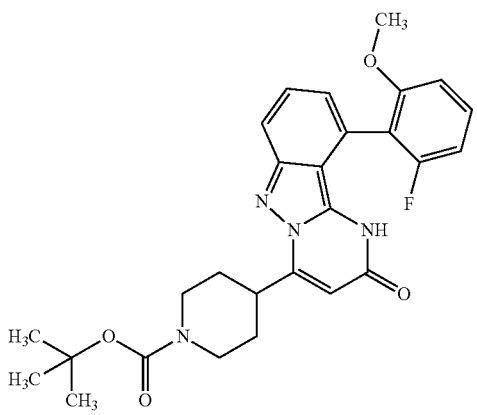 [SMILES: COc1cccc(F)c1-c1cccc2nn3c(C4CCN(C(=O)OC(C)(C)C)CC4)cc(=O)[nH]c3c12]

Under argon, tert-butyl 4-(10-bromo-2-oxo-1,2-dihydropyrimido[1,2-b]indazol-4-yl)piperidine-1-carboxylate (50 mg, 0.11 mmol) and (2-dicyclohexylphosphino-2',4',6'-triisopropyl-1,1'-biphenyl)[2-(2'-amino-1,1'-biphenyl)]palladium(II) methanesulfonate (104 mg, 0.12 mmol) were dissolved in degassed tetrahydrofuran (1.5 mL) and treated with potassium phosphate solution (1 M in water, degassed) (0.44 mL, 0.44 mmol). After stirring at RT for 15 min, a solution of 2-fluoro-6-methoxyboronic acid (38 mg, 0.22 mmol) and 1-bromo-3,5-difluorobenzene (43 mg, 0.22 mmol) in degassed tetrahydrofuran (0.5 mL) was added and stirring was resumed at RT for 15 min. The mixture was taken up in a mixture of water and ethyl acetate. The aqueous phase was extracted twice with ethyl acetate. The combined organic phases were washed with brine and dried over sodium sulfate. Separation via column chromatography (gradient cyclohexane/ethyl acetate) followed by preparative HPLC (Method 1A) afforded the title compound (21 mg, 36% of theory).

LC-MS (Method 1B): $R_t$=1.18 min, MS (ESIPos): m/z=493 [M+H]$^+$

Example 166A

Isomer mixture of 2-fluoro-6-(2H-1,2,3-triazol-2-yl)benzonitrile and 2-fluoro-6-(1H-1,2,3-triazol-1-yl)benzonitrile

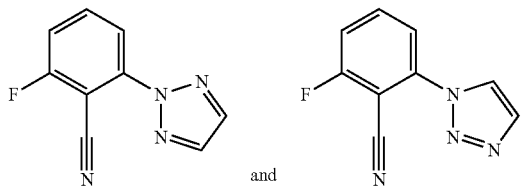 [SMILES: N#Cc1c(F)cccc1-n1nccn1 ; N#Cc1c(F)cccc1-n1ccnn1]

Under argon, 2,6-difluorobenzonitrile (5.00 g, 35.9 mmol) was dissolved in dimethylsulfoxide (20 mL), and 1,2,3-triazole (2.58 g, 37.4 mmol) and cesium carbonate (12.18 g, 37.4 mmol) were added. After stirring the mixture at 50° C. for 10 h, additional 1,2,3-triazole (1.25 g, 18.7 mmol) was added and stirring was resumed at 50° C. for 6 h. After cooling to RT, water (90 mL) was added and stirring was continued for 10 min. The mixture was extracted with ethyl acetate. The combined organic phases were washed with brine, dried over sodium sulfate, and concentrated in vacuo to afford a mixture of the isomers of the title compounds (ca 7:1, 9.73 g, 65% of theory) in a purity of 46%.

Major Isomer (2-fluoro-6-(2H-1,2,3-triazol-2-yl)benzonitrile): GC-MS (Method 1G): $R_t$=5.56 min, MS (ESIPos): m/z=188 [M+H]$^+$ Minor Isomer (2-fluoro-6-(1H-1,2,3-triazol-1-yl)benzonitrile): GC-MS (Method 1G): $R_t$=5.92 min, MS (ESIPos): m/z=188 [M+H]$^+$

Examples 167A and 168A 4-(2H-1,2,3-Triazol-2-yl)-1H-indazol-3-amine and 4-(1H-1,2,3-triazol-1-yl)-1H-indazol-3-amine

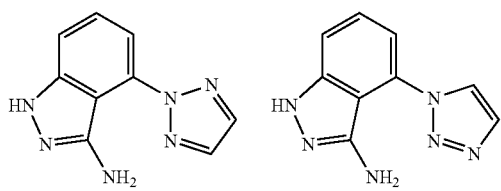

The 7:1 mixture of 2-fluoro-6-(2H-1,2,3-triazol-2-yl)benzonitrile and 2-fluoro-6-(1H-1,2,3-triazol-1-yl)benzonitrile obtained in Example 166A (purity 46%, 9.73 g, 23.8 mmol) was dissolved in ethanol (80 mL) and treated with hydrazine hydrate (7.25 g, 144.8 mmol). After stirring at 70° C. for 7 h, the mixture was cooled to RT and concentrated in vacuo. The residue was dissolved in a mixture of water and ethyl acetate. The aqueous layer was extracted twice with ethyl acetate. The combined organic layers were washed with water and with brine, dried over sodium sulfate and concentrated in vacuo. Separation and purification by column chromatography (eluent dichloromethane, then dichloromethane/ethanol) afforded the two isomers 4-(2H-1,2,3-triazol-2-yl)-1H-indazol-3-amine (1.13 g, 23% of theory) and 4-(1H-1,2,3-triazol-1-yl)-1H-indazol-3-amine (0.29 g, 6% of theory).

4-(2H-1,2,3-triazol-2-yl)-1H-indazol-3-amine: LC-MS (Method 2B): $R_t$=1.64 min, MS (ESIPos): m/z=201 [M+H]$^+$ 4-(1H-1,2,3-triazol-1-yl)-1H-indazol-3-amine: LC-MS (Method 2B): $R_t$=1.67 min, MS (ESIPos): m/z=201 [M+H]$^+$

Example 169A

Tert-butyl 4-[2-oxo-10-(2H-1,2,3-triazol-2-yl)-1,2-dihydropyrimido[1,2-b]indazol-4-yl]piperidine-1-carboxylate

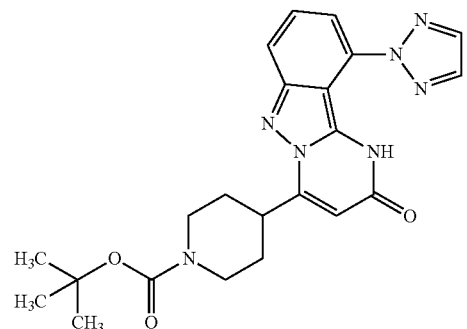

4-(2H-1,2,3-Triazol-2-yl)-1H-indazol-3-amine (500 mg, 2.37 mmol) and tert-butyl 4-[(2,2-dimethyl-4,6-dioxo-1,3-dioxan-5-yl)carbonyl]piperidine-1-carboxylate (0.93 g, 2.61 mmol) were dissolved in acetonitrile (8.5 mL) and refluxed for 4 h. After cooling to RT, the solvent was removed in vacuo and the residue was dissolved in 1-methoxy-2-propanol (20 mL). Potassium phosphate (0.94 g, 4.45 mmol) was added and the mixture was stirred at 50° C. for 4 h. After cooling to RT, water was added, and the mixture was neutralized with aqueous hydrogen chloride solution (1 M). The precipitate was collected via filtration, triturated with acetonitrile, and dried to afford the title compound (750 mg, 77% of theory).

LC-MS (Method 1B): $R_t$=1.11 min, MS (ESIPos): m/z=436 [M+H]$^+$

Example 170A

Tert-butyl 4-[2-oxo-10-(1H-1,2,3-triazol-1-yl)-1,2-dihydropyrimido[1,2-b]indazol-4-yl]piperidine-1-carboxylate

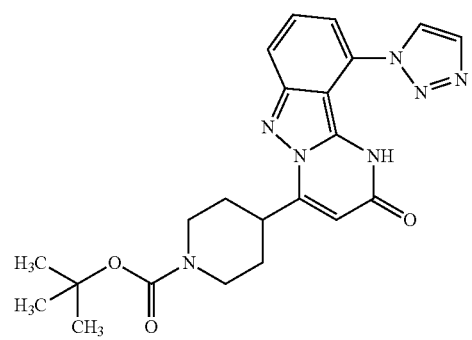 [SMILES: CC(C)(C)OC(=O)N1CCC(c2cc(=O)[nH]c3c4c(-n5ccnn5)cccc4nn23)CC1]

4-(1H-1,2,3-Triazol-1-yl)-1H-indazol-3-amine (280 mg, 2.37 mmol) and tert-butyl 4-[(2,2-dimethyl-4,6-dioxo-1,3- dioxan-5-yl)carbonyl]piperidine-1-carboxylate (0.53 g, 1.49 mmol) were dissolved in acetonitrile (8.5 mL) and refluxed for 4 h. Additional tert-butyl 4-[(2,2-dimethyl-4,6-dioxo-1,3-dioxan-5-yl)carbonyl]piperidine-1-carboxylate (0.24 g, 0.68 mmol) was added and the mixture was refluxed for another 6 h. After cooling to RT, the solvent was removed in vacuo and the residue was dissolved in 1-methoxy-2-propanol (20 mL). Potassium phosphate (0.70 g, 3.28 mmol) was added and the mixture was stirred at 110° C. for 4 h. After cooling to RT, water was added, and the mixture was neutralized with aqueous hydrogen chloride solution (1 M). The aqueous phase was washed with ethyl acetate and left standing over night. The precipitate was collected via filtration, washed with acetonitrile, and dried to afford the title compound (240 mg, 23% of theory).

LC-MS (Method 1B): $R_t$=1.01 min, MS (ESIPos): m/z=436 $[M+H]^+$

Example 171A

6-Chloro-2-fluoro-3-methylbenzaldehyde H$_3$C

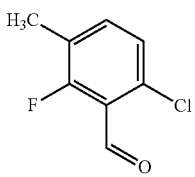

4-Chloro-2-fluorotoluene (5.00 g, 34.6 mmol) was dissolved in tetrahydrofuran (100 mL) and cooled to −78° C. Lithium diisopropyl amide (1.8 M in tetrahydrofuran, 21.1 mL, 38.0 mmol) was added. After stirring at −78° C. for 30 min, N,N-dimethylformamide (3.03 g, 41.5 mmol) was added. After stirring at −78° C. for an additional 15 min, acetic acid (8 mL) and water (100 mL) was added and the mixture was warmed to RT. After extraction with ethyl acetate, the organic phase was washed with 1 M hydrochloride acid solution and brine, and dried over magnesium sulfate. Concentration in vacuo afforded the title compound (5.93 g, 94% of theory).

GC-MS (Method 1G): $R_t$=3.86 min, MS (ESIPos): m/z=172 $[M+H]^+$

Example 172A

6-Chloro-2-fluoro-3-methylbenzonitrile

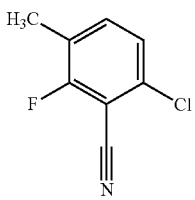

A mixture of 6-chloro-2-fluoro-3-methylbenzaldehyde (5.90 g, 34.2 mmol), sodium lauryl sulfate (1.97 g, 6.84 mmol), (Diacetoxyiodo)benzene (16.5 g, 51.3 mmol) and ammonium acetate (13.2 g, 170.9 mmol) in water (35 mL) was stirred at 70° C. for 30 min. After extraction with dichloromethane, the organic phase was dried over magnesium sulfate and concentrated in vacuo. Purification via preparative HPLC (Method 1A) afforded the title compound (1.12 g, 19% of theory).

GC-MS (Method 1G): $R_t$=3.90 min, MS (ESIPos): m/z=169 $[M+H]^+$

Example 173A

4-Chloro-7-methyl-1H-indazol-3-amine

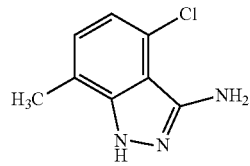

6-Chloro-2-fluoro-3-methylbenzonitrile (1.12 g, 6.60 mmol) was dissolved in ethanol (10 mL) and treated with hydrazine hydrate (1.32 g, 26.4 mmol). After stirring at 70° C. for 6 h, the mixture was cooled to RT and concentrated in vacuo. The residue was dissolved in a mixture of water and ethyl acetate. The aqueous layer was extracted once more with ethyl acetate. The combined organic layers were washed with water and with brine, dried over magnesium sulfate, concentrated in vacuo and dried to yield the title compound (1.25 g, 99% of theory) in a purity of 95%.

LC-MS (Method 2B): $R_t$=1.87 min, MS (ESIPos): m/z=182 $[M+H]^+$

Example 174A

Tert-butyl 4-(10-chloro-7-methyl-2-oxo-1,2-dihydropyrimido[1,2-b]indazol-4-yl)piperidine-1-carboxylate

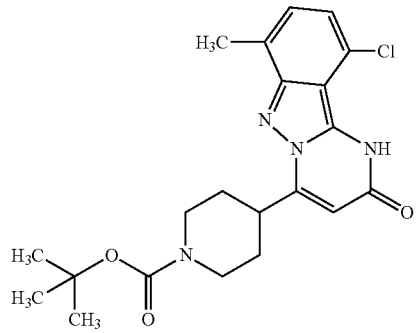 [SMILES: Cc1ccc(Cl)c2c1nn1c(C3CCN(C(=O)OC(C)(C)C)CC3)cc(=O)[nH]c21]

4-Chloro-7-methyl-1H-indazol-3-amine (purity 95%, 200 mg, 1.05 mmol) and tert-butyl 4-[(2,2-dimethyl-4,6-dioxo-1,3-dioxan-5-yl)carbonyl]piperidine-1-carboxylate (409 mg, 1.15 mmol) were dissolved in acetonitrile (10 mL) and refluxed for 2 h. After cooling to RT, the solvent was removed in vacuo and the residue was dissolved in 1-methoxy-2-propanol (10 mL). Potassium phosphate (0.30 g, 1.43 mmol) was added and the mixture was stirred at 110° C. for 4 h. After concentration in vacuo, purification via preparative HPLC (Method 1A) afforded the title compound (230 g, 77% of theory).

LC-MS (Method 1B): $R_t$=1.24 min, MS (ESIPos): m/z=417 [M+H]$^+$

Example 175A

Cis-methyl 2-methylpiperidine-4-carboxylate

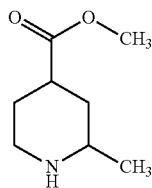

A solution of (+)-Cis-1-benzyl 4-methyl 2-methylpiperidine-1,4-dicarboxylate (21.15 g, 72.60 mmol) in ethanol (250 ml) was treated with palladium on charcoal 10% (1.54 g, 1.45 mmol) under hydrogen atmosphere at normal pressure and RT for 16 h. The mixture was filtered through celite and the filtrate was evaporated and dried under vacuo to yield the title compound (11.42 g, 95% of theory).

LC-MS (MCW-ZQ3-EXT-B): $R_t$=1.10 min, MS (ESIPos): m/z=158 [M+H]$^+$

Example 176A

Cis-1-tert-butyl 4-methyl 2-methylpiperidine-1,4-dicarboxylate

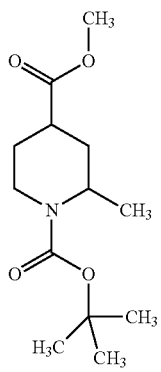 [SMILES: COC(=O)C1CCN(C(=O)OC(C)(C)C)C(C)C1]

To a solution of cis-methyl 2-methylpiperidine-4-carboxylate obtained in example 175A (11.70 g, 74.42 mmol) in tetrahydrofuran (250 ml) under argon atmosphere was added di-tert-butyl dicarbonate (19.49 g, 89.30 mmol) and the reaction mixture was stirred at RT overnight. The mixture was evaporated under vacuo and the crude product was dissolved in ethyl acetate and treated with a 10% citric acid aqueous solution. After separation of the layers the organic layer was washed with 10% citric acid aqueous solution, with a saturated aqueous solution of sodium hydrogen carbonate and finally with brine. The organic phase was dried over magnesium sulfate, filtered and evaporated to yield the title compound (23.69 g, 90% of theory, 73% pure according NMR). The crude product was used in the next step without further purification.

MS (ESIPos): m/z=258 [M+H]$^+$

Example 177A

Cis-1-(tert-butoxycarbonyl)-2-methylpiperidine-4-carboxylic Acid

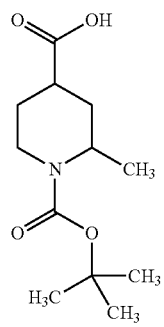 [SMILES: CC1CC(C(=O)O)CCN1C(=O)OC(C)(C)C]

To a solution of cis-1-tert-butyl 4-methyl 2-methylpiperidine-1,4-dicarboxylate obtained in example 176A (23.69 g, 92.06 mmol) in a mixture of tetrahydrofuran (250 ml) and water (125 ml) was added lithium hydroxide (8.82 g, 368.24 mmol) and the mixture was stirred overnight at RT. The mixture was evaporated under vacuo and was diluted in water and ethyl acetate. After separation of the layers the aqueous phase was treated with HCl 1M until pH 4 was achieved and then was extracted with ethyl acetate, dried over magnesium sulfate, filtered and evaporated under vacuo to yield the title compound (14.85 g, 66% of theory).

LC-MS (Method 2B): $R_t$=1.45 min, MS (ESIPos): m/z=242 [M–H]$^-$ $^1$H-NMR (400 MHz, DMSO-d$_6$): δ=12.33 (bs, 1H), 4.07-3.99 (m, 1H), 3.68-3.60 (m, 1H), 3.07-2.97 (m, 1H), 1.87-1.75 (m, 4H), 1.62-1.52 (m, 1H), 1.39 (s, 9H), 1.04 (d, 3H).

Example 178A (+)-Cis-tert-butyl 4-[(2,2-dimethyl-4,6-dioxo-1,3-dioxan-5-yl)carbonyl]-2-methylpiperidine-1-carboxylate

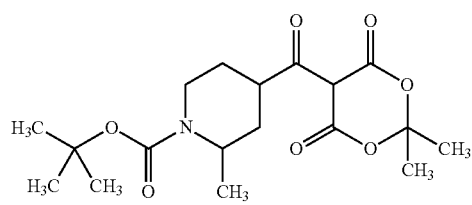 [SMILES: CC1CC(C(=O)C2C(=O)OC(C)(C)OC2=O)CCN1C(=O)OC(C)(C)C]

To a solution of cis-1-(tert-butoxycarbonyl)-2-methylpiperidine-4-carboxylic acid obtained in example 177A (1.00 g, 4.11 mmol) and 2,2-dimethyl-1,3-dioxane-4,6-dione (0.65 g, 4.52 mmol) in dichloromethane (10 ml) was added 4-dimethylaminopyridin (0.75 g, 6.16 mmol). After cooling the mixture to 0° C., 1-(3-dimethylaminopropyl)-3-ethylcarbodiimide hydrochloride (1.10 g, 5.75 mmol) was added in portions and then the reaction mixture was stirred at RT for 16 h. The mixture was diluted in dichloromethane and then treated with HCl 1M. After that the layers were separated. The organic layer was washed with HCl 1M, water and brine

Example 179A (+)-Cis-Tert-butyl 4-(10-chloro-2-oxo-1,2-dihydro-pyrimido[1,2-b]indazol-4-yl)-2-methylpiperidine-1-carboxylate [Enantiomerically Pure Cis-Isomer]

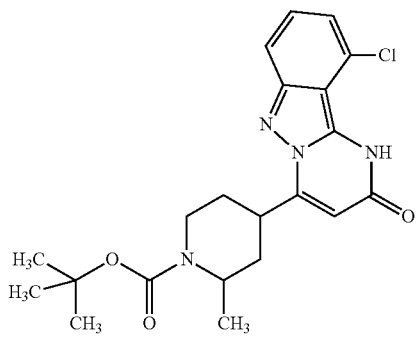 [SMILES: CC1CC(c2cc(=O)[nH]c3c4c(Cl)cccc4nn23)CCN1C(=O)OC(C)(C)C]

The title compound was prepared according to General Procedure 1A starting from 0.26 g (1.48 mmol) 4-chloro-1H-indazol-3-amine and 0.55 g (1.48 mmol) (+)-cis-tert-butyl 4-[(2,2-dimethyl-4,6-dioxo-1,3-dioxan-5-yl)carbonyl]-2-methylpiperidine-1-carboxylate. Then the mixture was diluted with water and was treated with 1N hydrochloric acid until pH 5 was achieved and finally extracted with ethyl acetate. The organic layer was washed with water, brine and dried over magnesium sulfate, filtered, evaporated and dried in vacuo. The crude was purified by preparative HPLC (Method 1A). The combined product fractions were evaporated and lyophilized overnight. Epimerization was observed obtaining a mixture of diastereomers which were separated by Method 5C to yield the title compound, which was after then stirred in acetonitrile. The resulting solid was filtered, washed with acetonitrile and dried overnight in vacuo at 60° C. to yield the title compound. The filtrate was purified by preparative HPLC (Method 1A).

The combined product fractions were evaporated and lyophilized overnight to yield the title compound (65 mg, 10% of theory).

LC-MS (Method 1B): RT=1.18 min, MS (ESIPos): m/z=417 (M+H)+

HPLC (Method 5E): $R_t$=7.19 min $[\alpha]^{20}$=+24.9 (c. 0.30, methanol) WL=589 nm

Example 180A (3-amino-1H-indazol-4-yl)acetonitrile

To a solution of 2-(cyanomethyl)-6-fluorobenzonitrile (1.00 g, 6.24 mmol) in ethanol (12 mL) under argon was added hydrazine hydrate (2.38 mL, 25.0 mmol) at RT. The mixture was heated to 70° C. for 5 h. The mixture was cooled to RT and concentrated in vacuo and then the residue was dissolved in a mixture of water and ethyl acetate. The aqueous layer was extracted once more with ethyl acetate. The combined organic layers were washed with water and with brine, dried over magnesium sulfate, concentrated in vacuo and dried in vacuo to yield the title compound (0.80 g, 62% of theory, 80% pure according LC-MS).

LC-MS (Method 2B): $R_t$=1.54 min, MS (ESIPos): m/z=173 [M+H]+

Example 181A

Tert-butyl 4-[10-(cyanomethyl)-2-oxo-1,2-dihydro-pyrimido[1,2-b]indazol-4-yl]piperidine-1-carboxylate

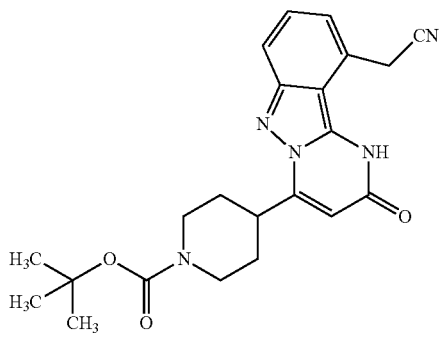 [SMILES: CC(C)(C)OC(=O)N1CCC(c2cc(=O)[nH]c3c4c(CC#N)cccc4nn23)CC1]

(3-amino-1H-indazol-4-yl)acetonitrile (purity 80%, 589 mg, 2.74 mmol) and tert-butyl 4-[(2,2-dimethyl-4,6-dioxo-1,3-dioxan-5-yl)carbonyl]piperidine-1-carboxylate (863 mg, 2.28 mmol) were dissolved in acetonitrile (8.6 mL) and stirred at 60° C. for 5 h. After cooling to RT, the solvent was removed in vacuo and the residue was dissolved in 1-methoxy-2-propanol (8.6 mL). Potassium phosphate (969 mg, 4.57 mmol) was added and the mixture was stirred at 110° C. for 1 h. The mixture was diluted with water, neutralized (pH 6) by the addition of 1N HCl and the resulting solid was filtered, washed with water and finally purified by preparative HPLC (Method 2A) to yield the title compound (15 mg, 2% of theory).

LC-MS (Method 1B): $R_t$=1.02 min, MS (ESIPos): m/z=408 [M+H]+

Example 182A tert-butyl 4-{2-oxo-10-[1-(tetrahydro-2H-pyran-2-yl)-1H-imidazol-5-yl]-1,2-dihydropyrimido[1,2-b]indazol-4-yl}piperidine-1-carboxylate

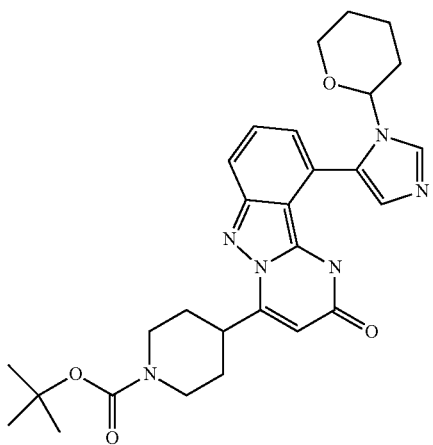 [SMILES: CC(C)(C)OC(=O)N1CCC(c2cc(=O)[nH]c3c4c(-c5cncn5C5CCCCO5)cccc4nn23)CC1]

tert-butyl 4-(10-bromo-2-oxo-1,2-dihydropyrimido[1,2-b]indazol-4-yl)piperidine-1-carboxylate (200 mg, 0.45 mmol) and 1-(tetrahydro-2H-pyran-2-yl)-5-(4,4,5,5-tetramethyl-1,3,2-dioxaborolan-2-yl)-1H-imidazole (187 mg, 0.67 mmol) were dissolved in N,N-Dimethylformamide (5 ml) and treated with sodium carbonate solution (2M in water, 0.89 ml). After degassing the solution 1,1'-Bis(diphenylphosphino)ferrocene-palladium(II)chloride (16.4 mg, 0.02 mmol) was added. After stirring at 80° C. for 16 h, the mixture was separated via reverse phase HPLC (gradient acetonitrile/water with 0.1% trifluoroacetic acid) which afforded the title compound (55.4 mg, 25% of theory).

LC-MS (Method 5B): $R_t$=0.84 min, MS (ESIPos): m/z=519.5 $[M+H]^+$

Example 183A tert-butyl 4-{10-[1-(tert-butoxycarbonyl)-1H-pyrrol-2-yl]-2-oxo-1,2-dihydropyrimido[1,2-b]indazol-4-yl}piperidine-1-carboxylate

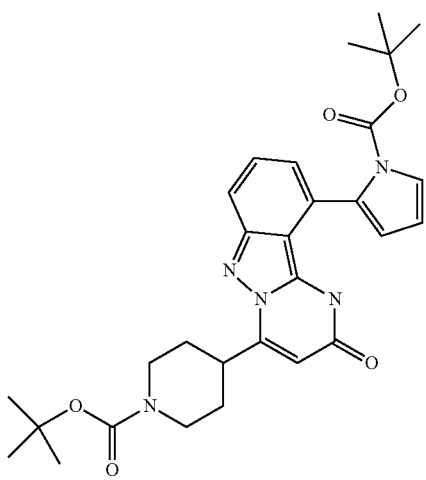 [SMILES: CC(C)(C)OC(=O)N1CCC(c2cc(=O)[nH]c3c4c(-c5cccn5C(=O)OC(C)(C)C)cccc4nn23)CC1]

tert-butyl 4-(10-bromo-2-oxo-1,2-dihydropyrimido[1,2-b]indazol-4-yl)piperidine-1-carboxylate (200 mg, 0.45 mmol) and [1-(tert-butoxycarbonyl)-1H-pyrrol-2-yl]boronic acid (142 mg, 0.67 mmol) were dissolved in N,N-Dimethylformamide (5 ml) and treated with sodium carbonate solution (2M in water, 0.89 ml). After degassing the solution 1,1'-Bis(diphenylphosphino)ferrocene-palladium(II)chloride (16.4 mg, 0.02 mmol) was added. After stirring at 80° C. for 16 h, the mixture was separated via reverse phase HPLC (gradient acetonitrile/water with 0.1% trifluoroacetic acid) which afforded the title compound (149 mg, 61% of theory).

LC-MS (Method 5B): $R_t$=1.26 min, MS (ESIPos): m/z=534.5 $[M+H]^+$

Example 184A

4-[1-(tert-butoxycarbonyl)piperidin-4-yl]-2-oxo-1,2-dihydropyrimido[1,2-b]indazole-10-carboxylic Acid

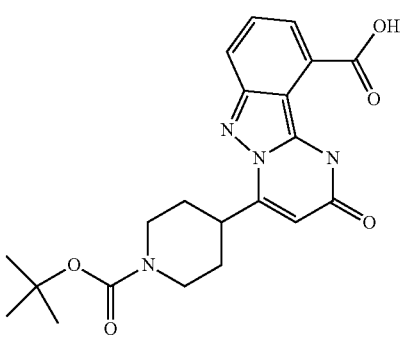 [SMILES: CC(C)(C)OC(=O)N1CCC(c2cc(=O)[nH]c3c4c(C(=O)O)cccc4nn23)CC1]

Tert-butyl 4-(10-cyano-2-oxo-1,2-dihydropyrimido[1,2-b]indazol-4-yl)piperidine-1-carboxylate (Example 78A) (200 mg, 0.51 mmol) and sodium hydroxide solution (2M in water, 25 ml, 50.8 mol) were dissolved in water (5 ml) and ethanol (40 ml). After stirring at 100° C. for 4 h and 2 d at rt, the mixture was worked up 3× with ethyl acetate and citric acid solution (10% in water). The organic phases were washed with water and dried with sodium sulfate. Drying in vacuo afforded the title compound (187 mg, 84% of theory).

LC-MS (Method 5B): $R_t$=0.95 min, MS (ESIPos): m/z=412.3 $[M+H]^+$

Example 185A tert-butyl 4-[2-oxo-10-(2,2,2-trifluoroethoxy)-1,2-dihydropyrimido[1,2-b]indazol-4-yl]piperidine-1-carboxylate

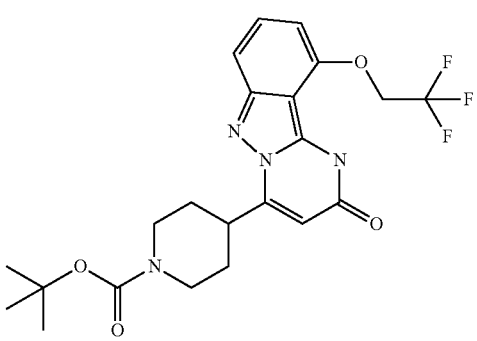 [SMILES: CC(C)(C)OC(=O)N1CCC(c2cc(=O)[nH]c3c4c(OCC(F)(F)F)cccc4nn23)CC1]

tert-butyl 4-[(2,2-dimethyl-4,6-dioxo-1,3-dioxan-5-yl)carbonyl]piperidine-1-carboxylate (338 mg, 0.95 mmol, 1.1 eq) and 4-(2,2,2-trifluoroethoxy)-2H-indazol-3-amine (200 mg, 0.86 mmol, 1 eq) were dissolved in acetonitrile (15 mL) and refluxed for 3 h. After cooling to RT, the solvent was removed in vacuo and the residue was dissolved in 1-methoxy-2-propanol (15 mL). Potassium phosphate (368 mg, 1.7 mmol, 2 eq.) was added and the mixture was stirred at 100° C. for 4 h. After concentration in vacuo, purification via reverse phase HPLC (gradient acetonitrile/water with 0.1% formic acid) afforded the title compound (190 mg, 47% of theory).

LC-MS (Method 1B): $R_t$=1.04 min, MS (ESIPos): m/z=467 [M+H]$^+$

Example 186A 4-(2,2,2-trifluoroethoxy)-1H-indazol-3-amine

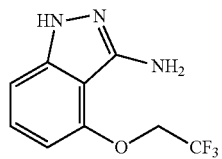

To a solution of 2-(2,2,2-trifluoroethoxy)-6-fluorobenzonitrile (1.00 g, 4.56 mmol, 1 eq) in ethanol (30 mL) was added hydrazine hydrate (0.88 mL, 18 mmol, 4 eq) at RT. The mixture was stirred at rt for 16 h and the heated to 70° C. over night. The solvents were removed in vacuo and the obtained residue purification via reverse phase HPLC (gradient acetonitrile/water with 0.1% trifluoro acetic acid) afforded the title compound (430 mg, 35% of theory).

LC-MS (Method 7B): $R_t$=1.89 min, MS (ESIPos): m/z=232 [M+H]$^+$

PREPARATION OF COMPOUND EXAMPLES

Example 1

4-(Piperidin-4-yl)pyrimido[1,2-b]indazol-2(1H)-one hydrochloride

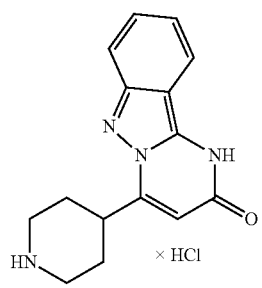 [SMILES: O=c1cc(C2CCNCC2)n2nc3ccccc3c2[nH]1]

Tert-butyl 4-(4-oxo-1,4-dihydropyrimido[1,2-b]indazol-2-yl)piperidine-1-carboxylate (1.50 g, 4.07 mmol) was dissolved in 4N HCl in dioxane (10 mL) and methanol (5 mL) and irradiated with ultrasound for 5 min. The resulting suspension was filtered, the residue was washed with dioxane (50 ml) and methanol (2 mL) and dried for 16 h at 50° C. in vacuo to yield the title compound (1.35 g, 92% purity, 4.07 mmol, 100% of theory).

LC-MS (Method 2B): $R_t$=1.19 min, MS (ESIPos): m/z=269 [M+H−xHCl]$^+$ $^1$H-NMR (400 MHz, D$_2$O): δ=7.57 (d, 2H), 7.41 (d-like, 2H), 7.00 (quint-like, 1H), 6.26 (s, 1H), 3.67 (d, 2H), 3.53 (t, 1H), 3.31 (t, 2H), 2.43 (d, 2H), 1.96 (qm, 2H).

Example 2

4-(Piperidin-4-yl)-9-(trifluoromethyl)pyrimido[1,2-b]indazol-2(1H)-one hydrochloride

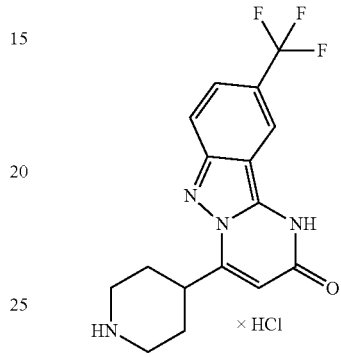

Tert-butyl 4-[2-oxo-9-(trifluoromethyl)-1,2-dihydropyrimido[1,2-b]indazol-4-yl]piperidine-1-carboxylate, 48.3 mg, 0.111 mmol) was dissolved in 4N HCl in dioxane (1.2 mL), stirred for 5 min and evaporated in vacuo. Methanol (5 mL) was added and the solution was evaporated again. The residue was dissolved in methanol (0.5 mL) and water (2 mL) and then lyophilized to give the title compound (38.7 mg, 94% of theory).

LC-MS (Method 1B): $R_t$=0.65 min, MS (ESIPos): m/z=337 [M+H−xHCl]$^+$ $^1$H-NMR (400 MHz, DMSO-d$_6$): δ=13.55 (br. S, 1H), 8.91 (br. s, 1H), 8.74 (br. S, 1H), 8.48 (s, 1H), 7.73 (d, 1H), 7.58 (d, 1H), 6.31 (s, 1H), 3.79 (m, 1H), 3.43 (d, 2H), 3.17 (q, 2H), 2.30 (d, 2H), 1.92 (q, 2H).

Example 3

10-Chloro-4-(piperidin-4-yl)pyrimido[1,2-b]indazol-2(1H)-one Hydrochloride

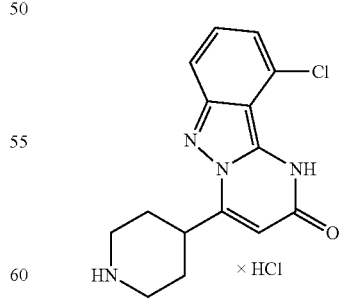

Tert-butyl 4-(10-chloro-4-oxo-1,4-dihydropyrimido[1,2-b]indazol-2-yl)piperidine-1-carboxylate, 47.3 mg, 0.12 mmol) was dissolved in 4N HCl in dioxane (1.3 mL), stirred for 5 min and evaporated in vacuo. Methanol (5 mL) was added and the solution was evaporated again. The residue was dissolved in methanol (0.5 mL) and water (2 mL) and then lyophilized to give the title compound (40.5 mg, 0.12 mmol, 100% of theory).

LC-MS (Method 2B): $R_t$=1.36 min, MS (ESIPos): m/z=303 [M+H−xHCl]$^+$ $^1$H-NMR (400 MHz, D$_2$O): δ=7.27 (d, 1H), 7.22 (dd, 1H), 6.85 (d, 1H), 6.34 (s, 1H), 3.68 (d, 2H), 3.52 (t, 1H), 3.32 (t, 2H), 2.44 (d, 2H), 1.97 (qm, 2H).

Example 4

10-Fluoro-4-(piperidin-4-yl)pyrimido[1,2-b]indazol-2(1H)-one Hydrochloride

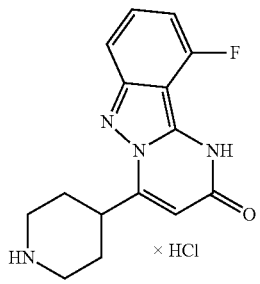 [SMILES: O=c1cc(C2CCNCC2)n2nc3cccc(F)c3c2[nH]1]

Tert-butyl 4-(10-fluoro-4-oxo-1,4-dihydropyrimido[1,2-b]indazol-2-yl)piperidine-1-carboxylate (80 mg, 0.21 mmol) was dissolved in 4N HCl in dioxane (1 mL) and methanol (1 mL) and irradiated with ultrasound for 15 min. The resulting suspension was diluted with dioxane (2 mL), filtered, the residue was washed with dioxane (2 ml) and dried for 16 h at 50° C. in vacuo to yield the title compound (64 mg, 95% of theory).

LC-MS (Method 2B): $R_t$=1.24 min, MS (ESIPos): m/z=287 [M+H−xHCl]$^+$ $^1$H-NMR (400 MHz, D$_2$O): δ=7.39 (q, 1H), 7.28 (d, 1H), 6.70 (dd, 1H), 6.38 (s, 1H), 3.72-3.59 (m, 3H), 3.31 (t, 2H), 2.46 (d, 2H), 1.99 (qm, 2H).

Example 5

9-Chloro-4-(piperidin-4-yl)pyrimido[1,2-b]indazol-2(1H)-one Hydrochloride

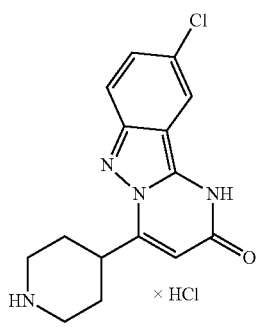

Tert-butyl 4-(9-chloro-4-oxo-1,4-dihydropyrimido[1,2-b]indazol-2-yl)piperidine-1-carboxylate, 26.5 mg, 0.066 mmol) was dissolved in 4N HCl in dioxane (1 mL), stirred for 1 min and evaporated in vacuo. Methanol (5 mL) was added and the solution was evaporated again. The residue was dissolved in methanol (0.5 mL) and water (2 mL) and then lyophilized to give the title compound (24 mg, 0.07 mmol, 100% of theory).

LC-MS (Method 1B): $R_t$=0.59 min, MS (ESIPos): m/z=303 [M+H−xHCl]$^+$ $^1$H-NMR (400 MHz, D$_2$O): δ=7.67 (s, 1H), 7.48 (d, 1H), 7.37 (d, 1H), 6.39 (s, 1H), 3.72-3.62 (m, 3H), 3.32 (t, 2H), 2.48 (d, 2H), 2.00 (qm, 2H).

Example 6

7,9-Dichloro-4-(piperidin-4-yl)pyrimido[1,2-b]indazol-2(1H)-one Hydrochloride

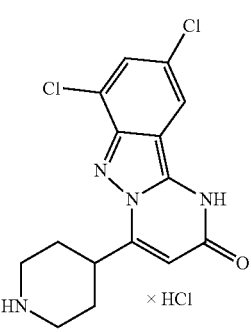 [SMILES: O=c1cc(C2CCNCC2)n2nc3c(Cl)cc(Cl)cc3c2[nH]1]

Tert-butyl 4-(8,10-dichloro-4-oxo-1,4-dihydropyrimido[1,2-b]indazol-2-yl)piperidine-1-carboxylate (15.5 mg, 0.035 mmol) was dissolved in 4N HCl in dioxane (0.9 mL) and methanol (0.1 mL), stirred for 30 min and evaporated in vacuo. Methanol (5 mL each) was added and the solution was evaporated two times to give the title compound (13.4 mg, 0.04 mmol, 100% of theory).

LC-MS (Method 1B): $R_t$=0.61 min, MS (ESIPos): m/z=337 [M+H−xHCl]$^+$ $^1$H-NMR (400 MHz, DMSO-d$_6$+TFA): δ=8.01 (d, J=1.8 Hz, 1H), 7.62 (d, J=1.8 Hz, 1H), 6.41 (s, 1H), 3.81 (tm, 1H), 2.10 (dm, 2H), 3.23 (tm, 2H), 2.33 (d, 2H), 1.91 (dq, 2H).

Example 7

9-Fluoro-4-(piperidin-4-yl)pyrimido[1,2-b]indazol-2(1H)-one Hydrochloride

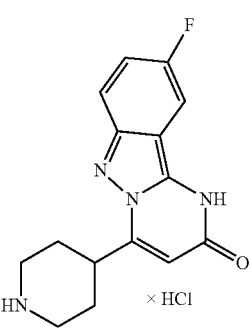 [SMILES: O=c1cc(C2CCNCC2)n2nc3ccc(F)cc3c2[nH]1]

Tert-butyl 4-(9-fluoro-4-oxo-1,4-dihydropyrimido[1,2-b]indazol-2-yl)piperidine-1-carboxylate (59 mg, 0.153 mmol) was dissolved in 4N HCl in dioxane (1 mL) and methanol (1 mL) and irradiated with ultrasound for 15 min. The resulting suspension was diluted with dioxane (2 mL) and filtered, the residue was washed with dioxane (2 ml) and dried for 16 h at 50° C. in vacuo to yield the title compound (53 mg, 92% purity, 99% of theory).

LC-MS (Method 2B): R$_t$=1.29 min, MS (ESIPos): m/z=287 [M+H−xHCl]$^+$ $^1$H-NMR (400 MHz, D$_2$O): δ=7.52 (dt, 1H), 7.34-7.25 (m, 2H), 6.34 (s, 1H), 3.71-3.60 (m, 3H), 3.31 (t, 2H), 2.46 (d, 2H), 1.99 (qm, 2H).

Example 8

10-Methoxy-4-(piperidin-4-yl)pyrimido[1,2-b]indazol-2(1H)-one Hydrochloride

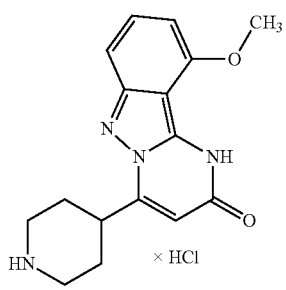 [SMILES: COc1cccc2nn3c(C4CCNCC4)cc(=O)[nH]c3c12]

Tert-butyl 4-(10-methoxy-4-oxo-1,4-dihydropyrimido[1,2-b]indazol-2-yl)piperidine-1-carboxylate (120 mg, 0.30 mmol) was dissolved in 4N HCl in dioxane (2 mL) and methanol (2 mL) and irradiated with ultrasound for 15 min. The resulting suspension was diluted with dioxane (2 mL) and filtered, the residue was washed with dioxane (2 ml) and dried for 16 h at 50° C. in vacuo to yield the title compound (102 mg, 98% purity, 99% of theory).

LC-MS (Method 2B): R$_t$=1.27 min, MS (ESIPos): m/z=299 [M+H−xHCl]$^+$ $^1$H-NMR (400 MHz, D$_2$O): δ=7.32 (t, 1H), 6.92 (d, 1H), 6.30 (d, 1H), 6.23 (s, 1H), 3.65 (d, 2H), 3.47 (t, 1H), 3.29 (t, 2H), 2.42 (d, 2H), 1.94 (dm, 2H).

Example 9

7-(Piperidin-4-yl)pyrido[3',2':3,4]pyrazolo[1,5-a]pyrimidin-9(10H)-one Hydrochloride

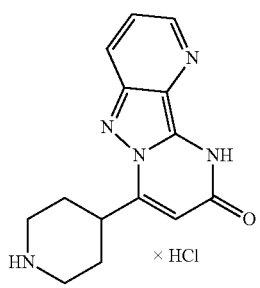 [SMILES: O=c1cc(C2CCNCC2)n2nc3cccnc3c2[nH]1]

Tert-butyl 4-(9-oxo-9,10-dihydropyrido[3',2':3,4]pyramzolo[1,5-a]pyrimidin-7-yl)piperidine-1-carboxylate (16 mg, 0.04 mmol) was dissolved in 4N HCl in dioxane (1 mL) and methanol (1 mL) and irradiated with ultrasound for 15 min. The resulting suspension was diluted with dioxane (2 mL) and filtered, the residue was washed with dioxane (2 ml) and dried for 16 h at 50° C. in vacuo to yield the title compound (16 mg, 92% purity, 99% of theory).

LC-MS (Method 2B): R$_t$=1.07 min, MS (ESIPos): m/z=270 [M+H−xHCl]$^+$ $^1$H-NMR (400 MHz, D$_2$O): δ=8.54 (d, 1H), 8.14 (d, 1H), 7.56 (dd, 1H), 6.51 (s, 1H), 3.82 (t, 1H), 3.66 (d, 2H), 3.32 (t, 2H), 2.49 (d, 2H), 2.02 (qm, 2H).

Example 10

10-Bromo-4-(piperidin-4-yl)pyrimido[1,2-b]indazol-2(1H)-one Hydrochloride

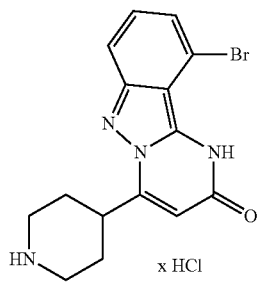 [SMILES: O=c1cc(C2CCNCC2)n2nc3cccc(Br)c3c2[nH]1]

Tert-butyl 4-(10-bromo-4-oxo-1,4-dihydropyrimido[1,2-b]indazol-2-yl)piperidine-1-carboxylate (190 mg, 0.425 mmol) was dissolved in 4N HCl in dioxane (4 mL) and methanol (4 mL) and irradiated with ultrasound for 15 min. The resulting suspension was filtered, the residue was washed with dioxane (5 ml) and dried for 16 h at 50° C. in vacuo to yield the title compound (175 mg, 93% purity, 99% of theory).

LC-MS (Method 2B): R$_t$=1.44 min, MS (ESIPos): m/z=347/349 [M+H−xHCl]$^+$ $^1$H-NMR (400 MHz, D$_2$O): δ=7.40 (d, 1H), 7.22 (dd, 1H), 7.11 (d, 1H), 6.39 (s, 1H), 3.67 (d, 2H), 3.60 (t, 1H), 3.32 (dd, 2H), 2.46 (d, 2H), 1.98 (qm, 2H).

Example 11

4-(Piperidin-4-yl)-8-(trifluoromethyl)pyrimido[1,2-b]indazol-2(1H)-one Hydrochloride

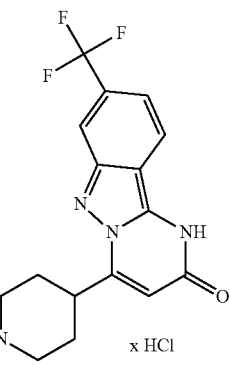

Tert-butyl 4-[2-oxo-8-(trifluoromethyl)-1,2-dihydropyrimido[1,2-b]indazol-4-yl]piperidine-1-carboxylate (353 mg, 0.810 mmol) was dissolved in methanol (8 mL), 4N HCl in dioxane (8 mL) was added and the mixture irradiated with ultrasound for 15 min. The resulting suspension was filtered, the residue was washed with dioxane (5 ml) and dried for 16 h at 50° C. in vacuo to yield the title compound (231 mg, 76% of theory).

LC-MS (Method 2B): $R_t$=1.61 min, MS (ESIPos): m/z=337 [M+H−xHCl]$^+$ $^1$H-NMR (400 MHz, D$_2$O): δ=7.78 (s, 1H), 7.74 (d, 1H), 7.16 (d, 1H), 6.35 (s, 1H), 3.68 (d, 2H), 3.63 (t, 1H), 3.32 (dd, 2H), 2.45 (d, 2H), 1.99 (dm, 2H).

Example 12

4-(Piperidin-4-yl)-10-(trifluoromethyl)pyrimido[1,2-b]indazol-2(1H)-one hydrochloride

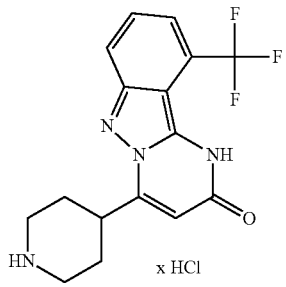 [SMILES: O=c1cc(C2CCNCC2)n2nc3cccc(C(F)(F)F)c3c2[nH]1]

Tert-butyl 4-(10-(trifluoromethyl)-4-oxo-1,4-dihydropyrimido[1,2-b]indazol-2-yl)piperidine-1-carboxylate (103 mg, 0.237 mmol) was dissolved in methanol (4 mL), 4N HCl in dioxane (4 mL) was added and the mixture irradiated with ultrasound for 15 min. The resulting suspension was diluted with methanol (2 mL), filtered, the residue was washed with methanol (3 ml) and dried for 16 h at 50° C. in vacuo to yield the title compound (90.6 mg, 97% purity, 99% of theory).

LC-MS (Method 2B): $R_t$=1.55 min, MS (ESIPos): m/z=337 [M+H−xHCl]$^+$ $^1$H-NMR (400 MHz, D$_2$O): δ=7.80 (d, 1H), 7.58-7.49 (m, 2H), 6.48 (s, 1H), 3.76 (t, 1H), 3.67 (d, 2H), 3.32 (dd, 2H), 2.47 (d, 2H), 2.00 (qm, 2H).

Example 13

8-tert-Butyl-4-(piperidin-4-yl)pyrido[2',3':3,4]pyrazolo[1,5-a]pyrimidin-2(1H)-one Hydrochloride

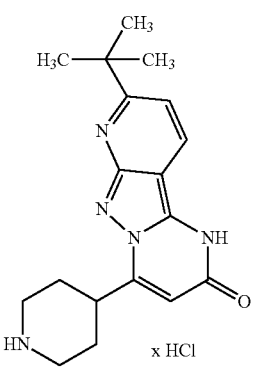 [SMILES: CC(C)(C)c1ccc2c(n1)nn1c(C3CCNCC3)cc(=O)[nH]c21]

Tert-butyl 4-(8-tert-butyl-4-oxo-1,4-dihydropyrido[2',3':3,4]pyrazolo[1,5-a]pyrimidin-2-yl)piperidine-1-carboxylate (64 mg, 0.152 mmol) was dissolved in methanol (2 mL), 4N HCl in dioxane (2 mL) was added and the mixture irradiated with ultrasound for 15 min. The resulting yellow solution was evaporated and the residue was triturated with 4 mL dioxane/methanol (20:1), filtered and dried for 16 h at 50° C. in vacuo to yield the title compound (51.4 mg, 90% purity, 76% of theory).

LC-MS (Method 2B): $R_t$=1.57 min, MS (ESIPos): m/z=326 [M+H−xHCl]$^+$ $^1$H-NMR (400 MHz, D$_2$O): δ=8.82 (d, 1H), 7.53 (d, 1H), 6.62 (s, 1H), 3.88 (t, 1H), 3.66 (d, 2H), 3.33 (dd, 2H), 2.49 (d, 2H), 2.05 (qm, 2H), 1.54 (s, 9H).

Example 14

10-Methyl-4-(piperidin-4-yl)-8-(trifluoromethyl)pyrido[2',3':3,4]pyrazolo[1,5-a]pyrimidin-2(1H)-one Hydrochloride

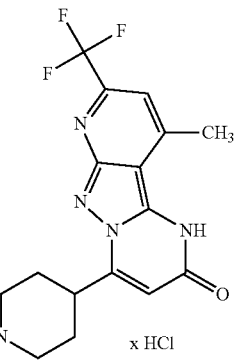

Tert-butyl 4-(8-(trifluoromethyl)-4-oxo-1,4-dihydropyrido[2',3':3,4]pyrazolo[1,5-a]pyrimidin-2-yl)piperidine-1-carboxylate (105 mg, 0.233 mmol) was dissolved in methanol (2 mL), 4N HCl in dioxane (2 mL) was added and the mixture irradiated with ultrasound for 15 min. The resulting suspension was filtered, the residue was washed with dioxane (5 ml) and dried for 16 h at 50° C. in vacuo to yield the title compound (71.8 mg, 72% of theory).

LC-MS (Method 1B): $R_t$=0.59 min, MS (ESIPos): m/z=352 [M+H−xHCl]$^+$ $^1$H-NMR (400 MHz, D$_2$O): δ=7.49 (s, 1H), 6.63 (s, 1H), 3.85 (dt-like, 1H), 3.67 (d, 2H), 3.34 (t, 2H), 2.77 (s, 3H), 2.50 (d, 2H), 2.05 (qm, 2H).

Example 15

9-Methyl-4-(piperidin-4-yl)pyrimido[1,2-b]indazol-2(1H)-one Hydrochloride

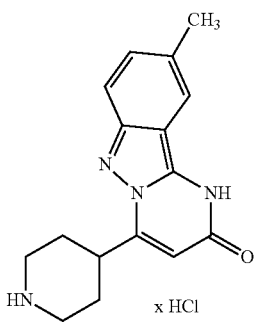 [SMILES: Cc1ccc2nn3c(C4CCNCC4)cc(=O)[nH]c3c2c1]

Tert-butyl 4-(9-methyl-4-oxo-1,4-dihydropyrimido[1,2-b]indazol-2-yl)piperidine-1-carboxylate (130 mg, 0.34 mmol) was dissolved in methanol (2 mL). 4N HCl in dioxane (2 mL) was added and the mixture was irradiated with ultrasound for 15 min. The resulting suspension was diluted with methanol (2 mL), filtered, the residue was washed with dioxane (2 ml) and dried for 16 h at 50° C. in vacuo to yield the title compound (108 mg, 98% of theory).

LC-MS (Method 1B): $R_t$=0.55 min, MS (ESIPos): m/z=283 [M+H−xHCl]$^+$ $^1$H-NMR (400 MHz, D$_2$O): δ=7.32-7.19 (m, 3H), 6.20 (br. S, 1H), 3.67 (d, 2H), 3.48 (t-like, 1H), 3.30 (t, 2H), 2.41 (d, 2H), 2.32 (s, 3H), 1.94 (qm, 2H).

Example 16

8-Amino-4-(piperidin-4-yl)pyrimido[1,2-b]indazol-2(1H)-one Hydrochloride

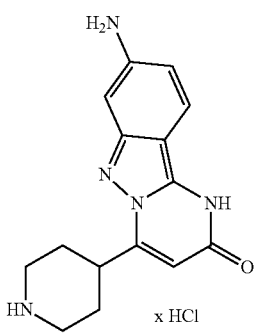 [SMILES: Nc1ccc2c(c1)nn1c(C3CCNCC3)cc(=O)[nH]c21]

Tert-butyl 4-(8-amino-4-oxo-1,4-dihydropyrimido[1,2-b]indazol-2-yl)piperidine-1-carboxylate (23 mg, 0.06 mmol) was dissolved in methanol (0.5 mL). 4N HCl in dioxane (0.5 mL) was added and the mixture was irradiated with ultrasound for 15 min. The resulting suspension was diluted with methanol (2 mL), filtered, the residue was washed with dioxane (2 ml) and dried for 16 h at 50° C. in vacuo to yield the title compound (14 mg, 64% of theory).

LC-MS (Method 1B): $R_t$=0.18 min, MS (ESIPos): m/z=284 [M+H−xHCl]$^+$ $^1$H-NMR (400 MHz, DMSO-d$_6$): δ=7.91 (d, 1H), 6.96 (d, 1H), 6.38 (s, 1H), 6.26 (s, 1H), 3.71 (t, 1H), 3.66 (d, 2H), 3.31 (dd, 2H), 2.47 (d, 2H), 1.99 (qm, 2H).

Example 17

3,4-Dimethyl-8-(piperidin-4-yl)pyrimido[1',2':1,5]pyrazolo[3,4-c]pyridazin-6(5H)-one Hydrochloride

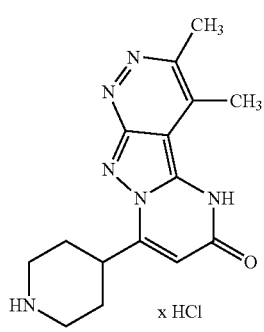 [SMILES: Cc1nnc2nn3c(C4CCNCC4)cc(=O)[nH]c3c2c1C]

Tert-butyl 4-(3,4-dimethyl-8-oxo-5,8-dihydropyrimido[1',2':1,5]pyrazolo[3,4-c]pyridazin-6-yl)piperidine-1-carboxylate (55 mg, 0.128 mmol) was dissolved in methanol (1 mL). 4N HCl in dioxane (1 mL) was added and the mixture was irradiated with ultrasound for 15 min. The resulting suspension was diluted with methanol (2 mL), filtered, the residue was washed with dioxane (2 ml) and dried for 16 h at 50° C. in vacuo to yield the title compound (43.6 mg, 85% of theory).

LC-MS (Method 2B): $R_t$=1.12 min, MS (ESIPos): m/z=299 [M+H−xHCl]$^+$ $^1$H-NMR (400 MHz, D$_2$O): δ=7.02 (s, 1H), 3.86 (t-like, 1H), 3.68 (d, 2H), 3.34 (dd, 2H), 3.06 (s, 3H), 2.81 (s, 3H), 2.51 (d, 2H), 2.08 (qm, 2H).

Example 18

8-Fluoro-4-(piperidin-4-yl)pyrimido[1,2-b]indazol-2(1H)-one Hydrochloride

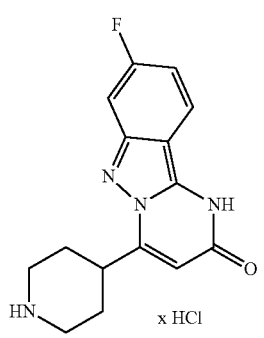 [SMILES: O=c1cc(C2CCNCC2)n2nc3cc(F)ccc3c2[nH]1]

Tert-butyl 4-(8-fluoro-4-oxo-1,4-dihydropyrimido[1,2-b]indazol-2-yl)piperidine-1-carboxylate (57.1 mg, 0.148 mmol) was dissolved in methanol (1 mL). 4N HCl in dioxane (1 mL) was added and the mixture was irradiated with ultrasound for 15 min. The resulting suspension was diluted with methanol (2 mL), filtered, the residue was washed with dioxane (2 ml) and dried for 16 h at 50° C. in vacuo to yield the title compound (40.3 mg, 84% of theory).

LC-MS (Method 2B): R$_t$=1.30 min, MS (ESIPos): m/z=287 [M+H−xHCl]$^+$ $^1$H-NMR (400 MHz, D$_2$O): δ=7.67 (dt, 1H), 7.05 (d, 1H), 6.82 (dt, 1H), 6.29 (s, 1H), 3.62 (d, 2H), 3.58 (t-like, 1H), 3.26 (dd, 2H), 2.40 (d, 2H), 1.93 (qm, 2H), 2 exchangeable protons not visible.

Example 19

9-Bromo-4-(piperidin-4-yl)pyrimido[1,2-b]indazol-2(1H)-one Hydrochloride

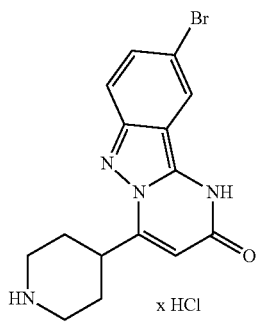 [SMILES: O=c1cc(C2CCNCC2)n2nc3ccc(Br)cc3c2[nH]1]

Tert-butyl 4-(9-bromo-4-oxo-1,4-dihydropyrimido[1,2-b]indazol-2-yl)piperidine-1-carboxylate (30 mg, 0.067 mmol) was dissolved in methanol (1 mL). 4N HCl in dioxane (1 mL) was added and the mixture was irradiated with ultrasound for 15 min. The resulting suspension was filtered, the residue was washed with methanol (0.5 mL) and dried for 16 h at 50° C. in vacuo to yield the title compound (11 mg, 42% of theory).

LC-MS (Method 2B): R$_t$=1.48 min, MS (ESIPos): m/z=347/349 [M+H−xHCl]$^+$ $^1$H-NMR (400 MHz, D$_2$O): δ=7.83 (s, 1H), 7.48 (d, 1H), 7.42 (d, 1H), 6.40 (s, 1H), 3.74-3.62 (m, 3H), 3.31 (t-like, 2H), 2.48 (d, 2H), 2.00 (qm, 2H).

Example 20

10-Iodo-4-(piperidin-4-yl)pyrimido[1,2-b]indazol-2(1H)-one Hydrochloride

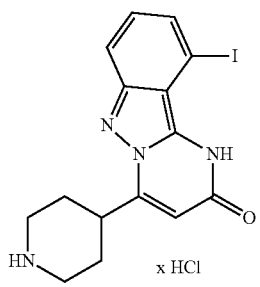

Tert-butyl 4-(10-iodo-4-oxo-1,4-dihydropyrimido[1,2-b]indazol-2-yl)piperidine-1-carboxylate (43 mg, 0.087 mmol) was dissolved in methanol (1 mL). 4N HCl in dioxane (1 mL) was added and the mixture was irradiated with ultrasound for 15 min. The resulting suspension was diluted with methanol (2 mL), filtered, the residue was washed with dioxane (2 mL) and dried for 16 h at 50° C. in vacuo to yield the title compound (34 mg, 90% of theory).

LC-MS (Method 2B): R$_t$=1.52 min, MS (ESIPos): m/z=395 [M+H−xHCl]$^+$ $^1$H-NMR (400 MHz, D$_2$O): δ=7.43 (d, 1H), 7.37 (d, 1H), 7.05 (dd, 1H), 6.43 (s, 1H), 3.68 (d, 2H), 3.61 (t-like, 1H), 3.32 (dd, 2H), 2.46 (d, 2H), 1.98 (qm, 2H).

Example 21

8-Bromo-4-(piperidin-4-yl)pyrimido[1,2-b]indazol-2(1H)-one Hydrochloride

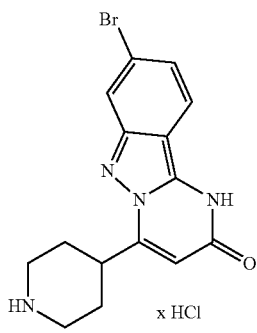 [SMILES: O=c1cc(C2CCNCC2)n2nc3cc(Br)ccc3c2[nH]1]

Tert-butyl 4-(8-bromo-4-oxo-1,4-dihydropyrimido[1,2-b]indazol-2-yl)piperidine-1-carboxylate (85 mg, 0.190 mmol) was dissolved in methanol (1 mL). 4N HCl in dioxane (1 mL) was added and the mixture was irradiated with ultrasound for 15 min. The resulting suspension was diluted with methanol (2 mL), filtered, the residue was washed with dioxane (2 mL) and dried for 16 h at 50° C. in vacuo to yield the title compound (58 mg, 78% of theory).

LC-MS (Method 2B): R$_t$=1.50 min, MS (ESIPos): m/z=347/349 [M+H−xHCl]$^+$ $^1$H-NMR (400 MHz, D$_2$O): δ=7.50 (s, 1H), 7.39 (d, 1H), 6.94 (d, 1H), 6.37 (s, 1H), 3.68 (d, 2H), 3.56 (t-like, 1H), 3.32 (dd, 2H), 2.47 (d, 2H), 1.99 (qm, 2H).

Example 22

7-Chloro-4-(piperidin-4-yl)pyrimido[1,2-b]indazol-2(1H)-one Hydrochloride

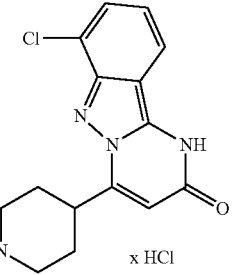

Tert-butyl 4-(7-chloro-4-oxo-1,4-dihydropyrimido[1,2-b]indazol-2-yl)piperidine-1-carboxylate (75 mg, 0.186 mmol) was suspended in methanol (1 mL). 4N HCl in dioxane (1 mL) was added and the mixture was irradiated with ultrasound for 30 min. The resulting yellow suspension was diluted with methanol (2 mL), filtered, the residue was washed with 2 mL dioxane/methanol (1:1) and dried for 16 h at 50° C. in vacuo to yield the title compound (60 mg, 95% of theory).

LC-MS (Method 2B): R$_t$=1.41 min, MS (ESIPos): m/z=303 [M+H−xHCl]$^+$ $^1$H-NMR (400 MHz, DMSO-d$_6$): δ=13.49 (br. s, 1H), 8.80 (br. s, 1H), 8.56 (br. s, 1H), 7.95 (d, 1H), 7.53 (d, 1H), 6.99 (dd, 1H), 6.28 (br. s, 1H), 3.81 (br. s, 1H), 3.44 (d, 2H), 3.28-3.14 (m, 2H), 2.33 (d, 2H), 1.90 (qm, 2H).

Example 23

8,10-Difluoro-4-(piperidin-4-yl)pyrimido[1,2-b]indazol-2(1H)-one Hydrochloride

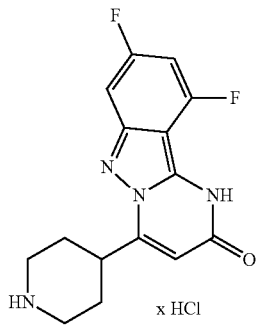 [SMILES: O=c1cc(C2CCNCC2)n2nc3cc(F)cc(F)c3c2[nH]1]

Tert-butyl 4-(8,10-difluoro-4-oxo-1,4-dihydropyrimido[1,2-b]indazol-2-yl)piperidine-1-carboxylate (26 mg, 0.064 mmol) was suspended in methanol (0.5 mL). 4N HCl in dioxane (0.5 mL) was added and the mixture was irradiated with ultrasound for 30 min. The resulting yellow suspension was filtered, the residue was washed with dioxane (2 mL) and dried for 16 h at 50° C. in vacuo to yield the title compound (13 mg, 95% purity, 57% of theory).

LC-MS (Method 2B): R$_t$=1.36 min, MS (ESIPos): m/z=305 [M+H−xHCl]$^+$ $^1$H-NMR (400 MHz, DMSO-d$_6$): δ=12.79 (br. s, 1H), 8.91 (br. d, 1H), 8.74 (br. d, 1H), 7.22 (d, 1H), 6.87 (dt, 1H), 6.66 (br. s, 1H), 3.85 (br. t, 1H), 3.44 (d, 2H), 3.18 (dd, 2H), 2.31 (d, 2H), 1.94 (dm, 2H).

Example 24

8-Methyl-4-(piperidin-4-yl)pyrido[2',3':3,4]pyrazolo[1,5-a]pyrimidin-2(1H)-one Hydrochloride

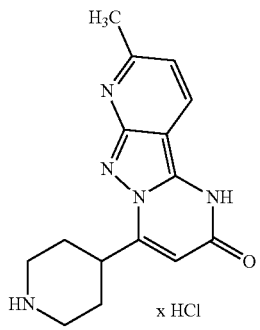 [SMILES: Cc1ccc2c(n1)nn1c(C3CCNCC3)cc(=O)[nH]c21]

Tert-butyl 4-(8-methyl-4-oxo-1,4-dihydropyrido[2',3':3,4]pyrazolo[1,5-a]pyrimidin-2-yl)piperidine-1-carboxylate (50 mg, 0.130 mmol) was dissolved in methanol (1 mL). 4N HCl in dioxane (1 mL) was added and the mixture was irradiated with ultrasound for 15 min. The resulting suspension was diluted with dioxane (2 mL), filtered, the residue was washed with dioxane (2 mL) and dried for 16 h at 50° C. in vacuo to yield the title compound (43 mg, 93% of theory).

LC-MS (Method 2B): R$_t$=1.12 min, MS (ESIPos): m/z=284 [M+H−xHCl]$^+$ $^1$H-NMR (400 MHz, D$_2$O): δ=8.82 (d, 1H), 7.32 (d, 1H), 6.65 (s, 1H), 3.83 (t-like, 1H), 3.65 (d, 2H), 3.31 (dd, 2H), 2.87 (s, 3H), 2.48 (d, 2H), 2.04 (qm, 2H).

Example 25

3-Fluoro-7-(piperidin-4-yl)pyrido[3',2':3,4]pyrazolo[1,5-a]pyrimidin-9(10H)-one Hydrochloride

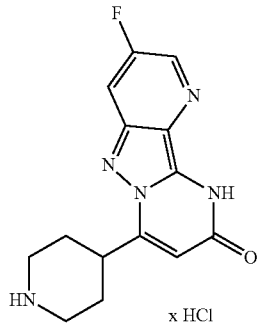 [SMILES: O=c1cc(C2CCNCC2)n2nc3cc(F)cnc3c2[nH]1]

Tert-butyl 4-(3-fluoro-9-oxo-9,10-dihydropyrido[3',2':3,4]pyrazolo[1,5-a]pyrimidin-7-yl)piperidine-1-carboxylate (50.9 mg, 0.131 mmol) was dissolved in methanol (1 mL). 4N HCl in dioxane (1 mL) was added and the mixture was irradiated with ultrasound for 15 min. The resulting suspension was diluted with dioxane (2 mL), filtered, the residue was washed with dioxane (2 mL) and dried for 16 h at 50° C. in vacuo to yield the title compound (38.9 mg, 82% of theory).

LC-MS (Method 2B): R$_t$=1.19 min, MS (ESIPos): m/z=270 [M+H−xHCl]$^+$ $^1$H-NMR (400 MHz, D$_2$O): δ=8.42 (s, 1H), 7.69 (dd, 1H), 6.46 (s, 1H), 3.76 (t-like, 1H), 3.66 (d, 2H), 3.31 (dd, 2H), 2.47 (d, 2H), 2.01 (qm, 2H).

Example 26

10-Ethoxy-4-(piperidin-4-yl)pyrimido[1,2-b]indazol-2(1H)-one Hydrochloride

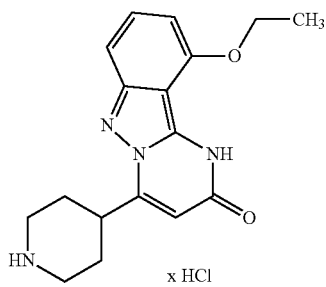 [SMILES: CCOc1cccc2nn3c(C4CCNCC4)cc(=O)[nH]c3c12]

Tert-butyl 4-(10-ethoxy-2-oxo-1,2-dihydropyrimido[1,2-b]indazol-4-yl)piperidine-1-carboxylate (135 mg, 0.327 mmol) was dissolved in methanol (2.5 mL). 4N HCl in dioxane (2.5 mL) was added and the mixture was irradiated with ultrasound for 15 min. The resulting suspension was diluted with dioxane (2 mL), filtered, the residue was washed with dioxane (2 mL) and dried for 16 h at 50° C. in vacuo to yield the title compound (120 mg, 95% purity, 0.33 mmol, 100% of theory).

LC-MS (Method 2B): $R_t$=1.40 min, MS (ESIPos): m/z=313 [M+H−xHCl]$^+$ $^1$H-NMR (400 MHz, D$_2$O): δ=7.35 (dd, 1H), 6.98 (d, 1H), 6.35 (d, 1H), 6.28 (s, 1H), 4.23 (q, 2H), 3.66 (d, 2H), 3.54 (t-like, 1H), 3.30 (dd, 2H), 2.44 (d, 2H), 1.96 (qm, 2H), 1.47 (t, 3H).

Example 27

7-Bromo-4-(piperidin-4-yl)pyrido[4',3':3,4]pyrazolo[1,5-a]pyrimidin-2(1H)-one Hydrochloride

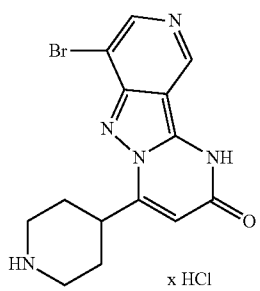 [SMILES: O=c1cc(C2CCNCC2)n2nc3c(Br)cncc3c2[nH]1]

Tert-butyl 4-(7-bromo-2-oxo-1,2-dihydropyrido[4',3':3,4]pyrazolo[1,5-a]pyrimidin-4-yl)piperidine-1-carboxylate (105 mg, 0.235 mmol) was dissolved in methanol (2 mL). 4N HCl in dioxane (2 mL) was added and the mixture was irradiated with ultrasound for 15 min. The resulting suspension was diluted with dioxane (2 mL), filtered, the residue was washed with dioxane (2 mL) and dried for 16 h at 50° C. in vacuo to yield the title compound (90 mg, 91% of theory).

LC-MS (Method 2B): $R_t$=1.18 min, MS (ESIPos): m/z=350 [M+H−xHCl]$^+$ $^1$H-NMR (400 MHz, DMSO-d$_6$): δ=12.88 (br. s, 1H), 9.29 (s, 1H), 9.02 (br. s, 1H), 8.92 (br. s, 1H), 8.32 (s, 1H), 6.98 (s, 1H), 3.95 (t-like, 1H), 3.46 (d, 2H), 3.20 (dd, 2H), 2.34 (d, 2H), 2.01 (dq, 2H).

Example 28

7-Fluoro-4-(piperidin-4-yl)pyrimido[1,2-b]indazol-2(1H)-one Hydrochloride

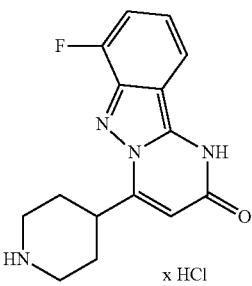 [SMILES: O=c1cc(C2CCNCC2)n2nc3c(F)cccc3c2[nH]1]

Tert-butyl 4-(7-fluoro-2-oxo-1,2-dihydropyrimido[1,2-b]indazol-4-yl)piperidine-1-carboxylate (82.6 mg, 0.214 mmol) was dissolved in methanol (1 mL). 4N HCl in dioxane (1 mL) was added and the mixture was irradiated with ultrasound for 15 min at 40° C. The resulting solution was evaporated in vacuo and triturated with dioxane (2 mL), filtered, and dried for 16 h at 50° C. in vacuo to give the title compound (69.4 mg, 0.21 mmol, 100% of theory) as the yellowish hydrochloride salt.

LC-MS (Method 2B): $R_t$=1.30 min, MS (ESIPos): m/z=287 [M+H−xHCl]$^+$ $^1$H-NMR (400 MHz, D$_2$O): δ=7.56 (d, 1H), 7.18 (dd, 1H), 7.01 (dt, 1H), 6.39 (s, 1H), 3.74.3.62 (m, 3H), 3.33 (dd, 2H), 2.48 (d, 2H), 2.00 (qm, 2H).

Example 29

4-(Piperidin-4-yl)pyrido[3',4':3,4]pyrazolo[1,5-a]pyrimidin-2(1H)-one Hydrochloride

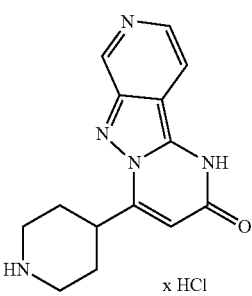 [SMILES: O=c1cc(C2CCNCC2)n2nc3cnccc3c2[nH]1]

Tert-butyl 4-(2-oxo-1,2-dihydropyrido[3',4':3,4]pyrazolo[1,5-a]pyrimidin-4-yl)piperidine-1-carboxylate (80.0 mg, 75% purity, 0.152 mmol) was dissolved in methanol (1 mL). 4N HCl in dioxane (1 mL) was added and the mixture was irradiated with ultrasound for 15 min at 40° C. The resulting suspension was diluted with dioxane (2 mL), filtered, and dried for 16 h at 50° C. in vacuo to give the title compound (42.4 mg, 79% of theory).

LC-MS (Method 2B): $R_t$=1.04 min, MS (ESIPos): m/z=270 [M+H−xHCl]+

$^1$H-NMR (400 MHz, D$_2$O): δ=9.50 (s, 1H), 8.46 (d, 1H), 8.14 (d, 1H), 6.78 (s, 1H), 3.93 (t-like, 1H), 3.67 (dd, 2H), 2.52 (d, 2H), 2.07 (qm, 2H).

Example 30

4-(Piperidin-4-yl)-7-(trifluoromethyl)pyrimido[1,2-b]indazol-2(1H)-one Hydrochloride

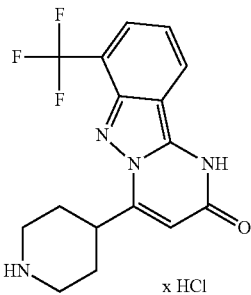 [SMILES: O=c1cc(C2CCNCC2)n2nc3c(C(F)(F)F)cccc3c2[nH]1]

Tert-butyl 4-[2-oxo-7-(trifluoromethyl)-1,2-dihydropyrimido[1,2-b]indazol-4-yl]piperidine-1-carboxylate (109 mg, 0.249 mmol) was dissolved in methanol (1 mL). 4N HCl in dioxane (2 mL) was added and the mixture was irradiated with ultrasound for 15 min at 40° C. The resulting solution was evaporated in vacuo and triturated with dioxane (2 mL), filtered, and dried for 16 h at 50° C. in vacuo to give the title compound (86 mg, 91% of theory).

LC-MS (Method 2B): $R_t$=1.62 min, MS (ESIPos): m/z=337 [M+H−xHCl]+

$^1$H-NMR (400 MHz, D$_2$O): δ=7.92 (d, 1H), 7.76 (d, 1H), 7.06 (dd, 1H), 6.38 (s, 1H), 3.79 (t-like, 1H), 3.65 (d, 2H), 3.34 (dd, 2H), 2.46 (d, 2H), 1.98 (qm, 2H).

Example 31

10-Nitro-4-(piperidin-4-yl)-8-(trifluoromethyl)pyrimido[1,2-b]indazol-2(1H)-one Hydrochloride

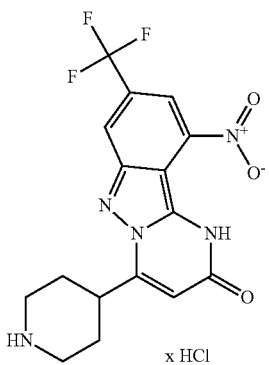 [SMILES: O=c1cc(C2CCNCC2)n2nc3cc(C(F)(F)F)cc([N+](=O)[O-])c3c2[nH]1]

Tert-butyl 4-[10-nitro-2-oxo-8-(trifluoromethyl)-1,2-dihydropyrimido[1,2-b]indazol-4-yl]piperidine-1-carboxylate (80 mg, 0.166 mmol) was dissolved in methanol (1.3 mL). 4N HCl in dioxane (1.3 mL) was added and the mixture was irradiated with ultrasound for 15 min. The resulting suspension was diluted with dioxane (2 mL), filtered, and dried for 16 h at 50° C. in vacuo. The crude product product was again was dissolved in methanol (1 mL). 4N HCl in dioxane (1 mL) was added and the mixture was irradiated with ultrasound for 15 min. The resulting suspension was evaporated in vacuo. Methanol (5 mL) was added and the solution was evaporated in vacuo. Methanol (5 mL) was added and the solution was evaporated in vacuo again to give the title compound (40 mg, 58% of theory).

LC-MS (Method 2B): $R_t$=1.71 min, MS (ESIPos): m/z=382 [M+H−xHCl]+

$^1$H-NMR (400 MHz, D$_2$O): δ=8.71 (s, 1H), 8.58 (s, 1H), 6.62 (s, 1H), 3.94 (t-like, 1H), 3.68 (d, 2H), 3.36 (dd, 2H), 2.52 (d, 2H), 2.05 (qm, 2H).

Example 32

8,10-Dimethyl-4-(piperidin-4-yl)pyrido[2',3':3,4]pyrazolo[1,5-a]pyrimidin-2(1H)-one Hydrochloride

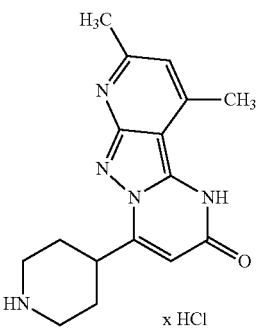 [SMILES: Cc1cc(C)c2c(n1)nn1c(C3CCNCC3)cc(=O)[nH]c21]

Tert-butyl 4-(8,10-dimethyl-4-oxo-1,4-dihydropyrido[2',3':3,4]pyrazolo[1,5-a]pyrimidin-2-yl)piperidine-1-carboxylate (79.6 mg, 0.200 mmol) was dissolved in methanol (2 mL). 4N HCl in dioxane (2 mL) was added and the mixture was irradiated with ultrasound for 15 min. The resulting suspension was diluted with methanol (2 mL), filtered, washed with methanol (3 mL) and dried for 16 h at 50° C. in vacuo to give the title compound (65.2 mg, 88% of theory).

LC-MS (Method 2B): $R_t$=1.39 min, MS (ESIPos): m/z=298 [M+H−xHCl]+

$^1$H-NMR (400 MHz, D$_2$O): δ=6.89 (s, 1H), 6.38 (s, 1H), 3.62 (d, 2H), 3.29-3.14 (3H), 2.86 (s, 3H), 2.71 (s, 3H), 2.33 (d, 2H), 2.04 (qm, 2H).

Example 33

2-Oxo-4-(piperidin-4-yl)-1,2-dihydropyrimido[1,2-b]indazole-10-carbonitrile Trifluoroacetate

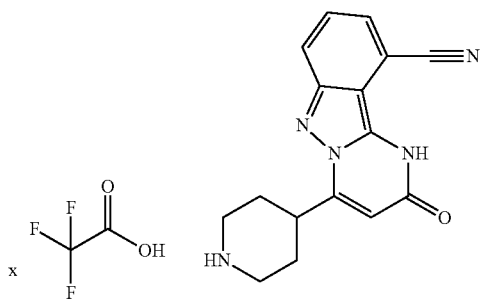 [SMILES: O=C(O)C(F)(F)F ; N#Cc1cccc2nn3c(C4CCNCC4)cc(=O)[nH]c3c12]

Tert-butyl 4-(10-cyano-2-oxo-1,2-dihydropyrimido[1,2-b]indazol-4-yl)piperidine-1-carboxylate (22 mg, 0.05 mmol) in dichloromethane (2 mL) was added TFA (0.1 mL) and the mixture was stirred for 16 h at RT. The resulting solution was evaporated in vacuo, dissolved in water (15 mL) and lyophilized to give the title compound (20 mg, 86% of theory).

LC-MS (Method 2B): $R_t$=1.34 min, MS (ESIPos): m/z=294 [M+H−xTFA]$^+$ $^1$H-NMR (400 MHz, DMSO-d$_6$): δ=12.62 (br. S, 1H), 8.75 (br. S, 1H), 8.44 (br. S, 1H), 8.02 (d, 1H), 7.70 (d, 1H), 7.62 (dd, 1H), 6.82 (s, 1H), 3.94 (t-like, 1H), 3.48 (d, 2H), 3.26-3.15 (m, 2H), 2.36 (d, 2H), 1.94 (qm, 2H).

Example 34

7-Bromo-4-(piperidin-4-yl)pyrimido[1,2-b]indazol-2(1H)-one Hydrochloride

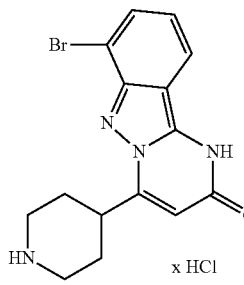

Tert-butyl 4-(7-bromo-2-oxo-1,2-dihydropyrimido[1,2-b]indazol-4-yl)piperidine-1-carboxylate (50.8 mg, 0.114 mmol) was dissolved in methanol (1.5 mL). 4N HCl in dioxane (1.5 mL) was added and the mixture was irradiated with ultrasound for 15 min. The resulting suspension was filtered, washed with dioxane (2 mL) and dried for 16 h at 50° C. in vacuo to give the title compound (40.8 mg, 94% of theory).

LC-MS (Method 1B): $R_t$=0.52 min, MS (ESIPos): m/z=347 [M+H−xHCl]$^+$ $^1$H-NMR (400 MHz, D$_2$O): δ=7.85 (d, 1H), 7.73 (d, 1H), 6.97 (dd, 1H), 6.40 (s, 1H), 3.83 (t-like, 1H), 3.66 (d, 2H), 3.35 (dd, 2H), 2.51 (d, 2H), 2.01 (qm, 2H).

Example 35

4-(Piperidin-4-yl)pyrido[2',3':3,4]pyrazolo[1,5-a]pyrimidin-2(1H)-one Hydrochloride

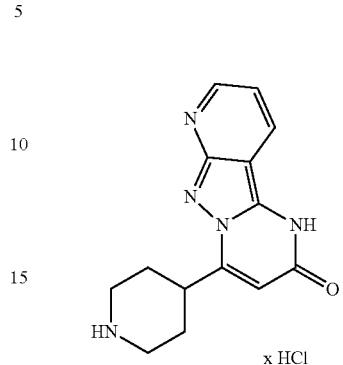

Tert-butyl 4-(2-oxo-1,2-dihydropyrido[2',3':3,4]pyrazolo[1,5-a]pyrimidin-4-yl)piperidine-1-carboxylate (35.9 mg, 0.087 mmol) was dissolved in methanol (1 mL). 4N HCl in dioxane (1 mL) was added and the mixture was irradiated with ultrasound for 15 min at 40° C. The resulting suspension was filtered, washed with dioxane (2 mL) and dried for 16 h at 50° C. in vacuo to give the title compound (5.7 mg, 18% of theory).

LC-MS (Method 2B): $R_t$=0.97 min, MS (ESIPos): m/z=270 [M+H−xHCl]$^+$ $^1$H-NMR (400 MHz, D$_2$O): δ=8.95-8.72 (m, 2H), 7.49-7.33 (m, 1H), 6.66 (s, 1H), 3.85 (t-like, 1H), 3.66 (d, 2H), 3.32 (dd, 2H), 2.48 (d, 2H), 2.16-1.95 (m, 2H).

Example 36

10-Methyl-4-(piperidin-4-yl)pyrimido[1,2-b]indazol-2(1H)-one Hydrochloride

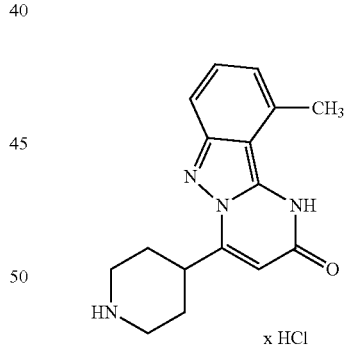

Tert-butyl 4-(10-methyl-2-oxo-1,2-dihydropyrimido[1,2-b]indazol-4-yl)piperidine-1-carboxylate (54.1 mg, 0.141 mmol) was dissolved in methanol (1 mL). 4N HCl in dioxane (1 mL) was added and the mixture was irradiated with ultrasound for 15 min at 40° C. The resulting suspension was filtered, washed with dioxane (2 mL) and dried for 16 h at 50° C. in vacuo to give the title compound (39.7 mg, 88% of theory).

LC-MS (Method 2B): $R_t$=1.35 min, MS (ESIPos): m/z=283 [M+H−xHCl]$^+$ $^1$H-NMR (400 MHz, D$_2$O): δ=7.33-7.26 (m, 2H), 6.75-6.70 (m, 1H), 6.32 (s, 1H), 3.67 (d, 2H), 3.60 (t-like, 1H), 3.32 (dd, 2H), 2.52 (s, 3H), 2.45 (d, 2H), 1.97 (qm, 2H).

Example 37

4-(Piperidin-4-yl)-10-(trifluoromethoxy)pyrimido[1,2-b]indazol-2(1H)-one Hydrochloride

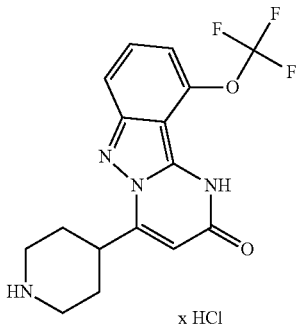 [SMILES: O=c1cc(C2CCNCC2)n2nc3cccc(OC(F)(F)F)c3c2[nH]1]

x HCl

Tert-butyl 4-[2-oxo-10-(trifluoromethoxy)-1,2-dihydropyrimido[1,2-b]indazol-4-yl]piperidine-1-carboxylate (52.3 mg, 0.116 mmol) was dissolved in methanol (2 mL). 4N HCl in dioxane (2 mL) was added and the mixture was irradiated with ultrasound for 15 min at 40° C. The resulting suspension was filtered, washed with dioxane (2 mL) and dried for 16 h at 50° C. in vacuo to give the title compound (43.8 mg, 93% of theory).

LC-MS (Method 2B): $R_t$=1.60 min, MS (ESIPos): m/z=353 [M+H−xHCl]$^+$ $^1$H-NMR (400 MHz, D$_2$O): δ=7.47-7.41 (m, 2H), 6.94 (br. s, 1H), 6.42 (s, 1H), 3.73-3.62 (m, 3H), 3.31 (dd, 2H), 2.47 (d, 2H), 2.00 (qm, 2H).

Example 38

7-(Piperidin-4-yl)pyrazino[2',3':3,4]pyrazolo[1,5-a]pyrimidin-9(10H)-one Hydrochloride

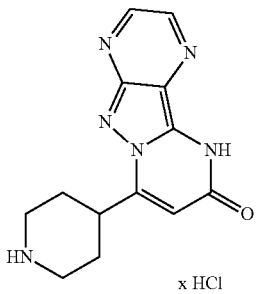 [SMILES: O=c1cc(C2CCNCC2)n2nc3nccnc3c2[nH]1]

x HCl

Tert-butyl 4-(9-oxo-9,10-dihydropyrazino[2',3':3,4]pyrazolo[1,5-a]pyrimidin-7-yl)piperidine-1-carboxylate (78.2 mg, 0.211 mmol) was dissolved in methanol (2 mL). 4N HCl in dioxane (2 mL) was added and the mixture was irradiated with ultrasound for 15 min at 40° C. The resulting suspension was filtered, washed with dioxane (2 mL) and dried for 16 h at 50° C. in vacuo to give the title (43.8 mg, 93% of theory).

LC-MS (Method 2B): $R_t$=0.87 min, MS (ESIPos): m/z=271 [M+H−xHCl]$^+$ $^1$H-NMR (400 MHz, D$_2$O): δ=8.71 (br. s, 1H), 8.52 (br. s, 1H), 6.55 (br. s, 1H), 3.90-3.56 (m, 3H), 3.35 (br. s, 2H), 2.49 (br. s, 2H), 2.04 (br. s, 2H).

Example 39

8-Chloro-4-(piperidin-4-yl)pyrimido[1,2-b]indazol-2(1H)-one Hydrochloride

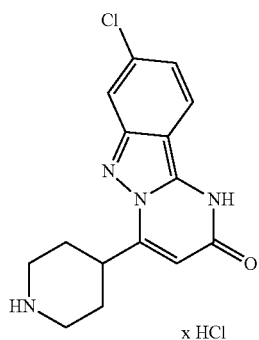 [SMILES: O=c1cc(C2CCNCC2)n2nc3cc(Cl)ccc3c2[nH]1]

x HCl

Tert-butyl 4-(8-chloro-4-oxo-1,4-dihydropyrimido[1,2-b]indazol-2-yl)piperidine-1-carboxylate, 2.1 mg, 0.005 mmol) was dissolved in 4N HCl in dioxane (1 mL), stirred for 1 min and evaporated in vacuo. Methanol (5 mL) was added and the solution was evaporated again. The residue was dissolved in methanol (0.5 mL) and water (2 mL) and then lyophilized to give the title compound (2.0 mg, 0.005 mmol, 100% of theory).

$^1$H-NMR (400 MHz, D$_2$O): δ=7.44 (dd, 1H), 7.28 (d, 1H), 6.79 (d, 1H), 6.32 (s, 1H), 3.68 (d, 2H), 3.51 (t, 1H), 3.32 (t, 2H), 2.45 (d, 2H), 1.98 (q, 2H), 2 exchangeable protons not visible.

Example 40

10-(Dimethylamino)-4-(piperidin-4-yl)pyrido[2',3':3,4]pyrazolo[1,5-a]pyrimidin-2(1H)-one hydrochloride

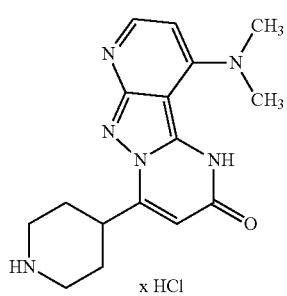 [SMILES: CN(C)c1ccnc2nn3c(C4CCNCC4)cc(=O)[nH]c3c12]

x HCl

A solution of tert-Butyl 4-[10-(dimethylamino)-2-oxo-1,2-dihydropyrido[2',3':3,4]pyrazolo[1,5-a]pyrimidin-4-yl]piperidine-1-carboxylate (8 mg, 0.02 mmol) in methanol (0.06 ml) was treated with HCl 4N in dioxane (0.06 ml) and the reaction mixture was left without stirring for 16 h at RT. The resulting precipitate was filtrated and dried under vacuo to yield the title compound (3.8 mg, 49% of theory).

LC-MS (Method 2B): $R_t$=1.21 min, MS (ESIPos): m/z=313 [M+H−xHCl]$^+$

¹H-NMR (400 MHz, D₂O): δ=7.88 (d, 1H), 6.61 (s, 1H), 6.39 (d, 1H), 3.75-3.48 (m, 9H), 3.30 (dd, 2H), 2.45 (d, 2H), 2.01 (dd, 2H).

Example 41

10-Chloro-4-(piperidin-4-yl)-8-(trifluoromethyl)pyrimido[1,2-b]indazol-2(1H)-one Hydrochloride

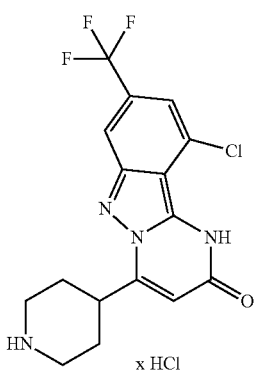 [SMILES: O=c1cc(C2CCNCC2)n2nc3cc(C(F)(F)F)cc(Cl)c3c2[nH]1]

A solution of tert-Butyl 4-[10-chloro-2-oxo-8-trifluoromethy)-1,2-dihydropyrimido[1,2-b]indazol-4-yl]piperidine-1-carboxylate (83 mg, 0.18 mmol) in methanol (0.51 ml) was treated with HCl 4N in dioxane (0.51 ml) and the reaction mixture was left without stirring for 16 h at RT. The resulting precipitate was filtrated and dried under vacuo to yield the title compound (40 mg, 54% of theory).

LC-MS (Method 1B): R$_t$=0.67 min, MS (ESIPos): m/z=371[M+H−xHCl]⁺

¹H-NMR (400 MHz, DMSO-d₆): δ=12.75 (br. s, 1H), 9.06 (br. s, 1H), 8.04 (s, 1H), 7.36 (s, 1H), 6.87 (br. s, 1H), 3.91 (dd, 1H), 3.45 (d, 2H), 3.19 (dd, 2H), 2.34 (d, 2H), 2.00 (dd, 2H).

Example 42

8-(4-Fluorophenyl)-4-(piperidin-4-yl)-10-(trifluoromethyl)pyrido[2',3':3,4]pyrazolo[1,5-a]pyrimidin-2(1H)-one Hydrochloride

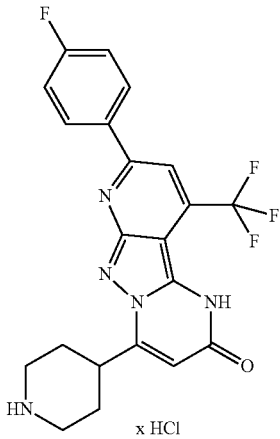 [SMILES: O=c1cc(C2CCNCC2)n2nc3nc(-c4ccc(F)cc4)cc(C(F)(F)F)c3c2[nH]1]

A solution of tert-Butyl 4-[8-(4-fluorophenyl)-2-oxo-10-(trifluoromethyl)-1,2-dihydropyrido[2',3':3,4]pyrazolo[1,5-a]pyrimidin-4-yl]piperidine-1-carboxylate (8 mg, 0.09 mmol) in methanol (0.26 ml) was treated with HCl 4N in dioxane (0.26 ml) and the reaction mixture was left without stirring for 16 h at RT. The resulting precipitate was filtrated and dried under vacuo (21 mg, 49% of theory).

LC-MS (Method 1B): R$_t$=0.74 min, MS (ESIPos): m/z=432 [M+H−xHCl]⁺

¹H-NMR (400 MHz, DMSO-d₆): δ=8.75 (br. s, 1H), 8.50 (br. s, 1H), 8.41 (dd, 2H), 8.06 (s, 1H), 7.42 (dd, 2H), 6.88 (s, 1H), 3.96 (dd, 1H), 3.50 (d, 2H), 3.24 (d, 2H), 2.40-2.33 (m, 2H), 1.98 (dd, 2H).

Example 43

10-Bromo-4-(piperidin-4-yl)pyrido[3',4':3,4]pyrazolo[1,5-a]pyrimidin-2(1H)-one hydrochloride

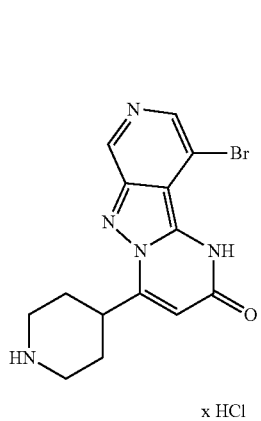 [SMILES: O=c1cc(C2CCNCC2)n2nc3cncc(Br)c3c2[nH]1]

A suspension of tert-Butyl 4-(10-bromo-2-oxo-1,2-dihydropyrido[3',4':3,4]pyrazolo[1,5-a]pyrimidin-4-yl)piperidine-1-carboxylate (164 mg, 0.37 mmol) in methanol (3.0 ml) was treated with HCl 4N in dioxane (3.0 ml) and then the reaction mixture was sonicated at RT for 15 min. The resulting precipitate was filtrated, washed with dioxane and dried under vacuo 16 h at 50° C. to yield the title compound (143 mg, 91% of theory).

LC-MS (Method 1B): R$_t$=0.33 min, MS (ESIPos): m/z=350 [M+H−xHCl]⁺

¹H-NMR (400 MHz, DMSO-d₆): δ=9.24 (s, 1H), 8.95 (br. s, 1H), 8.91 (br. s, 1H), 8.30 (s, 1H), 6.95 (s, 1H), 3.95 (dd, 1H), 3.20 (dd, 2H), 2.35 (d, 2H), 1.98 (dd, 2H).

Example 44

8-Phenyl-4-(piperidin-4-yl)pyrido[2',3':3,4]pyrazolo[1,5-a]pyrimidin-2(1H)-one Hydrochloride

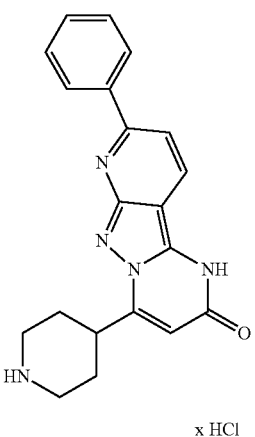 [SMILES: O=c1cc(C2CCNCC2)n2nc3nc(-c4ccccc4)ccc3c2[nH]1]

x HCl

A suspension of tert-Butyl 4-(2-oxo-8-phenyl-1,2-dihydropyrido[2',3':3,4]pyrazolo[1,5-a]pyrimidin-4-yl)piperidine-1-carboxylate (91 mg, 0.20 mmol) in methanol (0.59 ml) was treated with HCl 4N in dioxane (0.59 ml) and then the reaction mixture was left without stirring for 16 h at RT. The resulting precipitate was filtrated and dried under vacuo to yield the title compound (68 mg, 90% of theory).

LC-MS (Method 2B): $R_t$=1.55 min, MS (ESIPos): m/z=346 [M+H−xHCl]$^+$ $^1$H-NMR (400 MHz, DMSO-d$_6$): δ=8.77 (br. s, 1H), 8.57 (br. s, 1H), 8.46 (d, 1H), 8.20 (d, 1H), 7.73 (d, 1H), 7.57-7.52 (m, 3H), 6.34 (br. s, 1H), 3.80 (br. s, 1H), 3.46 (d, 2H), 3.19 (dd, 2H), 2.35 (d, 2H), 1.94 (dd, 1H).

Example 45

9-Phenyl-4-(piperidin-4-yl)pyrido[2',3':3,4]pyrazolo[1,5-a]pyrimidin-2(1H)-one Hydrochloride

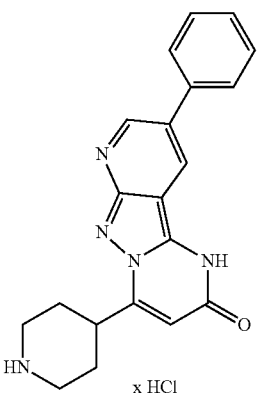 [SMILES: O=c1cc(C2CCNCC2)n2nc3ncc(-c4ccccc4)cc3c2[nH]1]

x HCl

A suspension of tert-Butyl 4-(2-oxo-9-phenyl-1,2-dihydropyrido[2',3':3,4]pyrazolo[1,5-a]pyrimidin-4-yl)piperidine-1-carboxylate (57 mg, 0.13 mmol) in methanol (0.37 ml) was treated with HCl 4N in dioxane (0.37 ml) and then the reaction mixture was left without stirring for 16 h at RT. The resulting precipitate was filtrated and dried under vacuo to yield the title compound (45 mg, 93% of theory).

LC-MS (Method 2B): $R_t$=1.54 min, MS (ESIPos): m/z=346 [M+H−xHCl]$^+$ $^1$H-NMR (400 MHz, DMSO-d$_6$): δ=9.08 (d, 1H), 8.95 (br. s, 1H), 8.75 (br. s, 1H), 8.65 (s, 1H), 7.74 (d, 2H), 7.54 (dd, 2H), 7.42 (dd, 1H), 6.43 (br. s, 1H), 3.82 (dd, 1H), 3.46 (d, 2H), 3.20 (dd, 2H), 2.32 (d, 2H), 1.96 (dd, 2H).

Example 46

10-Phenyl-4-(piperidin-4-yl)pyrido[2',3':3,4]pyrazolo[1,5-a]pyrimidin-2(1H)-one Hydrochloride

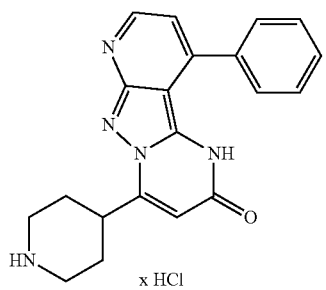 [SMILES: O=c1cc(C2CCNCC2)n2nc3nccc(-c4ccccc4)c3c2[nH]1]

x HCl

A suspension of tert-Butyl 4-(2-oxo-10-phenyl-1,2-dihydropyrido[2',3':3,4]pyrazolo[1,5-a]pyrimidin-4-yl)piperidine-1-carboxylate (39 mg, 0.09 mmol) in methanol (0.25 ml) was treated with HCl 4N in dioxane (0.25 ml) and then the reaction mixture was left without stirring at RT for 16 h. The resulting precipitate was filtrated and dried under vacuo to yield the title compound (32 mg, 97% of theory).

LC-MS (Method 2B): $R_t$=1.5 min, MS (ESIPos): m/z=346 [M+H−xHCl]$^+$ $^1$H-NMR (400 MHz, D$_2$O): δ=8.66 (d, 1H), 7.76 (d, 2H), 7.62 (dd, 1H), 7.56 (dd, 2H), 7.34 (d, 1H), 6.83 (s, 1H), 3.76 (dd, 1H), 3.61 (d, 2H), 3.26 (dd, 2H), 2.38 (d, 2H), 1.99 (dd, 2H).

Example 47

10-methyl-4-(piperidin-4-yl)pyrido[2',3':3,4]pyrazolo[1,5-a]pyrimidin-2(1H)-one Hydrochloride

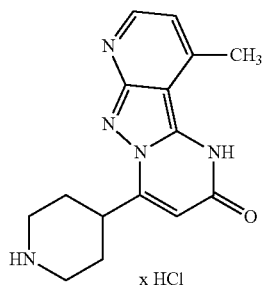 [SMILES: Cc1ccnc2nn3c(C4CCNCC4)cc(=O)[nH]c3c12]

x HCl

A suspension of tert-butyl 4-(10-methyl-2-oxo-1,2-dihydropyrido[2',3':3,4]pyrazolo[1,5-a]pyrimidin-4-yl)piperidine-1-carboxylate (40 mg, 0.11 mmol) in methanol (0.30 ml) was treated with HCl 4N in dioxane (0.30 ml) and then the reaction mixture was left without stirring for 16 h at RT.

Example 48

9-Iodo-4-(piperidin-4-yl)pyrimido[1,2-b]indazol-2(1H)-one Hydrochloride

The resulting precipitate was filtrated and dried under vacuo to yield the title compound (27 mg, 81% of theory).

LC-MS (Method 2B): $R_t$=1.14 min, MS (ESIPos): m/z=284 [M+H−xHCl]$^+$ $^1$H-NMR (400 MHz, D$_2$O): δ=8.52 (s, 1H), 7.23 (s, 1H), 6.88 (s, 1H), 3.89-3.80 (m, 1H), 3.62 (m, 2H), 3.31 (s, 3H), 2.97-2.94 (m, 2H), 2.46 (s, 2H), 2.08-1.98 (m, 2H).

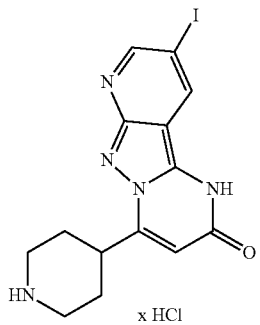 [SMILES: O=c1cc(C2CCNCC2)n2nc3ncc(I)cc3c2[nH]1]

x HCl

A suspension of tert-Butyl 4-(9-iodo-2-oxo-1,2-dihydropyrimido[1,2-b]indazol-4-yl)piperidine-1-carboxylate (83 mg, 0.17 mmol) in methanol (0.48 ml) was treated with HCl 4N in dioxane (0.48 ml) and then the reaction mixture was left without stirring for 16 h at RT. The resulting precipitate was filtrated and dried under vacuo to yield the title compound: 77 mg (100% of theory).

LC-MS (Method 1B): $R_t$=0.59 min, MS (ESIPos): m/z=395 [M+H−xHCl]$^+$ $^1$H-NMR (400 MHz, TFA): δ=8.85 (s, 1H), 8.53 (d, 1H), 7.94 (br. s, 1H), 7.90 (d, 1H), 7.76 (br. s, 1H), 7.28 (s, 1H), 4.35 (dd, 1H), 4.20 (d, 2H), 3.96 (dd, 2H), 2.91 (d, 2H), 2.68 (dd, 2H).

Example 49

4-(Piperidin-4-yl)pyrido[4',3':3,4]pyrazolo[1,5-a]pyrimidin-2(1H)-one

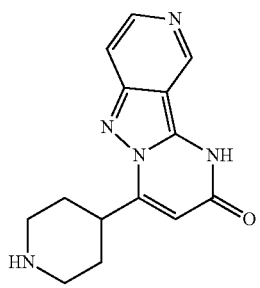 [SMILES: O=c1cc(C2CCNCC2)n2nc3ccncc3c2[nH]1]

A suspension of compound tert-Butyl 4-(2-oxo-1,2-dihydropyrido[4',3':3,4]pyrazolo[1,5-a]pyrimidin-4-yl)piperidine-1-carboxylate (100 mg, 0.27 mmol) in methanol (0.78 ml) was treated with HCl 4N in dioxane (0.78 ml) and then the reaction mixture was left without stirring for 16 h at RT.

The resulting precipitate was filtrated and dried under vacuo. The solid was diluted in small amount of water and treated with ammonia. The resulting precipitate was filtrated and dried under vacuo to yield the title compound (24 mg, 33% of theory).

LC-MS (Method 2B): $R_t$=1.03 min, MS (ESIPos): m/z=270 [M+H−xHCl]$^+$ $^1$H-NMR (400 MHz, TFA): δ=9.98 (s, 1H), 8.50 (d, 1H), 8.28 (d, 1H), 7.91 (br. s, 1H), 7.51 (br. s, 1H), 7.33 (s, 1H), 4.39 (dd, 1H), 4.19 (d, 2H), 3.84 (dd, 2H), 2.93 (d, 2H), 2.65 (dd, 1H).

Example 50

(−)-trans-10-Bromo-4-(2-methylpiperidin-4-yl)pyrimido[1,2-b]indazol-2(1H)-one Hydrochloride

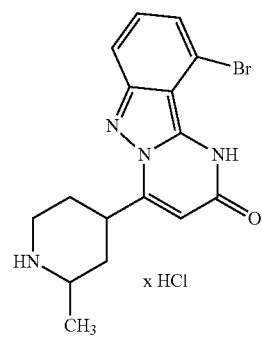 [SMILES: CC1CC(c2cc(=O)[nH]c3c4c(Br)cccc4nn23)CCN1]

x HCl

A suspension of tert-butyl-4-(10-bromo-2-oxo-1,2-dihydropyrimido[1,2-b]indazol-4-yl)-2-methylpiperidine-1-carboxylate (Example 74A, enantiomerically pure trans-Isomer) (1.07 g, 2.32 mmol) in methanol (11.0 ml) was treated with HCl 4N in dioxane (11.0 ml). The reaction mixture was sonicated at RT for 30 minutes. The mixture was evaporated and the crude product was stirred in a mixture of dioxane/methanol 1/1. The solid was filtered, washed with dioxane and dried overnight under vacuo at 70° C. After that the solid was dissolved in water and lyophilized overnight to yield the title compound (373 mg, 40% of theory).

LC-MS (Method 1B): $R_t$=0.58 min, MS (ESIPos): m/z=363 [M+H−xHCl]$^+$ $[α]^{20}$=−13.16 (c. 0.380, methanol) WL=436 nm $^1$H-NMR (400 MHz, DMSO-d$_6$): δ 12.40 (br. s, 1H), 9.38 (s, 1H), 8.99 (s, 1H), 7.65 (d, 1H), 7.40-7.33 (m, 1H), 7.29 (d, 1H), 6.86 (s, 1H), 4.12-4.01 (m, 1H), 3.41-3.26 (m, 1H), 3.25-3.14 (m, 1H), 2.34-2.20 (m, 2H), 2.20-2.09 (m, 2H), 1.42 (d, 3H)

Example 51

(−)-trans-4-(2-Methylpiperidin-4-yl)-10-phenylpyrido[2',3':3,4]pyrazolo[1,5-a]pyrimidin-2(1H)-one Hydrochloride

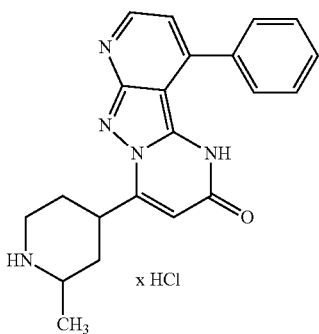 [SMILES: CC1CC(c2cc(=O)[nH]c3c4c(-c5ccccc5)ccnc4nn23)CCN1]

A suspension of tert-Butyl 2-methyl-4-(2-oxo-10-phenyl-1,2-dihydropyrido[2',3':3,4]pyrazolo[1,5-a]pyrimidin-4-yl)piperidine-1-carboxylate (Example 76A, enantiomerically pure trans-Isomer) (73 mg, 0.16 mmol) in methanol (0.46 ml) was treated with HCl 4N in dioxane (0.46 ml). The reaction mixture was left without stirring at RT for 16 h. The resulting solid was filtered and washed with dioxane and finally dried under vacuo to yield the title compound (48 mg, 77% of theory).

LC-MS (Method 1B): $R_t$=0.50 min, MS (ESIPos): m/z=360 [M+H−xHCl]$^+$

[α]$^{20}$=−26.80 (c. 0.49, methanol) WL=589 nm $^1$H-NMR (400 MHz, DMSO-d$_6$): δ 9.21 (br. s, 1H), 8.87 (d, 1H), 8.00-7.89 (m, 2H), 7.65-7.55 (m, 3H), 7.32-7.31 (m, 1H), 7.05-6.95 (m, 1H), 4.14-4.03 (m, 1H), 3.76-3.66 (m, 1H), 3.41-3.30 (m, 1H), 3.28-3.18 (m, 1H), 2.34-2.11 (m, 4H), 1.44 (s, 3H).

Example 52

(−)-trans-10-Ethoxy-4-(2-methylpiperidin-4-yl)pyrimido[1,2-b]indazol-2(1H)-one Hydrochloride

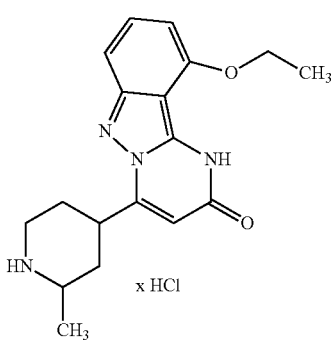 [SMILES: CCOc1cccc2nn3c(C4CCNC(C)C4)cc(=O)[nH]c3c12]

A suspension of tert-butyl 4-(10-ethoxy-2-oxo-1,2-dihydropyrimido[1,2-b]indazol-4-yl)-2-methylpiperidine-1-carboxylate (Example 75A, enantiomerically pure trans-Isomer) (90 mg, 0.21 mmol) in methanol (0.61 ml) was treated with HCl 4N in dioxane (0.61 ml). The reaction mixture was left without stirring at RT for 16 h. The mixture was evaporated and the residue was sonicated in dioxane. The salt was filtered, washed with dioxane and dried overnight under vacuo to yield the title compound (66 mg, 85% of theory).

LC-MS (Method 1B): $R_t$=0.54 min, MS (ESIPos): m/z=327 [M+H−xHCl]$^+$

[α]$^{20}$=−6.420 (c. 0.405, methanol) WL=578 nm $^1$H-NMR (400 MHz, DMSO-d$_6$): δ 9.00 (br. s, 1H), 8.71 (br. s, 1H), 7.28 (t, 1H), 7.04 (d, 1H), 6.35 (d, 1H), 4.24 (q, 2H), 3.74-3.65 (br. s, 1H), 3.35-3.19 (m, 2H), 2.30-2.00 (m, 4H), 1.15 (t, 3H), 1.40 (d, 3H).

Example 53

2-Oxo-4-(piperidin-4-yl)-1,2-dihydropyrimido[1,2-b]indazole-10-carbonitrile Hydrochloride

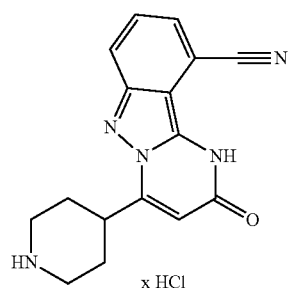 [SMILES: N#Cc1cccc2nn3c(C4CCNCC4)cc(=O)[nH]c3c12]

Tert-butyl 4-(10-cyano-2-oxo-1,2-dihydropyrimido[1,2-b]indazol-4-yl)piperidine-1-carboxylate (320 mg, 0.81 mmol) was dissolved in 1,4-dioxane (2 mL) and treated with hydrochloric acid (4 M solution in 1,4-dioxane, 2.0 mL, 8.1 mmol). The mixture was stirred at RT for 16 h. The resulting solid was filtered and washed with 1,4-dioxane to afford the title compound (275 mg, 92% of theory).

LC-MS (Method 1B): $R_t$=0.46 min, MS (ESIPos): m/z=294 [M+H−xHCl]$^+$ $^1$H-NMR (400 MHz, DMSO-d$_6$): δ=12.65 (br. s, 1H), 9.13-8.70 (m, 2H), 8.03 (d, 1H), 7.71 (d, 1H), 7.62 (dd, 1H), 6.85 (s, 1H), 4.00-3.86 (m, 1H), 3.45 (d, 2H), 3.20 (d, 2H), 2.35 (d, 2H), 1.99 (d, 2H).

Example 54

10-(4-Methoxyphenyl)-4-(piperidin-4-yl)pyrimido[1,2-b]indazol-2(1H)-one hydrochloride

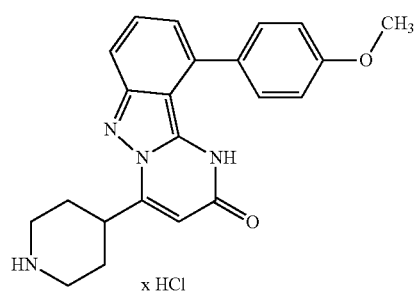 [SMILES: COc1ccc(-c2cccc3nn4c(C5CCNCC5)cc(=O)[nH]c4c23)cc1]

Tert-butyl-4-[10-(4-methoxyphenyl)-2-oxo-1,2-dihydropyrimido[1,2-b]indazol-4-yl]piperidin-1-carboxylat (312 mg, 0.66 mmol) was dissolved in 1,4-dioxane (2 mL) and treated with hydrochloric acid (4 M solution in 1,4-dioxane, 1.6 mL, 6.6 mmol). The mixture was stirred at RT for 16 h. The resulting solid was filtered and washed with 1,4-dioxane and diethyl ether to afford the title compound (244 mg, 78% of theory).

LC-MS (Method 1B): $R_t$=0.70 min, MS (ESIPos): m/z=375 [M+H−xHCl]$^+$ $^1$H-NMR (400 MHz, DMSO-d$_6$): δ=9.04-8.77 (m, 2H), 7.64 (d, 2H), 7.59 (d, 1H), 7.49 (dd, 1H), 7.05 (d, 2H), 6.95 (d, 1H), 6.63 (br. s, 1H), 3.57 (s, 3H), 3.46 (d, 2H), 3.21 (d, 2H), 2.36 (d, 2H), 1.98 (d, 2H).

Example 55

4-(Piperidin-4-yl)-10-[4-(trifluoromethyl)phenyl]pyrimido[1,2-b]indazol-2(1H)-one Hydrochloride

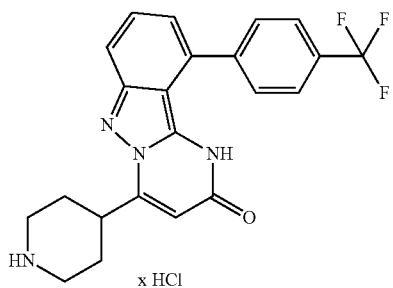 [SMILES: O=c1cc(C2CCNCC2)n2nc3cccc(-c4ccc(C(F)(F)F)cc4)c3c2[nH]1]

x HCl

Tert-butyl 4-{2-oxo-10-[4-(trifluoromethyl)phenyl]-1,2-dihydropyrimido[1,2-b]indazol-4-yl}piperidine-1-carboxylate (180 mg, 0.35 mmol) was dissolved in 1,4-dioxane (2 mL) and treated with hydrochloric acid (4 M solution in 1,4-dioxane, 0.9 mL, 3.5 mmol). The mixture was stirred at RT for 16 h. The resulting solid was filtered and washed with 1,4-dioxane and diethyl ether to afford the title compound (144 mg, 84% of theory).

LC-MS (Method 1B): $R_t$=0.80 min, MS (ESIPos): m/z=413 [M+H−xHCl]$^+$ $^1$H-NMR (400 MHz, DMSO-d$_6$): δ=9.06-8.81 (m, 2H), 7.94 (d, 2H), 7.83 (d, 2H), 7.71 (d, 1H), 7.57 (dd, 1H), 7.09 (d, 1H), 6.68 (br. s, 1H), 3.46 (d, 2H), 3.22 (d, 2H), 2.36 (d, 2H), 1.99 (dd, 2H).

Example 56

10-Phenyl-4-(piperidin-4-yl)pyrimido[1,2-b]indazol-2(1H)-one Hydrochloride

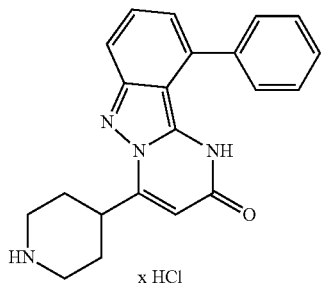 [SMILES: O=c1cc(C2CCNCC2)n2nc3cccc(-c4ccccc4)c3c2[nH]1]

x HCl

Tert-butyl 4-(2-oxo-10-phenyl-1,2-dihydropyrimido[1,2-b]indazol-4-yl)piperidine-1-carboxylate (470 mg, 1.06 mmol) was dissolved in 1,4-dioxane (2 mL) and treated with hydrochloric acid (4 M solution in 1,4-dioxane, 2.6 mL, 10.6 mmol). The mixture was stirred at RT for 16 h. The resulting solid was filtered and washed with 1,4-dioxane and diethyl ether to afford the title compound (375 mg, 85% of theory).

LC-MS (Method 1B): $R_t$=0.69 min, MS (ESIPos): m/z=345 [M+H−xHCl]$^+$ $^1$H-NMR (400 MHz, DMSO-d$_6$): δ=9.07 (br. s., 2H), 7.83-7.59 (m, 3H), 7.58-7.33 (m, 4H), 7.00 (d, 1H), 6.66 (br. s., 1H), 4.07-3.85 (m, 1H), 3.45 (d, 2H), 3.21 (d, 2H), 2.36 (d, 2H), 2.00 (d, 2H).

Example 57

10-(2-Fluorophenyl)-4-(piperidin-4-yl)pyrimido[1,2-b]indazol-2(1H)-one hydrochloride

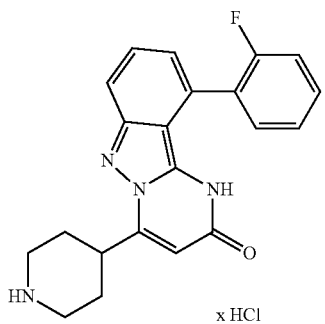 [SMILES: O=c1cc(C2CCNCC2)n2nc3cccc(-c4ccccc4F)c3c2[nH]1]

x HCl

Tert-butyl 4-[10-(2-fluorophenyl)-2-oxo-1,2-dihydropyrimido[1,2-b]indazol-4-yl]piperidine-1-carboxylate (590 mg, 1.28 mmol) was dissolved in 1,4-dioxane (5 mL) and treated with hydrochloric acid (4 M solution in 1,4-dioxane, 3.2 mL, 12.8 mmol). The mixture was stirred at RT for 16 h. The resulting solid was filtered and washed with 1,4-dioxane and diethyl ether to afford the title compound (501 mg, 90% of theory).

LC-MS (Method 1B): $R_t$=0.62 min, MS (ESIPos): m/z=363 [M+H−xHCl]$^+$ $^1$H-NMR (400 MHz, DMSO-d$_6$): δ=9.02 (br. s., 2H), 7.69 (d, 1H), 7.61-7.44 (m, 3H), 7.40-7.23 (m, 2H), 6.98 (d, 1H), 6.67 (br. s., 1H), 4.04-3.87 (m, 1H), 3.45 (d, 2H), 3.21 (d, 2H), 2.36 (d, 2H), 1.99 (dd, 2H).

Example 58

4-(Piperidin-4-yl)-10-(pyridin-3-yl)pyrimido[1,2-b]indazol-2(1H)-one Hydrochloride

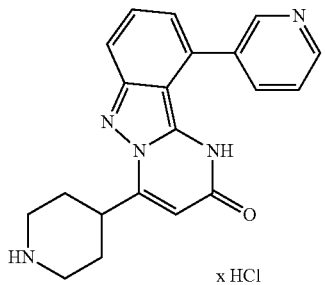 [SMILES: O=c1cc(C2CCNCC2)n2nc3cccc(-c4cccnc4)c3c2[nH]1]

x HCl

Tert-butyl 4-[2-oxo-10-(pyridin-3-yl)-1,2-dihydropyrimido[1,2-b]indazol-4-yl]piperidine-1-carboxylate (450 mg, 1.01 mmol) was dissolved in 1,4-dioxane (2 mL) and treated with hydrochloric acid (4 M solution in 1,4-dioxane, 2.5 mL, 10.1 mmol). The mixture was stirred at RT for 16 h. The resulting solid was filtered and washed with 1,4-dioxane and diethyl ether to afford the title compound (349 mg, 83% of theory).

LC-MS (Method 1B): $R_t$=0.36 min, MS (ESIPos): m/z=346 [M+H−xHCl]$^+$ $^1$H-NMR (400 MHz, DMSO-d$_6$): δ=9.27 (s, 1H), 9.06 (br. s., 1H), 8.98 (d, 1H), 8.91-8.80 (m, 1H), 8.13 (dd, 1H), 7.81 (d, 1H), 7.64 (dd, 1H), 7.24 (d, 1H), 6.75 (br. s, 1H), 4.04-3.90 (m, 1H), 3.46 (d, 2H), 3.31-3.10 (m, 2H), 2.35 (d, 2H), 2.09-1.87 (m, 2H)

Example 59

4-(Piperidin-4-yl)-10-(pyridin-4-yl)pyrimido[1,2-b]indazol-2(1H)-one Hydrochloride

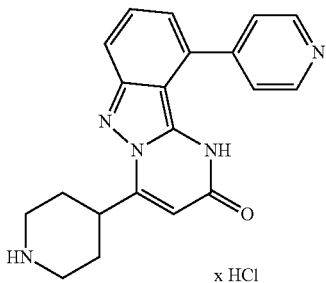 [SMILES: O=c1cc(C2CCNCC2)n2nc3cccc(-c4ccncc4)c3c2[nH]1]

x HCl

Tert-butyl 4-[2-oxo-10-(pyridin-4-yl)-1,2-dihydropyrimido[1,2-b]indazol-4-yl]piperidine-1-carboxylate (33 mg, 0.07 mmol) was dissolved in 1,4-dioxane (1 mL) and treated with hydrochloric acid (4 M solution in 1,4-dioxane, 0.3 mL, 0.74 mmol). The mixture was stirred at RT for 16 h. The resulting solid was filtered and washed with 1,4-dioxane. The residue was dissolved in methanol and concentrated in vacuo to afford the title compound (30 mg, 97% of theory).

LC-MS (Method 1B): $R_t$=0.25 min, MS (ESIPos): m/z=346 [M+H−xHCl]$^+$ $^1$H-NMR (500 MHz, D$_2$O): δ=8.85 (d, 2H), 8.19 (d, 2H), 7.81 (d, 1H), 7.66 (dd, 1H), 7.32 (d, 1H), 6.53 (s, 1H), 3.80 (t, 1H), 3.69 (d, 2H), 3.35 (dd, 2H), 2.50 (d, 2H), 2.10-1.96 (m, 2H)

Example 60

10-Bromo-4-(piperidin-4-yl)pyrimido[1,2-b]indazol-2(1H)-one Hydrochloride

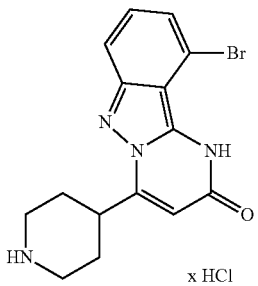 [SMILES: O=c1cc(C2CCNCC2)n2nc3cccc(Br)c3c2[nH]1]

x HCl

Tert-butyl 4-(10-bromo-2-oxo-1,2-dihydropyrimido[1,2-b]indazol-4-yl)piperidine-1-carboxylate (860 mg, 1.92 mmol) was dissolved in 1,4-dioxane (20 mL) and treated with hydrochloric acid (4 M solution in 1,4-dioxane, 4.8 mL, 19.2 mmol). The mixture was stirred at RT for 16 h. The resulting solid was filtered and washed with 1,4-dioxane to afford the title compound (805 mg, 100% of theory).

LC-MS (Method 3B): $R_t$=1.40 min, MS (ESIPos): m/z=349 [M+H−xHCl]$^+$ $^1$H-NMR (400 MHz, DMSO-d$_6$): δ=8.97-8.65 (m, 1H), 7.65 (d, 1H), 7.37 (dd, 1H), 7.31 (d, 1H), 6.75 (br. s, 1H), 3.50-3.39 (m, 2H), 3.28-3.11 (m, 2H), 2.40-2.27 (m, 2H), 2.04-1.88 (m, 2H).

Example 61

10-Cyclopropyl-4-(piperidin-4-yl)pyrimido[1,2-b]indazol-2(1H)-one Hydrochloride

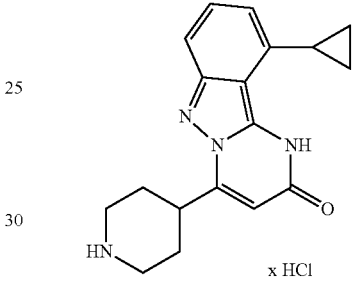

x HCl

Tert-butyl 4-(10-cyclopropyl-2-oxo-1,2-dihydropyrimido[1,2-b]indazol-4-yl)piperidine-1-carboxylate (25 mg, 0.06 mmol) was dissolved in 1,4-dioxane (2 mL) and treated with hydrochloric acid (4 M solution in 1,4-dioxane, 0.15 mL, 0.61 mmol). The mixture was stirred at RT for 72 h. The resulting solid was filtered and washed with 1,4-dioxane to afford the title compound (22 mg, 94% of theory).

LC-MS (Method 1B): $R_t$=0.57 min, MS (ESIPos): m/z=309 [M+H−xHCl]$^+$ $^1$H-NMR (500 MHz, D$_2$O): δ=7.36-7.26 (m, 2H), 6.72-6.65 (m, 1H), 6.40-6.35 (m, 1H), 3.72-3.57 (m, 3H), 3.39-3.25 (m, 2H), 2.51-2.39 (m, 2H), 2.24-2.15 (m, 1H), 2.06-1.88 (m, 2H), 1.15-1.03 (m, 2H), 0.76-0.69 (m, 2H).

Example 62

10-Isopropyl-4-(piperidin-4-yl)pyrimido[1,2-b]indazol-2(1H)-one Hydrochloride

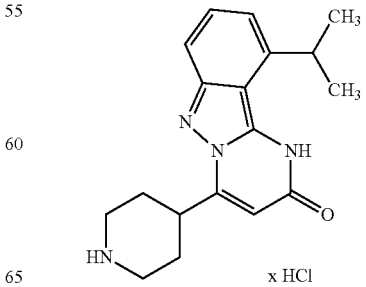

x HCl

Tert-butyl 4-(10-isopropyl-2-oxo-1,2-dihydropyrimido[1,2-b]indazol-4-yl)piperidine-1-carboxylate (33 mg, 0.08 mmol) was dissolved in 1,4-dioxane (1 mL) and treated with hydrochloric acid (4 M solution in 1,4-dioxane, 0.2 mL, 0.80 mmol). The mixture was stirred at RT for 16 h. The resulting solid was filtered and washed with 1,4-dioxane to afford the title compound (30 mg, 97% of theory).

LC-MS (Method 2B): $R_t$=1.63 min, MS (ESIPos): m/z=311 [M+H−xHCl]$^+$ $^1$H-NMR (400 MHz, DMSO-d$_6$): δ=9.01-8.67 (m, 2H), 7.44 (s, 2H), 6.94 (d, 1H), 6.66 (br. s, 1H), 3.51-3.39 (m, 2H), 3.30-3.11 (m, 2H), 2.41-2.29 (m, 2H), 2.06-1.88 (m, 2H), 1.35 (d, 6H).

Example 63

10-Cyclopentyl-4-(piperidin-4-yl)pyrimido[1,2-b]indazol-2(1H)-one Hydrochloride

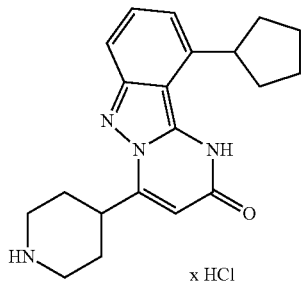 [SMILES: O=c1cc(C2CCNCC2)n2nc3cccc(C4CCCC4)c3c2[nH]1]

Tert-butyl 4-(10-cyclopentyl-2-oxo-1,2-dihydropyrimido[1,2-b]indazol-4-yl)piperidine-1-carboxylate (23 mg, 0.05 mmol) was dissolved in 1,4-dioxane (1 mL) and treated with hydrochloric acid (4 M solution in 1,4-dioxane, 0.1 mL, 0.53 mmol). The mixture was stirred at RT for 16 h. The resulting solid was filtered and washed with 1,4-dioxane to afford the title compound (21 mg, 97% of theory).

LC-MS (Method 1B): $R_t$=0.68 min, MS (ESIPos): m/z=337 [M+H−xHCl]$^+$ $^1$H-NMR (400 MHz, DMSO-d$_6$): δ=8.94-8.80 (m, 1H), 8.78-8.57 (m, 1H), 7.47-7.32 (m, 2H), 6.94 (d, 1H), 6.64 (br. s, 1H), 4.28-4.08 (m, 1H), 4.01-3.86 (m, 1H), 3.77-3.62 (m, 3H), 3.28-3.11 (m, 2H), 2.42-2.29 (m, 2H), 2.25-2.07 (m, 2H), 2.05-1.59 (m, 7H)

Example 64

10-(2-Chlorophenyl)-4-(piperidin-4-yl)pyrimido[1,2-b]indazol-2(1H)-one Hydrochloride

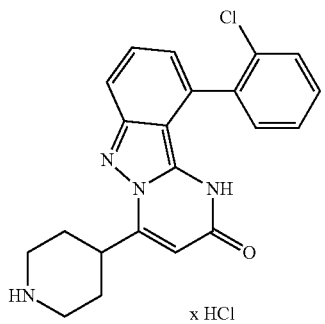 [SMILES: O=c1cc(C2CCNCC2)n2nc3cccc(-c4ccccc4Cl)c3c2[nH]1]

Tert-butyl 4-[10-(2-chlorophenyl)-2-oxo-1,2-dihydropyrimido[1,2-b]indazol-4-yl]piperidine-1-carboxylate (300 mg, 0.63 mmol) was dissolved in 1,4-dioxane (12 mL) and treated with hydrochloric acid (4 M solution in 1,4-dioxane, 1.6 mL, 6.26 mmol). The mixture was stirred at RT for 16 h. The resulting solid was filtered and washed with 1,4-dioxane to afford the title compound (220 mg, 78% of theory).

LC-MS (Method 1B): $R_t$=0.70 min, MS (ESIPos): m/z=379 [M+H−xHCl]$^+$ $^1$H-NMR (500 MHz, DMSO-d$_6$): δ=9.24-9.06 (m, 1H), 7.69 (d, 1H), 7.58 (d, 1H), 7.54 (dd, 1H), 7.50-7.41 (m, 3H), 6.89 (d, 1H), 6.66 (br. s., 1H), 3.95 (t, 1H), 3.45 (d, 2H), 3.27-3.13 (m, 2H), 2.36 (d, 2H), 2.01 (d, 2H).

Example 65

10-(2-Methoxyphenyl)-4-(piperidin-4-yl)pyrimido[1,2-b]indazol-2(1H)-one hydrochloride

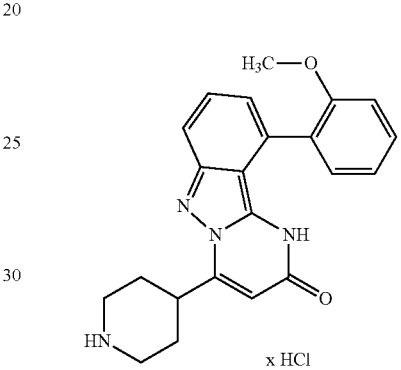

Tert-butyl 4-[10-(2-methoxyphenyl)-2-oxo-1,2-dihydropyrimido[1,2-b]indazol-4-yl]piperidine-1-carboxylate (200 mg, 0.42 mmol) was dissolved in 1,4-dioxane (8 mL) and treated with hydrochloric acid (4 M solution in 1,4-dioxane, 1.1 mL, 4.21 mmol). The mixture was stirred at RT for 16 h. The resulting solid was filtered and washed with 1,4-dioxane to afford the title compound (22 mg, 12% of theory).

LC-MS (Method 1B): $R_t$=0.66 min, MS (ESIPos): m/z=375 [M+H−xHCl]$^+$ $^1$H-NMR (500 MHz, D$_2$O): δ=7.51 (br. s., 3H), 7.29-6.96 (m, 3H), 6.83 (br. s., 1H), 6.35 (br. s., 1H), 3.33 (br. s., 2H), 2.43 (br. s., 2H), 1.99 (br. s., 2H)

Example 66

10-Chloro-4-(piperidin-4-yl)pyrimido[1,2-b]indazol-2(1H)-one

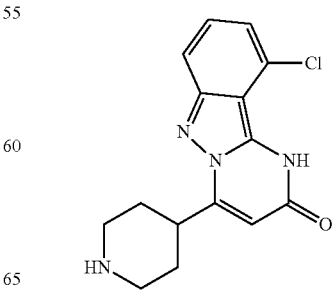

10-chloro-4-(piperidin-4-yl)pyrimido[1,2-b]indazol-2(1H)-one hydrochloride (4.00 g, 11.8 mmol) was dissolved in hydrochloric acid (1.0 M in water) and treated with sodium hydroxide solution (1.0 M in water). The precipitate was collected by filtration, washed with water, and dried under vacuo to afford the title compound (3.05 g, 85% of theory).

LC-MS (Method 1B): $R_t$=0.47 min, MS (ESIPos): m/z=303 [M+H]$^+$ $^1$H-NMR (500 MHz, DCOOD): δ=7.50 (d, 1H), 7.41-7.33 (m, 1H), 7.05 (d, 1H), 6.58 (s, 1H), 3.83 (t, 1H), 3.76 (d, 2H), 3.39 (dd, 2H), 2.47 (d, 2H), 2.16-2.02 (m, 2H).

Example 67

4-(Piperidin-4-yl)-10-[2-(trifluoromethyl)phenyl]pyrimido[1,2-b]indazol-2(1H)-one Hydrochloride

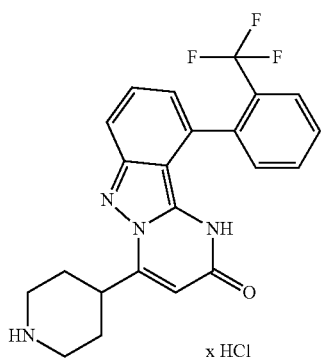 [SMILES: O=c1cc(C2CCNCC2)n2nc3cccc(-c4ccccc4C(F)(F)F)c3c2[nH]1]

Tert-butyl 4-{2-oxo-10-[2-(trifluoromethyl)phenyl]-1,2-dihydropyrimido[1,2-b]indazol-4-yl}piperidine-1-carboxylate (200 mg, 0.39 mmol) was dissolved in 1,4-dioxane (8 mL) and treated with hydrochloric acid (4 M solution in 1,4-dioxane, 1.0 mL, 3.90 mmol). The mixture was stirred at RT for 16 h. The resulting solid was filtered and washed with 1,4-dioxane to afford the title compound (102 mg, 54% of theory).

LC-MS (Method 1B): $R_t$=0.73 min, MS (ESIPos): m/z=413 [M+H−xHCl]$^+$ $^1$H-NMR (500 MHz, D$_2$O): δ=7.95 (s, 1H), 7.72 (s, 2H), 7.64 (d, 1H), 7.52 (br. s, 1H), 7.29 (br. s, 1H), 6.90 (br. s, 1H), 6.36 (s, 1H), 3.77 (t, 1H), 3.66 (d, 2H), 3.32 (dd, 2H), 2.44 (d, 2H), 2.06-1.89 (m, 2H).

Example 68

(−)-trans-10-Chloro-4-(2-methylpiperidin-4-yl)pyrimido[1,2-b]indazol-2(1H)-one Hydrochloride

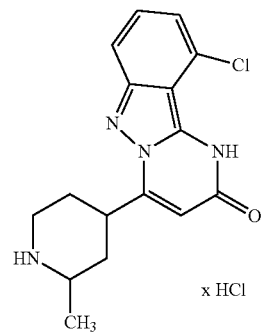 [SMILES: CC1CC(c2cc(=O)[nH]c3c4c(Cl)cccc4nn23)CCN1]

A suspension of tert-butyl 4-(10-chloro-2-oxo-1,2-dihydropyrimido[1,2-b]indazol-4-yl)-2-methylpiperidine-1-carboxylate (Example 49A, enantiomerically pure trans-Isomer) (270 mg, 0.65 mmol) in methanol (1.8 ml) was treated with HCl 4N in dioxane (1.8 ml). The reaction mixture was left at RT without stirring for 16 h. The mixture was evaporated and the crude product was stirred in dioxane. The solid was filtered, washed with dioxane and dried overnight under vacuo at 60° C. After that the solid was dissolved in water and methanol and lyophilized overnight to yield the title compound (117 mg, 77% of theory).

LC-MS (Method 1B): RT=0.53 min, MS (ESIPos): m/z=317 [M+H−xHCl]$^+$

[α]$^{20}$=−3.04 (c. 0.46, methanol) WL=589 nm $^1$H-NMR (400 MHz, DMSO-d$_6$): δ 12.44 (br. s, 1H), 9.22 (br. s, 1H), 8.87 (br. s, 1H), 7.60 (d, 1H), 7.73 (t, 1H), 7.10 (d, 1H), 6.86 (br. s, 1H), 4.13-3.97 (m, 1H), 3.76-3.64 (m, 1H), 3.26-3.12 (m, 1H), 2.35-2.20 (m, 2H), 2.21-2.06 (m, 2H), 1.42 (d, 3H).

Example 69

10-Chloro-9-methyl-4-(piperidin-4-yl)pyrimido[1,2-b]indazol-2(1H)-one Hydrochloride

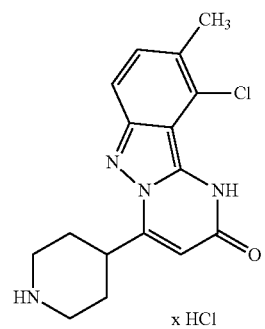 [SMILES: Cc1ccc2nn3c(C4CCNCC4)cc(=O)[nH]c3c2c1Cl]

Tert-butyl 4-(10-chloro-9-methyl-2-oxo-1,2-dihydropyrimido[1,2-b]indazol-4-yl)piperidine-1-carboxylate (220 mg, 0.53 mmol) was dissolved in 1,4-dioxane (2 mL) and treated with hydrochloric acid (4 M solution in 1,4-dioxane, 1.3 mL, 5.3 mmol). The mixture was stirred at RT for 16 h.

The resulting solid was filtered and washed with 1,4-dioxane to afford the title compound (182 mg, 89% of theory).

LC-MS (Method 1B): $R_t$=0.52 min, MS (ESIPos): m/z=317 [M+H−xHCl]$^+$ $^1$H-NMR (400 MHz, DMSO-d$_6$): δ=9.10-8.80 (m, 2H), 7.53 (d, 1H), 7.42 (d, 1H), 6.64 (br. s, 1H), 3.97-3.81 (m, 1H), 3.44 (d, 1H), 3.18 (dd, 2H), 2.42 (s, 2H), 2.33 (d, 2H), 2.06-1.86 (m, 2H).

Example 70

10-Bromo-9-fluoro-4-(piperidin-4-yl)pyrimido[1,2-b]indazol-2(1H)one Hydrochloride

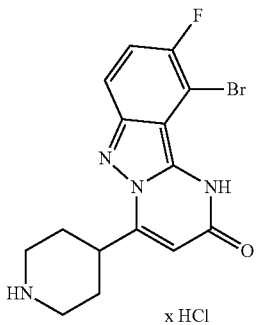 [SMILES: O=c1cc(C2CCNCC2)n2nc3ccc(F)c(Br)c3c2[nH]1]

Tert-butyl 4-(10-bromo-9-fluoro-2-oxo-1,2-dihydropyrimido[1,2-b]indazol-4-yl)piperidine-1-carboxylate (376 mg, 0.81 mmol) was dissolved in 1,4-dioxane (3 mL) and treated with hydrochloric acid (4 M solution in 1,4-dioxane, 2.0 mL, 8.1 mmol). The mixture was stirred at RT for 16 h. The resulting solid was filtered and washed with 1,4-dioxane to afford the title compound (350 mg, 99% of theory).

LC-MS (Method 1B): $R_t$=0.51 min, MS (ESIPos): m/z=365 [M+H−xHCl]$^+$ $^1$H-NMR (400 MHz, DMSO-d$_6$): δ=9.14-8.87 (m, 1H), 7.73 (dd, 1H), 7.53 (dd, 1H), 6.78 (br. s., 1H), 3.44 (d, 2H), 3.18 (d, 2H), 2.33 (d, 2H), 1.99 (d, 2H).

Example 71

10-Bromo-7-fluoro-4-(piperidin-4-yl)pyrimido[1,2-b]indazol-2(1H)-one Hydrochloride

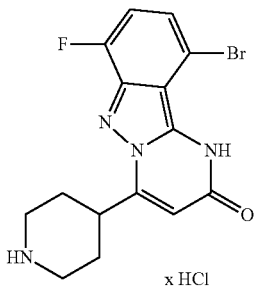 [SMILES: O=c1cc(C2CCNCC2)n2nc3c(F)ccc(Br)c3c2[nH]1]

Tert-butyl 4-(10-bromo-7-fluoro-2-oxo-1,2-dihydropyrimido[1,2-b]indazol-4-yl)piperidine-1-carboxylate (424 mg, 0.91 mmol) was dissolved in 1,4-dioxane (3 mL) and treated with hydrochloric acid (4 M solution in 1,4-dioxane, 2.3 mL, 9.1 mmol). The mixture was stirred at RT for 16 h.

The resulting solid was filtered and washed with methanol and 1,4-dioxane to afford the title compound (330 mg, 83% of theory).

LC-MS (Method 1B): $R_t$=0.52 min, MS (ESIPos): m/z=365 [M+H−xHCl]$^+$ $^1$H-NMR (400 MHz, DMSO-d$_6$): δ=12.69-12.49 (m, 1H), 8.91 (br. s, 1H), 8.70 (br. s, 1H), 7.32-7.17 (m, 2H), 6.84 (br. s, 1H), 4.04-3.88 (m, 1H), 3.45 (d, 2H), 3.29-3.14 (m, 2H), 2.34 (d, 2H), 2.06-1.88 (m, 2H).

Example 72

10-sec-Butyl-4-(piperidin-4-yl)pyrimido[1,2-b]indazol-2(11H)-one Hydrochloride

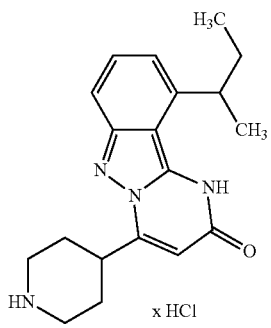 [SMILES: CCC(C)c1cccc2nn3c(C4CCNCC4)cc(=O)[nH]c3c12]

Tert-butyl 4-(10-sec-butyl-2-oxo-1,2-dihydropyrimido[1,2-b]indazol-4-yl)piperidine-1-carboxylate (27 mg, 0.06 mmol) was dissolved in 1,4-dioxane (1 mL) and treated with hydrochloric acid (4 M solution in 1,4-dioxane, 0.2 mL, 0.64 mmol). The mixture was stirred at RT for 16 h. The resulting solid was filtered and washed with methanol and 1,4-dioxane to afford the title compound (26 mg, 100% of theory).

LC-MS (Method 1B): $R_t$=0.70 min, MS (ESIPos): m/z=325 [M+H−xHCl]$^+$ $^1$H-NMR (400 MHz, DMSO-d$_6$): δ=9.04-8.93 (m, 1H), 8.91-8.76 (m, 1H), 7.50-7.35 (m, 2H), 6.91 (d, 1H), 6.66 (br. s, 1H), 4.00-3.87 (m, 2H), 3.45 (d, 2H), 3.22 (br. s., 2H), 2.35 (d, 2H), 2.06-1.90 (m, 2H), 1.89-1.62 (m, 2H), 1.32 (d, 3H), 0.85 (t, 3H).

Example 73

10-Isobutyl-4-(piperidin-4-yl)pyrimido[1,2-b]indazol-2(1H)-one Hydrochloride

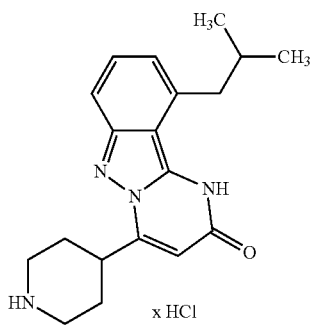 [SMILES: CC(C)Cc1cccc2nn3c(C4CCNCC4)cc(=O)[nH]c3c12]

Tert-butyl 4-(10-isobutyl-2-oxo-1,2-dihydropyrimido[1,2-b]indazol-4-yl)piperidine-1-carboxylate (92 mg, 0.22 mmol) was dissolved in 1,4-dioxane (2 mL) and treated with hydrochloric acid (4 M solution in 1,4-dioxane, 0.6 mL, 2.2 mmol). The mixture was stirred at RT for 16 h. The resulting solid was filtered and washed with methanol and 1,4-dioxane to afford the title compound (85 mg, 99% of theory).

LC-MS (Method 2B): $R_t$=1.73 min, MS (ESIPos): m/z=325 [M+H−xHCl]$^+$ $^1$H-NMR (400 MHz, DMSO-$d_6$): δ=9.07-8.80 (m, 1H), 7.45 (d, 1H), 7.37 (dd, 1H), 6.80 (d, 1H), 6.66 (br. s., 1H), 3.45 (d, 2H), 3.20 (d, 2H), 3.08 (d, 2H), 2.35 (d, 2H), 2.14-2.05 (m, 1H), 1.98 (dd, 2H), 0.94 (d, 6H).

Example 74

10-Bromo-9-methyl-4-(piperidin-4-yl)pyrimido[1,2-b]indazol-2(1H)-one Hydrochloride

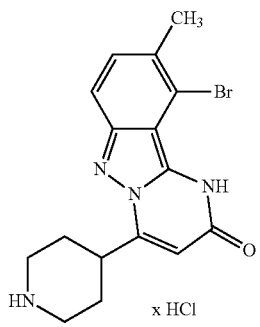 [SMILES: Cc1ccc2nn3c(C4CCNCC4)cc(=O)[nH]c3c2c1Br]

Tert-butyl 4-(10-bromo-9-methyl-2-oxo-1,2-dihydropyrimido[1,2-b]indazol-4-yl)piperidine-1-carboxylate (220 mg, 0.48 mmol) was treated with hydrochloric acid (4 M solution in 1,4-dioxane, 20.0 mL, 80 mmol). The mixture was stirred at RT for 16 h. The resulting solid was filtered and washed with methanol and 1,4-dioxane to afford the title compound (184 mg, 97% of theory).

LC-MS (Method 1B): $R_t$=0.56 min, MS (ESIPos): m/z=361 [M+H−xHCl]$^+$ $^1$H-NMR (400 MHz, DMSO-$d_6$): δ=9.09-8.79 (m, 2H), 7.58 (d, 1H), 7.43 (d, 1H), 6.70 (s, 1H), 3.99-3.83 (m, 1H), 3.44 (d, 2H), 3.18 (d, 2H), 2.46 (s, 3H), 2.33 (d, 2H), 1.97 (d, 2H).

Example 75

10-Bromo-7-methyl-4-(piperidin-4-yl)pyrimido[1,2-b]indazol-2(1H)-one Hydrochloride

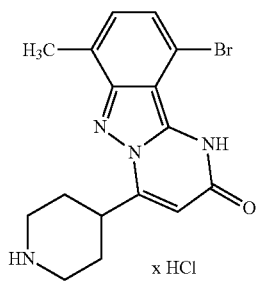 [SMILES: Cc1ccc(Br)c2c1nn1c(C3CCNCC3)cc(=O)[nH]c21]

Tert-butyl 4-(10-bromo-7-methyl-2-oxo-1,2-dihydropyrimido[1,2-b]indazol-4-yl)piperidine-1-carboxylate (220 mg, 0.48 mmol) was treated with hydrochloric acid (4 M solution in 1,4-dioxane, 20.0 mL, 80 mmol). The mixture was stirred at RT for 16 h. The resulting solid was filtered and washed with methanol and 1,4-dioxane to afford the title compound (145 mg, 76% of theory).

LC-MS (Method 1B): $R_t$=0.62 min, MS (ESIPos): m/z=361 [M+H−xHCl]$^+$ $^1$H-NMR (400 MHz, DMSO-$d_6$): δ=8.97-8.84 (m, 1H), 8.83-8.66 (m, 1H), 7.23-7.13 (m, 2H), 6.74 (s, 1H), 3.99-3.86 (m, 1H), 3.46 (d, 2H), 3.30-3.12 (m, 2H), 2.53 (br. s., 3H), 2.38 (d, 2H), 2.06-1.89 (m, 2H).

Example 76

10-Isopropoxy-4-(piperidin-4-yl)pyrimido[1,2-b]indazol-2(1H)-one Hydrochloride

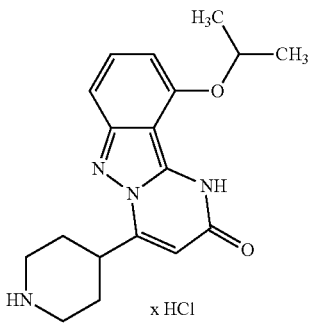 [SMILES: CC(C)Oc1cccc2nn3c(C4CCNCC4)cc(=O)[nH]c3c12]

Tert-butyl 4-(10-isopropoxy-2-oxo-1,2-dihydropyrimido[1,2-b]indazol-4-yl)piperidine-1-carboxylate (134 mg, 0.31 mmol) was dissolved in 1,4-dioxane (5 mL) and treated with hydrochloric acid (4 M solution in 1,4-dioxane, 3.6 mL, 14.4 mmol). The mixture was stirred at RT for 16 h. The resulting solid was filtered and washed with methanol and 1,4-dioxane to afford the title compound (125 mg, 99% of theory).

LC-MS (Method 1B): $R_t$=1.55 min, MS (ESIPos): m/z=327 [M+H−xHCl]$^+$ $^1$H-NMR (500 MHz, $D_2O$): δ=7.35 (dd, 1H), 6.97 (d, 1H), 6.39 (d, 1H), 6.27 (s, 1H), 4.83-4.76 (m, 1H), 3.70-3.62 (m, 2H), 3.58-3.49 (m, 1H), 3.35-3.26 (m, 2H), 2.47-2.39 (m, 2H), 2.01-1.90 (m, 2H), 1.45 (d, 6H).

Example 77

9-Fluoro-10-phenyl-4-(piperidin-4-yl)pyrimido[1,2-b]indazol-2(1H)-one hydrochloride

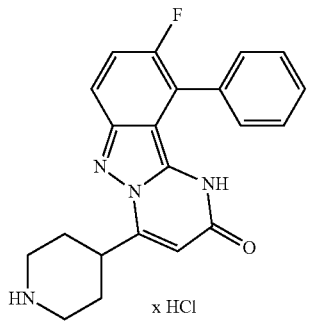 [SMILES: O=c1cc(C2CCNCC2)n2nc3ccc(F)c(-c4ccccc4)c3c2[nH]1]

x HCl

Tert-butyl 4-(9-fluoro-2-oxo-10-phenyl-1,2-dihydropyrimido[1,2-b]indazol-4-yl)piperidine-1-carboxylate (67 mg, 0.15 mmol) was dissolved in 1,4-dioxane (2 mL) and treated with hydrochloric acid (4 M solution in 1,4-dioxane, 1.6 mL, 6.7 mmol). The mixture was stirred at RT for 4 h. The resulting solid was filtered and washed with methanol and 1,4-dioxane to afford the title compound (62 mg, 98% of theory).

LC-MS (Method 2B): $R_t$=1.70 min, MS (ESIPos): m/z=363 [M+H−xHCl]$^+$ $^1$H-NMR (500 MHz, D$_2$O): δ=7.56 (dd, 3H), 7.49 (dd, 1H), 7.34-7.26 (m, 3H), 6.32 (s, 1H), 3.69-3.59 (m, 3H), 3.33-3.23 (m, 2H), 2.39-2.29 (m, 2H), 1.98-1.85 (m, 2H).

Example 78

10-(2,6-Difluorophenyl)-4-(piperidin-4-yl)pyrimido[1,2-b]indazol-2(1H)-one Hydrochloride

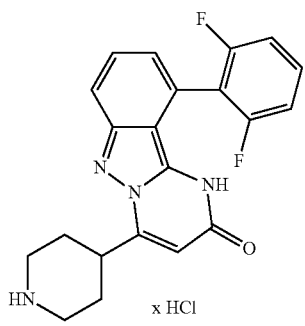 [SMILES: O=c1cc(C2CCNCC2)n2nc3cccc(-c4c(F)cccc4F)c3c2[nH]1]

x HCl

Tert-butyl 4-[10-(2,6-difluorophenyl)-2-oxo-1,2-dihydropyrimido[1,2-b]indazol-4-yl]piperidine-1-carboxylate (105 mg, 0.22 mmol) was treated with hydrochloric acid (4 M solution in 1,4-dioxane, 20.0 mL, 80.0 mmol). The mixture was stirred at RT for 16 h. The resulting solid was filtered and washed with methanol and 1,4-dioxane to afford the title compound (66 mg, 73% of theory).

LC-MS (Method 1B): $R_t$=0.67 min, MS (ESIPos): m/z=381 [M+H−xHCl]$^+$ $^1$H-NMR (500 MHz, D$_2$O): δ=7.59 (br. s, 1H), 7.54-7.37 (m, 2H), 7.09 (br. s, 2H), 6.89 (br. s, 1H), 6.39 (s, 1H), 3.73-3.59 (m, 3H), 3.37-3.24 (m, 2H), 2.43-2.28 (m, 2H), 2.02-1.86 (m, 2H).

Example 79

10-Chloro-8-methyl-4-(piperidin-4-yl)pyrimido[1,2-b]indazol-2(1H)-one Hydrochloride

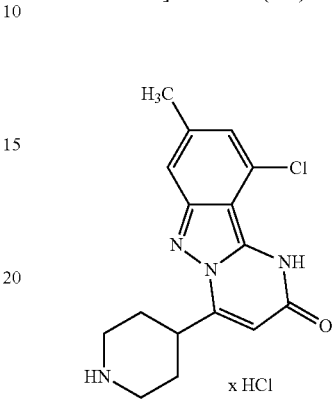

x HCl

Tert-butyl 4-(10-chloro-8-methyl-2-oxo-1,2-dihydropyrimido[1,2-b]indazol-4-yl)piperidine-1-carboxylate (320 mg, 0.77 mmol) was dissolved in 1,4-dioxane (10 mL) and treated with hydrochloric acid (4 M solution in 1,4-dioxane, 8.8 mL, 35.3 mmol). The mixture was stirred at RT for 4 h. The resulting solid was filtered and washed with methanol and 1,4-dioxane to afford the title compound (290 mg, 97% of theory).

LC-MS (Method 2B): $R_t$=1.50 min, MS (ESIPos): m/z=317 [M+H−xHCl]$^+$ $^1$H-NMR (500 MHz, D$_2$O): δ=6.95 (s, 1H), 6.64 (s, 1H), 6.27 (s, 1H), 3.68 (d, 2H), 3.56-3.47 (m, 1H), 3.37-3.25 (m, 2H), 2.43 (d, 2H), 2.25 (s, 3H), 2.03-1.91 (m, 2H).

Example 80

4-(Piperidin-4-yl)-10-[2-(trifluoromethoxy)phenyl]pyrimido[1,2-b]indazol-2(1H)-on Hydrochloride

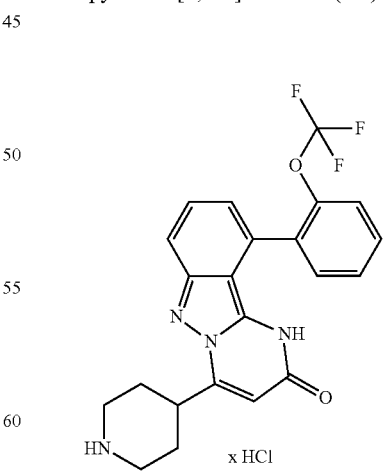

x HCl

Tert-butyl 4-{2-oxo-10-[2-(trifluoromethoxy)phenyl]-1,2-dihydropyrimido[1,2-b]indazol-4-yl}piperidine-1-carboxylate (107 mg, 0.20 mmol) was dissolved in 1,4-dioxane (5 mL) and treated with hydrochloric acid (4 M solution in 1,4-dioxane, 5.0 mL, 20.0 mmol). The mixture was stirred at RT for 16 h. The resulting solid was filtered and washed with 1,4-dioxane to afford the title compound (70 mg, 74% of theory).

LC-MS (Method 1B): $R_t$=0.73 min, MS (ESIPos): m/z=429 [M+H−xHCl]$^+$ $^1$H-NMR (400 MHz, DMSO-d$_6$): δ=11.81 (br. s, 1H), 8.93-8.71 (m, 1H), 8.70-8.48 (m, 1H), 7.72-7.45 (m, 6H), 6.94 (d, 1H), 6.63 (br. s, 1H), 4.06-3.87 (m, 1H), 3.51-3.39 (m, 2H), 3.32-3.12 (m, 2H), 2.43-2.28 (m, 2H), 2.04-1.84 (m, 2H).

Example 81

10-Bromo-8-fluoro-4-(piperidin-4-yl)pyrimido[1,2-b]indazol-2(1H)-one Hydrochloride

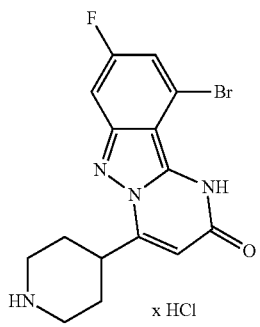 [SMILES: O=c1cc(C2CCNCC2)n2nc3cc(F)cc(Br)c3c2[nH]1]

Tert-butyl 4-(10-bromo-8-fluoro-2-oxo-1,2-dihydropyrimido[1,2-b]indazol-4-yl)piperidine-1-carboxylate (23 mg, 0.05 mmol) was dissolved in 1,4-dioxane (1 mL) and treated with hydrochloric acid (4 M solution in 1,4-dioxane, 0.6 mL, 2.3 mmol). The mixture was stirred at RT for 4 h. Concentration in vacuo afforded the title compound (21 mg, 97% of theory).

LC-MS (Method 1B): $R_t$=0.57 min, MS (ESIPos): m/z=365 [M+H−xHCl]$^+$ $^1$H-NMR (400 MHz, DMSO-d$_6$): δ=9.03-8.75 (m, 1H), 7.42 (dd, 1H), 7.31 (dd, 1H), 6.77 (br. s, 1H), 3.96-3.83 (m, 1H), 3.45 (d, 2H), 3.26-3.10 (m, 2H), 2.32 (d, 2H), 2.05-1.87 (m, 2H).

Example 82

4-(Piperidin-4-yl)-10-(pyridin-2-yl)pyrimido[1,2-b]indazol-2(1H)-one Hydrochloride

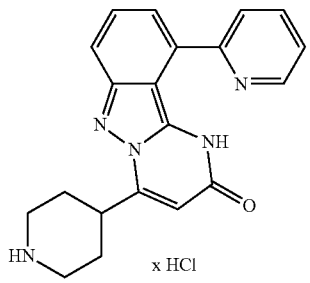 [SMILES: O=c1cc(C2CCNCC2)n2nc3cccc(-c4ccccn4)c3c2[nH]1]

Tert-butyl 4-[2-oxo-10-(pyridin-2-yl)-1,2-dihydropyrimido[1,2-b]indazol-4-yl]piperidine-1-carboxylate (339 mg, 0.76 mmol) was dissolved in 1,4-dioxane (5 mL) and treated with hydrochloric acid (4 M solution in 1,4-dioxane, 3.8 mL, 15.2 mmol). The mixture was stirred at RT for 4 h. The resulting solid was filtered and washed with 1,4-dioxane to afford the title compound (306 mg, 96% of theory).

LC-MS (Method 1B): $R_t$=0.59 min, MS (ESIPos): m/z=346 [M+H−xHCl]$^+$ $^1$H-NMR (400 MHz, DMSO-d$_6$): δ=8.89 (br. s., 3H), 8.40 (d, 1H), 8.27-8.15 (m, 1H), 7.87-7.80 (m, 1H), 7.79-7.64 (m, 2H), 7.56 (dd, 1H), 6.40 (s, 1H), 3.91-3.80 (m, 1H), 3.43 (d, 2H), 3.26-3.11 (m, 2H), 2.31 (d, 2H), 2.04-1.88 (m, 2H).

Example 83

4-(Piperidin-4-yl)-10-(1,3-thiazol-2-yl)pyrimido[1,2-b]indazol-2(1H)-one Hydrochloride

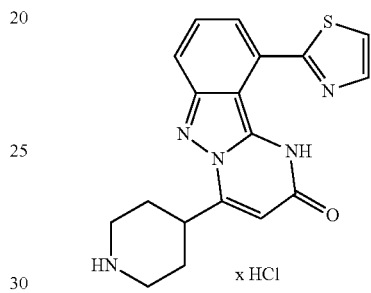

Tert-butyl 4-[2-oxo-10-(1,3-thiazol-2-yl)-1,2-dihydropyrimido[1,2-b]indazol-4-yl]piperidine-1-carboxylate (279 mg, 0.62 mmol) was dissolved in 1,4-dioxane (5 mL) and treated with hydrochloric acid (4 M solution in 1,4-dioxane, 3.8 mL, 15.2 mmol). The mixture was stirred at RT for 4 h. The resulting solid was filtered and washed with 1,4-dioxane to afford the title compound (259 mg, 99% of theory).

LC-MS (Method 1B): $R_t$=0.61 min, MS (ESIPos): m/z=352 [M+H−xHCl]$^+$ $^1$H-NMR (400 MHz, DMSO-d$_6$): δ=13.64 (br. s, 1H), 9.13-8.67 (m, 2H), 8.22 (d, 1H), 8.01 (d, 1H), 7.78-7.70 (m, 2H), 7.51 (dd, 1H), 6.34 (s, 1H), 3.87-3.76 (m, 1H), 3.44 (d, 2H), 3.26-3.10 (m, 2H), 2.32 (d, 2H), 1.96 (d, 2H).

Example 84

4-(Piperidin-4-yl)-10-(3-thienyl)pyrimido[1,2-b]indazol-2(1H)-one Hydrochloride

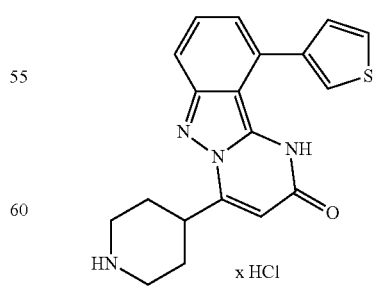

Tert-butyl 4-[2-oxo-10-(3-thienyl)-1,2-dihydropyrimido[1,2-b]indazol-4-yl]piperidine-1-carboxylate (98 mg, 0.22 mmol) was dissolved in 1,4-dioxane (8 mL) and treated with hydrochloric acid (4 M solution in 1,4-dioxane, 1.1 mL, 4.4 mmol). The mixture was stirred at RT for 4 h. The resulting solid was filtered and washed with 1,4-dioxane to afford the title compound (34 mg, 40% of theory). LC-MS (Method 1B): R$_t$=0.61 min, MS (ESIPos): m/z=351 [M+H−xHCl]$^+$ $^1$H-NMR (500 MHz, D$_2$O): δ=7.59 (br. s, 1H), 7.34 (br. s., 1H), 7.30-7.20 (m, 2H), 7.05 (br. s, 1H), 6.81-6.72 (m, 1H), 6.23 (br. s., 1H), 3.64 (d, 2H), 3.48-3.37 (m, 1H), 3.31-3.15 (m, 2H), 2.28 (d, 2H), 1.97-1.79 (m, 2H).

Example 85

10-(2-Methylphenyl)-4-(piperidin-4-yl)pyrimido[1,2-b]indazol-2(1H)-one Hydrochloride

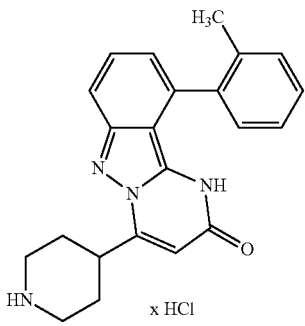 [SMILES: Cc1ccccc1-c1cccc2nn3c(C4CCNCC4)cc(=O)[nH]c3c12]

Tert-butyl 4-[10-(2-methylphenyl)-2-oxo-1,2-dihydropyrimido[1,2-b]indazol-4-yl]piperidine-1-carboxylate (150 mg, 0.33 mmol) was dissolved in 1,4-dioxane (13 mL) and treated with hydrochloric acid (4 M solution in 1,4-dioxane, 1.6 mL, 6.5 mmol). The mixture was stirred at RT for 4 h. Concentration in vacuo afforded the title compound (123 mg, 95% of theory).

LC-MS (Method 1B): R$_t$=0.67 min, MS (ESIPos): m/z=359 [M+H−xHCl]$^+$ $^1$H-NMR (500 MHz, D$_2$O): δ=7.58 (d, 1H), 7.54-7.48 (m, 1H), 7.47-7.39 (m, 2H), 7.30 (t, 1H), 7.09 (d, 1H), 6.78 (d, 1H), 6.35 (s, 1H), 3.87-3.62 (m, 3H), 3.37-3.27 (m, 2H), 2.48-2.38 (m, 2H), 2.00 (s, 5H).

Example 86

10-(1-Methyl-1H-pyrazol-5-yl)-4-(piperidin-4-yl)pyrimido[1,2-b]indazo-2(1H)-one Hydrochloride

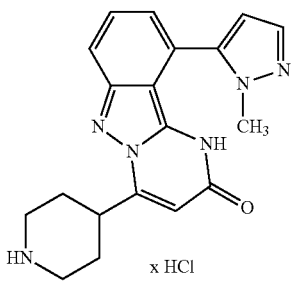 [SMILES: Cn1nccc1-c1cccc2nn3c(C4CCNCC4)cc(=O)[nH]c3c12]

Tert-butyl 4-[10-(1-methyl-1H-pyrazol-5-yl)-2-oxo-1,2-dihydropyrimido[1,2-b]indazol-4-yl]piperidine-1-carboxylate (140 mg, 0.31 mmol) was dissolved in 1,4-dioxane (6 mL) and treated with hydrochloric acid (4 M solution in 1,4-dioxane, 3.6 mL, 14.4 mmol). The mixture was stirred at RT for 4 h. Concentration in vacuo afforded the title compound (110 mg, 92% of theory).

LC-MS (Method 1B): R$_t$=0.52 min, MS (ESIPos): m/z=349 [M+H−xHCl]$^+$ $^1$H-NMR (500 MHz, D$_2$O): δ=7.85 (d, 1H), 7.71 (d, 1H), 7.59 (dd, 1H), 7.10 (d, 1H), 6.56 (d, 1H), 6.47 (s, 1H), 3.79 (s, 4H), 3.69 (d, 2H), 3.39-3.30 (m, 2H), 2.47 (d, 2H), 2.07-1.95 (m, 2H).

Example 87

10-(1-Methyl-1H-pyrazol-4-yl)-4-(piperidin-4-yl)pyrimido[1,2-b]indazol-2(1H)-one Hydrochloride

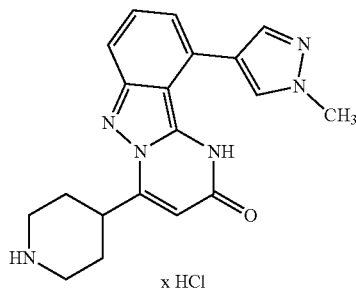 [SMILES: Cn1cc(-c2cccc3nn4c(C5CCNCC5)cc(=O)[nH]c4c23)cn1]

Tert-butyl 4-[10-(1-methyl-1H-pyrazol-4-yl)-2-oxo-1,2-dihydropyrimido[1,2-b]indazol-4-yl]piperidine-1-carboxylate (121 mg, 0.27 mmol) was dissolved in 1,4-dioxane (6 mL) and treated with hydrochloric acid (4 M solution in 1,4-dioxane, 3.1 mL, 12.4 mmol). The mixture was stirred at RT for 4 h. Concentration in vacuo afforded the title compound (128 mg, 99% of theory).

LC-MS (Method 1B): R$_t$=0.53 min, MS (ESIPos): m/z=349 [M+H−xHCl]$^+$ $^1$H-NMR (500 MHz, D$_2$O): δ=7.93 (s, 1H), 7.79 (s, 1H), 7.05 (dd, 1H), 6.97 (d, 1H), 6.57 (d, 1H), 6.24 (s, 1H), 3.89 (s, 3H), 3.71 (d, 2H), 3.33-3.24 (m, 2H), 3.24-3.15 (m, 1H), 2.26 (d, 2H), 1.92-1.80 (m, 2H).

Example 88

4-(Piperidin-4-yl)-10-(2-thienyl)pyrimido[1,2-b]indazol-2(1H)-one Hydrochloride

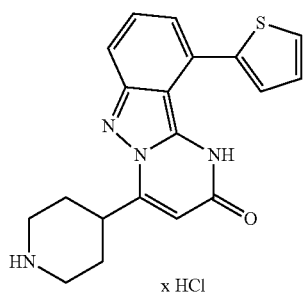 [SMILES: O=c1cc(C2CCNCC2)n2nc3cccc(-c4cccs4)c3c2[nH]1]

Tert-butyl 4-[2-oxo-10-(2-thienyl)-1,2-dihydropyrimido[1,2-b]indazol-4-yl]piperidine-1-carboxylate (101 mg, 0.22 mmol) was dissolved in 1,4-dioxane (5 mL) and treated with hydrochloric acid (4 M solution in 1,4-dioxane, 2.6 mL, 10.3 mmol). The mixture was stirred at RT for 4 h. Concentration in vacuo afforded the title compound (85 mg, 98% of theory).

LC-MS (Method 1B): $R_t$=0.66 min, MS (ESIPos): m/z=351 [M+H−xHCl]$^+$ $^1$H-NMR (500 MHz, D$_2$O): δ=7.51 (d, 1H), 7.28 (d, 1H), 7.23 (dd, 1H), 7.16 (dd, 1H), 7.08 (d, 1H), 6.82 (d, 1H), 6.23 (s, 1H), 3.59 (d, 2H), 3.52-3.42 (m, 1H), 3.20 (t, 2H), 2.27 (d, 2H), 1.91-1.77 (m, 2H).

Example 89

10-Bromo-8-methyl-4-(piperidin-4-yl)pyrimido[1,2-b]indazol-2(1H)-one Hydrochloride

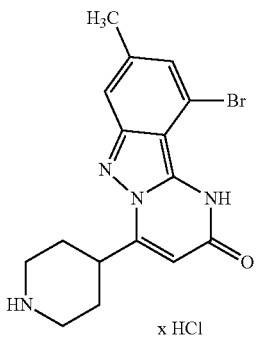 [SMILES: Cc1cc(Br)c2c(c1)nn1c(C3CCNCC3)cc(=O)[nH]c21]

Tert-butyl 4-(10-bromo-8-methyl-2-oxo-1,2-dihydropyrimido[1,2-b]indazol-4-yl)piperidine-1-carboxylate (404 mg, 0.88 mmol) was dissolved in 1,4-dioxane (18 mL) and treated with hydrochloric acid (4 M solution in 1,4-dioxane, 10.0 mL, 40.0 mmol). The mixture was stirred at RT for 4 h. Concentration in vacuo afforded the title compound (360 mg, 95% of theory).

LC-MS (Method 1B): $R_t$=0.60 min, MS (ESIPos): m/z=361 [M+H−xHCl]$^+$ $^1$H-NMR (500 MHz, D$_2$O): δ=6.87 (s, 1H), 6.62 (s, 1H), 6.25 (s, 1H), 3.74-3.66 (m, 2H), 3.51-3.42 (m, 1H), 3.36-3.27 (m, 2H), 2.44-2.37 (m, 2H), 2.18 (s, 3H), 2.03-1.91 (m, 2H).

Example 90

10-Chloro-9-fluoro-4-(piperidin-4-yl)pyrimido[1,2-b]indazol-2(1H)-one Hydrochloride

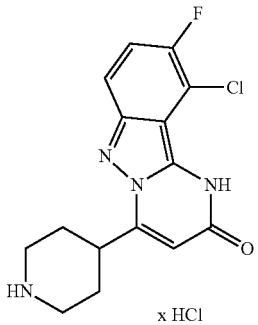 [SMILES: O=c1cc(C2CCNCC2)n2nc3ccc(F)c(Cl)c3c2[nH]1]

Tert-butyl 4-(10-chloro-9-fluoro-2-oxo-1,2-dihydropyrimido[1,2-b]indazol-4-yl)piperidine-1-carboxylate (428 mg, 1.02 mmol) was dissolved in 1,4-dioxane (20 mL) and treated with hydrochloric acid (4 M solution in 1,4-dioxane, 11.7 mL, 46.7 mmol). The mixture was stirred at RT for 4 h. Concentration in vacuo afforded the title compound (378 mg, 91% of theory).

LC-MS (Method 1B): $R_t$=0.55 min, MS (ESIPos): m/z=321 [M+H−xHCl]$^+$ $^1$H-NMR (500 MHz, D$_2$O): δ=7.23 (dd, 1H), 7.12 (dd, 1H), 6.38 (s, 1H), 3.69 (d, 2H), 3.57-3.48 (m, 1H), 3.36-3.28 (m, 2H), 2.44 (d, 2H), 2.05-1.94 (m, 2H).

Example 91

4-(Piperidin-4-yl)-10-(1H-1,2,4-triazol-1-yl)pyrimido[1,2-b]indazol-2(1H)-one hydrochloride

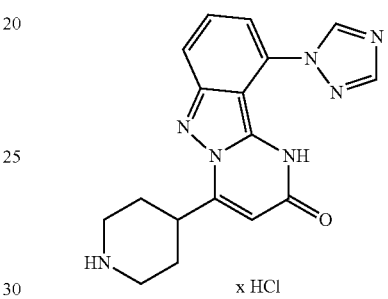

Tert-butyl 4-[2-oxo-10-(1H-1,2,4-triazol-1-yl)-1,2-dihydropyrimido[1,2-b]indazol-4-yl]piperidine-1-carboxylate (96 mg, 0.22 mmol) was dissolved in 1,4-dioxane (2.2 mL) and treated with hydrochloric acid (4 M solution in 1,4-dioxane, 0.55 mL, 2.2 mmol). The mixture was stirred at RT for 16 h. The resulting solid was filtered and washed with 1,4-dioxane to afford the title compound (72 mg, 87% of theory).

LC-MS (Method 1B): $R_t$=0.43 min, MS (ESIPos): m/z=336 [M+H−xHCl]$^+$ $^1$H-NMR (500 MHz, D$_2$O): δ=9.07 (s, 1H), 8.24 (s, 1H), 7.35-7.26 (m, 2H), 7.15 (d, 1H), 6.34 (s, 1H), 3.69 (d, 2H), 3.60-3.50 (m, 1H), 3.39-3.28 (m, 2H), 2.43 (d, 2H), 2.05-1.91 (m, 2H).

Example 92

9-Fluoro-10-(2-fluorophenyl)-4-(piperidin-4-yl)pyrimido[1,2-b]indazol-2(1H)-one Hydrochloride

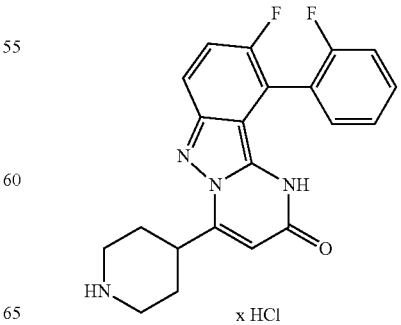

Tert-butyl 4-[9-fluoro-10-(2-fluorophenyl)-2-oxo-1,2-dihydropyrimido[1,2-b]indazol-4-yl]piperidine-1-carboxylate (42 mg, 0.09 mmol) was dissolved in 1,4-dioxane (1 mL) and treated with hydrochloric acid (4 M solution in 1,4-dioxane, 1.0 mL, 4.0 mmol). The mixture was stirred at RT for 4 h. Concentration in vacuo afforded the title compound (36 mg, 86% of theory).

LC-MS (Method 1B): $R_t$=0.70 min, MS (ESIPos): m/z=381 [M+H−xHCl]$^+$ $^1$H-NMR (500 MHz, D$_2$O): δ=7.63-7.52 (m, 2H), 7.37-7.29 (m, 3H), 7.27-7.20 (m, 1H), 6.35 (s, 1H), 3.69-3.60 (m, 3H), 3.34-3.24 (m, 2H), 2.40-2.30 (m, 2H), 1.98-1.86 (m, 2H).

Example 93

10-(2-Ethoxyphenyl)-4-(piperidin-4-yl)pyrimido[1,2-b]indazol-2(1H)-one Hydrochloride

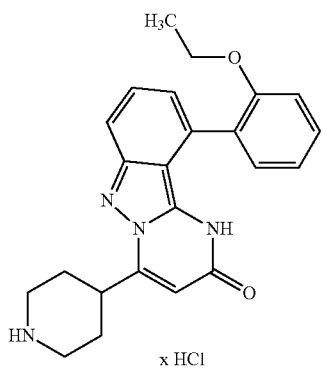 [SMILES: CCOc1ccccc1-c1cccc2nn3c(C4CCNCC4)cc(=O)[nH]c3c12]

Tert-butyl 4-[10-(2-ethoxyphenyl)-2-oxo-1,2-dihydropyrimido[1,2-b]indazol-4-yl]piperidine-1-carboxylate (150 mg, 0.31 mmol) was dissolved in 1,4-dioxane (6 mL) and treated with hydrochloric acid (4 M solution in 1,4-dioxane, 3.5 mL, 14.1 mmol). The mixture was stirred at RT for 4 h. Concentration in vacuo afforded the title compound (173 mg).

LC-MS (Method 1B): $R_t$=0.68 min, MS (ESIPos): m/z=389 [M+H−xHCl]$^+$ $^1$H-NMR (400 MHz, DMSO-d$_6$): δ=9.07-8.76 (m, 1H), 7.60 (d, 1H), 7.51 (d, 1H), 7.41 (dd, 1H), 7.33 (dd, 1H), 7.12 (d, 1H), 7.03 (dd, 1H), 6.90 (d, 1H), 6.60 (br. s, 1H), 4.00 (q, 2H), 3.61-3.53 (m, 1H), 3.45 (d, 2H), 3.29-3.12 (m, 2H), 2.36 (d, 2H), 2.04-1.87 (m, 2H), 0.78 (t, 3H)

Example 94

10-(2-Isopropoxyphenyl)-4-(piperidin-4-yl)pyrimido[1,2-b]indazol-2(1H)-one Hydrochloride

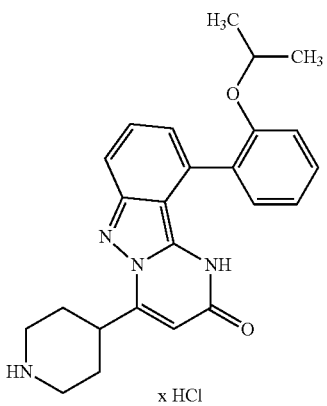 [SMILES: CC(C)Oc1ccccc1-c1cccc2nn3c(C4CCNCC4)cc(=O)[nH]c3c12]

Tert-butyl 4-[10-(2-isopropoxyphenyl)-2-oxo-1,2-dihydropyrimido[1,2-b]indazol-4-yl]piperidine-1-carboxylate (130 mg, 0.26 mmol) was dissolved in 1,4-dioxane (5 mL) and treated with hydrochloric acid (4 M solution in 1,4-dioxane, 3.0 mL, 12.0 mmol). The mixture was stirred at RT for 4 h. Concentration in vacuo afforded the title compound (153 mg).

LC-MS (Method 1B): $R_t$=0.72 min, MS (ESIPos): m/z=403 [M+H−xHCl]$^+$ $^1$H-NMR (400 MHz, DMSO-d$_6$): δ=9.07-8.80 (m, 1H), 7.59 (d, 1H), 7.49 (dd, 1H), 7.39 (dd, 1H), 7.32 (dd, 1H), 7.11 (d, 1H), 7.02 (dd, 1H), 6.90 (d, 1H), 6.55 (br. s, 1H), 4.55-4.46 (m, 1H), 3.57 (s, 1H), 3.45 (d, 2H), 3.22 (m, 2H), 2.35 (d, 2H), 2.03-1.88 (m, 2H), 0.96 (d, 6H).

Example 95

10-(2-Fluorophenyl)-4-(piperidin-4-yl)pyrimido[1,2-b]indazol-2(1H)-one

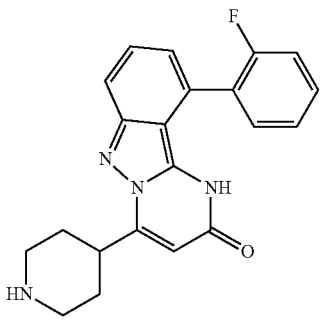 [SMILES: O=c1cc(C2CCNCC2)n2nc3cccc(-c4ccccc4F)c3c2[nH]1]

10-(2-fluorophenyl)-4-(piperidin-4-yl)pyrimido[1,2-b]indazol-2(1H)-one hydrochloride (100 mg, 0.23 mmol) was dissolved in hydrochloric acid (1.0 M in water) and treated with sodium hydroxide solution (1.0 M in water). The precipitate was collected by filtration, washed with water, and dried under vacuo to afford the title compound (35 mg, 42% of theory).

Example 96

4-(Piperidin-4-yl)-10-(1H-pyrazol-1-yl)pyrimido[1,2-b]indazol-2(1H)-one hydrochloride

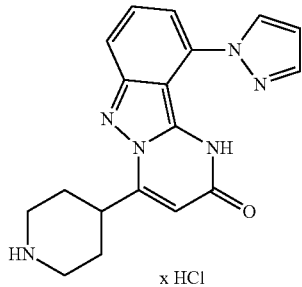 [SMILES: O=c1cc(C2CCNCC2)n2nc3cccc(-n4cccn4)c3c2[nH]1]

x HCl

Tert-butyl 4-[2-oxo-10-(1H-pyrazol-1-yl)-1,2-dihydropyrimido[1,2-b]indazol-4-yl]piperidine-1-carboxylate (380 mg, 0.87 mmol) was dissolved in 1,4-dioxane (14 mL) and treated with hydrochloric acid (4 M solution in 1,4-dioxane, 5.0 mL, 20.0 mmol). The mixture was stirred at RT for 8 h. Concentration in vacuo and trituration with acetonitrile afforded the title compound (338 mg).

$^1$H-NMR (500 MHz, D$_2$O): δ=7.67 (s, 1H), 7.24 (s, 1H), 6.67 (dd, 1H), 6.52 (d, 1H), 6.28 (s, 1H), 6.20 (d, 1H), 5.94 (s, 1H), 3.68-3.59 (m, 2H), 3.26-3.15 (m, 2H), 3.09-2.98 (m, 1H), 2.23-2.14 (m, 2H), 1.88-1.76 (m, 2H).

Example 97

10-(2-Fluoro-6-methoxyphenyl)-4-(piperidin-4-yl)pyrimido[1,2-b]indazol-2(1H)-one Hydrochloride

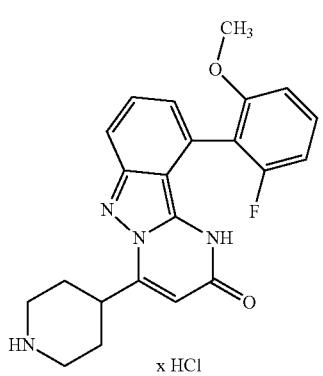 [SMILES: COc1cccc(F)c1-c1cccc2nn3c(C4CCNCC4)cc(=O)[nH]c3c12]

x HCl

Tert-butyl 4-[10-(2-fluoro-6-methoxyphenyl)-2-oxo-1,2-dihydropyrimido[1,2-b]indazol-4-yl]piperidine-1-carboxylate (21 mg, 0.043 mmol) was dissolved in 1,4-dioxane (0.6 mL) and treated with hydrochloric acid (4 M solution in 1,4-dioxane, 0.2 mL, 0.8 mmol). The mixture was stirred at RT for 4 h. Concentration in vacuo afforded the title compound (18 mg, 96% of theory).

LC-MS (Method 1B): R$_t$=0.66 min, MS (ESIPos): m/z=393 [M+H−xHCl]$^+$ $^1$H-NMR (500 MHz, D$_2$O): δ=8.46 (s, 1H), 7.73-7.66 (m, 1H), 7.66-7.52 (m, 2H), 7.17-6.99 (m, 3H), 6.42 (s, 1H), 3.88-3.78 (m, 1H), 3.77-3.71 (m, 3H), 3.70-3.61 (m, 2H), 3.40-3.27 (m, 2H), 2.56-2.43 (m, 2H), 2.09-1.94 (m, 2H).

Example 98

4-(Piperidin-4-yl)-10-(2H-1,2,3-triazol-2-yl)pyrimido[1,2-b]indazol-2(1H)-one Hydrochloride

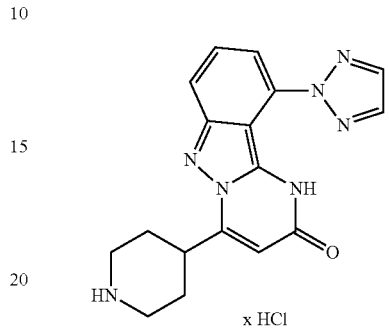

x HCl

Tert-butyl 4-[2-oxo-10-(2H-1,2,3-triazol-2-yl)-1,2-dihydropyrimido[1,2-b]indazol-4-yl]piperidine-1-carboxylate (750 mg, 1.71 mmol) was dissolved in 1,4-dioxane (25 mL) and treated with hydrochloric acid (4 M solution in 1,4-dioxane, 8.0 mL, 32.0 mmol). The mixture was stirred at RT for 16 h. Concentration in vacuo afforded the title compound (730 mg, 96% of theory).

LC-MS (Method 1B): R$_t$=0.58 min, MS (ESIPos): m/z=336 [M+H−xHCl]$^+$ $^1$H-NMR (400 MHz, DMSO-d$_6$): δ=12.24 (br. s, 1H), 8.94 (br. s, 1H), 8.75 (br. s, 1H), 8.45 (s, 2H), 7.80 (d, 1H), 7.66 (d, 1H), 7.55 (dd, 1H), 6.38 (s, 1H), 3.84 (br. s., 1H), 3.44 (d, 2H), 3.19 (d, 2H), 2.32 (d, 2H), 1.94 (d, 2H).

Example 99

4-(Piperidin-4-yl)-10-(1H-1,2,3-triazol-1-yl)pyrimido[1,2-b]indazol-2(1H)-one Hydrochloride

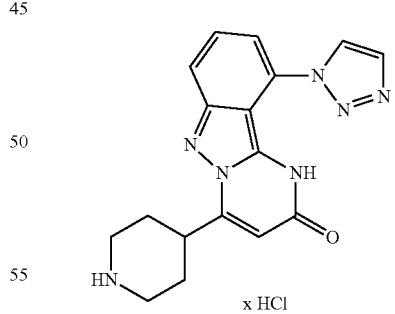

x HCl

Tert-butyl 4-[2-oxo-10-(1H-1,2,3-triazol-1-yl)-1,2-dihydropyrimido[1,2-b]indazol-4-yl]piperidine-1-carboxylate (237 mg, 0.54 mmol) was dissolved in 1,4-dioxane (8 mL) and treated with hydrochloric acid (4 M solution in 1,4-dioxane, 1.4 mL, 5.6 mmol). The mixture was stirred at 60° C. for 6 h. The precipitate was collected by filtration and dried to afford the title compound (210 mg, 88% of theory).

LC-MS (Method 1B): R$_t$=0.44 min, MS (ESIPos): m/z=336 [M+H−xHCl]$^+$ $^1$H-NMR (500 MHz, D$_2$O): δ=8.39 (s, 1H), 7.88 (s, 1H), 7.12-7.05 (m, 2H), 6.91-6.83 (m, 1H), 6.26 (s, 1H), 3.70 (d, 2H), 3.42 (t, 1H), 3.31 (t, 2H), 2.40 (d, 2H), 2.04-1.92 (m, 2H).

Example 100

10-Chloro-7-methyl-4-(piperidin-4-yl)pyrimido[1,2-b]indazol-2(1H)-one Hydrochloride

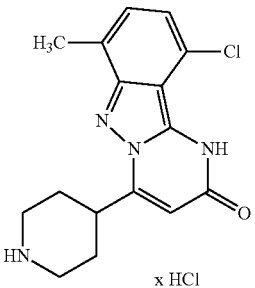 [SMILES: Cc1ccc(Cl)c2c1nn1c(C3CCNCC3)cc(=O)[nH]c21]

x HCl

Tert-butyl 4-(10-chloro-7-methyl-2-oxo-1,2-dihydropyrimido[1,2-b]indazol-4-yl)piperidine-1-carboxylate (230 mg, 0.55 mmol) was dissolved in 1,4-dioxane (2 mL) and treated with hydrochloric acid (4 M solution in 1,4-dioxane, 1.4 mL, 5.6 mmol). The mixture was stirred at RT for 16 h. The precipitate was collected by filtration, washed with dioxane, and dried to afford the title compound (194 mg, 90% of theory).

LC-MS (Method 1B): R$_t$=0.58 min, MS (ESIPos): m/z=317 [M+H−xHCl]$^+$ $^1$H-NMR (400 MHz, DMSO-d$_6$): δ=9.01-8.71 (m, 1H), 7.21 (d, 1H), 7.01 (d, 1H), 6.67 (br. s, 1H), 3.98-3.83 (m, 1H), 3.21 (d, 2H), 2.37 (d, 2H), 1.98 (d, 2H).

Example 101

(+)-Cis-10-Chloro-4-(2-methylpiperidin-4-yl)pyrimido[1,2-b]indazol-2(1H)-one Hydrochloride [Enantiomerically Pure Cis-Isomer]

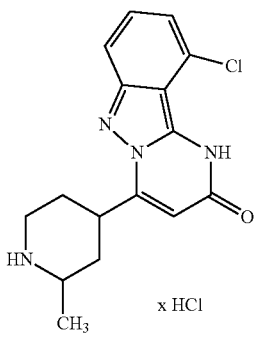

x HCl

A suspension of (+)-cis-Tert-butyl 4-(10-chloro-2-oxo-1,2-dihydropyrimido[1,2-b]indazol-4-yl)-2-methylpiperidine-1-carboxylate [enantiomerically pure cis-Isomer] (40 mg, 0.09 mmol) in methanol (0.053 ml) was treated with HCl 4N in dioxane (0.35 ml). The reaction mixture was stirred 1 h at rt. The mixture was evaporated and the crude was stirred in dichloromethane, evaporated and dried under vacuo to yield the title compound (22 mg, 66% of theory).

LC-MS (Method 5B): RT=0.54 min, MS (ESIPos): m/z=317 [M+H−xHCl]$^+$

[α]$^{20}$=+0.37 (c. 0.27, methanol) WL=589 nm $^1$H-NMR (400 MHz, MeOD): δ 7.41 (d, 1H), 7.27 (t, 1H), 6.96 (d, 1H), 6.41 (s, 1H), 4.08-3.98 (m, 1H), 3.83-3.74 (m, 1H), 3.57 (dm, 1H), 3.45-3.36 (m, 1H), 3.30-3.24 (m, 1H), 2.39-2.31 (m, 1H), 2.21 (dd, 1H), 2.08-1.98 (m, 1H), 1.47 (d, 3H).

Example 102

[2-oxo-4-(piperidin-4-yl)-1,2-dihydropyrimido[1,2-b]indazol-10-yl]acetonitrile Hydrocloride

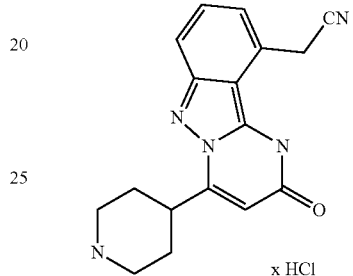

x HCl

Tert-butyl 4-[10-(cyanomethyl)-2-oxo-1,2-dihydropyrimido[1,2-b]indazol-4-yl]piperidine-1-carboxylate (12 mg, 0.03 mmol) was dissolved in methanol (0.08 mL) and then 4N HCl in dioxane (0.07 mL) was added and the mixture was stirred at room temperature overnight. The resulting suspension was filtered and the solid was washed with methanol and dried for 16 h in vacuo to give the title compound (5 mg, 53% of theory).

LC-MS (Method 3B): R$_t$=1.30 min, MS (ESIPos): m/z=307 [M+H−xHCl]$^+$ $^1$H-NMR (400 MHz, D$_2$O): δ=7.32 (d, 1H), 7.24 (dd, 1H), 6.76 (d, 1H), 6.39 (s, 1H), 3.98 (s, 2H), 3.60 (d, 2H), 3.51 (dd, 1H), 3.25 (dd, 2H), 2.35 (d, 2H), 1.89 (dd, 2H)

Example 103

10-(1H-imidazol-5-yl)-4-(piperidin-4-yl)pyrimido[1,2-b]indazol-2(1H)-one Hydrochloride

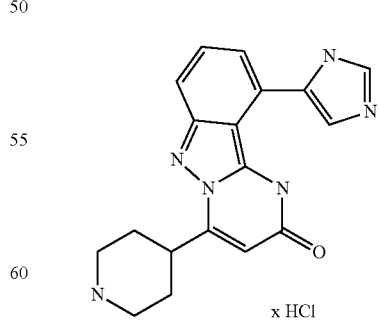

x HCl tert-butyl 4-{2-oxo-10-[1-(tetrahydro-2H-pyran-2-yl)-1H-imidazol-5-yl]-1,2-dihydropyrimido[1,2-b]indazol-4-yl}piperidine-1-carboxylate (55 mg, 0.11 mmol) was dissolved in 1,4-dioxane (1.5 mL) and treated with hydrochloric acid (4 M solution in 1,4-dioxane, 0.53 mL, 2.12 mmol). The solvent was removed and the residue treated with acetonitrile. The resulting solid was filtered and washed with acetonitrile to afford the title compound (36.5 mg, 82% of theory).

LC-MS (Method 6B): $R_t$=0.90 min, MS (ESIPos): m/z=335 [M+H−xHCl]$^+$ $^1$H-NMR (400 MHz, DMSO-d$_6$): δ=ppm 15.89 (br. s, 1H), 9.09-9.39 (m, 3H), 8.65 (s, 1H), 7.70-7.83 (m, 2H), 7.60 (d, 1H), 6.83 (s, 1H), 3.84-4.06 (m, 1H), 3.44 (m, 2H), 3.00-3.28 (m, 2H), 2.30-2.41 (m, 2H), 1.99-2.15 (m, 2H).

Example 104

4-(piperidin-4-yl)-10-(1H-pyrrol-2-yl)pyrimido[1,2-b]indazol-2(1H)-one hydrochloride

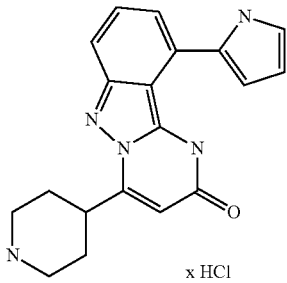 [SMILES: O=c1cc(C2CCNCC2)n2nc3cccc(-c4ccc[nH]4)c3c2[nH]1]

x HCl tert-butyl 4-{10-[1-(tert-butoxycarbonyl)-1H-pyrrol-2-yl]-2-oxo-1,2-dihydropyrimido[1,2-b]indazol-4-yl}piperidine-1-carboxylate (140 mg, 0.26 mmol) was dissolved in 1,4-dioxane (2.5 mL) and treated with hydrochloric acid (4 M solution in 1,4-dioxane, 1.3 mL, 5.2 mmol). The solvent was removed and the residue treated with acetonitrile. The resulting solid was filtered and washed with acetonitrile to afford the title compound (79.4 mg, 74% of theory).

LC-MS (Method 5B): $R_t$=1.48 min, MS (ESIPos): m/z=334 [M+H−xHCl]$^+$ $^1$H-NMR (400 MHz, DMSO-d$_6$): δ=ppm 13.39 (br. s, 1H), 9.18 (br. s., 2H), 7.34-7.64 (m, 3H), 7.15 (br. s., 1H), 6.96 (br. s, 1H), 6.82 (s, 1H), 6.24 (d, 1H), 4.00 (t, 1H), 3.45 (d, 2H), 3.06-3.29 (m, 2H), 2.38 (d, 2H), 1.88-2.13 (m, 2H).

Example 105

10-hydroxy-4-(piperidin-4-yl)pyrimido[1,2-b]indazol-2(1H)-one Hydrobromide

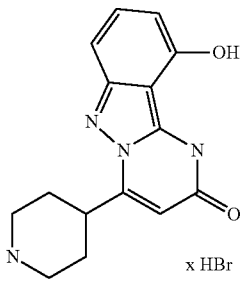 [SMILES: O=c1cc(C2CCNCC2)n2nc3cccc(O)c3c2[nH]1]

x HBr

10-Methoxy-4-(piperidin-4-yl)pyrimido[1,2-b]indazol-2(1H)-one hydrochloride (Example 8) (25 mg, 0.08 mmol) was dissolved in acetic acid (2 mL) and treated with hydrobromic acid (58% in water, 0.5 mL, 9.2 mmol). The mixture was heated to 125° C. for 16h, then the solvents were removed and the resulting solid was dried in high vacuum to afford the title compound (32.5 mg, quant.).

LC-MS (Method 7B): $R_t$=1.14 min, MS (ESIPos): m/z=285.1 [M+H−xHBr]$^+$ $^1$H-NMR (400 MHz, D$_2$O-d$_6$): δ=ppm 6.89-7.04 (m, 1H), 6.56 (d, 1H), 6.02 (s, 1H), 5.93-5.99 (m, 1H), 3.50-3.63 (m, 2H), 3.19 (br. s., 3H), 2.20-2.31 (m, 2H), 1.72-1.89 (m, 2H).

Example 106

2-oxo-4-(piperidin-4-yl)-1,2-dihydropyrimido[1,2-b]indazole-10-carboxylic Acid Hydrochloride

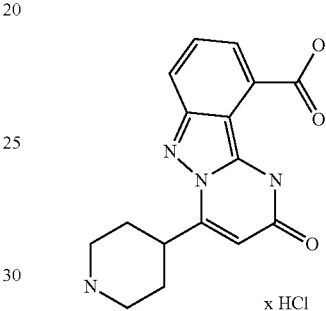

x HCl

4-[1-(tert-butoxycarbonyl)piperidin-4-yl]-2-oxo-1,2-dihydropyrimido[1,2-b]indazole-10-carboxylic acid (185 mg, 0.45 mmol) was dissolved in 1,4-dioxane (2 mL) and treated with hydrochloric acid (4 M solution in 1,4-dioxane, 2.2 mL, 9.0 mmol) for 18h at rt. The resulting solid was filtered and washed with acetonitrile to afford the title compound (99.5 mg, 64% of theory).

LC-MS (Method 5B): $R_t$=0.33 min, MS (ESIPos): m/z=313.2 [M+H−xHCl]$^+$ $^1$H-NMR (400 MHz, DMSO-d$_6$): δ=ppm 13.90-14.33 (br. s, 1H), 11.84 (br. s., 1H), 9.02 (br. s, 1H), 8.85 (br. s, 1H), 7.90 (d, 1H), 7.81 (d, 1H), 7.52 (t, 1H), 6.32 (s, 1H), 3.73-3.87 (m, 1H), 3.43 (m, 3H), 3.17 (m, 2H), 2.30 (d, 2H), 1.95 (m, 2H).

Example 107

4-(piperidin-4-yl)-10-(2,2,2-trifluoroethoxy)pyrimido[1,2-b]indazol-2(1H)-one Hydrochloride

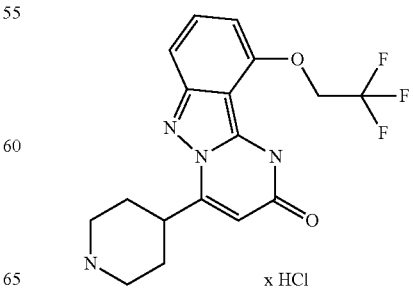

x HCl tert-butyl 4-[2-oxo-10-(2,2,2-trifluoroethoxy)-1,2-dihydropyrimido[1,2-b]indazol-4-yl]piperidine-1-carboxylate (188 mg, 0.40 mmol) was dissolved in 1,4-dioxane (2.5 mL) and treated with hydrochloric acid (4 M solution in 1,4-dioxane, 1.3 mL, 5.2 mmol). The resulting solid was filtered and washed with acetonitrile to afford the title compound (150 mg, 92% of theory).

LC-MS (Method 8B): $R_t$=0.71 min, MS (ESIPos): m/z=367 [M+H−xHCl]$^+$ $^1$H-NMR (400 MHz, DMSO-$d_6$): δ=ppm (br. s, 2H), 7.30-7.44 (m, 1H), 7.21 (d, 1H), 6.61 (d, 1H), 6.44 (br. s, 1H), 4.98 (q, 2H), 3.75-3.91 (m, 1H), 3.42 (d, 2H), 3.16 (m, 2H), 2.31 (d, 2H), 1.98 (d, 2H).

Example 108

10-amino-4-(piperidin-4-yl)pyrimido[1,2-b]indazol-2(1H)-one Hydrochloride

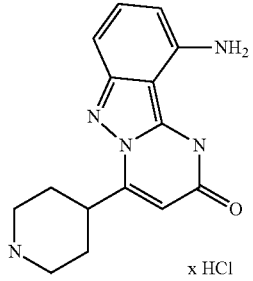 [SMILES: Nc1cccc2nn3c(C4CCNCC4)cc(=O)[nH]c3c12]

x HCl tert-butyl 4-{10-[(tert-butoxycarbonyl)amino]-2-oxo-1,2-dihydropyrimido[1,2-b]indazol-4-yl}piperidine-1-carboxylate (80 mg, 0.17 mmol) was dissolved in 1,4-dioxane (2 mL) and treated with hydrochloric acid (4 M solution in 1,4-dioxane, 1.3 mL, 5.2 mmol) for 3 d. The resulting solid was filtered and washed with 1,4-dioxane and acetonitrile to afford the title compound (46 mg, 78% of theory).

LC-MS (Method 7B): $R_t$=1.13 min, MS (ESIPos): m/z=384 [M+H−xHCl]$^+$ $^1$H-NMR (400 MHz, DMSO-$d_6$): δ=ppm 9.12 (br. s., 2H), 7.26 (br. s., 1H), 6.88-7.07 (m, 1H), 6.53-6.69 (m, 1H), 6.28-6.49 (m, 1H), 3.73-3.97 (m, 1H), 3.43 (m, 2H), 3.17 (m, 2H), 2.32 (m, 2H), 1.99 (m, 2H).

X-Ray Diffractometry:

Synthesis of 10-Chloro-4-(piperidin-4-yl)pyrimido[1,2-b]indazol-2(1H)-one (example 66) maleate Approximately 100 mg of 10-Chloro-4-(piperidin-4-yl)pyrimido[1,2-b]indazol-2(1H)-one (example 66) were solved in hexafluoroisopropanol without any heating. This solution was added to a solution of an equimolar amount of maleic acid solved in water. This solution was evaporated at room temperature and atmospheric pressure. The resulting solid was analyzed by x ray powder diffraction and corresponds to 10-Chloro-4-(piperidin-4-yl)pyrimido[1,2-b]indazol-2(1H)-one (example 66) in form of its maleate.

Synthesis of 10-Chloro-4-(piperidin-4-yl)pyrimido[1,2-b]indazol-2(1H)-one (example 66) Acetate Approximately 100 mg of 10-Chloro-4-(piperidin-4-yl)pyrimido[1,2-b]indazol-2(1H)-one (example 66) were solved in hexafluoroisopropanol without any heating. This solution was added to a solution of an equimolar amount of acetic acid solved in water. This solution was evaporated at room temperature and atmospheric pressure. The resulting solid was analyzed by x ray powder diffraction and corresponds to 10-Chloro-4-(piperidin-4-yl)pyrimido[1,2-b]indazol-2(1H)-one (example 66) in form of its acetate.

Synthesis of 10-Chloro-4-(piperidin-4-yl)pyrimido[1,2-b]indazol-2(1H)-one (example 66) Sulfate Approximately 100 mg of 10-Chloro-4-(piperidin-4-yl)pyrimido[1,2-b]indazol-2(1H)-one (example 66) were solved in hexafluoroisopropanol without any heating. This solution was added to a solution of an equimolar amount of sulfuric acid solved in water. This solution was evaporated at room temperature and atmospheric pressure. The resulting solid was analyzed by x ray powder diffraction and corresponds to 10-Chloro-4-(piperidin-4-yl)pyrimido[1,2-b]indazol-2(1H)-one (example 66) in form of its sulfate.

Measurement Conditions of X-Ray Diffractometry:

Transmission diffractometer PANalytical X'Pert PRO with PIXcel counter (multichannel):

| Source of raw data | XRPD measurement |
|---|---|
| Scan-Axis | Gonio |
| Starting position [°2Th.] | 2.0066 |
| End position [°2Th.] | 37.9906 |
| Material of anode | Cu |
| Wavelength K-Alpha1 [Å] | 1.54060 |
| Wavelength K-Alpha2 [Å] | 1.54443 |
| K-A2/K-A1 ratio | 0.50000 |
| Generator | 40 mA, 40 kV |
| Primary monochromator | focussing X-ray mirror |
| Sample rotation | yes |

TABLE 1

X-ray diffractogram of the maleate, acetate, and sulfate of 10-Chloro-4-(piperidin-4-yl)pyrimido[1,2-b]indazol-2(1H)-one (example 66)

| Peak List [°2 Theta] | | |
|---|---|---|
| Maleate | Acetate | Sulfate |
| 9.6 | 8.3 | 5.6 |
| 13.5 | 9.1 | 10.7 |
| 17.4 | 12.3 | 13.8 |
| 22.1 | 24.3 | 20.3 |
| 23.1 | 25.0 | 20.8 |
| 23.7 | 26.7 | 25.8 |
| 26.7 | 28.3 | 27.6 |

B. ASSESSMENT OF THE PHARMACOLOGICAL ACTIVITY

The following abbreviations are used:
Brij polyoxyethylene lauryl ether
$CaCl_2$ calciumchloride
CFT clot formation time
CM5 carboxymethylated dextran biosensor chips
CT clotting time
DMSO dimethylsulfoxide
EDC N-ethyl-N'-(3-dimethylaminopropyl)-carbodiimide hydrochloride
FVIII factor eight
HEPES hydroxyethyl-piperazineethanesulfonic acid
HCl hydrochloric acid
$IC_{50}$ half-maximal inhibitory concentration
$K_D$ dissociation constant MCF maximum clot firmness
ML maximum lysis
NaCl sodium chloride
NHS N-hydroxysuccinimide
OD optical density
PBS phosphate buffered saline
P-20 hybond P20
Rmax response at saturation
RU response units
SPR surface plasmon resonance
TF tissue factor
tPA tissue plasminogen activator
v/v volume/volume The pharmacological effect of the compounds of formula (I-A) or (I-B) according to the invention can be shown in the following assays:
B-1. Biacore Assay
Assay Description Surface Plasmon Resonance Plasminogen Inh.

Definitions

The term "surface plasmon resonance", as used herein, refers to an optical phenomenon that allows for the analysis of the reversible associations of biological molecules in real time within a biosensor matrix, for example using the Biacore® system (GE Healthcare Biosciences, Uppsala, Sweden). Biacore® uses the optical properties of surface plasmon resonance (SPR) to detect alterations in the refractive index of a buffer, which changes as molecules in solution interact with the target immobilized on the surface. In brief, proteins are covalently bound to the dextran matrix at a known concentration and a ligand for the protein is injected through the dextran matrix. Near infrared light, directed onto the opposite side of the sensor chip surface is reflected and also induces an evanescent wave in the gold film, which in turn, causes an intensity dip in the reflected light at a particular angle known as the resonance angle. If the refractive index of the sensor chip surface is altered (e.g. by compound binding to the protein bound to the surface) a shift occurs in the resonance angle. This angle shift can be measured. These changes are displayed with respect to time along the y-axis of a sensorgram, which depicts the association and dissociation of any biological reaction. For further descriptions see Jinsson U et al., 1993 Ann Biol Clin.; 51(1):19-26.; Johnsson B et al, Anal Biochem. 1991; 198(2):268-77.; Day Y et al, Protein Science, 2002; 11, 1017-1025; Myskza D G, Anal Biochem., 2004; 329, 316-323

The term "$K_D$", as used herein, is intended to refer to the dissociation constant of a particular compound/target protein complex.
Biological Activity The biological activity (e.g. as inhibitors of plasminogen) of the compounds of the invention can be measured using the assays set forth in the examples below, for example the surface plasmon resonance (SPR) experiments described in Example 1. The level of activity exhibited by a given compound in the SPR assay can be defined in terms of the $K_D$ value.

Example 1

The ability of the compounds of the invention to bind human plasminogen protein may be determined using surface plasmon resonance (SPR). $K_D$ values may be measured using a Biacore® T200 or Biacore® 4000 instrument (GE Healthcare, Uppsala, Sweden).

Cloning, expression, and purification of recombinant human plasminogen kringle 1 domain protein is performed according to a protocol based on published methods (Menhart et al, Biochemistry, 1991, 30, 1948-1957) with modifications as follows: Briefly, an E. coli expression construct coding for the amino acid sequence MKYLLPTAAAGLLL-LAAQPAMAHHHHHHHHHHMDYDIPTTENLYFQG followed by the human plasminogen kringle 1 domain protein sequence amino acids 101 to 181 (numbering based on Uniprot acc no P00747) and a stop codon is synthesized (GeneArt, Regensburg, Germany) and cloned into a modified pET22b vector (Novagen, Darmstadt, Germany), allowing for periplasmatic expression in E. coli and immobilized metal ion affinity chromatography employing a deca-histidine tag. E. coli BL21DE3 cells (Novagen) are transformed, grown and harvested and their periplasmatic fraction released using a buffer comprising 50 mM Tris pH 8 and 500 mM sucrose (modified from Menhart et al, Biochemistry, 1991, 30, 1948-1957). The periplasmatic fraction is then sequentially filtered using 8 µm, 3 µm and 1.2 µm cellulose nitrate filters (Sartorius Stedim, Gtittingen, Germany) and the filtrate subjected to Ni-Sepharose HP chromatography (GE Healthcare) according to the manufacturer's instructions. The resulting eluate is then subjected to a Desalting Hi Prep 26/10 column (GE Healthcare) equilibrated in buffer (100 mM sodium phosphate pH 8, 300 mM NaCl) followed by a lysine sepharose 4B (GE Healthcare) chromatography step according to the manufacturer's instructions. The resulting fractions of highly purified protein at concentrations of approximately 0.5 mg/ml are buffer exchanged against buffer (100 mM sodium phosphate pH 8, 300 mM NaCl) and stored at −80° C.

For SPR measurements, recombinant human plasminogen kringle 1 protein is immobilized using standard amine coupling (Johnsson B et al, Anal Biochem. 1991 Nov. 1; 198(2):268-77). Briefly, carboxymethylated dextran biosensor chips (CM5, GE Healthcare) are activated with N-ethyl-N'-(3-dimethylaminopropyl)-carbodiimide hydrochloride (EDC) and N-hydroxysuccinimide (NHS) according to the supplier's instructions. Purified recombinant human plasminogen kringle 1 protein is diluted in 10 mM sodium acetate pH 4.5 into 10 µg/ml and injected on the activated chip surface. Subsequently, 1 M ethanolamine-HCl (GE Healthcare) is injected to block unreacted groups, resulting in approximately 400 response units (RU) of immobilized protein. A reference surface is generated by treatment with NHS-EDC and ethanolamine-HCl. Compounds are dissolved in an aqueous 1% v/v acetic acid solution to a concentration of 20 mM, followed by addition of 1 vol of 100% dimethylsulfoxide (DMSO, Sigma-Aldrich, Germany) resulting in a compound concentration of 10 mM and subsequently diluted in running buffer (PBS pH 7.4, 0.05% v/v Surfactant P-20 (GE Healthcare), 1% v/v DMSO). For affinity measurements, five-fold serial dilutions of compound (0.64 nM to 10 µM) are injected over immobilized protein. The resulting sensorgrams are double-referenced against the reference surface as well as against blank injections. The double-referenced steady state responses are plotted against the test compound concentration and a fit using the equation Response=Rmax*[compound]/([compound]+$K_D$)+offset is generated. Parameters Rmax (response at saturation), $K_D$ (dissociation constant) and the offset parameter are calculated using a nonlinear least squares fit as implemented in the Biacore® evaluation software (GE Healthcare).

B-2. Plasma-Based Clot Lysis Assay (5%)

The clot-lysis test system configures the kinetics of clot formation and degradation in vitro and allows quantifying modulation of the process by selected test compounds.

The test compounds were dissolved in 1% acetic acid and further complemented with an equal volume of DMSO. The resulting stock solutions were serially diluted in 0.5% acetic acid/50% DMSO. 1 µL aliquots of these solutions were placed into 384 well microplates (Greiner, black, transparent bottom), followed by 30 µL of diluted human citrated plasma (platelet-poor, final concentration: 5%; supplemented with fibrinogen, final concentration: 3 µM; dilution buffer: 20 mM HEPES, 150 mM NaCl, 0.01% Brij (pH 7)). The reactions were started by addition of 20 µL of $CaCl_2$ (final concentration: 10 mM), and tPA (tissue plasminogen activator, final concentration: 0.2 nM) in dilution buffer, followed by an additional volume of 20 µL dilution buffer for improved mixing. The reactions were incubated at 37° C. Clot formation and degradation was monitored spectrophotometrically by kinetic optical density measurements at 405 nm. IC50 values were determined by comparing the resulting time courses with the time course of a blank control reaction.

Results B-2.

| Example | IC50 (nM) | Example | IC50 (nM) | Example | IC50 (nM) |
|---|---|---|---|---|---|
| 1 | 51 | 2 | 30 | 3 | 28 |
| 4 | 28 | 5 | 37 | 6 | 94 |
| 7 | 95 | 8 | 46 | 9 | 36 |
| 10 | 34 | 11 | 26 | 12 | 32 |
| 13 | 31 | 14 | 50 | 15 | 48 |
| 16 | 34 | 17 | 22 | 18 | 38 |
| 19 | 26 | 20 | 22 | 21 | 30 |
| 22 | 26 | 23 | 28 | 24 | 34 |
| 25 | 21 | 26 | 29 | 27 | 13 |
| 28 | 33 | 29 | 28 | 30 | 46 |
| 31 | 97 | 32 | 210 | 33 | 21 |
| 36 | 18 | 37 | 44 | 38 | 60 |
| 39 | 24 | 40 | 38 | 41 | 23 |
| 42 | 110 | 43 | 100 | 44 | 48 |
| 45 | 37 | 46 | 17 | 47 | 24 |
| 48 | 36 | 49 | 36 | 50 | 14 |
| 51 | 15 | 52 | 13 | 53 | 10 |
| 54 | 15 | 55 | 14 | 56 | 14 |
| 57 | 13 | 58 | 15 | 59 | 16 |
| 60 | 14 | 61 | 24 | 62 | 18 |
| 63 | 13 | 64 | 19 | 65 | 25 |
| 66 | 15 | 67 | 13 | 68 | 25 |
| 69 | 20 | 70 | 35 | 71 | 15 |
| 72 | 14 | 73 | 23 | 74 | 15 |
| 75 | 16 | 76 | 15 | 77 | 11 |
| 78 | 15 | 79 | 11 | 80 | 18 |
| 81 | 16 | 82 | 20 | 83 | 41 |
| 84 | 23 | 85 | 18 | 86 | 15 |
| 87 | 25 | 88 | 26 | 89 | 36 |
| 90 | 24 | 91 | 27 | 92 | 27 |
| 93 | 28 | 94 | 35 | 95 | 18 |
| 96 | 26 | 97 | 30 | 98 | 27 |
| 99 | 29 | 100 | 30 | 101 | 35 |
| 103 | 110 | 104 | 35 | 105 | 74 |
| 106 | 420 | 107 | 34 | 108 | 35 |

B-3. Plasma-Based Clot Lysis Assay (85%)

For induction of clot formation and subsequent clot lysis (fibrinolysis) a mixture of tissue factor (1 µM) and tissue plasminogen activator (tPA, 0.04 µM) was added to human plasma (final concentration 85%). The test compounds or saline controls were added simultaneously to TF and tPA. The functional activity is triggered with $CaCl_2$ (12.5 mM) and was monitored by measuring the optical density at 405 nM ($OD_{405}$). Fibrinolysis was evaluated as a relative decrease of OD after maximal clot formation. (Sperzel M, Huetter J, 2007, J Thromb Haemost 5(10): 2113-2118).

B-4. Thrombelastometry

Whole blood Thrombelastometry measurements are performed to confirm the potency of the compounds in inhibiting fibrinolysis and improving firmness of the clots (as seen in plasma based assays), for example using the ROTEM® system (Tem International GmbH, Munich, Germany). The ROTEM® system is a diagnostic (viscoelastic) technique which provides information on hemostasis. It includes a four-channel instrument, a computer, activators and disposable cups and pins. Kinetic changes in the blood sample are detected optically (light reflection) and data obtained from the reflected light is then processed into a graphical output by an integrated computer. Characteristic curves and numeric paremeters are generated. Thrombelastographic parameters of ROTEM® hemostatic systems include: Clotting Time (CT), which reflects the reaction time (the time required to obtain 2 mm amplitude following the initiation of data collection) to initiate blood clotting; Clot Formation Time (CFT), provides information about the kinetics of clot formation; the alpha angle to reflect clotting propagation. Maximum Clot Firmess (MCF) is defined as maximum amplitude which reflects the firmness of the clot (clot quality) and Maximum Lysis (ML) indicates fibrinolysis. For induction of clot formation and subsequent clot lysis a mixture of tissue factor (TF) and tissue plasminogen activator (tPA) is added to 300 µL freshly drawn citrated whole blood. Blood from patients with coagulation disorders and antibodies against coagulation factors (e.g. to neutralize FVIII activity and render the blood hemophilic) may be used. TF and tPA concentrations are adjusted dependent on the different conditions and species the whole blood is drawn from. Data are collected for 2 hours using a computer-controlled ROTEM® system.

For induction of clot formation and subsequent clot lysis in human whole blood or human Factor VIII depleted whole blood, a mixture of tissue factor (final concentration 0.5 µM) and tissue plasminogen activator (tPA, final concentration 10 nM) is added to 300 µL citrated human whole blood. The test compounds or controls are added simultaneously to TF and tPA.

For induction of clot formation and subsequent clot lysis (fibrinolysis) in rat whole blood, a mixture of tissue factor (final concentration 1 µM) and tissue plasminogen activator (tPA, final concentration 50 nM) is added to 300 µL citrated rat whole blood. The test compounds or controls are added simultaneously to TF and tPA. Or in the case of ex vivo experiments the test compounds are dosed to the animal, blood is drawn at different time points after administration and added to the test cup.

For induction of clot formation and subsequent clot lysis (fibrinolysis) in hemophilia A dog plasma or whole blood, a mixture of tissue factor (TF) and tissue plasminogen activator (tPA) is added to 300 µL citrated hemophilia A whole blood or plasma. TF and tPA concentrations are titrated and adjusted according to the current needs and technical requirements. Different concentrations of rFVIII are added to the test system in vitro (1-100%). The test compounds or controls are added simultaneously to TF and tPA. In the case of ex vivo experiments the test compounds are dosed to the animal, blood is drawn at different time points after administration and added to the test cup.

B-5. In Vivo Assays

To determine the protective effect of compounds on clot stability and blood loss in vivo, different bleeding models in different species are employed. Animals may be anticoagulated with different anticoagulants to induce a bleeding tendency. Genetically modified animals to mimick blood coagulation disorders may be used or antibodies to neutralize activity of different coagulation factors may be administered. Compounds of the invention are administered orally or parenterally at various indicated doses, at varying time courses prior to the injury. Injuries and endpoints may vary dependent on the mimicked disease condition.

B-5.1 Tail Bleeding in Hyperfibrinolytic Rats

In anaesthetized rats hyperfibrinolysis is induced by a continuous infusion of tPA (8 mg/kg/h) for twenty-five minutes via the right jugular vein. The right jugular vein is exposed and cannulated with saline-filled polyethylene catheters. The catheter is connected to a syringe pump (Braun, Melsungen, Germany) for the infusion of tPA. Hemostatic efficacy is evaluated in a rat bleeding model, where 8 mg/kg/h tPA is continuously infused to prolong bleeding time beyond control values. Test compounds or vehicle are administered by oral gavage at different time points before induction of anesthesia or intravenously through a second catheter in the contralateral jugular vein starting ten minutes after initiating tPA infusion. All infusions are stopped twenty-five minutes after onset of tPA administration. Twenty-five minutes after starting the tPA infusion, the rat tail is fully transected 2 mm from the tip of the tail. The tail is submerged in 37° C. physiological saline and bleeding is observed for 30 minutes. The time of bleeding is defined as the interval between the initial transection and the visual cessation of bleeding. A value of 30 minutes is assigned to those animals where bleeding does not stop during the entire observation period.

B-5.2 Tail Bleeding in Dabigatran-Anticoagulated Rats Animals are treated orally at different time points prior to induction of bleeding. In anaesthetized, anticoagulated rats bleeding is induced by a bolus and continuous infusion (jugular vein) of the thrombin-inhibitor Dabigatran (bolus 1 mg/kg followed by an infusion of 0.3 mg/kg/ml/h) for 15 minutes. 15 minutes after Dabigatran infusion the rat tail is fully transected 2 mm from the tip of the tail. Bleeding is observed for 30 minutes after the tail is submerged in 37° C. physiological saline. Blood loss is evaluated visually in 30 second intervals utilizing a scoring system (0=no blood flow; 1=weak, breaking to no blood flow; 2=reduced blood flow; 3=continuous blood flow; 4=strong, continuous blood flow). Initial bleeding time until the first visual cessation of bleeding as well as cumulative bleeding time over the entire observation period of 30 minutes is evaluated.

C. EXEMPLARY EMBODIMENTS OF PHARMACEUTICAL COMPOSITIONS

The compounds of formula (I-A) or (I-B) according to the invention can be converted into pharmaceutical preparations in the following ways:

Tablet:
Composition:
100 mg of the compound according to the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm.

Production:

The mixture of compound according to the invention, lactose and starch is granulated with a 5% strength solution (m/m) of the PVP in water. The granules are dried and then mixed with the magnesium stearate for 5 minutes. This mixture is compressed in a conventional tablet press (see above for format of the tablet). A guideline compressive force for the compression is 15 kN.

Suspension which can be Administered Orally:
Composition:
1000 mg of the compound according to the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound according to the invention.

Production:

The Rhodigel is suspended in ethanol, and the compound according to the invention is added to the suspension. The water is added while stirring. The mixture is stirred for about 6 h until the swelling of the Rhodigel is complete.

Solution which can be Administered Orally:
Composition:
500 mg of the compound according to the invention, 2.5 g of polysorbate and 97 g of polyethylene glycol 400. 20 g of oral solution correspond to a single dose of 100 mg of the compound according to the invention.

Production:

The compound according to the invention is suspended in the mixture of polyethylene glycol and polysorbate with stirring. The stirring process is continued until the compound according to the invention has completely dissolved.

i.v. Solution:

The compound according to the invention is dissolved in a concentration below the saturation solubility in a physiologically tolerated solvent (e.g. isotonic saline, 5% glucose solution and/or 30% PEG 400 solution). The solution obtained is sterilized by filtration and used to fill sterile and pyrogen-free injection containers.

The invention claimed is:

1. A method of prophylaxis of bleeding in a human or animal having a disease associated with bleeding, or at risk of bleeding during or after a medical intervention, the method comprising administering an effective amount of a compound of a formula (I-A)

(I-A)

in which
R$^1$ is selected from the group consisting of hydrogen and C$_1$-C$_4$ alkyl;
X$^1$ is selected from the group consisting of nitrogen and C—R$^2$;
X$^2$ is selected from the group consisting of nitrogen and C—R$^3$;
X$^3$ is selected from the group consisting of nitrogen and C—R$^4$;
X$^4$ is selected from the group consisting of nitrogen and C—R$^5$;

with a proviso that 0, 1 or 2 of $X^1$ to $X^4$ are nitrogen; and $R^2$, $R^3$, $R^4$, and $R^5$ are independently from each other selected from the group consisting of hydrogen,
halogen, $C_1$-$C_4$ alkyl, $C_1$-$C_4$ alkenyl, $C_1$-$C_4$ haloalkyl, $C_1$-$C_4$ alkoxy, $C_1$-$C_4$ haloalkoxy, cyano, amino, nitro, mono- or dialkylamino, hydroxy, thiol, carboxyl, $C_3$-$C_7$ cycloalkyl, and 5 to 6 membered heteroaryl, the 5 to 6 membered heteroaryl being optionally substituted with one, two, or three substituents selected from the group consisting of $C_1$-$C_4$ alkyl and phenyl, the phenyl being optionally substituted with one, two, or three substituents selected from the group consisting of halogen, $C_1$-$C_4$ alkyl, $C_1$-$C_4$ haloalkyl, $C_1$-$C_4$ alkoxy, and $C_1$-$C_4$ haloalkoxy, or a group of a formula selected from the group consisting of —CO—$NR^7R^8$, —NH—CO—$R^9$, —CO—O—$R^9$, —CO—$R^9$, —$SO_2R^{10}$, —$SO_2NR^{11}R^{12}$, —$SR^{10}$, $CH_2CN$, —$CH_2NR^{11}R^{12}$, and —$CH_2OR^{10}$, wherein
$R^7$ and $R^8$ independently from each other represent hydrogen, $C_1$-$C_4$ alkyl, $C_6$ aryl, or 5-6 membered heteroaryl;
$R^9$ represents $C_1$-$C_4$ alkyl, $C_6$ aryl, or 5-6 membered heteroaryl;
$R^{10}$ represents $C_1$-$C_4$ alkyl;
$R^{11}$ and $R^{12}$ independently from each other represent hydrogen or $C_1$-$C_4$ alkyl;
with a proviso that zero, one, two, or three of $R^2$ to $R^5$ are different from hydrogen, or a salt thereof.

2. The method of claim 1, wherein in the compound of the formula (I-A):
$R^1$ is selected from the group consisting of hydrogen and $C_1$-$C_4$ alkyl;
$X^1$ is selected from the group consisting of nitrogen and C—$R^2$;
$X^2$ is selected from the group consisting of nitrogen and C—$R^3$;
$X^3$ is selected from the group consisting of nitrogen and C—$R^4$;
$X^4$ is selected from the group consisting of nitrogen and C—$R^5$;
with a proviso that 0, 1 or 2 of $X^1$ to $X^4$ are nitrogen; and $R^2$, $R^3$, $R^4$, and $R^5$ are independently from each other selected from the group consisting of hydrogen, halogen, $C_1$-$C_4$ alkyl, $C_1$-$C_4$ alkenyl, $C_1$-$C_4$ haloalkyl, $C_1$-$C_4$ alkoxy, $C_1$-$C_4$ haloalkoxy, cyano, amino, nitro, mono- or dialkylamino, hydroxy, carboxyl, $C_3$-$C_7$ cycloalkyl, and 5 to 6 membered heteroaryl, the 5 to 6 membered heteroaryl being optionally substituted with one, two, or three substituents selected from the group consisting of $C_1$-$C_4$ alkyl and phenyl, the phenyl being optionally substituted with one, two, or three substituents selected from the group consisting of halogen, $C_1$-$C_4$ alkyl, $C_1$-$C_4$ haloalkyl, $C_1$-$C_4$ alkoxy, and $C_1$-$C_4$ haloalkoxy;
with a proviso that zero, one, two, or three of $R^2$ to $R^5$ are different from hydrogen, or a salt thereof.

3. The method of claim 1, wherein in the compound of the formula (I-A):
$R^1$ is selected from the group consisting of hydrogen and methyl;
$X^1$ is C—$R^2$
$X^2$ is C—$R^3$
$X^3$ is C—$R^4$
$X^4$ is C—$R^5$; and
$R^2$, $R^3$, and $R^4$ are independently from each other selected from the group consisting of hydrogen and fluorine; $R^5$ is selected from the group consisting of hydrogen, halogen, $C_1$-$C_4$ alkyl, $C_1$-$C_4$ haloalkyl, $C_1$-$C_4$ alkoxy, $C_1$-$C_4$ haloalkoxy, cyano, amino, nitro, dialkylamino, hydroxy, carboxyl, $C_3$-$C_7$ cycloalkyl, triazolyl (bonded via N), thiazolyl, thienyl, pyridyl, imidazolyl, pyrrolyl, and pyrazolyl (bonded via N or C), the pyrazolyl being optionally substituted with one or two substituents selected from the group consisting of $C_1$-$C_4$ alkyl and phenyl, the phenyl being optionally substituted with one or two substituents selected from the group consisting of halogen, $C_1$-$C_4$ alkyl, $C_1$-$C_4$ haloalkyl, $C_1$-$C_4$ alkoxy, and $C_1$-$C_4$ haloalkoxy;
with a proviso that zero, one, or two of $R^2$ to $R^5$ are different from hydrogen,
or a salt thereof.

4. The method of claim 1, wherein in the compound of the formula (I-A):
$R^1$ is hydrogen;
$X^1$ is C—$R^2$
$X^2$ is C—$R^3$
$X^3$ is C—$R^4$
$X^4$ is C—$R^5$
$R^2$ to $R^4$ are hydrogen, and
$R^5$ is chlorine;
or a salt thereof thereof.

5. The method of claim 1, wherein the bleeding disease or medical intervention is selected from the group consisting of menorrhagia, postpartum hemorrhage, hemorrhagic shock, trauma, surgery, otolaryngological surgery, dental surgery, urinary surgery, prostatic surgery, gynaecological surgery, cardiovascular surgery, and spinal surgery.

6. The method of claim 5, wherein the medical intervention is selected from the group consisting of liver or lung transplantation, gynaecological surgery, cardiovascular surgery, and spinal surgery.

7. The method of claim 1, wherein the bleeding disease is selected from the group consisting of stroke, liver diseases, hereditary angioedema, nosebleed, and synovitis and cartilage damage following hemarthrosis.

8. A method of prophylaxis of bleeding in a human or animal having a disease associated with bleeding, or at risk of bleeding during or after a medical intervention, the method comprising administering an effective amount of a compound of a formula (I-B)

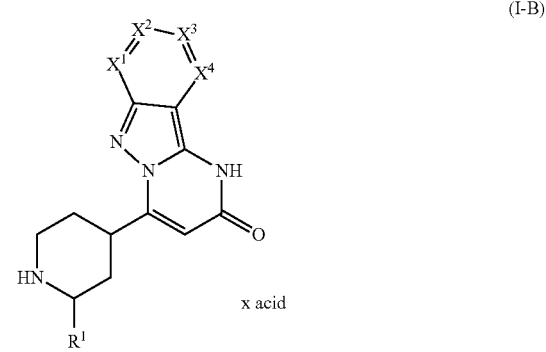

(I-B)

in which
$R^1$ is selected from the group consisting of hydrogen and $C_1$-$C_4$ alkyl;
$X^1$ is selected from the group consisting of nitrogen and C—$R^2$;
$X^2$ is selected from the group consisting of nitrogen and C—$R^3$;

$X^3$ is selected from the group consisting of nitrogen and C—$R^4$;

$X^4$ is selected from the group consisting of nitrogen and C—$R^5$;

with a proviso that 0, 1 or 2 of $X^1$ to $X^4$ are nitrogen; and $R^2$, $R^3$, $R^4$, and $R^5$ are independently from each other selected from the group consisting of hydrogen, halogen, $C_1$-$C_4$ alkyl, $C_1$-$C_4$ alkenyl, $C_1$-$C_4$ haloalkyl, $C_1$-$C_4$ alkoxy, $C_1$-$C_4$ haloalkoxy, cyano, amino, nitro, mono- or dialkylamino, hydroxy, thiol, carboxyl, $C_3$-$C_7$ cycloalkyl, and 5 to 6 membered heteroaryl, the 5 to 6 membered heteroaryl being optionally substituted with one, two, or three substituents selected from the group consisting of $C_1$-$C_4$ alkyl and phenyl, the phenyl being optionally substituted with one, two, or three substituents selected from the group consisting of halogen, $C_1$-$C_4$ alkyl, $C_1$-$C_4$ haloalkyl, $C_1$-$C_4$ alkoxy, and $C_1$-$C_4$ haloalkoxy, or a group of a formula selected from the group consisting of —CO—$NR^7R^8$, —NH—CO—$R^9$, —CO—O—$R^9$, —$SO^2R^{10}$, —$SO_2NR^{11}R^{12}$, —$SR^{10}$, $CH_2CN$, —$CH_2NR^{11}R^{12}$, and —$CH_2OR^{10}$, wherein $R^7$ and $R^8$ independently from each other represent hydrogen, $C_1$-$C_4$ alkyl, $C_6$ aryl, or 5-6 membered heteroaryl;

$R^9$ represents $C_1$-$C_4$ alkyl, $C_6$ aryl, or 5-6 membered heteroaryl;

$R^{10}$ represents $C_1$-$C_4$ alkyl;

$R^{11}$ and $R^{12}$ independently from each other represent hydrogen or $C_1$-$C_4$ alkyl;

with a proviso that zero, one, two, or three of $R^2$ to $R^5$ are different from hydrogen, or a salt thereof, and wherein x acid is a ratio of the compound to the acid which is from 10:1 to 1:10.

9. The method of claim 8, wherein in the compound of the formula (I-B):

$R^1$ is selected from the group consisting of hydrogen and $C_1$-$C_4$ alkyl;

$X^1$ is selected from the group consisting of nitrogen and C—$R^2$;

$X^2$ is selected from the group consisting of nitrogen and C—$R^3$;

$X^3$ is selected from the group consisting of nitrogen and C—$R^4$;

$X^4$ is selected from the group consisting of nitrogen and C—$R^5$;

with a proviso that 0, 1 or 2 of $X^1$ to $X^4$ are nitrogen; and $R^2$, $R^3$, $R^4$, and $R^5$ are independently from each other selected from the group consisting of hydrogen, halogen, $C_1$-$C_4$ alkyl, $C_1$-$C_4$ alkenyl, $C_1$-$C_4$ haloalkyl, $C_1$-$C_4$ alkoxy, $C_1$-$C_4$ haloalkoxy, cyano, amino, nitro, mono- or dialkylamino, hydroxy, carboxyl, $C_3$-$C_7$ cycloalkyl, and 5 to 6 membered heteroaryl, the 5 to 6 membered heteroaryl being optionally substituted with one, two, or three substituents selected from the group consisting of $C_1$-$C_4$ alkyl and phenyl, the phenyl being optionally substituted with one, two, or three substituents selected from the group consisting of halogen, $C_1$-$C_4$ alkyl, $C_1$-$C_4$ haloalkyl, $C_1$-$C_4$ alkoxy, and $C_1$-$C_4$ haloalkoxy;

with a proviso that zero, one, two, or three of $R^2$ to $R^5$ are different from hydrogen, or a salt thereof.

10. The method of claim 8, wherein in the compound of the formula (I-B):

$R^1$ is selected from the group consisting of hydrogen and methyl;

$X^1$ is C—$R^2$ $X^2$ is C—$R^3$ $X^3$ is C—$R^4$ $X^4$ is C—$R^5$; and $R^2$, $R^3$, and $R^4$ are independently from each other selected from the group consisting of hydrogen and fluorine; $R^5$ is selected from the group consisting of hydrogen, halogen, $C_1$-$C_4$ alkyl, $C_1$-$C_4$ haloalkyl, $C_1$-$C_4$ alkoxy, $C_1$-$C_4$ haloalkoxy, cyano, amino, nitro, dialkylamino, hydroxy, carboxyl, $C_3$-$C_7$ cycloalkyl, triazolyl (bonded via N), thiazolyl, thienyl, pyridyl, imidazolyl, pyrrolyl, and pyrazolyl (bonded via N or C), the pyrazolyl being optionally substituted with one or two substituents selected from the group consisting of $C_1$-$C_4$ alkyl and phenyl, the phenyl being optionally substituted with one or two substituents selected from the group consisting of halogen, $C_1$-$C_4$ alkyl, $C_1$-$C_4$ haloalkyl, $C_1$-$C_4$ alkoxy, and $C_1$-$C_4$ haloalkoxy;

with a proviso that zero, one, or two of $R^2$ to $R^5$ are different from hydrogen, or a salt thereof.

11. The method of claim 8, wherein in the compound of the formula (I-B):

$R^1$ is hydrogen;

$X^1$ is C—$R^2$ $X^2$ is C—$R^3$ $X^3$ is C—$R^4$ $X^4$ is C—$R^5$ $R^2$ to $R^4$ are hydrogen, and $R^5$ is chlorine;

or a salt thereof.

12. The method of claim 8, wherein the bleeding disease or medical intervention is selected from the group consisting of menorrhagia, postpartum hemorrhage, hemorrhagic shock, trauma, surgery, otolaryngological surgery, dental surgery, urinary surgery, prostatic surgery, gynaecological surgery, cardiovascular surgery, and spinal surgery.

13. The method of claim 12, wherein the medical intervention is selected from the group consisting of liver or lung transplantation, gynaecological surgery, cardiovascular surgery, and spinal surgery.

14. The method of claim 8, wherein the bleeding disease is selected from the group consisting of stroke, liver diseases, hereditary angioedema, nosebleed, and synovitis and cartilage damage following hemarthrosis.

15. The method of claim 8, wherein x acid is a ratio of the compound to an acid in a range of from 5:1 to 1:5.

16. The method of claim 8, wherein x acid is a ratio of the compound to an acid in a range of from 1.5:1 to 1:1.5.

17. The method of claim 11, wherein the compound of the formula (I-B) is a hydrochloride salt thereof.

* * * * *